US011669678B2

(12) United States Patent
Rao et al.

(10) Patent No.: US 11,669,678 B2
(45) Date of Patent: Jun. 6, 2023

(54) SYSTEM WITH REPORT ANALYSIS AND METHODS FOR USE THEREWITH

(71) Applicant: Enlitic, Inc., San Francisco, CA (US)

(72) Inventors: Shankar Rao, San Francisco, CA (US); Kevin Lyman, Fords, NJ (US)

(73) Assignee: Enlitic, Inc., Fort Collins, CO (US)

( * ) Notice: Subject to any disclaimer, the term of this patent is extended or adjusted under 35 U.S.C. 154(b) by 79 days.

(21) Appl. No.: 17/173,587

(22) Filed: Feb. 11, 2021

(65) Prior Publication Data

US 2022/0253592 A1    Aug. 11, 2022

(51) Int. Cl.
| | |
|---|---|
| *G06F 17/00* | (2019.01) |
| *G06F 40/166* | (2020.01) |
| *G16H 40/20* | (2018.01) |
| *G16H 70/60* | (2018.01) |
| *G16H 30/20* | (2018.01) |
| *G16H 50/70* | (2018.01) |
| *G06F 40/279* | (2020.01) |
| *G16H 30/40* | (2018.01) |
| *H04W 4/14* | (2009.01) |
| *G16H 10/20* | (2018.01) |

(52) U.S. Cl.
CPC .......... *G06F 40/166* (2020.01); *G06F 40/279* (2020.01); *G16H 30/20* (2018.01); *G16H 30/40* (2018.01); *G16H 40/20* (2018.01); *G16H 50/70* (2018.01); *G16H 70/60* (2018.01); *G16H 10/20* (2018.01); *H04W 4/14* (2013.01)

(58) Field of Classification Search
CPC ..... G06F 40/166; G06F 40/279; G16H 30/20; G16H 30/40; G16H 40/20; G16H 50/70; G16H 70/60; G16H 10/20; G16H 15/00; H04W 4/14

USPC ........................................................ 715/256
See application file for complete search history.

(56) References Cited

U.S. PATENT DOCUMENTS

| | | | |
|---|---|---|---|
| 6,466,687 | B1 | 10/2002 | Uppaluri |
| 6,524,246 | B1 | 2/2003 | Kelly |

(Continued)

FOREIGN PATENT DOCUMENTS

| | | |
|---|---|---|
| CN | 106295139 A | 1/2017 |
| CN | 106551704 A | 4/2017 |

(Continued)

OTHER PUBLICATIONS

Chaudhry, 'Systematic Review: Impact of Health Information Technology on Quality, Efficiency, and Costs of Medical Care', Acpjournal.org, published 2006 (Year: 2006).*

(Continued)

*Primary Examiner* — Stephen S Hong
*Assistant Examiner* — Matthew J Ludwig
(74) *Attorney, Agent, or Firm* — Cochran Freund & Young LLC

(57) ABSTRACT

A method includes receiving a medical report created by a medical professional at a creation time. Prior to elapsing of a fixed-length time frame starting at the creation time, report analysis data for the medical report is automatically generated via performance of a report processing function. Correction requirement notification data is generated based on the report analysis data indicating at least one correction requirement. Communication of the correction requirement notification data to the medical professional is facilitated.

7 Claims, 61 Drawing Sheets

(56) References Cited

U.S. PATENT DOCUMENTS

| | | | |
|---|---|---|---|
| 6,819,790 | B2 | 11/2004 | Suzuki |
| 6,937,776 | B2 | 8/2005 | Li |
| 7,123,762 | B2 | 10/2006 | Giger |
| 7,418,123 | B2 | 8/2008 | Giger |
| 7,813,822 | B1 | 10/2010 | Hoffberg |
| 8,121,362 | B2 | 2/2012 | Zhan |
| 8,303,505 | B2 | 11/2012 | Webler |
| 8,331,637 | B2 | 12/2012 | Bar-Aviv |
| 8,379,950 | B2 | 2/2013 | Ye |
| 8,447,627 | B1* | 5/2013 | Cruise ............ G06Q 40/08 705/2 |
| 8,600,133 | B2 | 12/2013 | Buelow |
| 8,885,898 | B2 | 11/2014 | Liu |
| 9,165,360 | B1 | 10/2015 | Bates |
| 9,349,178 | B1 | 5/2016 | Itu |
| 9,501,863 | B1 | 11/2016 | Fram |
| 9,569,736 | B1 | 2/2017 | Ghesu |
| 9,579,518 | B2 | 2/2017 | Gertner |
| 9,760,978 | B1 | 9/2017 | Lu |
| 9,916,420 | B2* | 3/2018 | Cardoza ............ G16H 40/20 |
| 10,140,421 | B1 | 11/2018 | Bernard |
| 10,304,198 | B2 | 5/2019 | Yan |
| 10,340,041 | B2 | 7/2019 | Chan |
| 10,553,311 | B2* | 2/2020 | Lyman ............ A61B 5/0022 |
| 11,176,840 | B2* | 11/2021 | Ogawa ............ G09B 5/06 |
| 11,275,985 | B2* | 3/2022 | Neumann ............ G06N 5/02 |
| 11,380,211 | B2* | 7/2022 | Dohring ............ G09B 5/06 |
| 11,443,648 | B2* | 9/2022 | Brinton ............ G09B 7/00 |
| 11,487,802 | B1* | 11/2022 | Klein ............ G06Q 50/01 |
| 2002/0186818 | A1 | 12/2002 | Amaud |
| 2003/0016850 | A1 | 1/2003 | Kaufman |
| 2004/0064029 | A1 | 4/2004 | Summers |
| 2004/0147840 | A1 | 7/2004 | Duggirala |
| 2004/0181431 | A1 | 9/2004 | Kuth |
| 2004/0252870 | A1 | 12/2004 | Reeves |
| 2005/0027566 | A1 | 2/2005 | Haskell |
| 2005/0207630 | A1 | 9/2005 | Chan |
| 2005/0283450 | A1 | 12/2005 | Matsugu |
| 2007/0004980 | A1 | 1/2007 | Warner |
| 2008/0004505 | A1 | 1/2008 | Kapit |
| 2008/0015418 | A1 | 1/2008 | Jarrell |
| 2008/0021834 | A1 | 1/2008 | Holla |
| 2008/0205717 | A1 | 8/2008 | Reeves |
| 2008/0243539 | A1 | 10/2008 | Barish et al. |
| 2008/0267483 | A1 | 10/2008 | Zhan |
| 2009/0177495 | A1 | 7/2009 | Abousy |
| 2009/0222388 | A1 | 9/2009 | Hua |
| 2009/0228299 | A1 | 9/2009 | Kangarloo |
| 2010/0088117 | A1 | 4/2010 | Belden |
| 2010/0191546 | A1* | 7/2010 | Kanamarlapudi ..... G06Q 10/10 707/E17.014 |
| 2010/0278405 | A1 | 11/2010 | Kakadiaris |
| 2012/0130734 | A1 | 5/2012 | White |
| 2013/0073344 | A1* | 3/2013 | Parent ............ G06Q 10/04 705/7.39 |
| 2013/0124527 | A1 | 5/2013 | Lee |
| 2013/0262364 | A1* | 10/2013 | Verbeek ............ G06N 5/02 706/46 |
| 2014/0219500 | A1 | 8/2014 | Moehrle |
| 2014/0328517 | A1 | 11/2014 | Gluncic |
| 2014/0335497 | A1* | 11/2014 | Gal ............ G09B 7/00 434/323 |
| 2014/0341471 | A1 | 11/2014 | Ono et al. |
| 2014/0379386 | A1* | 12/2014 | Drennan, III ...... G06Q 10/10 705/4 |
| 2015/0031979 | A1 | 1/2015 | Rappaport et al. |
| 2015/0063667 | A1 | 3/2015 | Sprencz |
| 2015/0230773 | A1 | 8/2015 | Cho |
| 2015/0254843 | A1 | 9/2015 | Brown |
| 2015/0305706 | A1 | 10/2015 | Kanik |
| 2016/0019695 | A1 | 1/2016 | Chukka |
| 2016/0027175 | A1 | 1/2016 | Kim et al. |
| 2016/0048972 | A1 | 2/2016 | Kam |
| 2016/0071226 | A1* | 3/2016 | Karale ............ G16H 10/60 705/3 |
| 2016/0104281 | A1 | 4/2016 | Grady |
| 2016/0174902 | A1 | 6/2016 | Georgescu |
| 2016/0203281 | A1 | 7/2016 | Zalis |
| 2016/0260211 | A1 | 9/2016 | Gillies |
| 2016/0314588 | A1* | 10/2016 | Harper ............ G06F 16/447 |
| 2016/0343127 | A1 | 11/2016 | Miller |
| 2016/0350919 | A1 | 12/2016 | Steigauf |
| 2016/0364862 | A1 | 12/2016 | Reicher |
| 2017/0004619 | A1 | 1/2017 | Liang |
| 2017/0024517 | A1 | 1/2017 | Biegert |
| 2017/0068780 | A1 | 3/2017 | Dobrean |
| 2017/0116497 | A1 | 4/2017 | Georgescu |
| 2017/0330320 | A1 | 11/2017 | Lynch |
| 2017/0337343 | A1 | 11/2017 | Kakadiaris |
| 2018/0025255 | A1 | 1/2018 | Poole |
| 2018/0033144 | A1 | 2/2018 | Risman |
| 2018/0060535 | A1 | 3/2018 | Reicher |
| 2018/0060691 | A1 | 3/2018 | Bernal |
| 2018/0114595 | A1 | 4/2018 | Stern |
| 2018/0204111 | A1 | 7/2018 | Zadeh |
| 2018/0301222 | A1* | 10/2018 | Dew, Sr. ............ G16H 15/00 |
| 2018/0315182 | A1* | 11/2018 | Rapaka ............ G16H 50/70 |
| 2018/0342055 | A1 | 11/2018 | Lyman |
| 2019/0142519 | A1 | 5/2019 | Siemionow |
| 2020/0294640 | A1* | 9/2020 | Ginsburg ............ G16H 40/20 |
| 2022/0005565 | A1* | 1/2022 | Lyman ............ G16H 15/00 |
| 2022/0068449 | A1* | 3/2022 | Klassen ............ G06F 40/40 |

FOREIGN PATENT DOCUMENTS

| | | |
|---|---|---|
| GB | 2457022 A | 8/2009 |
| KR | 1020100014065 A | 2/2010 |

OTHER PUBLICATIONS

Rubin, 'Knowledge Representation and Tool Support for Critiquing Clinical Trial Protocols', AMIA, 2000 (Year: 2000).*

Andersch, Michael; Inference: The Next Step in GPU-Accelerated Deep Learning; https://devblogs.nvidia.com/parallelforall/inference-next-step-gpu-accelerated-deep-learning/; Nov. 11, 2015; 7 pages.

Attaluri, et al.; Efficient and Accurate Abnormality Mining from Radiology Reports with Customized False Positive Reduction: arXiv:1810.000967v1; Oct. 1, 2018.

Choi, Y., Chiu, C. Y. I., & Sontag, D. (2016). Learning low-dimensional representations of medical concepts. AM IA Summits on Translational Science Proceedings, 2016, 41. (Year: 2016).

International Searching Authority; International Search Report and Written Opinion; International Application No. PCT/US2018/032927; dated Sep. 14, 2018; 9 pgs.

Jamie A. Weydert, MD, Barry R. De Young, MD and Michael B. Cohen, MD, A preliminary Diagnosis Service Provides Prospective Blinded Dual-Review of All General Surgical Pathology Cases in an Academic Practice, 2005, Am J Surg Pathol, vol. 29, pp. 801-805 (Year: 2005).

Long, Jonathan, Evan Shelhamer, and Trevor Darrell. "Fully convolutional networks for semantic segmentation." Proceedings of the IEEE conference on computer vision and pattern recognition. 2015. (Year: 2015).

Minnaar, Alex; Deep Learning Basics: Neural Networks, Backpropagation and Stochastic Gradient Descent; http://alexminnaar.com/deep-learning-basics-neural-networks-backpropagation-and-stochastic-gradient-descent.html; Feb. 14, 2015; 11 pages.

Pham, A.-D., Neveol, A., Lavergne, T., Yasunaga, D., Clement, O., Meyer, G., . . . Burgun, A. (2014). Natural language processing of radiology reports for the detection of thromboembolic diseases and clinically relevant incidental findings. BMC Bioinformatics, 15(1). doi: 10.1186/1471-2105-15-266 (Year: 2014).

Pons, E., Braun, L. M. M., Hunink, M. G. M., & Kors, J. A. (2016). Natural Language Processing in Radiology: A Systematic Review. Radiology, 279(2), 329-343. doi: 10.1148/radiol.16142770.

Pre Conference Proceedings of the 7th MICCAI BraTS Challenge (2018); BraTS Multimodal Brain Tumor Segmentation Challenge; Granada, Spain; Sep. 16, 2018; 578 pages.

(56) References Cited

OTHER PUBLICATIONS

Reid, Stuart; 10 misconceptions about Neural Networks; http://www.turingfinance.com/misconceptions-about-neural-networks/; May 8, 2014; 24 pages.
S. Ted Sandler, Regularlized Learning with Feature Networks (Year: 2010).
What Not to Include in a Medical Record. (Jun. 6, 2012). Retrieved from https://www.texmed.org/Template.aspx?id=1741. (Year 2012).
Wikipedia: Backpropagation; https://en.wikipedia.org/wiki/Backpropagation#Assumptions_about_the_loss_function; downloaded from the internet on 18/15/18; 12 pages.
Wikipedia; Convolutional neural network; https://en.wikipedia.org/wiki/Convolutional_neural_network#Pooling_layer; downloaded from the internet on Jan. 15, 2018; 21 pages.
Yao, Li, et al. "Weakly supervised medical diagnosis and localization from multiple resolutions." arXiv preprint arXiv: 1803.07703 (2018). (Year: 2018).
Yoo Jae Chern, Remote medical-diagnosis system and method. 2010. Translated by IP.com (Year 2010).

\* cited by examiner

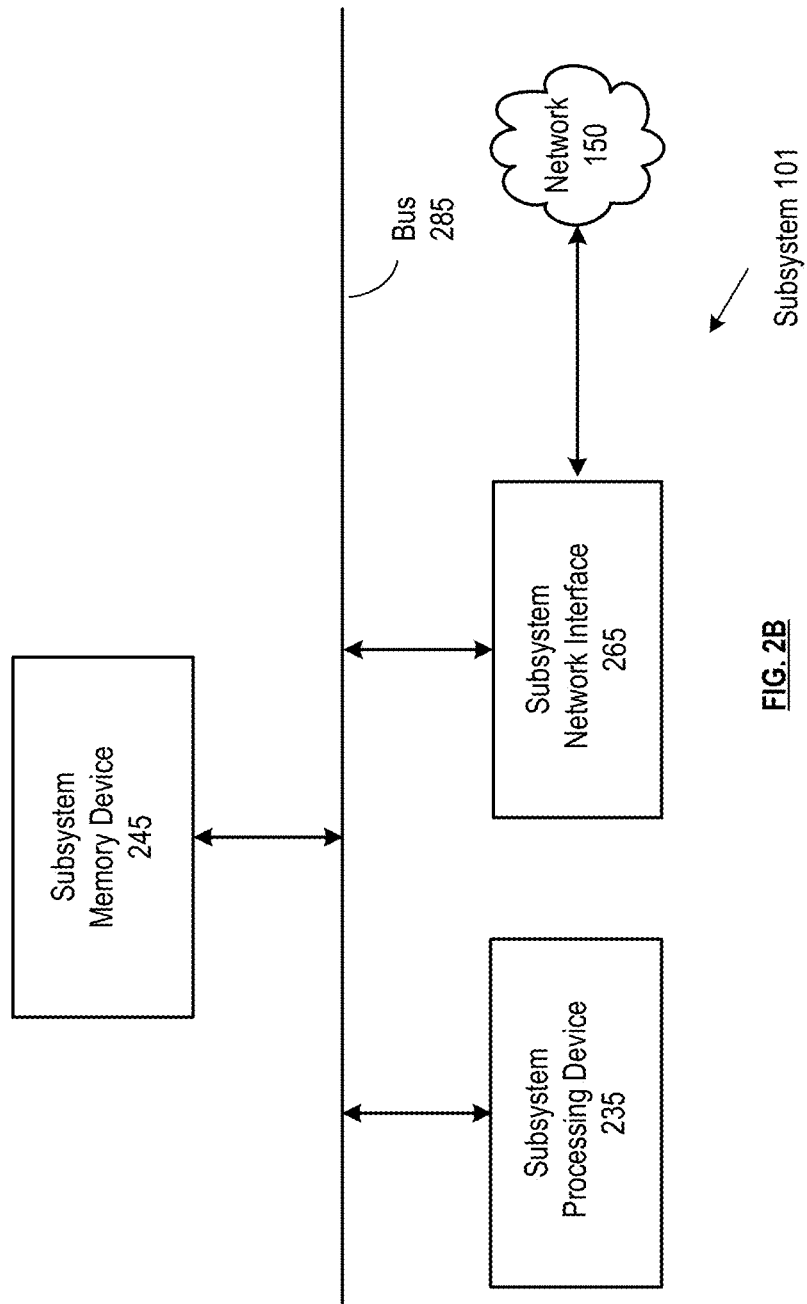

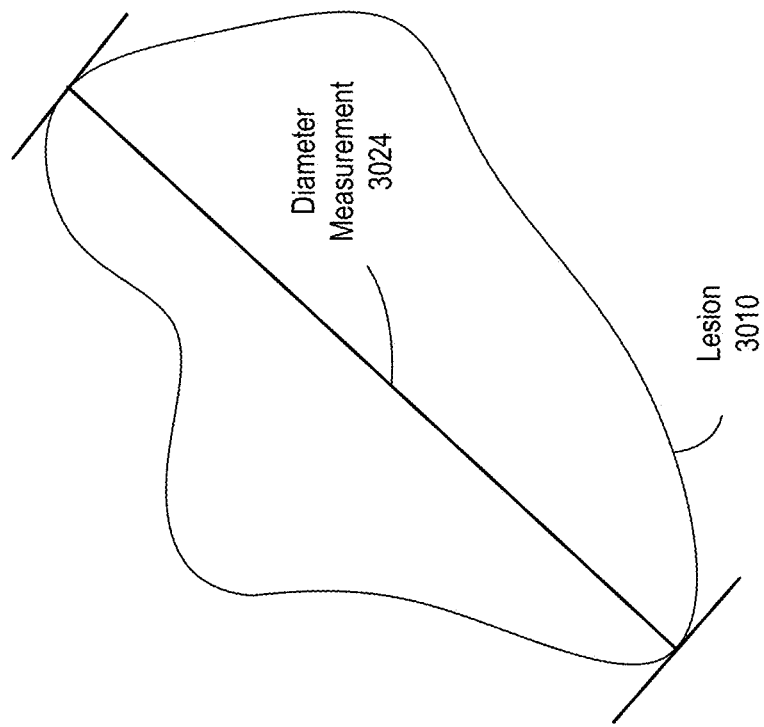
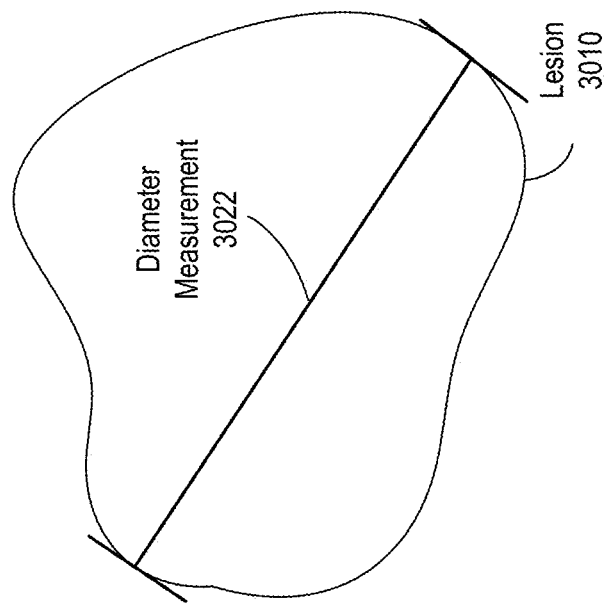
FIG. 12B

| | 3102-2 |
|---|---|
| Discrepancy noted! See below | |
| User XABC | System |
| Scan normal<br>Change?<br>Yes [x] No [ ] | Scan abnormal |
| No Pneumothorax<br>Change?<br>Yes [x] No [ ] | Pneumothorax present |
| ... | ... |
| No Cardiomegaly | No Cardiomegaly |

3106-2 →

3104 → (chest X-ray image labeled "pneumothorax")

FIG. 13C

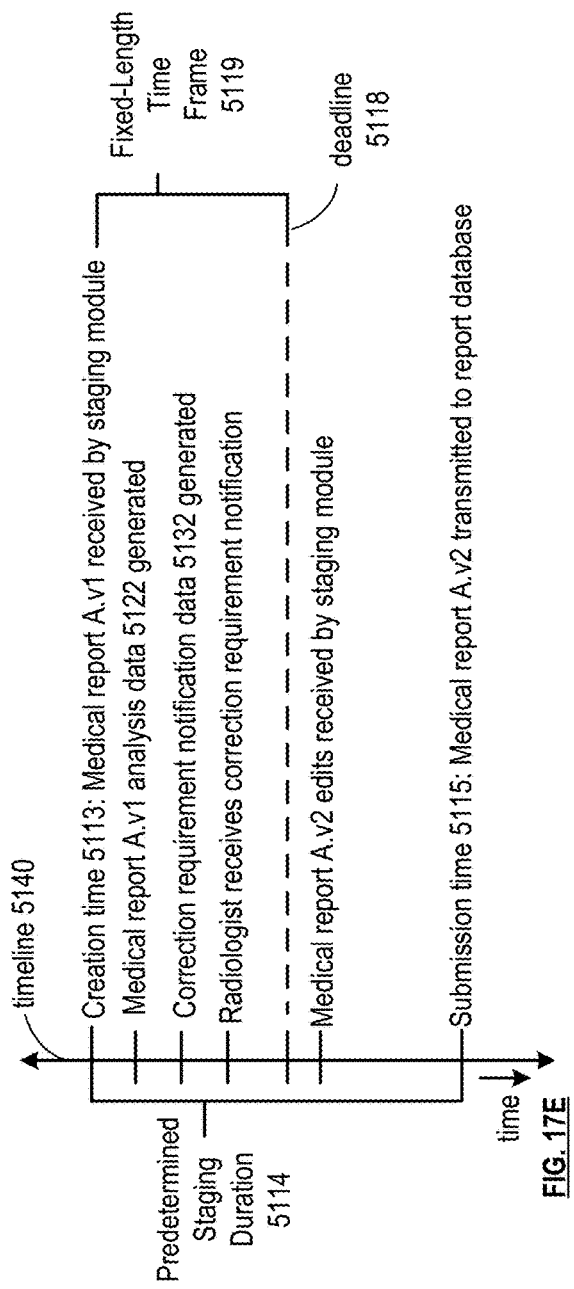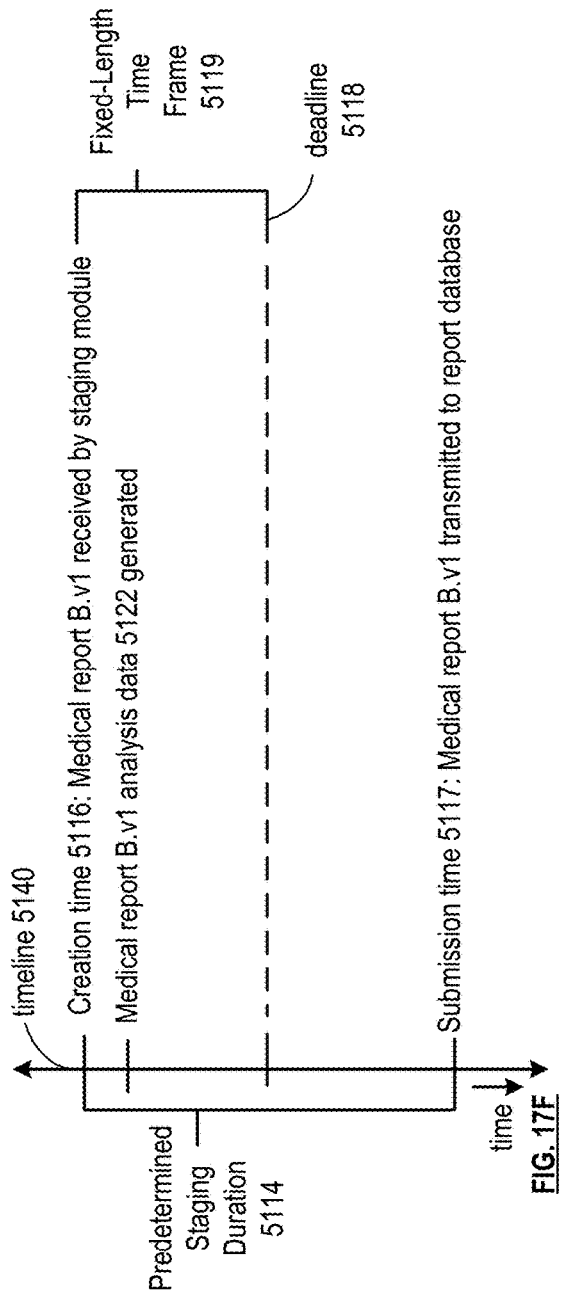

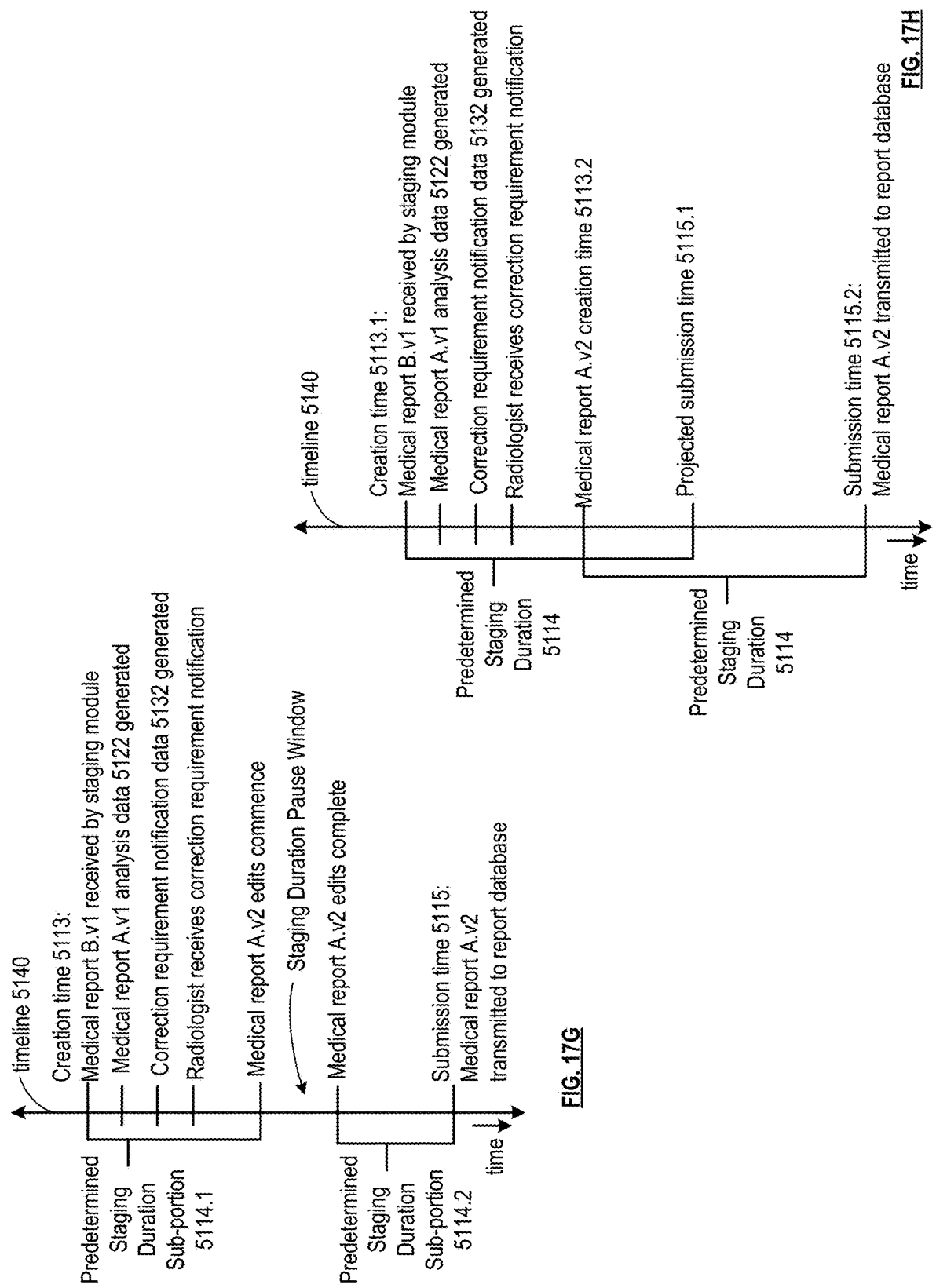

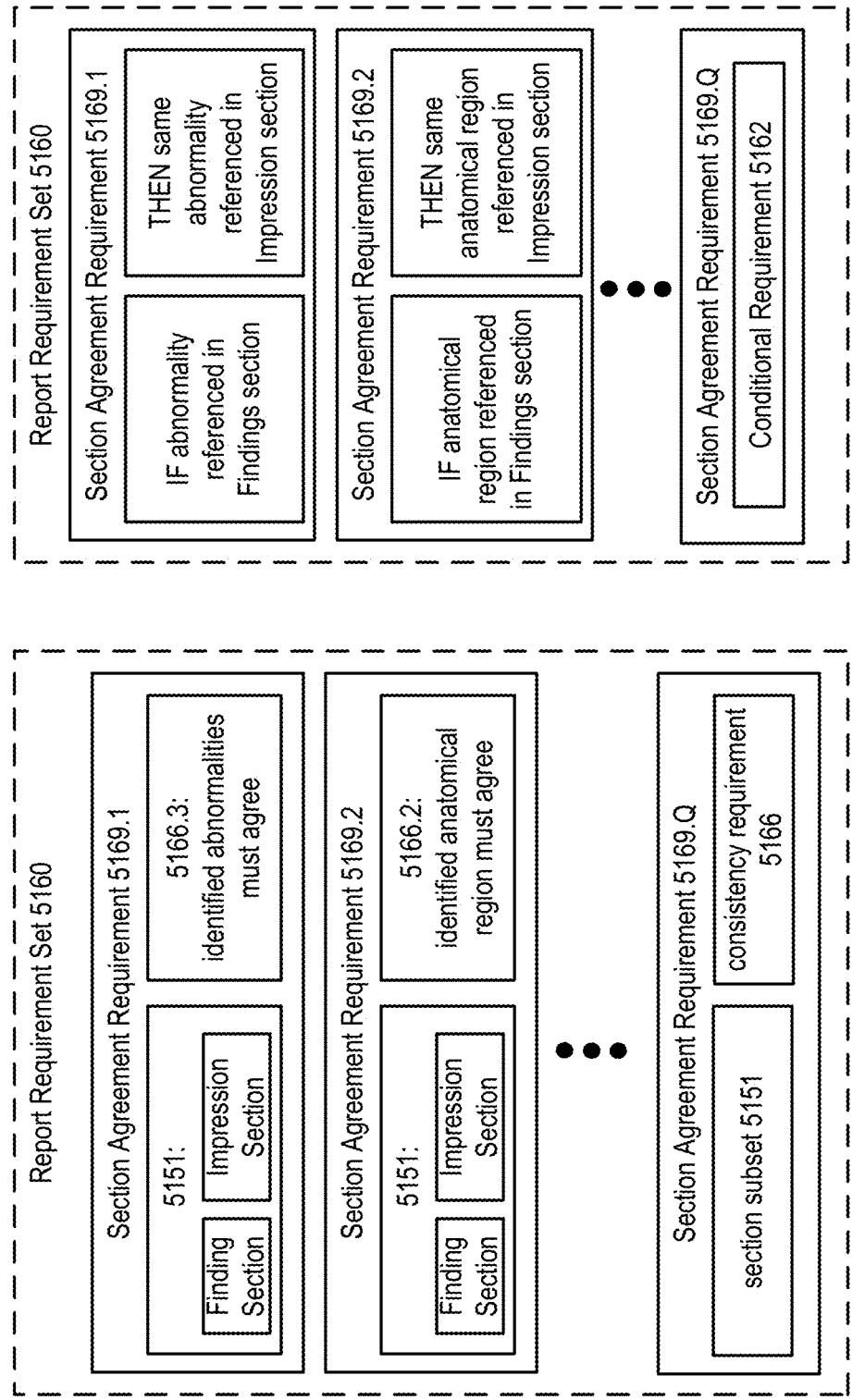

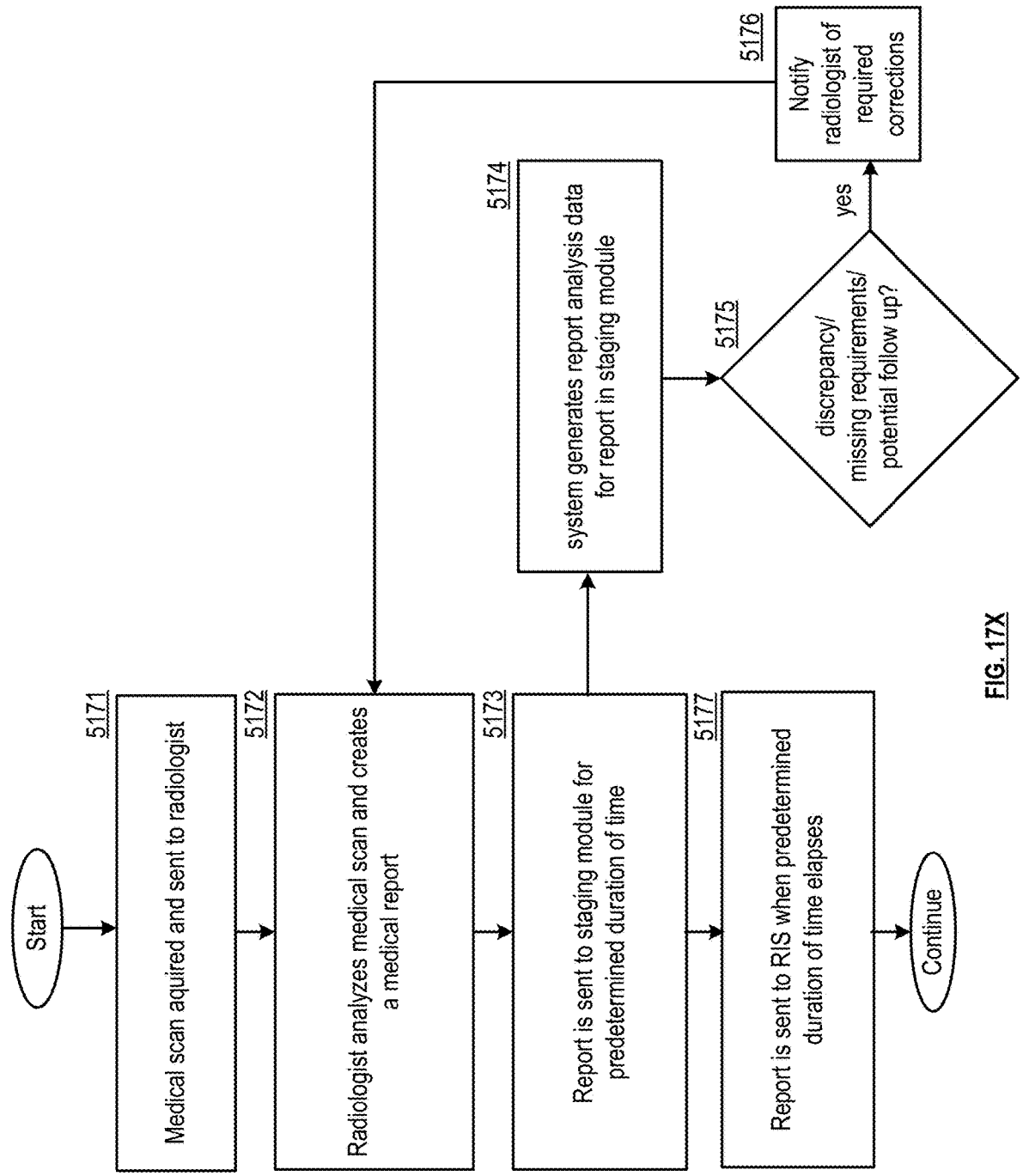

SYSTEM WITH REPORT ANALYSIS AND METHODS FOR USE THEREWITH

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISC

Not applicable.

BACKGROUND

Technical Field

This invention relates generally to medical imaging devices and knowledge-based systems used in conjunction with client/server network architectures.

DESCRIPTION OF RELATED ART

Brief Description of the Several Views of the Drawing(s)

FIG. 2B is a schematic block diagram of one or more subsystems in accordance with various embodiments;

Figure 11:
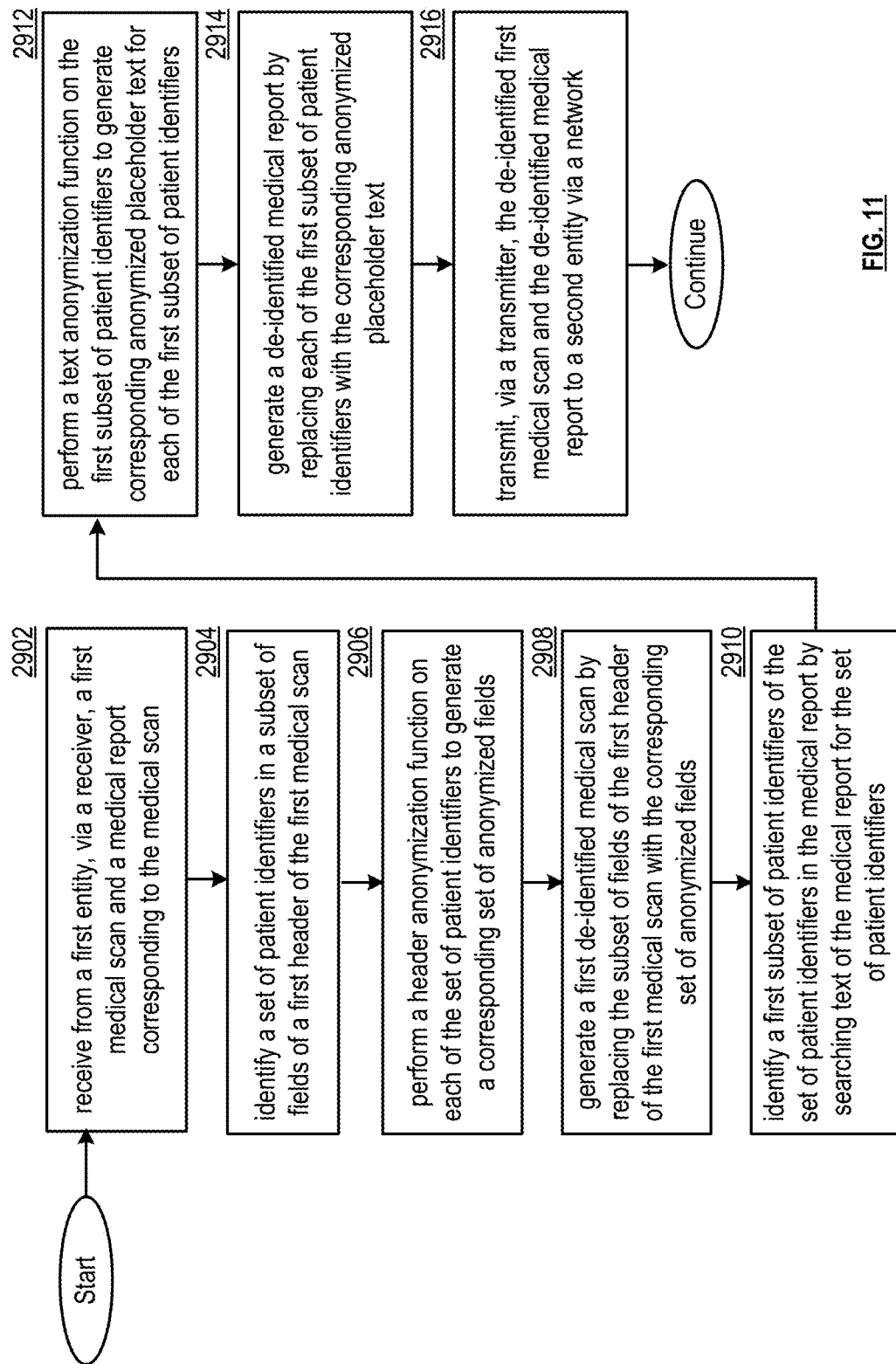
Figure 12A:
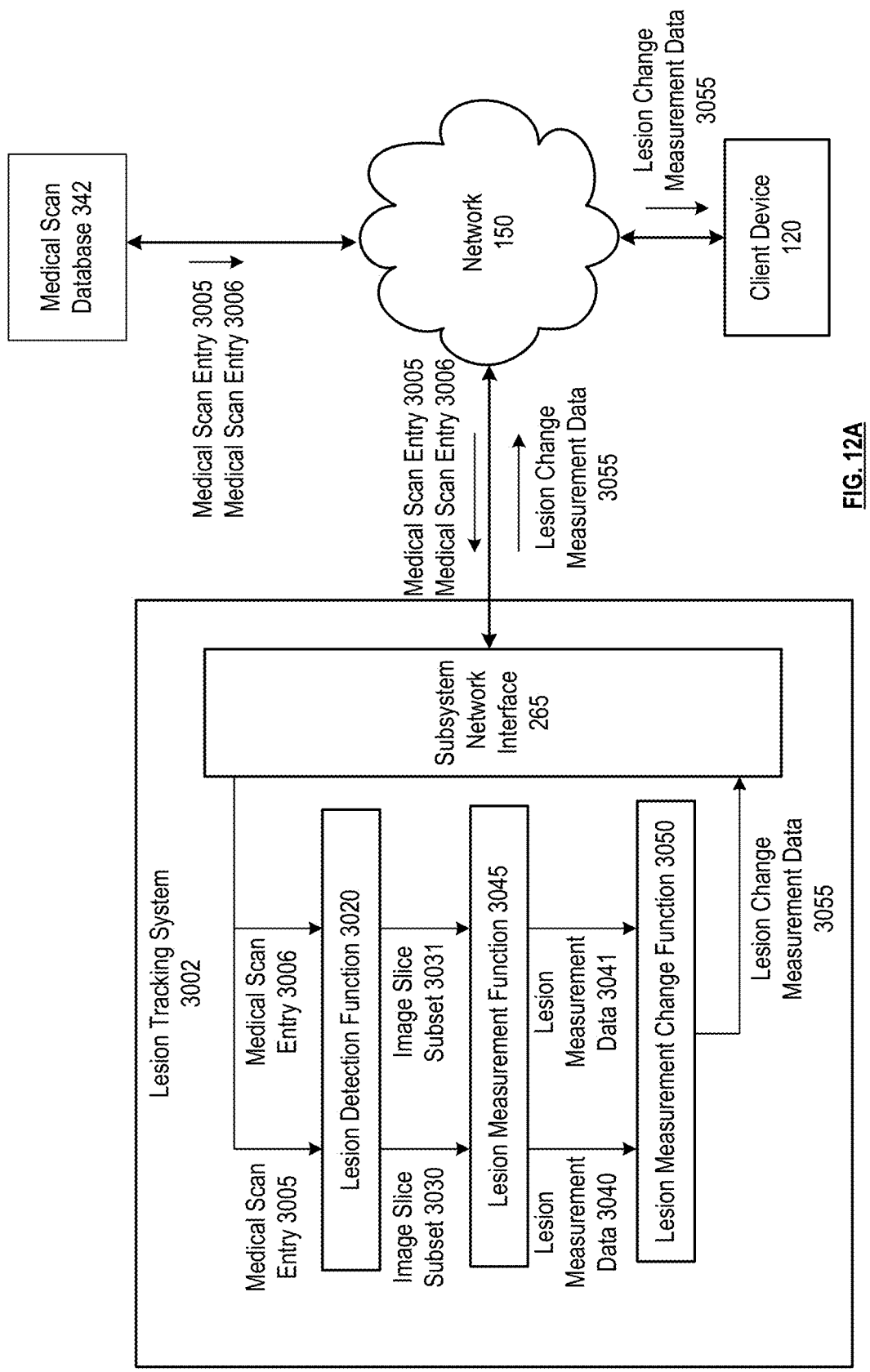
Figure 12C:
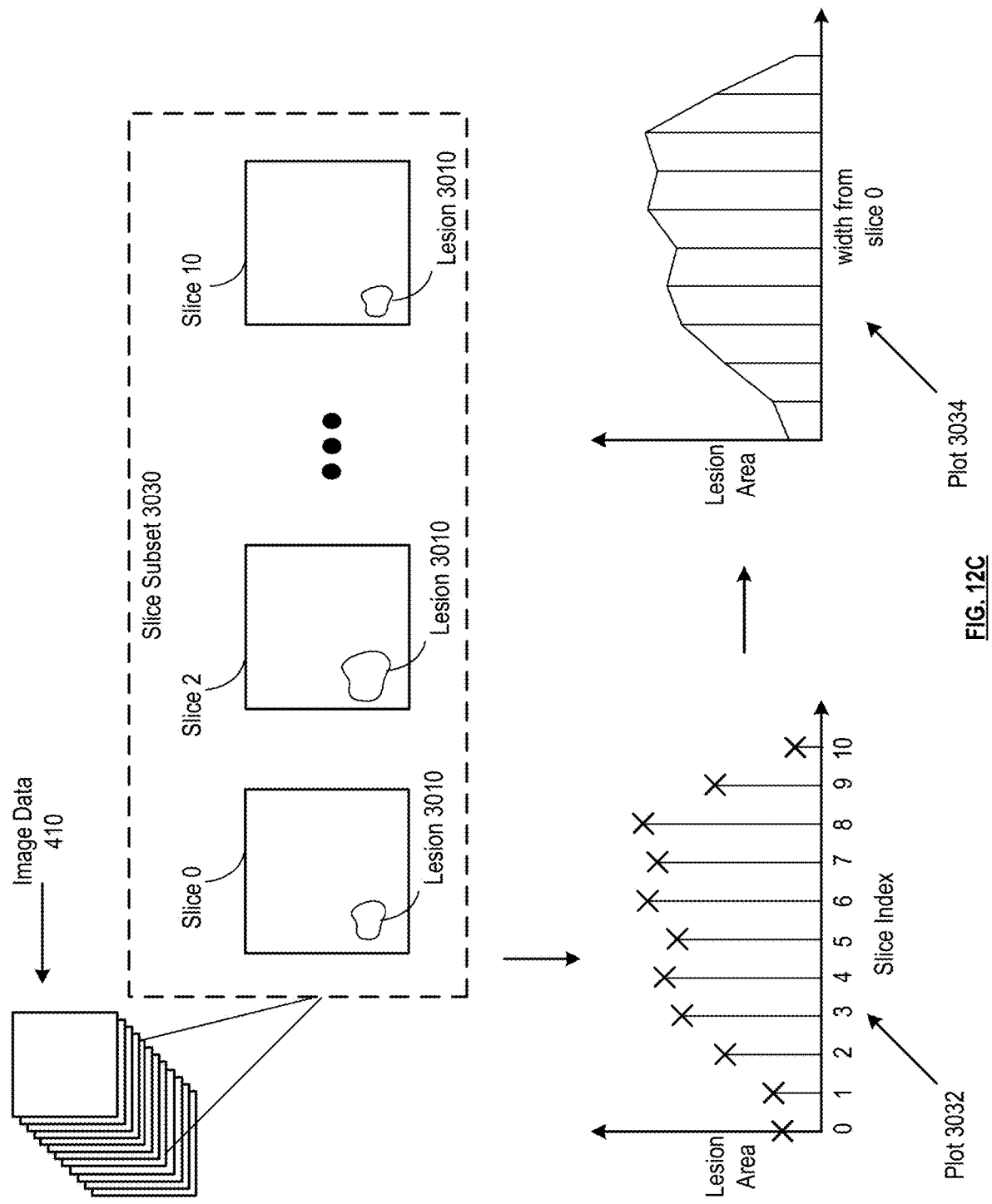
Figure 12D:
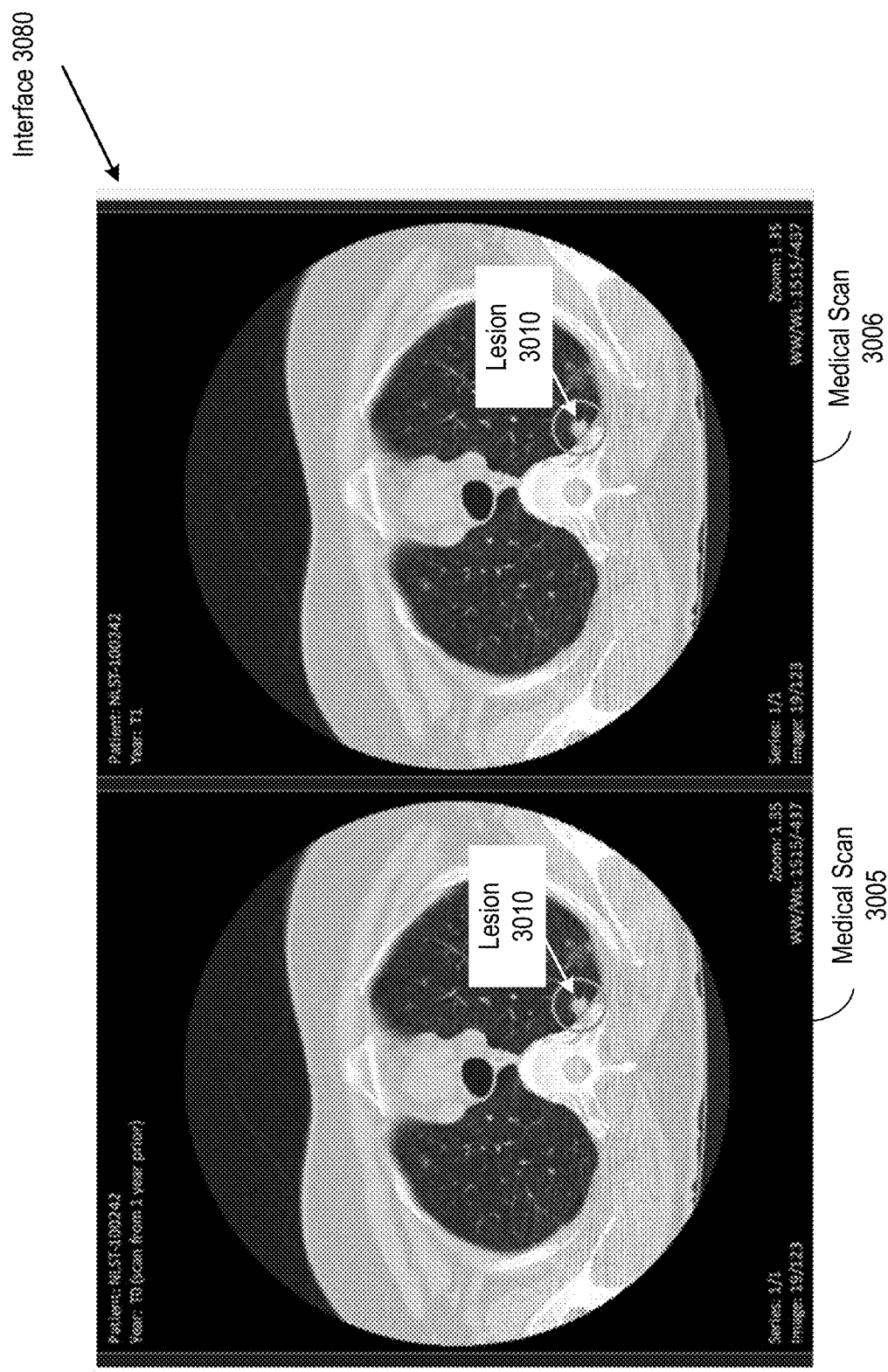
Figure 13A:
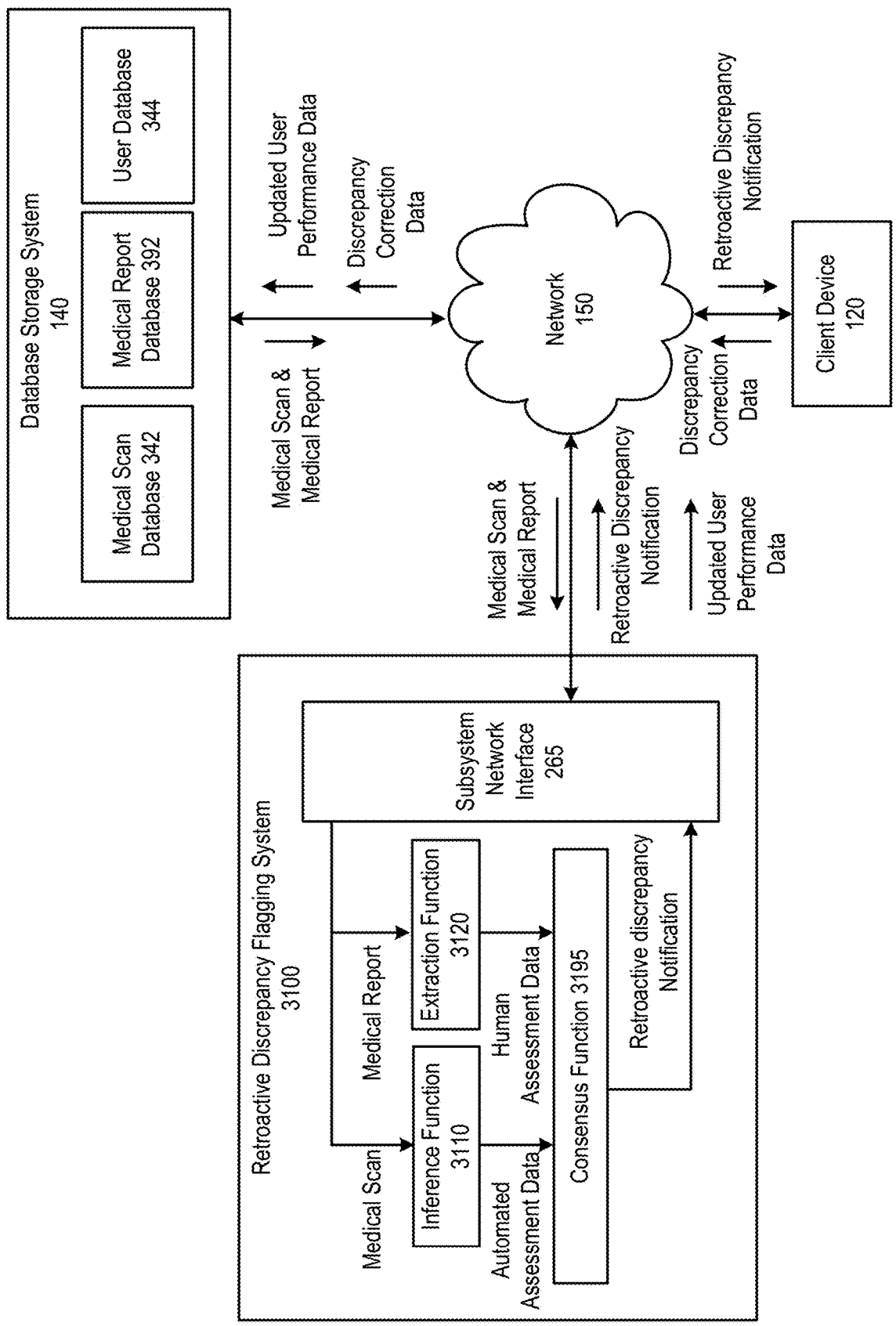
Figure 13B:
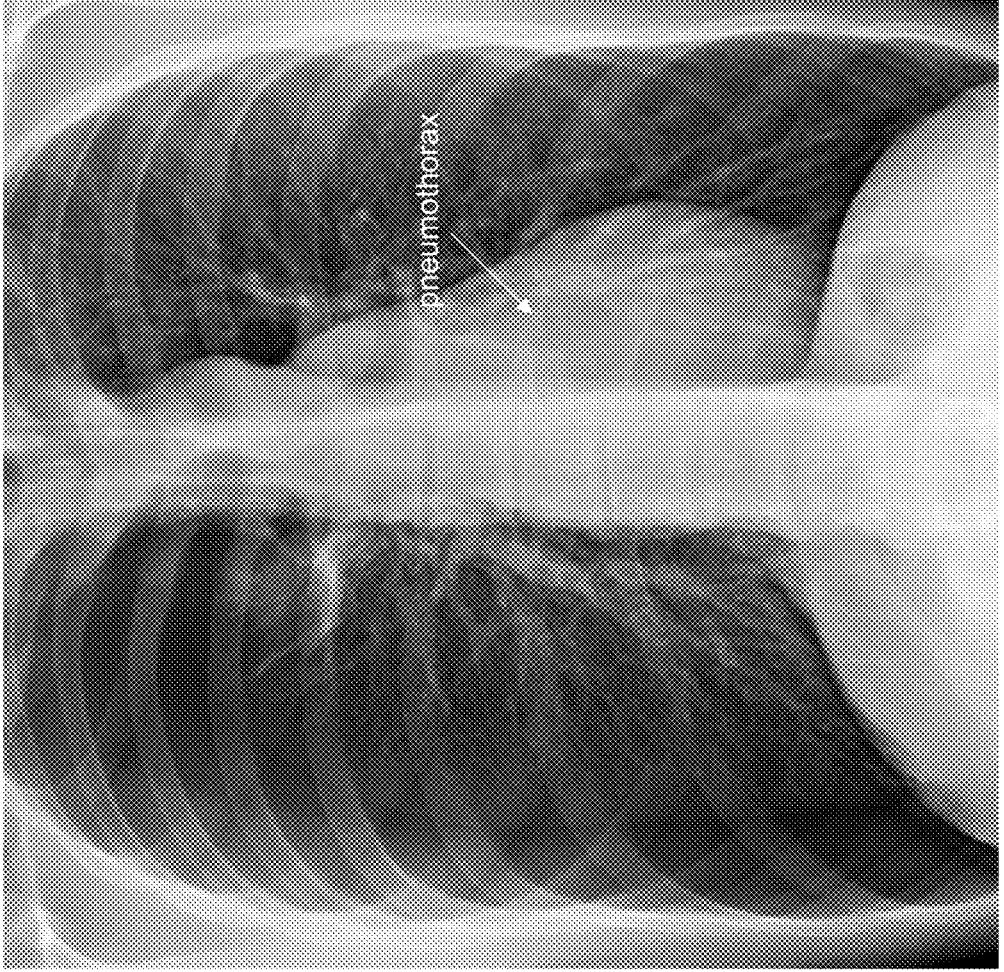
Figure 13D:
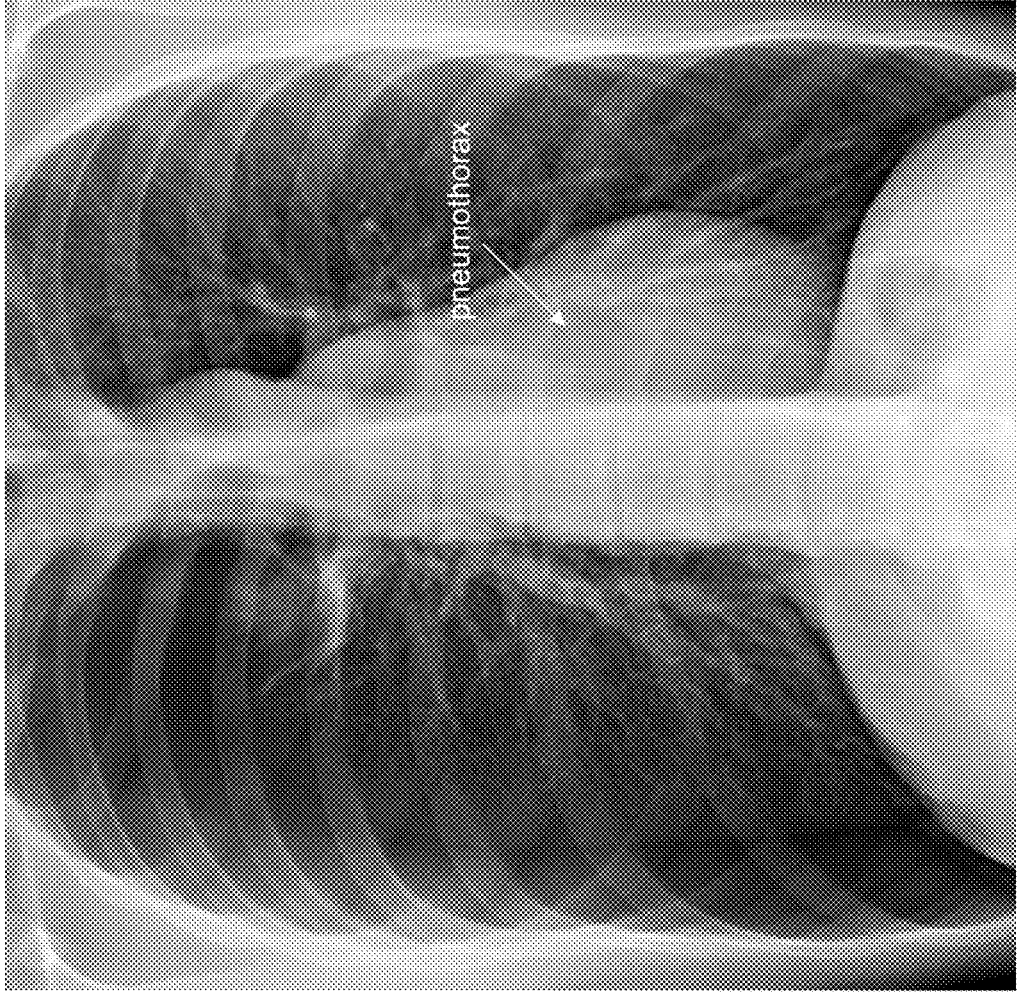
Figure 13E:
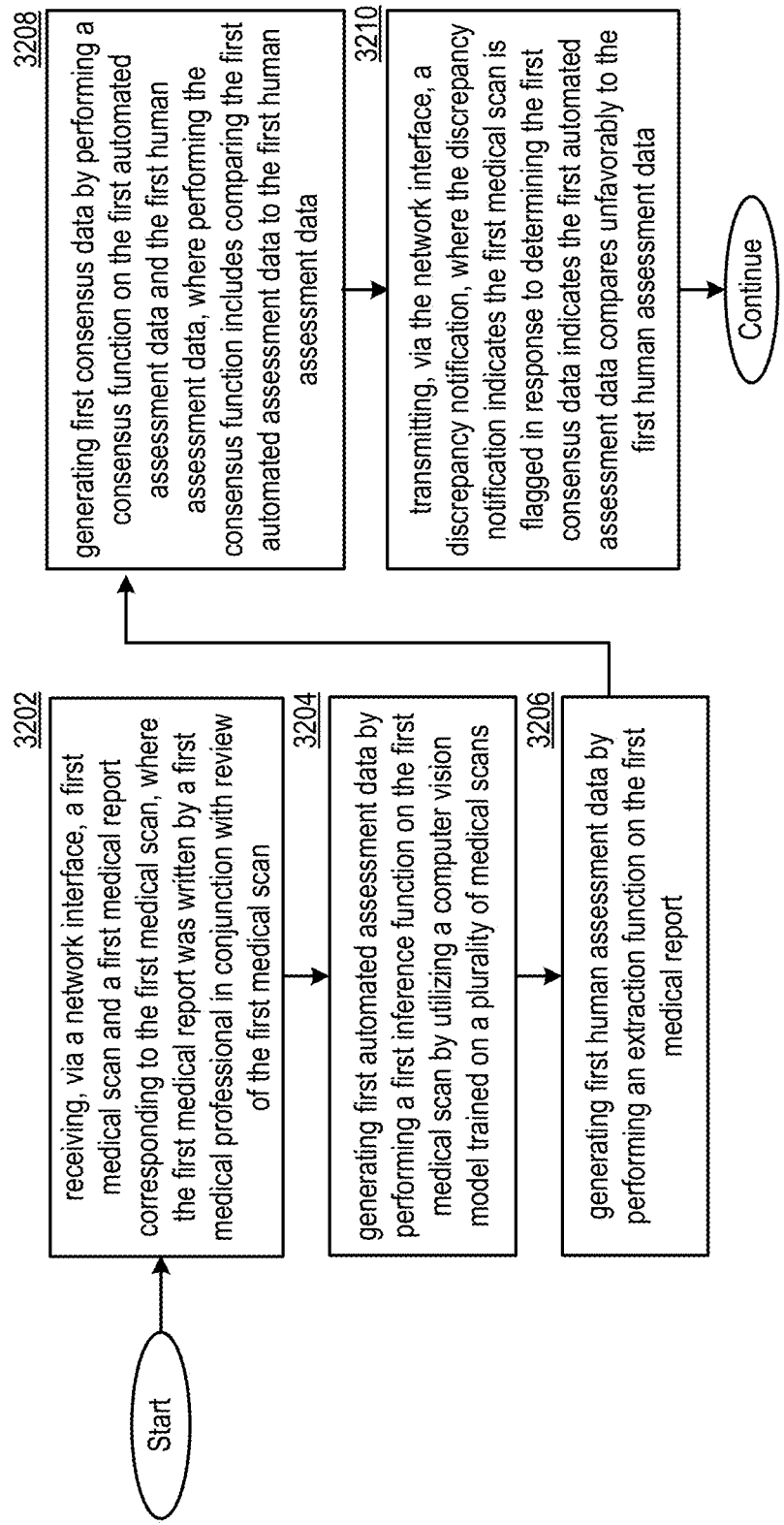
Figure 14A:
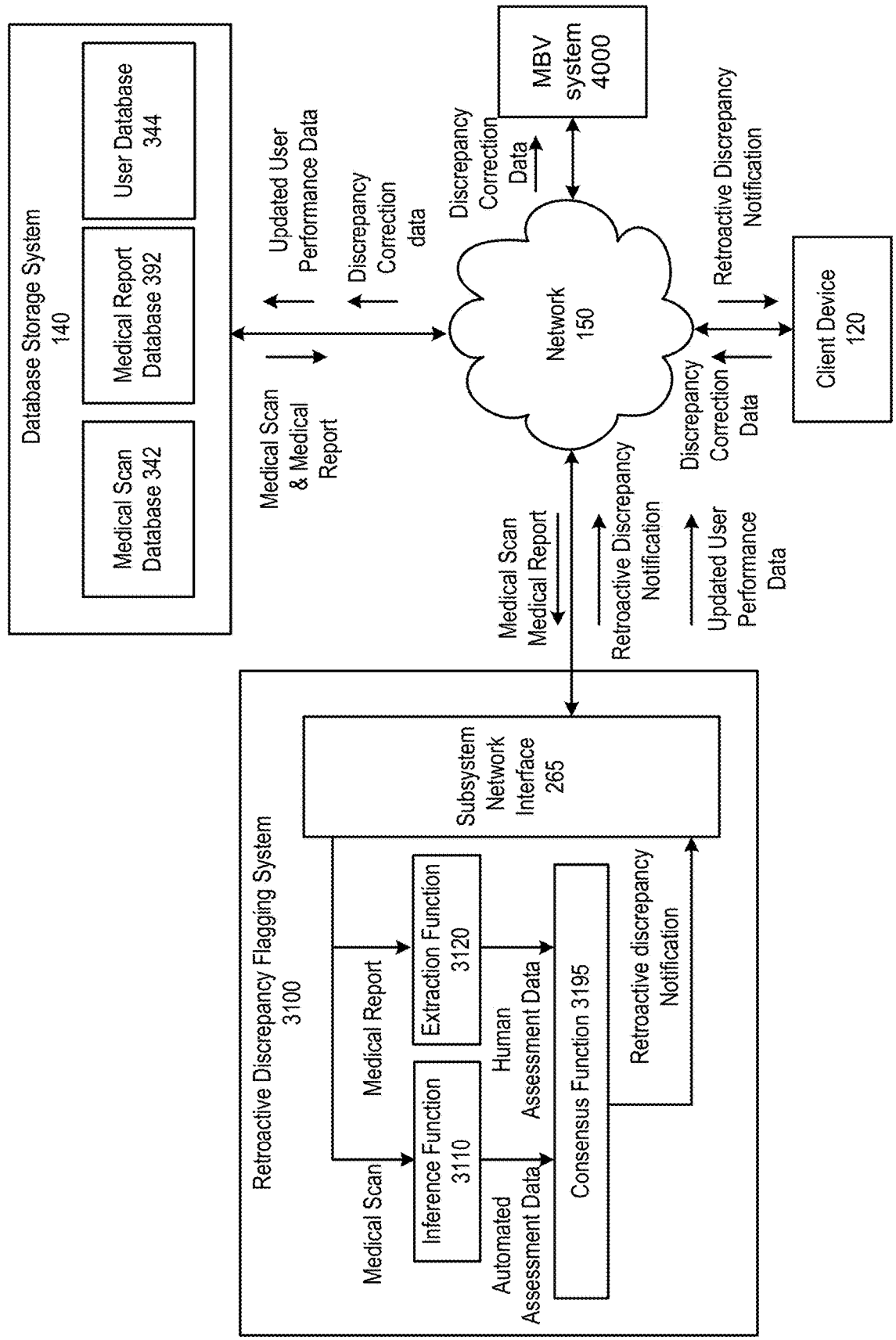
Figure 14B:
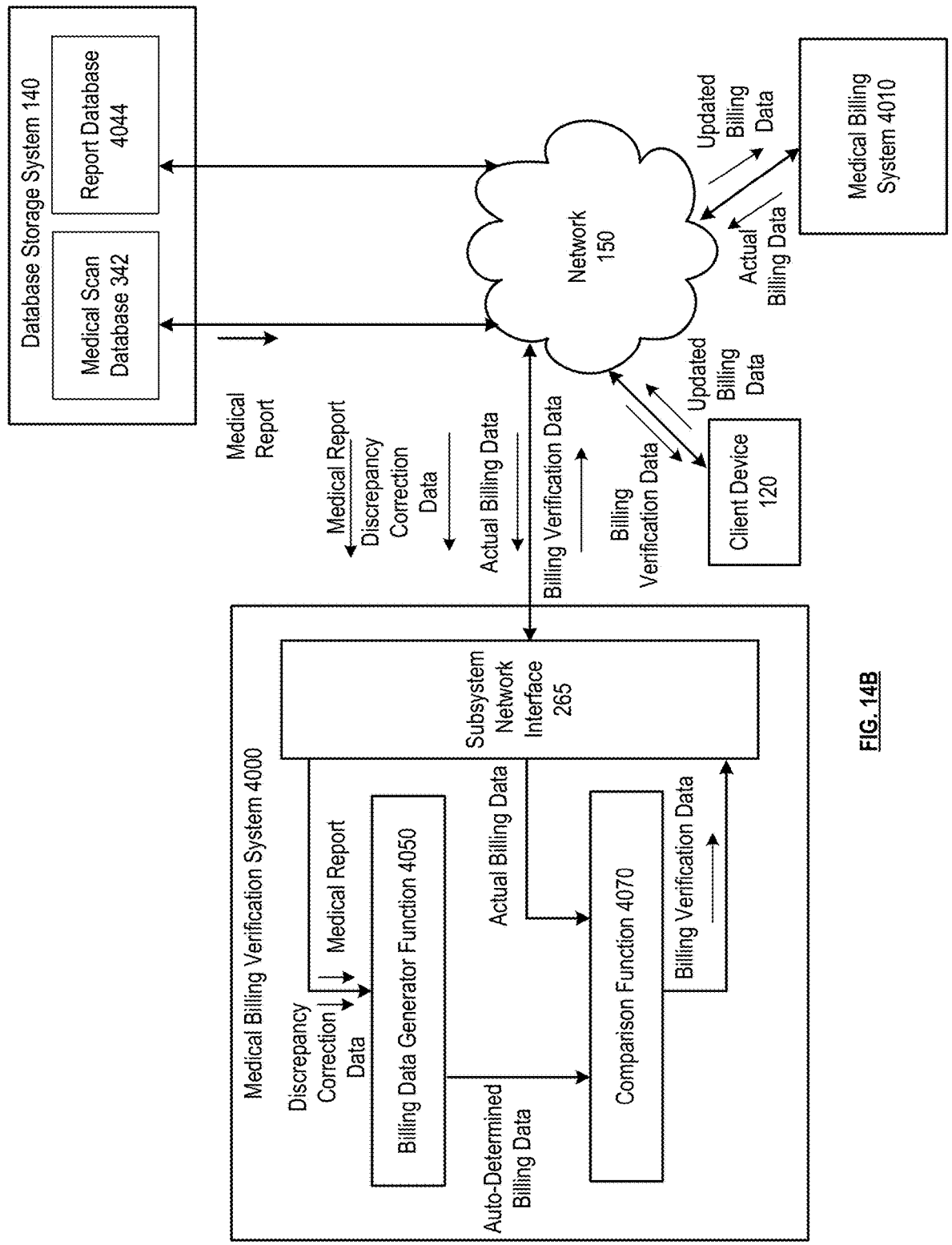
Figure 14C:
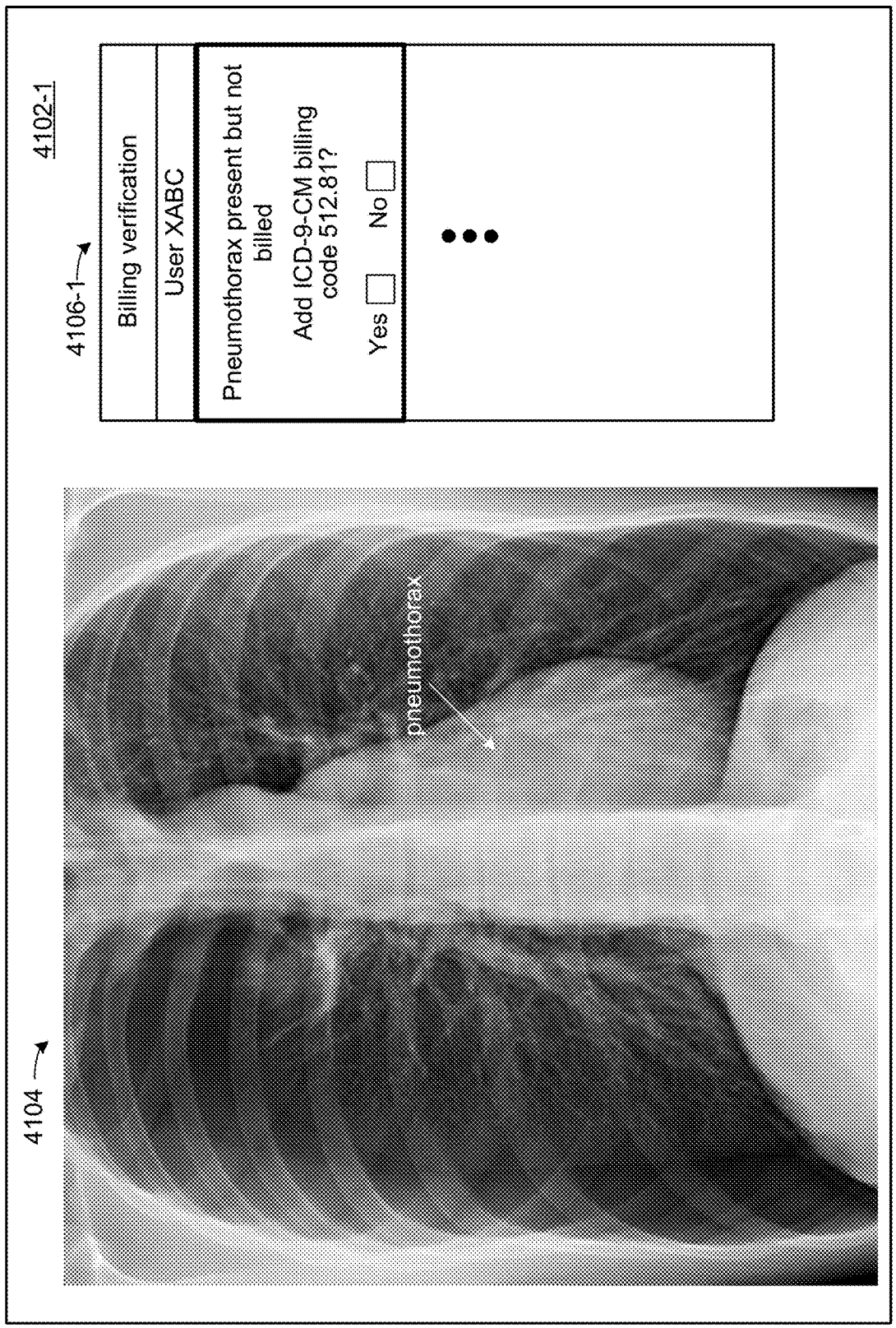
Figure 14D:
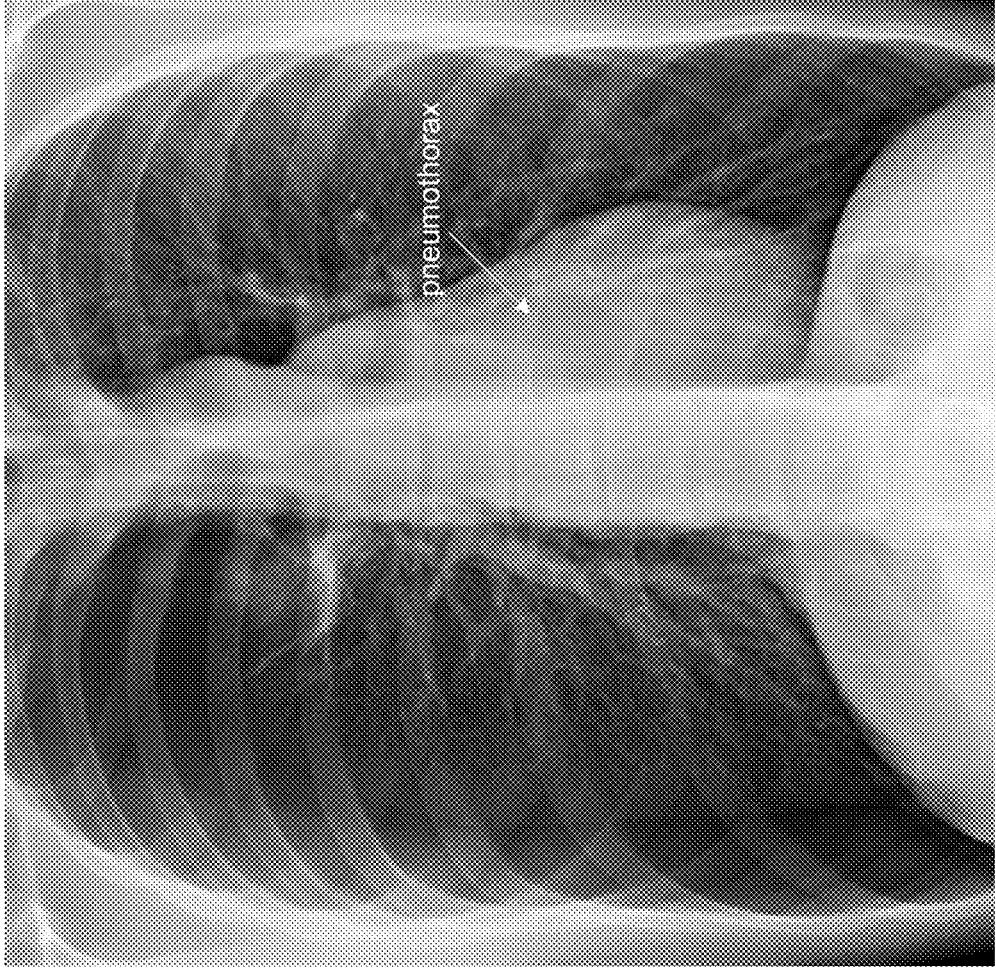
Figure 14E:
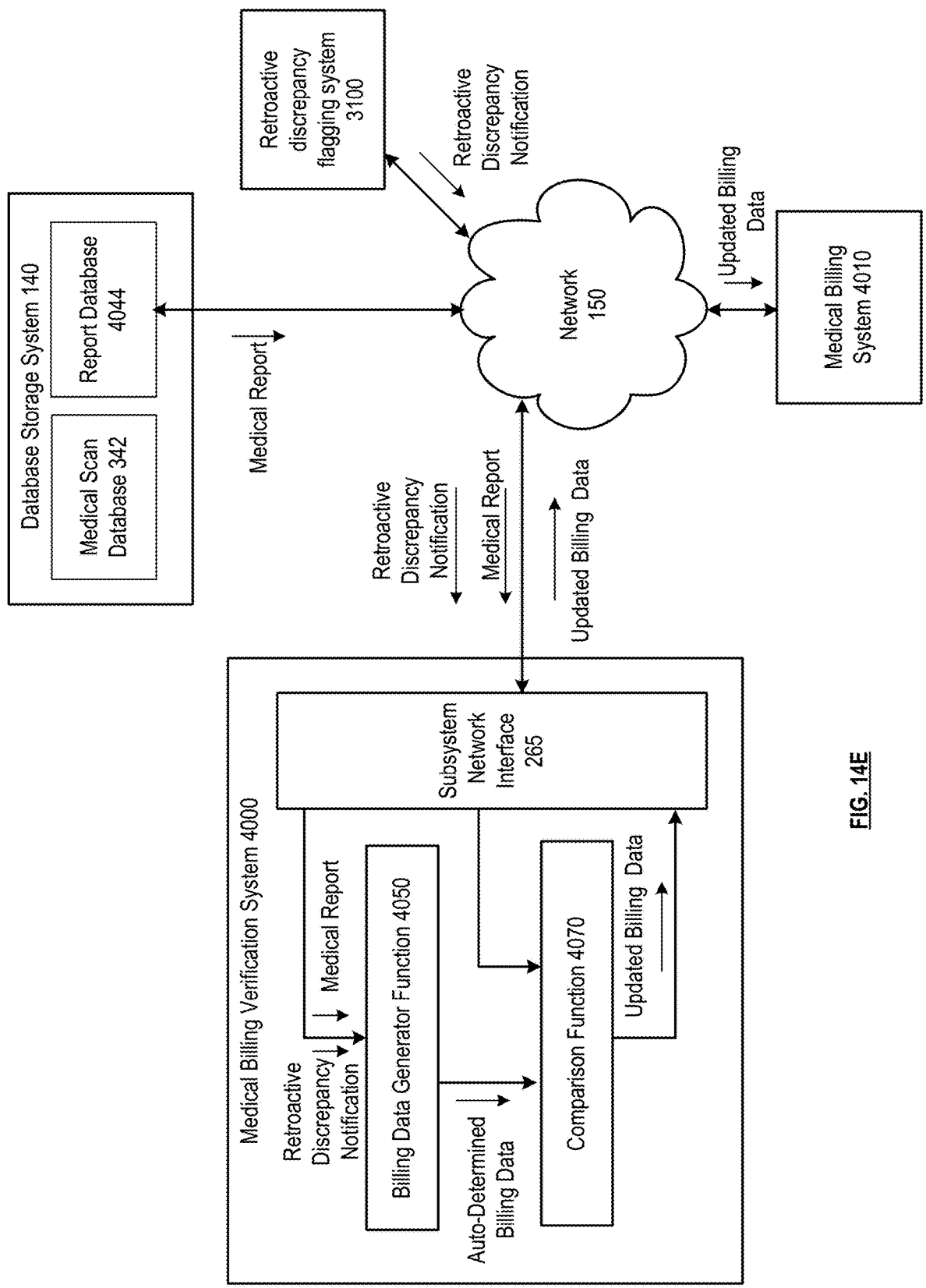
Figure 14F:
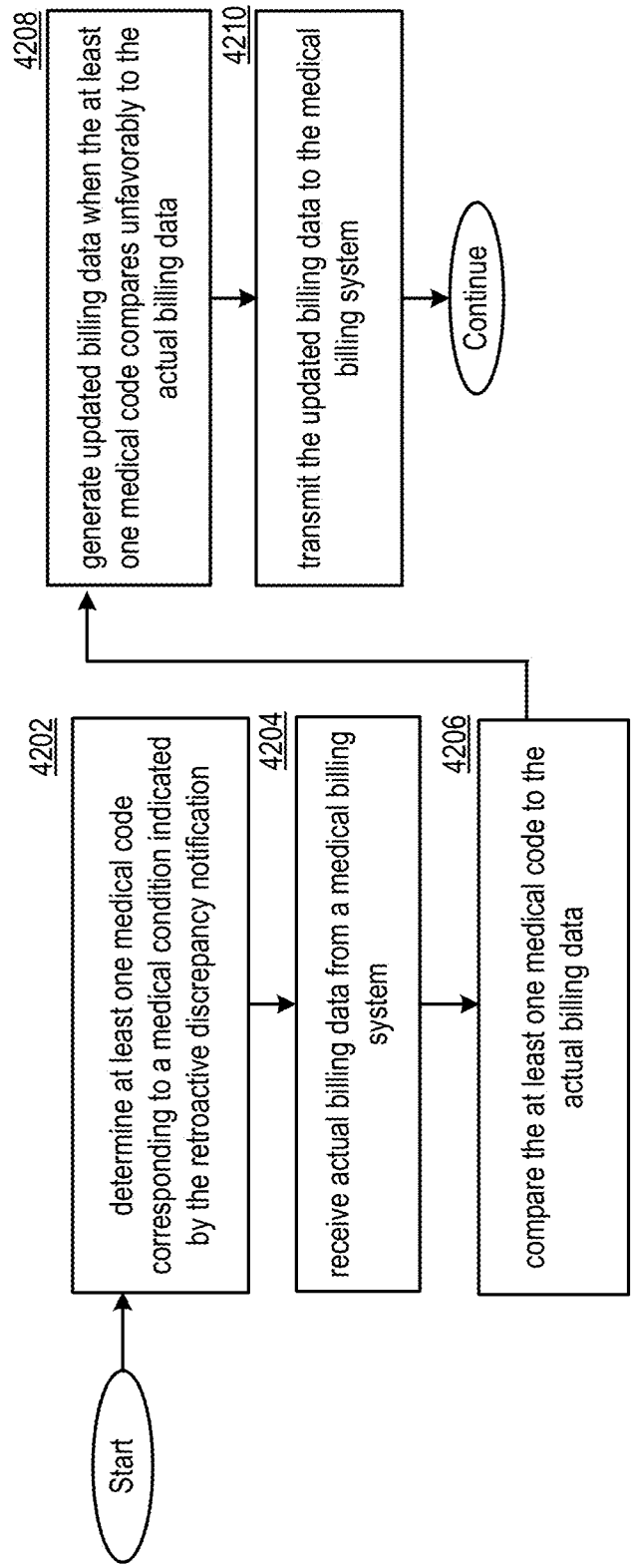
Figure 15A:
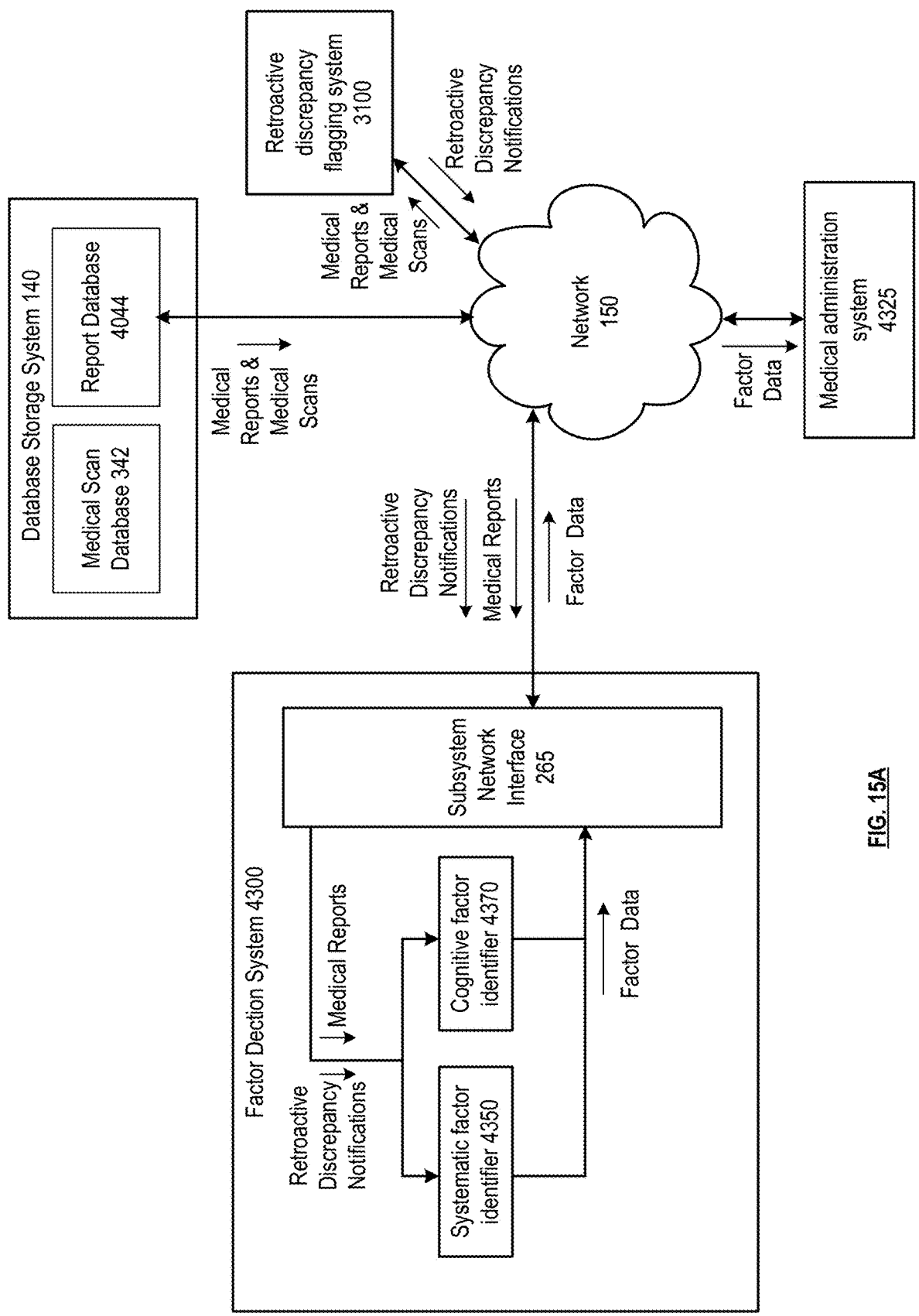
Figure 15B:
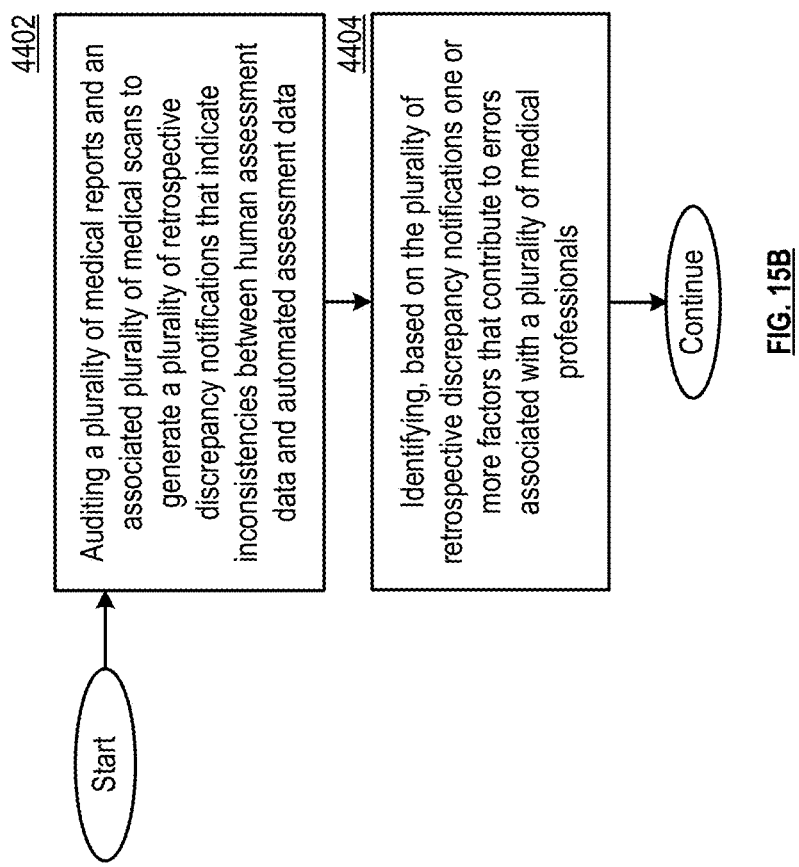
Figure 16A:
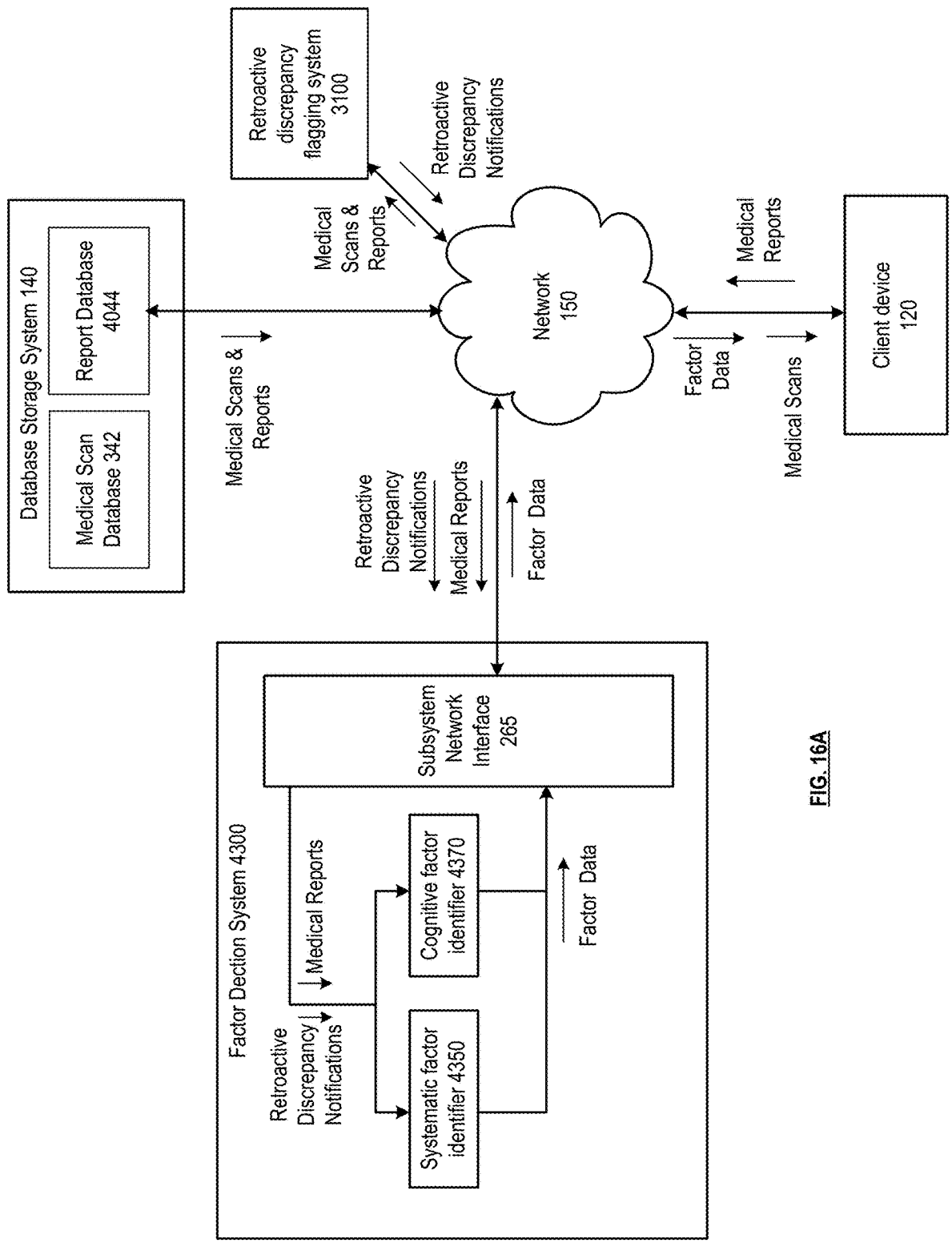
Figure 16B:
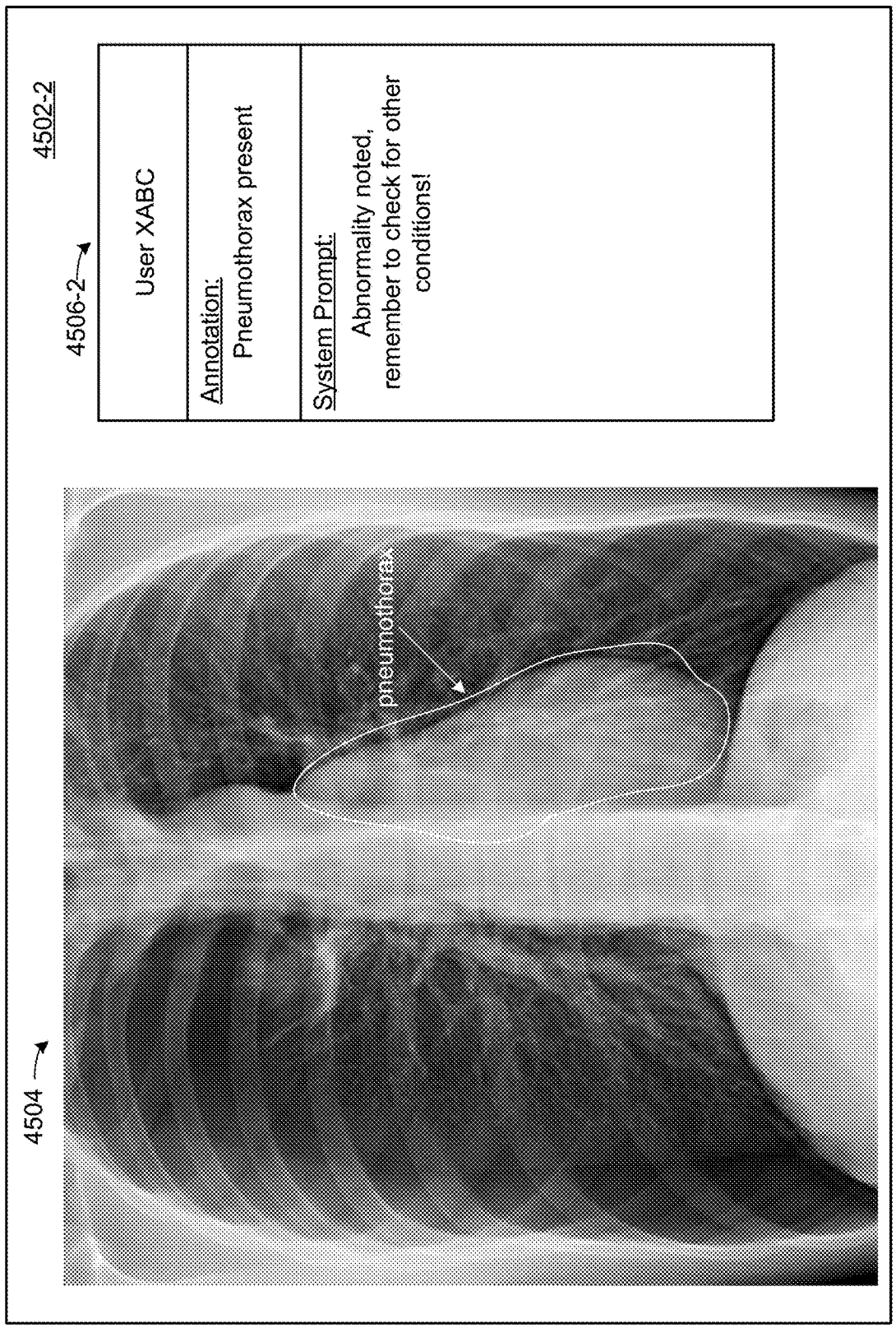
Figure 16C:
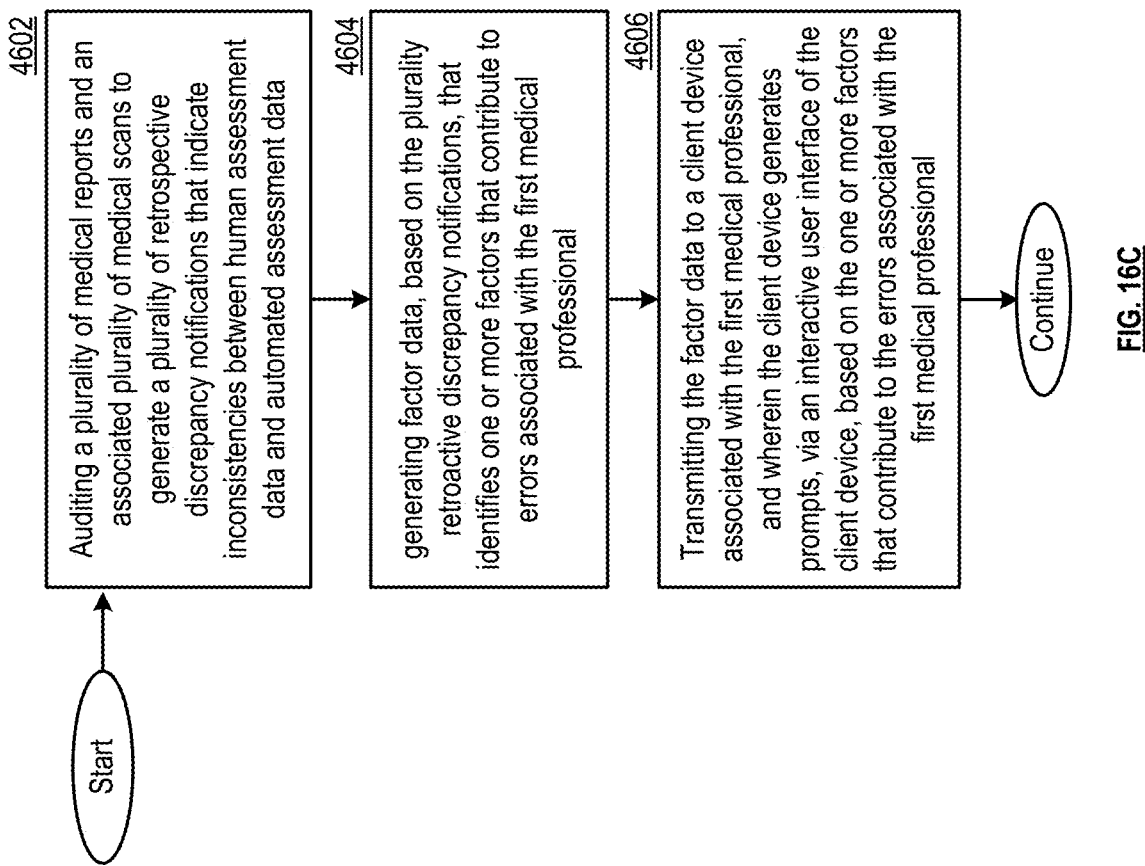
Figure 17A:
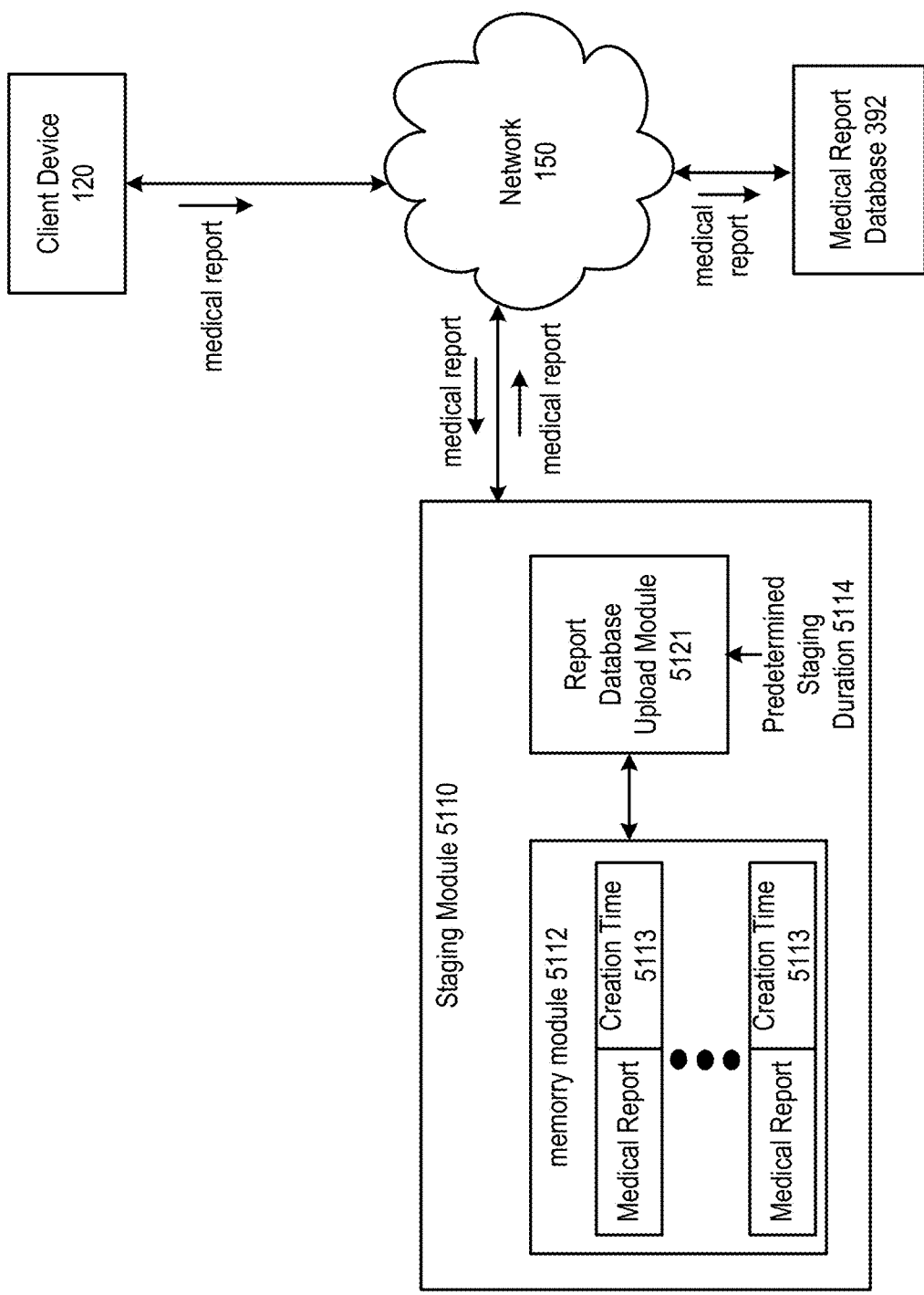
Figure 17B:
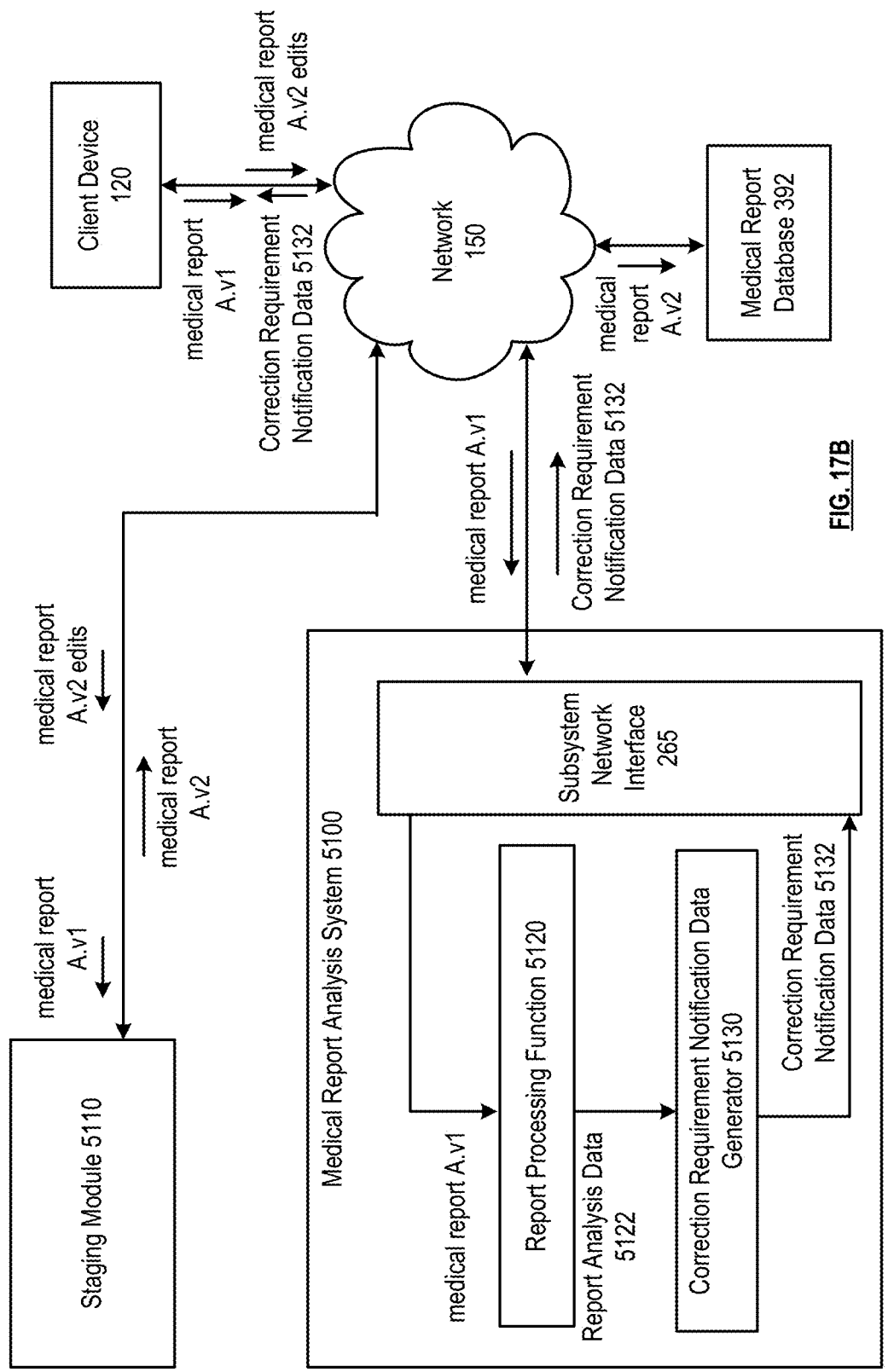
Figure 17C:
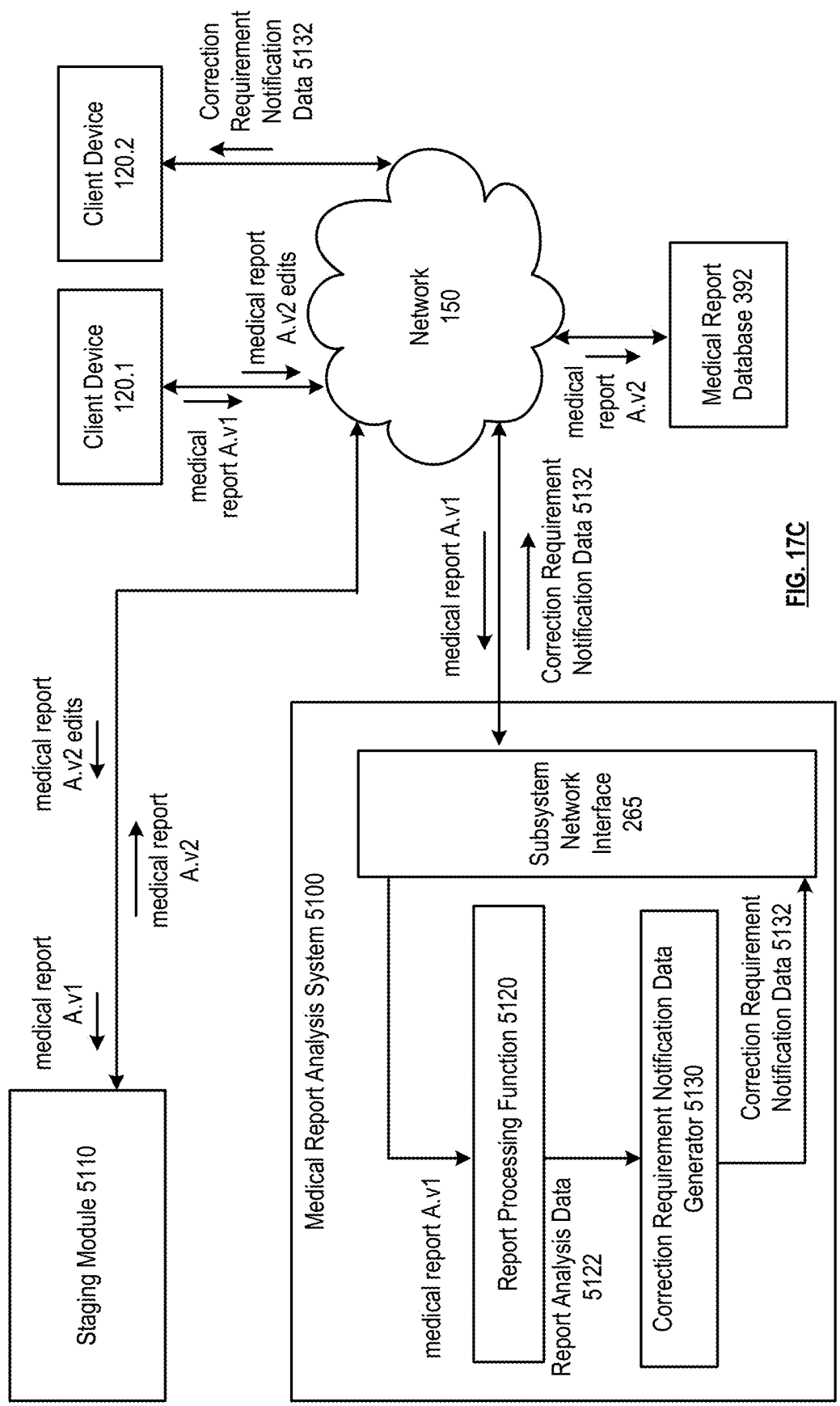
Figure 17D:
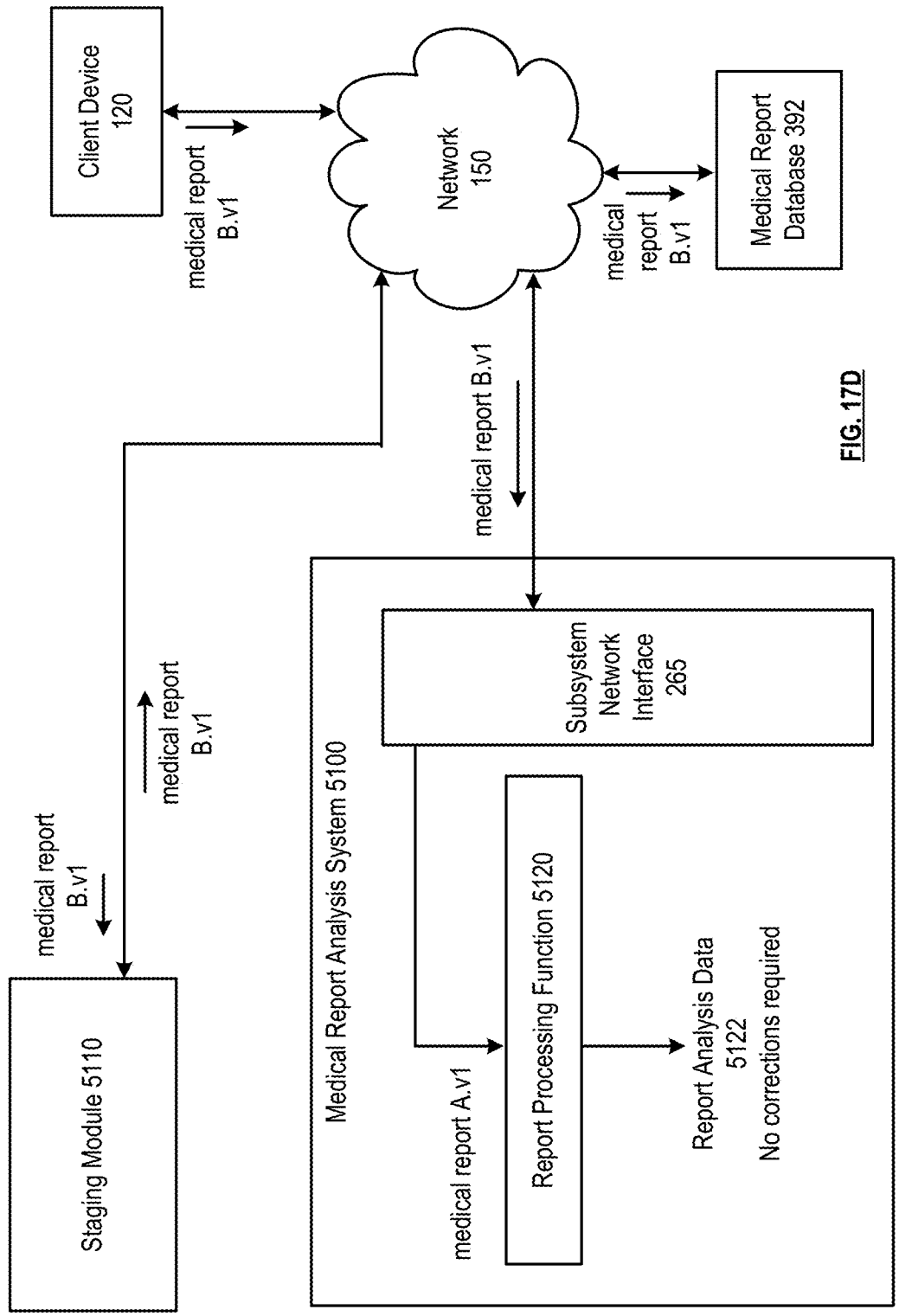
Figure 171:
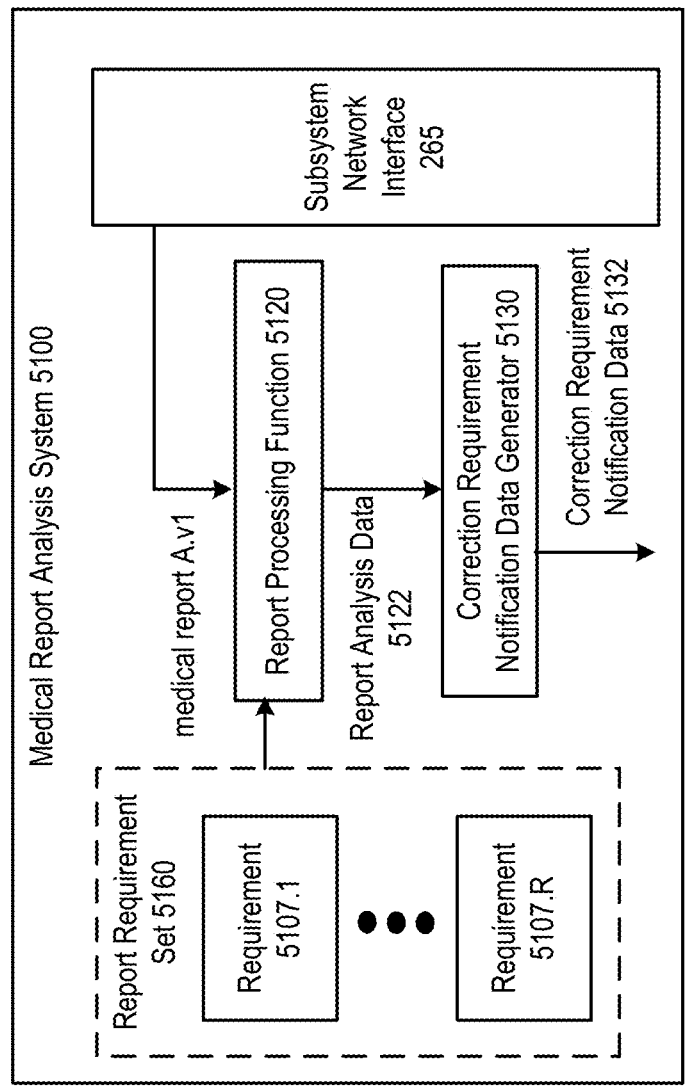
Figure 17K:
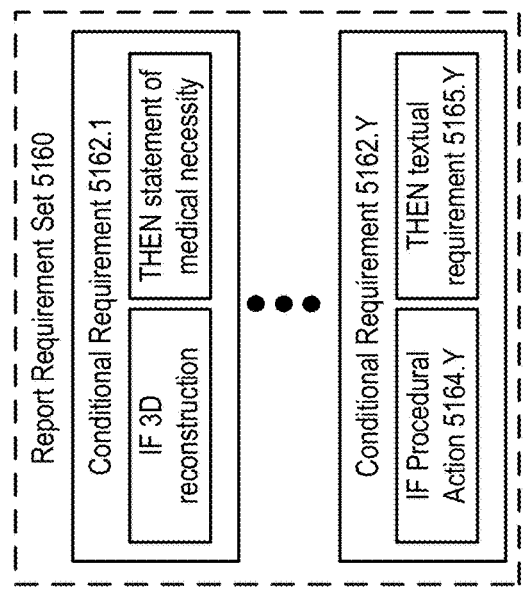
Figure 17M:
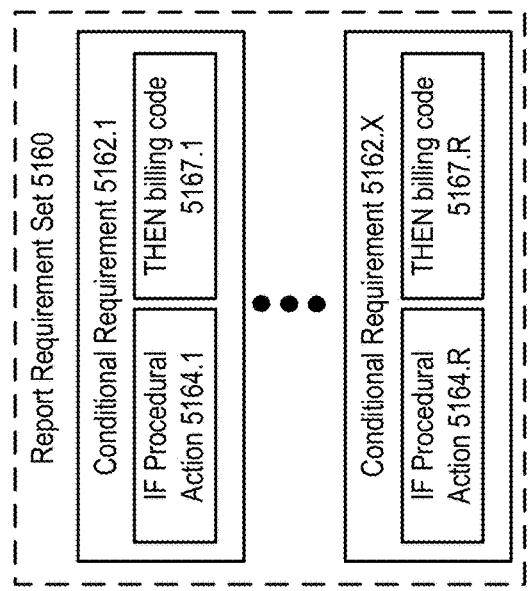
Figure 17J:
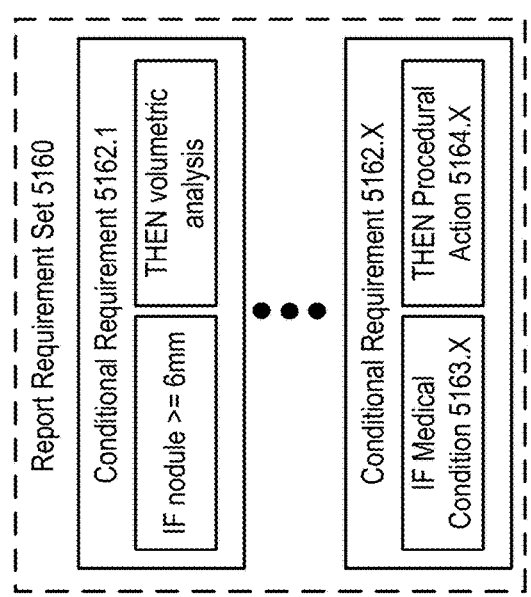
Figure 17L:
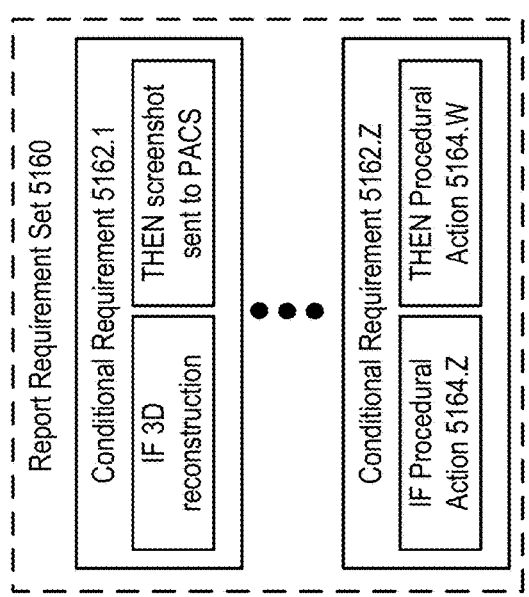
Figure 17N:
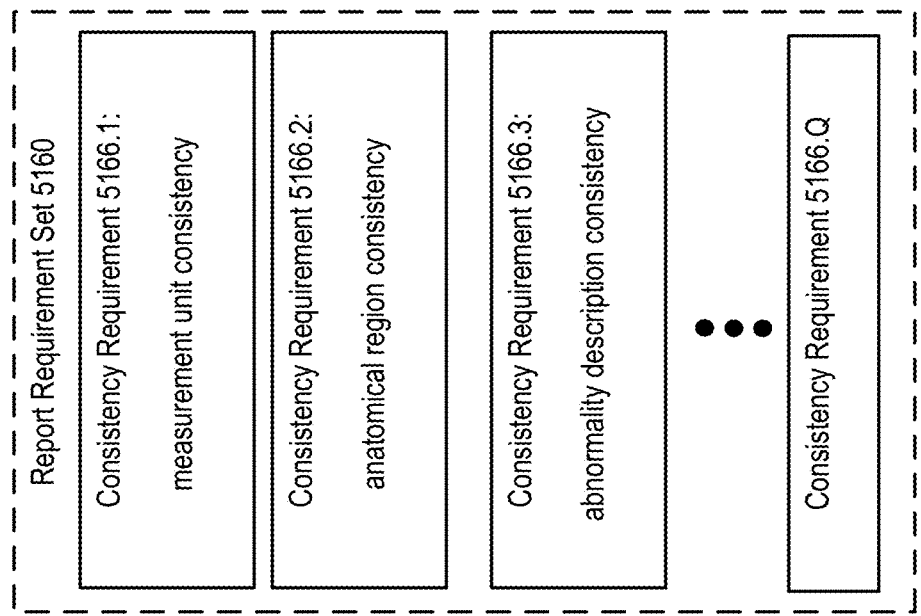
Figure 17Q:
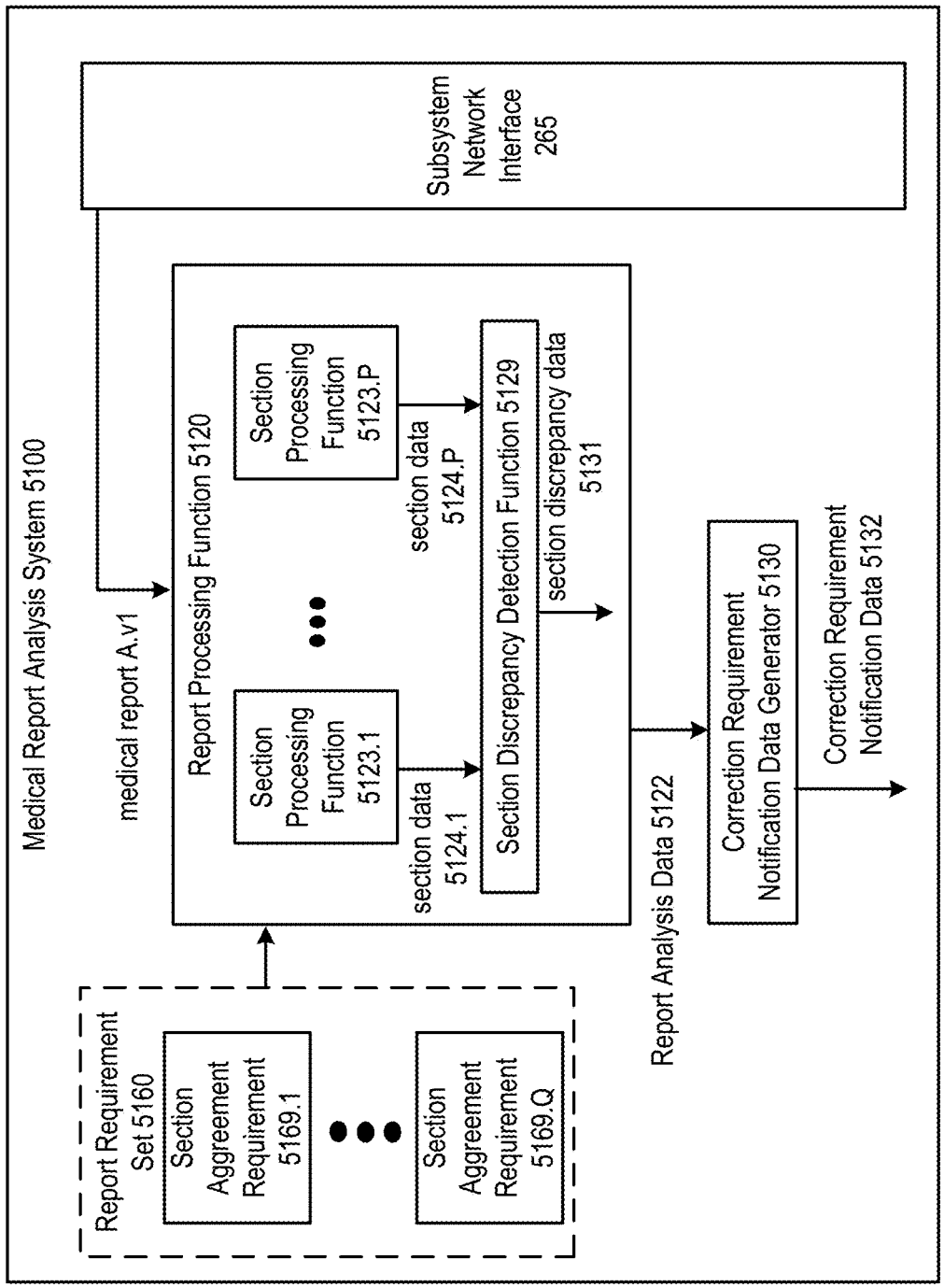
Figure 17R:
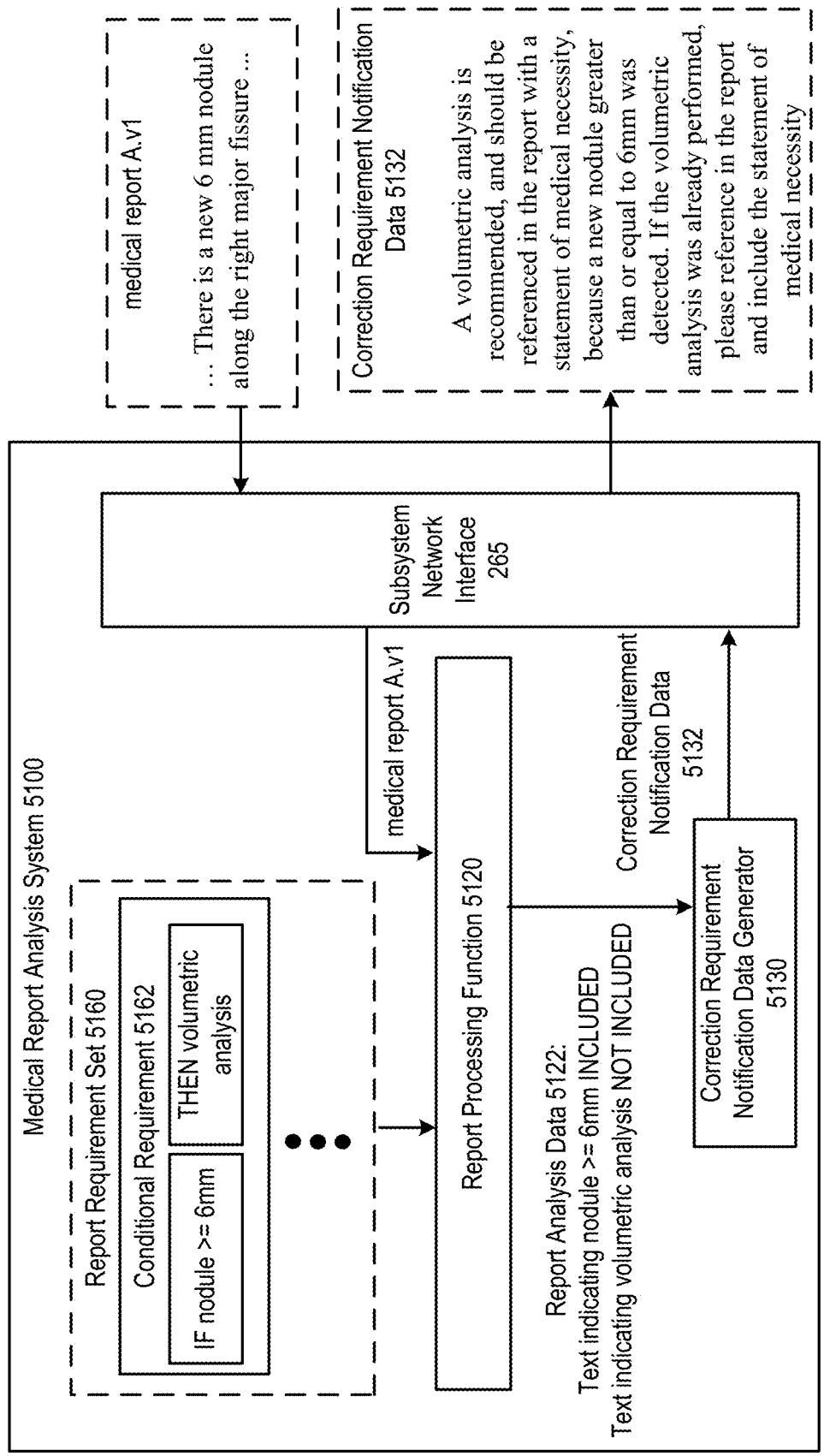
Figure 17S:
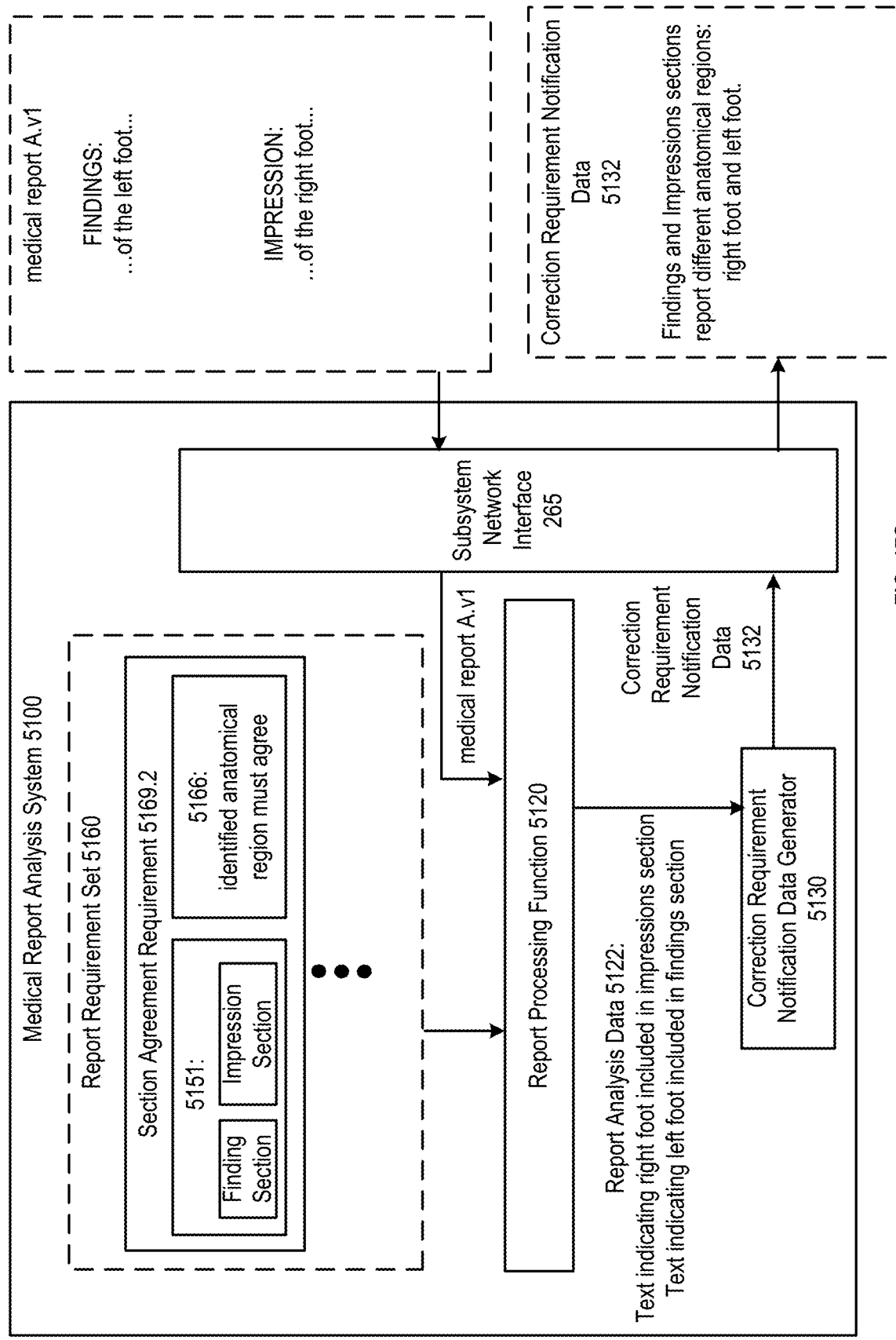
Figure 17T:
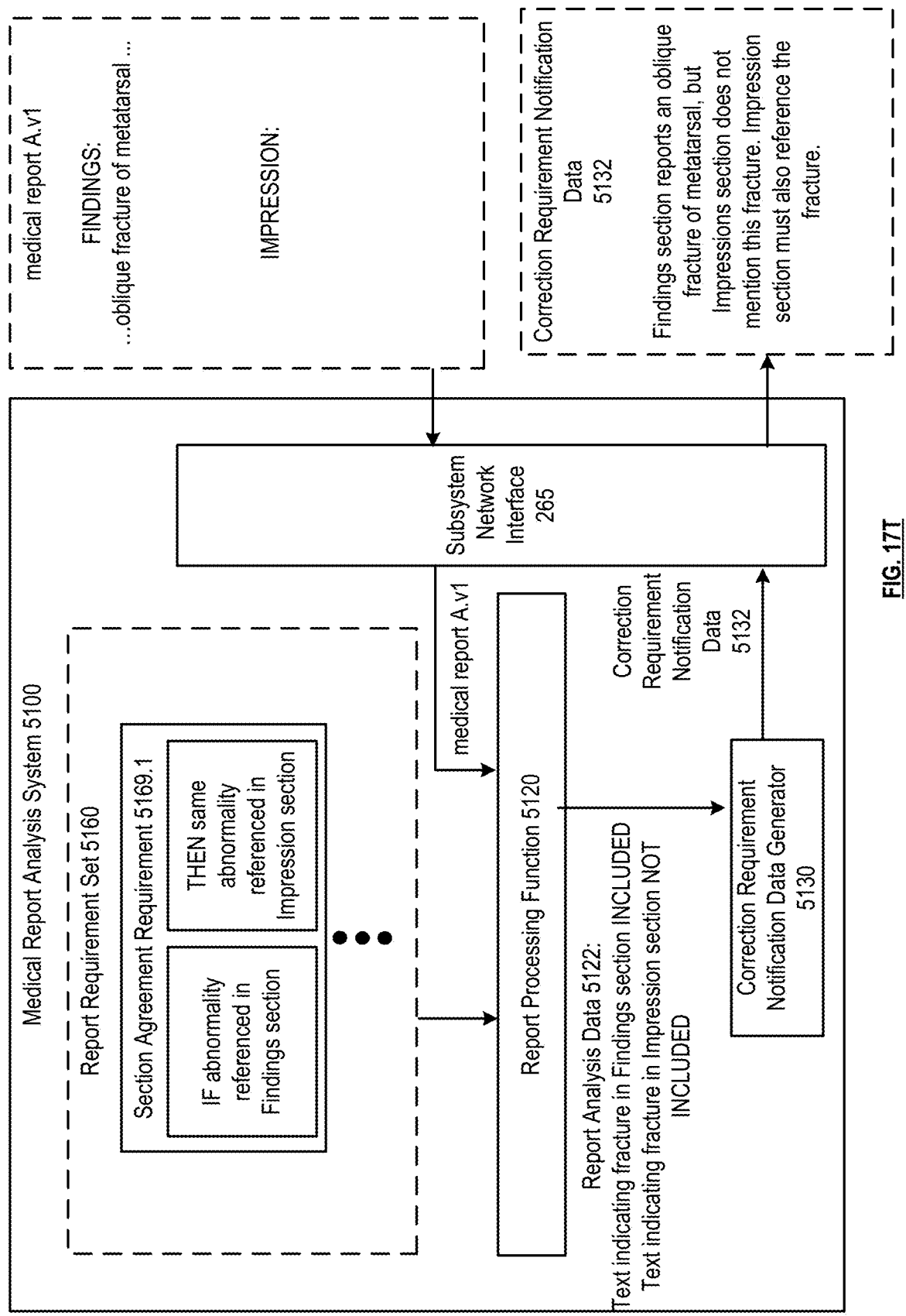
Figure 17U:
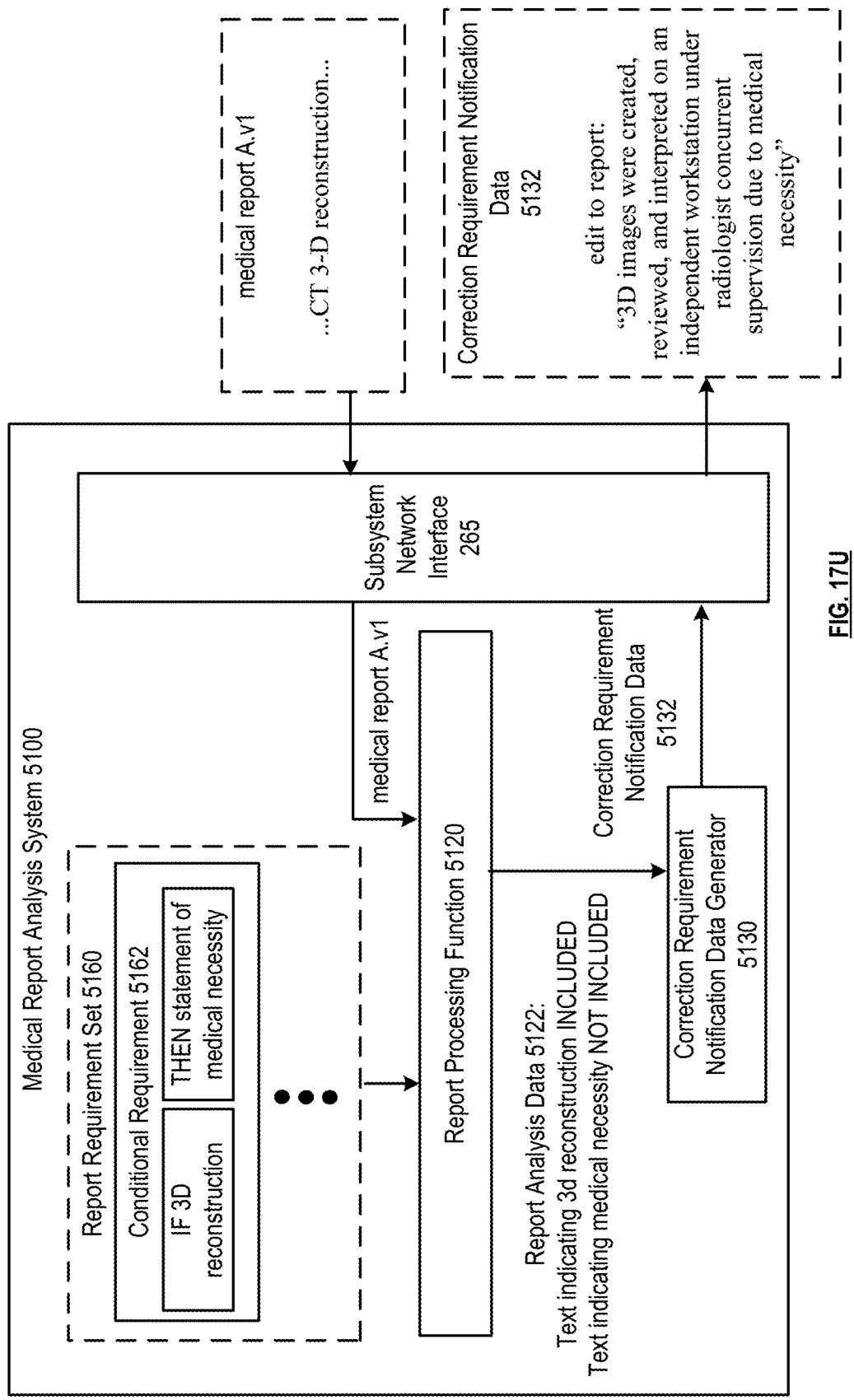
Figure 17V:
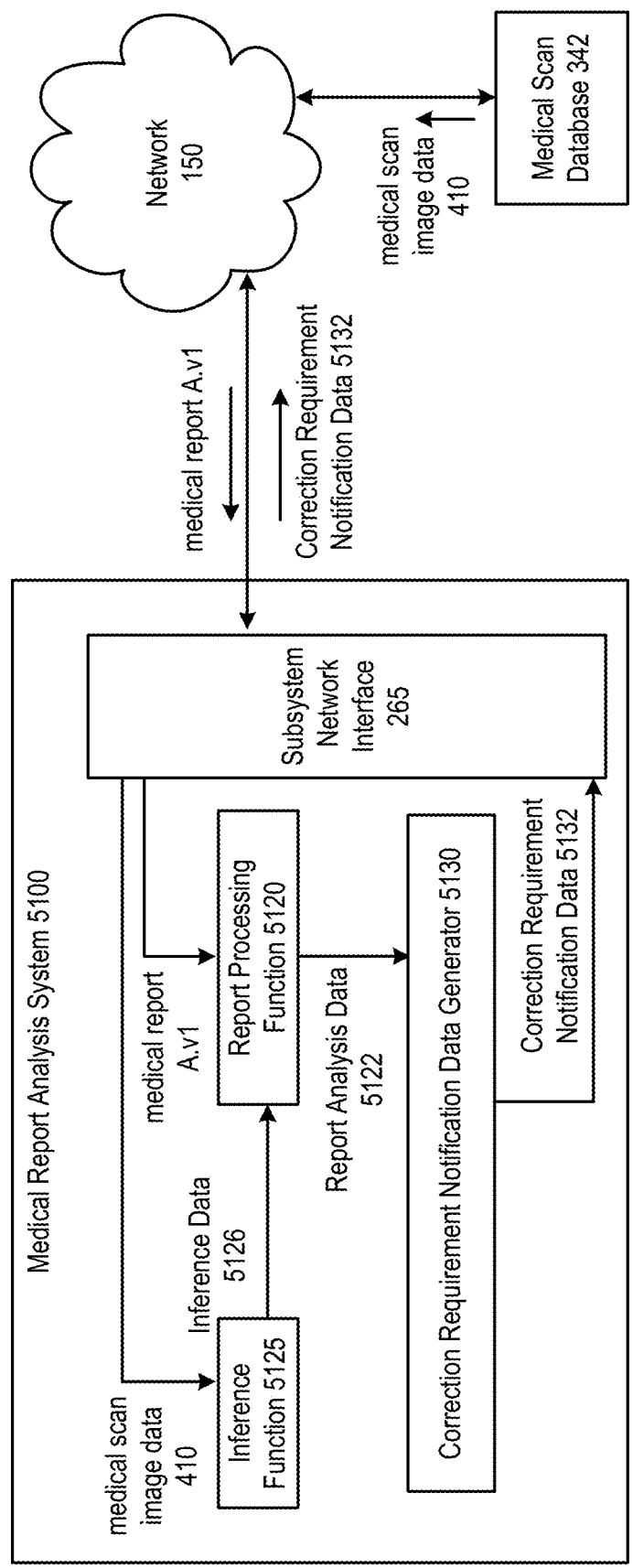
Figure 17W:
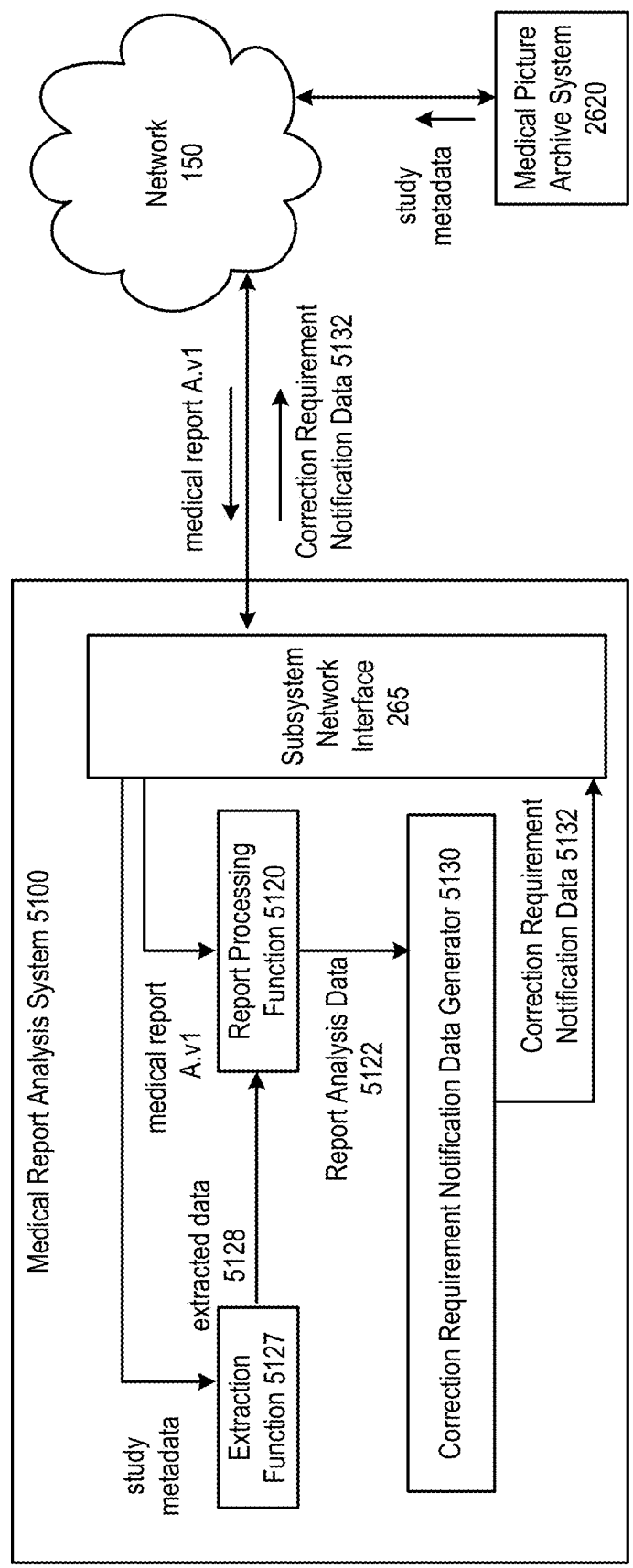
Figure 17Y:
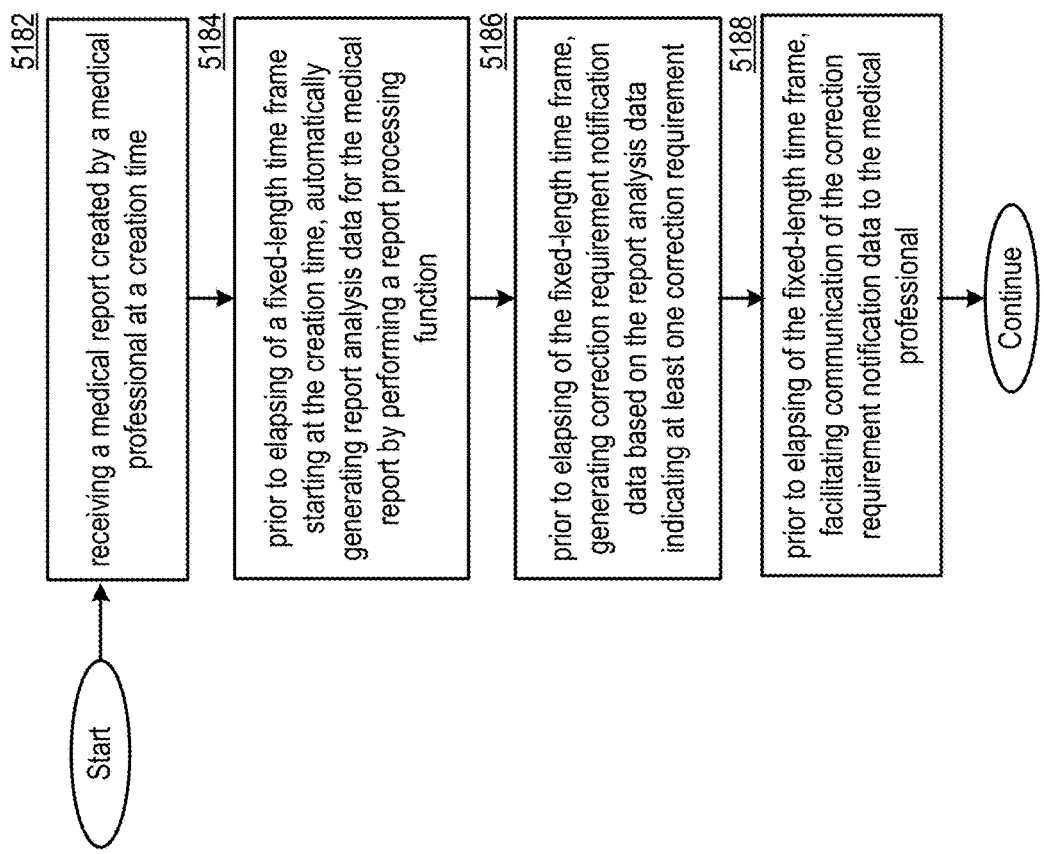

FIG. 11 presents a flowchart illustrating a method for execution by a de-identification system in accordance with various embodiments;

FIG. 12A is a schematic block diagram of a lesion tracking system in accordance with various embodiments;

FIG. 12B is an illustration of an example of a lesion diameter measurement in accordance with various embodiments;

FIG. 12C is a flowchart illustration of performing a lesion volume measurement function in accordance with various embodiments;

FIG. 12D is an illustration of an example interface displayed by a display device in accordance with various embodiments;

FIG. 13A is a schematic block diagram of a retroactive discrepancy flagging system in accordance with various embodiments;

FIGS. 13B-13D are illustrations of example interfaces displayed by a display device in accordance with various embodiments;

FIG. 13E presents a flowchart illustrating a method in accordance with various embodiments;

FIG. 14A is a schematic block diagram of a retroactive discrepancy flagging system in accordance with various embodiments;

FIG. 14B is a schematic block diagram of a medical billing verification system in accordance with various embodiments;

FIGS. 14C-14D are illustrations of example interfaces displayed by a display device in accordance with various embodiments;

FIG. 14E is a schematic block diagram of a medical billing verification system in accordance with various embodiments;

FIG. 14F presents a flowchart illustrating a method in accordance with various embodiments;

FIG. 15A is a schematic block diagram of a factor detection system in accordance with various embodiments;

FIG. 15B presents a flowchart illustrating a method in accordance with various embodiments;

FIG. 16A is a schematic block diagram of a factor detection system in accordance with various embodiments;

FIG. 16B is an illustration of an example interface displayed by a display device in accordance with various embodiments;

FIG. 16C presents a flowchart illustrating a method in accordance with various embodiments;

FIG. 17A is a schematic block diagram of a staging module that receives and transmits medical reports in accordance with various embodiments;

FIGS. 17B-17D are schematic block diagrams of a medical report analysis system that generates report analysis data in accordance with various embodiments;

FIGS. 17E-17H illustrate example timelines of report creation and transmission in accordance with various embodiments;

FIG. 17I is a schematic block diagram of a medical report analysis system that generates report analysis data based on a report requirement set in accordance with various embodiments;

FIGS. 17J-17P illustrate example report requirement sets in accordance with various embodiments;

FIG. 17Q is a schematic block diagram of a medical report analysis system that generates report analysis data based on a report requirement set in accordance with various embodiments;

FIGS. 17R-17U are schematic block diagrams of a medical report analysis system that generate example correction requirement notification data for example reports;

FIG. 17V is a schematic block diagram of a medical report analysis system that generates report analysis data based on medical scan image data;

FIG. 17W is a schematic block diagram of a medical report analysis system that generates report analysis data based on study metadata; and FIGS. 17X-17Y present flowcharts illustrating methods in accordance with various embodiments.

DETAILED DESCRIPTION

The present U.S. Utility patent application is related to U.S. Utility application Ser. No. 15/627,644, entitled "MEDICAL SCAN ASSISTED REVIEW SYSTEM", filed 20 Jun. 2017, which claims priority pursuant to 35 U.S.C. § 119(e) to U.S. Provisional Application No. 62/511,150, entitled "MEDICAL SCAN ASSISTED REVIEW SYSTEM AND METHODS", filed 25 May 2017, both of which are hereby incorporated herein by reference in their entirety and made part of the present U.S. Utility patent application for all purposes.

Figure 1:
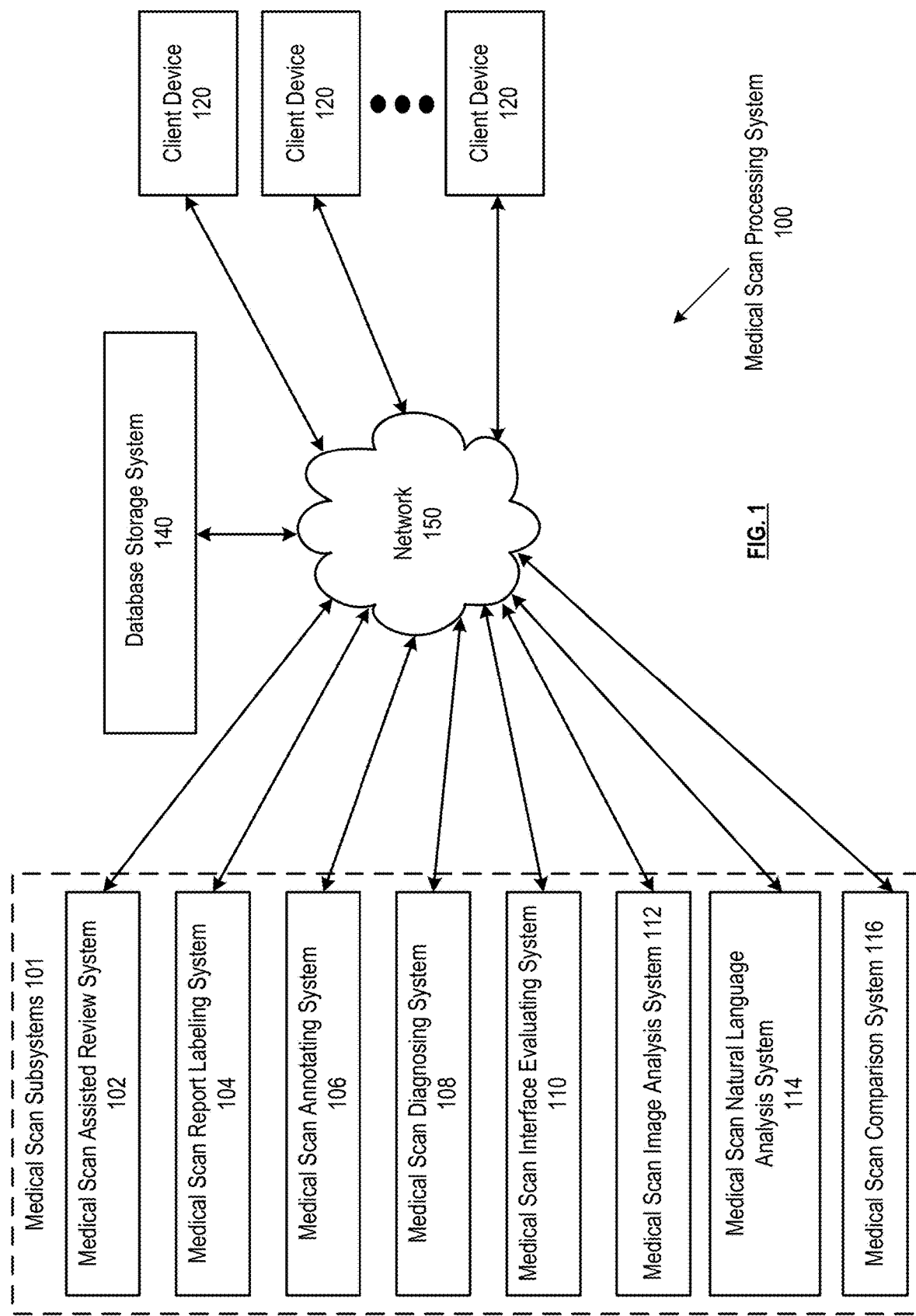
FIG. 1 is a schematic block diagram of an embodiment of a medical scan processing system.

FIG. 1 presents a medical scan processing system 100, which can include one or more medical scan subsystems 101 that communicate bidirectionally with one or more client devices 120 via a wired and/or wireless network 150. The medical scan subsystems 101 can include a medical scan assisted review system 102, medical scan report labeling system 104, a medical scan annotator system 106, a medical scan diagnosing system 108, a medical scan interface feature evaluator system 110, a medical scan image analysis system 112, a medical scan natural language analysis system 114, and/or a medical scan comparison system 116. Some or all of the subsystems 101 can utilize the same processing devices, memory devices, and/or network interfaces, for example, running on a same set of shared servers connected to network 150. Alternatively or in addition, some or all of the subsystems 101 be assigned their own processing devices, memory devices, and/or network interfaces, for example, running separately on different sets of servers connected to network 150. Some or all of the subsystems 101 can interact directly with each other, for example, where one subsystem's output is transmitted directly as input to another subsystem via network 150. Network 150 can include one or more wireless and/or wired communication systems; one or more non-public intranet systems and/or public internet systems; and/or one or more local area networks (LAN) and/or wide area networks (WAN).

The medical scan processing system 100 can further include a database storage system 140, which can include one or more servers, one or more memory devices of one or more subsystems 101, and/or one or more other memory devices connected to network 150. The database storage system 140 can store one or more shared databases and/or one or more files stored on one or more memory devices that include database entries as described herein. The shared databases and/or files can each be utilized by some or all of the subsystems of the medical scan processing system, allowing some or all of the subsystems and/or client devices to retrieve, edit, add, or delete entries to the one or more databases and/or files.

The one or more client devices 120 can each be associated with one or more users of one or more subsystems of the medical scan processing system. Some or all of the client devices can be associated with hospitals or other medical institutions and/or associated with medical professionals, employees, or other individual users for example, located at one or more of the medical institutions. Some of the client devices 120 can correspond to one or more administrators of one or more subsystems of the medical scan processing system, allowing administrators to manage, supervise, or override functions of one or more subsystems for which they are responsible.

Some or all of the subsystems 101 of the medical scan processing system 100 can include a server that presents a website for operation via a browser of client devices 120. Alternatively or in addition, each client device can store application data corresponding to some or all subsystems, for example, a subset of the subsystems that are relevant to the user in a memory of the client device, and a processor of the client device can display the interactive interface based on instructions in the interface data stored in memory. For example, the website presented by a subsystem can operate via the application. Some or all of the web sites presented can correspond to multiple subsystems, for example, where the multiple subsystems share the server presenting the website. Furthermore, the network 150 can be configured for secure and/or authenticated communications between the medical scan subsystems 101, the client devices 120 and the database storage system 140 to protect the data stored in the database storage system and the data communicated between the medical scan subsystems 101, the client devices 120 and the database storage system 140 from unauthorized access.

Some or all of the medical scan subsystems 101 described herein can perform some of all of their respective functionality by utilizing at least one artificial intelligence algorithm and/or technique. Some or all of the medical scan subsystems 101 described herein can perform some of all of their respective functionality by utilizing at least one machine learning algorithm and/or technique. For example, some or all of the medical scan subsystems 101 can perform some or all functionality described herein by utilizing a computer vision techniques and/or natural language processing techniques in accordance with artificial intelligence and/or machine learning.

The medical scan assisted review system 102 can be used to aid medical professionals or other users in diagnosing, triaging, classifying, ranking, and/or otherwise reviewing medical scans by presenting a medical scan for review by a user by transmitting medical scan data of a selected medical scan and/or interface feature data of selected interface features of to a client device 120 corresponding to a user of the medical scan assisted review system for display via a display device of the client device. The medical scan assisted review system 102 can generate scan review data for a medical scan based on user input to the interactive interface displayed by the display device in response to prompts to provide the scan review data, for example, where the prompts correspond to one or more interface features.

The medical scan assisted review system 102 can be operable to receive, via a network, a medical scan for review. Abnormality annotation data can be generated by identifying one or more of abnormalities in the medical scan by utilizing a computer vision model that is trained on a plurality of training medical scans. The abnormality annotation data can include location data and classification data for each of the plurality of abnormalities and/or data that facilitates the visualization of the abnormalities in the scan image data. Report data including text describing each of the plurality of abnormalities is generated based on the abnormality data. The visualization and the report data, which can collectively be displayed annotation data, can be transmitted to a client device. A display device associated with the client device can display the visualization in conjunction with the medical scan via an interactive interface, and the display device can further display the report data via the interactive interface.

In various embodiments, longitudinal data, such as one or more additional scans of longitudinal data 433 of the medical scan or of similar scans, can be displayed in conjunction with the medical scan automatically, or in response to the user electing to view longitudinal data via user input. For example, the medical scan assisted review system can retrieve a previous scan or a future scan for the patient from a patient database or from the medical scan database automatically or in response to the user electing to view past patient data. One or more previous scans can be displayed in one or more corresponding windows adjacent to the current medical scan. For example, the user can select a past scan from the longitudinal data for display. Alternatively or in addition, the user can elect longitudinal parameters such as amount of time elapsed, scan type, electing to select the most recent and/or least recent scan, electing to select a future scan, electing to select a scan at a date closest to the scan, or other criteria, and the medical scan assisted review system can automatically select a previous scan that compares most favorably to the longitudinal parameters. The selected additional scan can be displayed in an adjacent window alongside the current medical scan. In some embodiments, multiple additional scans will be selected and can be displayed in multiple adjacent windows.

In various embodiments, a first window displaying an image slice 412 of the medical scan and an adjacent second window displaying an image slice of a selected additional scan will display image slices 412 determined to correspond with the currently displayed slice 412 of the medical scan. As described with respect to selecting a slice of a selected similar medical scan for display, this can be achieved based on selecting the image slice with a matching slice number, based on automatically determining the image slice that most closely matches the anatomical region corresponding to the currently displayed slice of the current scan, and/or based on determining the slice in the previous scan with the most similar view of the abnormality as the currently displayed slice. The user can use a single scroll bar or other single user input indication to jump to a different image slice, and the multiple windows can simultaneously display the same numbered image slice, or can scroll or jump by the same number of slices if different slice numbers are initially displayed. In some embodiments, three or more adjacent windows corresponding to the medical scan and two or more additional scans are displayed, and can all be controlled with the single scroll bar in a similar fashion.

The medical scan assisted review system 102 can automatically detect previous states of the identified abnormalities based on the abnormality data, such as the abnormality location data. The detected previous states of the identified abnormality can be circled, highlighted, or otherwise indicated in their corresponding window. The medical scan assisted review system 102 can retrieve classification data for the previous state of the abnormality by retrieving abnormality annotation data 442 of the similar abnormality mapped to the previous scan from the medical scan database 342. This data may not be assigned to the previous scan, and the medical scan assisted review system can automatically determine classification or other diagnosis data for the previous medical scan by utilizing the medical scan image analysis system as discussed. Alternatively or in addition, some or all of the abnormality classification data 445 or other diagnosis data 440 for the previous scan can be assigned values determined based on the abnormality classification data or other diagnosis data determined for the current scan. Such abnormality classification data 445 or other diagnosis data 440 determined for the previous scan can be mapped to the previous scan, and or mapped to the longitudinal data 433, in the database and/or transmitted to a responsible entity via the network.

The medical assisted review system can automatically generate state change data such as a change in size, volume, malignancy, or other changes to various classifiers of the abnormality. This can be achieved by automatically comparing image data of one or more previous scans and the current scan and/or by comparing abnormality data of the previous scan to abnormality data of the current scan. In some embodiments, such metrics can be calculated by utilizing the medical scan similarity analysis function, for example, where the output of the medical scan similarity analysis function such as the similarity score indicates distance, error, or other measured discrepancy in one or more abnormality classifier categories 444 and/or abnormality pattern categories 446. This calculated distance, error, or other measured discrepancy in each category can be used to quantify state change data, indicate a new classifier in one or more categories, to determine if a certain category has become more or less severe, or otherwise determine how the abnormality has changed over time. In various embodiments, this data can be displayed in one window, for example, where an increase in abnormality size is indicated by overlaying or highlighting an outline of the current abnormality over the corresponding image slice of the previous abnormality, or vice versa. In various embodiments where several past scans are available, such state change data can be determined over time, and statistical data showing growth rate changes over time or malignancy changes over time can be generated, for example, indicating if a growth rate is lessening or worsening over time. Image slices corresponding to multiple past scans can be displayed in sequence, for example, where a first scroll bar allows a user to scroll between image slice numbers, and a second scroll bar allows a user to scroll between the same image slice over time. In various embodiments the abnormality data, heat map data, or other interface features will be displayed in conjunction with the image slices of the past image data.

The medical scan report labeling system 104 can be used to automatically assign medical codes to medical scans based on user identified keywords, phrases, or other relevant medical condition terms of natural text data in a medical scan report of the medical scan, identified by users of the medical scan report labeling system 104. The medical scan report labeling system 104 can be operable to transmit a medical report that includes natural language text to a first client device for display. Identified medical condition term data can be received from the first client device in response. An alias mapping pair in a medical label alias database can be identified by determining that a medical condition term of the alias mapping pair compares favorably to the identified medical condition term data. A medical code that corresponds to the alias mapping pair and a medical scan that corresponds to the medical report can be transmitted to a second client device of an expert user for display, and accuracy data can be received from the second client device in response. The medical code is mapped to the first medical scan in a medical scan database when the accuracy data indicates that the medical code compares favorably to the medical scan.

The medical scan annotator system 106 can be used to gather annotations of medical scans based on review of the medical scan image data by users of the system such as radiologists or other medical professionals. Medical scans that require annotation, for example, that have been triaged from a hospital or other triaging entity, can be sent to multiple users selected by the medical scan annotator system 106, and the annotations received from the multiple medical professionals can be processed automatically by a processing system of the medical scan annotator system, allowing the medical scan annotator system to automatically determine a consensus annotation of each medical scan. Furthermore, the users can be automatically scored by the medical scan annotator system based on how closely their annotation matches to the consensus annotation or some other truth annotation, for example, corresponding to annotations of the medical scan assigned a truth flag. Users can be assigned automatically to annotate subsequent incoming medical scans based on their overall scores and/or based on categorized scores that correspond to an identified category of the incoming medical scan.

The medical scan annotator system 106 can be operable to select a medical scan for transmission via a network to a first client device and a second client device for display via an interactive interface, and annotation data can be received from the first client device and the second client device in response. Annotation similarity data can be generated by comparing the first annotation data to the second annotation data, and consensus annotation data can be generated based on the first annotation data and the second annotation data in response to the annotation similarity data indicating that the difference between the first annotation data and the second annotation data compares favorably to an annotation discrepancy threshold. The consensus annotation data can be mapped to the medical scan in a medical scan database.

A medical scan diagnosing system 108 can be used by hospitals, medical professionals, or other medical entities to automatically produce inference data for given medical scans by utilizing computer vision techniques, natural language processing techniques, other artificial intelligence techniques, and/or other machine learning techniques. This automatically generated inference data can be used to generate and/or update diagnosis data or other corresponding data of corresponding medical scan entries in a medical scan database. The medical scan diagnosing system can utilize a medical scan database, user database, and/or a medical scan analysis function database by communicating with the database storage system 140 via the network 150, and/or can utilize another medical scan database, user database, and/or function database stored in local memory.

The medical scan diagnosing system 108 can be operable to receive a medical scan. Diagnosis data of the medical scan can be generated by performing a medical scan inference function on the medical scan. The first medical scan can be transmitted to a first client device associated with a user of the medical scan diagnosing system in response to the diagnosis data indicating that the medical scan corresponds to a non-normal diagnosis. The medical scan can be displayed to the user via an interactive interface displayed by a display device corresponding to the first client device. Review data can be received from the first client device, where the review data is generated by the first client device in response to a prompt via the interactive interface. Updated diagnosis data can be generated based on the review data. The updated diagnosis data can be transmitted to a second client device associated with a requesting entity.

A medical scan interface feature evaluating system 110 can be used evaluate proposed interface features or currently used interface features of an interactive interface to present medical scans for review by medical professionals or other users of one or more subsystems 101. The medical scan interface feature evaluator system 110 can be operable to generate an ordered image-to-prompt mapping by selecting a set of user interface features to be displayed with each of an ordered set of medical scans. The set of medical scans and the ordered image-to-prompt mapping can be transmitted to a set of client devices. A set of responses can be generated by each client device in response to sequentially displaying each of the set of medical scans in conjunction with a mapped user interface feature indicated in the ordered image-to-prompt mapping via a user interface. Response score data can be generated by comparing each response to truth annotation data of the corresponding medical scan. Interface feature score data corresponding to each user interface feature can be generated based on aggregating the response score data, and is used to generate a ranking of the set of user interface features.

A medical scan image analysis system 112 can be used to generate and/or perform one or more medical scan image analysis functions by utilizing a computer vision-based learning algorithm 1350 on a training set of medical scans with known annotation data, diagnosis data, labeling and/or medical code data, report data, patient history data, patient risk factor data, and/or other metadata associated with medical scans. These medical scan image analysis functions can be used to generate inference data for new medical scans that are triaged or otherwise require inferred annotation data, diagnosis data, labeling and/or medical code data, and/or report data. For example, some medical scan image analysis functions can correspond to medical scan inference functions of the medical scan diagnosing system or other medical scan analysis functions of a medical scan analysis function database. The medical scan image analysis functions can be used to determine whether or not a medical scan is normal, to detect the location of an abnormality in one or more slices of a medical scan, and/or to characterize a detected abnormality. The medical scan image analysis system can be used to generate and/or perform computer vision based medical scan image analysis functions utilized by other subsystems of the medical scan processing system as described herein, aiding medical professionals to diagnose patients and/or to generate further data and models to characterize medical scans. The medical scan image analysis system can include a processing system that includes a processor and a memory that stores executable instructions that, when executed by the processing system, facilitate performance of operations.

The medical scan image analysis system 112 can be operable to receive a plurality of medical scans that represent a three-dimensional anatomical region and include a plurality of cross-sectional image slices. A plurality of three-dimensional subregions corresponding to each of the plurality of medical scans can be generated by selecting a proper subset of the plurality of cross-sectional image slices from each medical scan, and by further selecting a two-dimensional subregion from each proper subset of cross-sectional image slices. A learning algorithm can be performed on the plurality of three-dimensional subregions to generate a neural network. Inference data corresponding to a new medical scan received via the network can be generated by performing an inference algorithm on the new medical scan by utilizing the neural network. An inferred abnormality can be identified in the new medical scan based on the inference data. The learning algorithm can be performed in accordance with computer vision processing techniques, at least one artificial intelligence algorithm and/or technique, and/or at least one machine learning algorithm and/or technique. The inference algorithm can be performed in accordance with natural language processing techniques, at least one artificial intelligence algorithm and/or technique, and/or at least one machine learning algorithm and/or technique.

The medical scan natural language analysis system 114 can determine a training set of medical scans with medical codes determined to be truth data. Corresponding medical reports and/or other natural language text data associated with a medical scan can be utilized to train a medical scan natural language analysis function by generating a medical report natural language model. The medical scan natural language analysis function can be utilized to generate inference data for incoming medical reports for other medical scans to automatically determine corresponding medical codes, which can be mapped to corresponding medical scans. Medical codes assigned to medical scans by utilizing the medical report natural language model can be utilized by other subsystems, for example, to train other medical scan analysis functions, to be used as truth data to verify annotations provided via other subsystems, to aid in diagnosis, or otherwise be used by other subsystems as described herein. The medical report natural language model can be generated in accordance with natural language processing techniques, at least one artificial intelligence algorithm and/or technique, and/or at least one machine learning algorithm and/or technique. The medical scan natural language analysis function can be performed in accordance with natural language processing techniques, at least one artificial intelligence algorithm and/or technique, and/or at least one machine learning algorithm and/or technique.

A medical scan comparison system 116 can be utilized by one or more subsystems to identify and/or display similar medical scans, for example, to perform or determine function parameters for a medical scan similarity analysis function, to generate or retrieve similar scan data, or otherwise compare medical scan data. The medical scan comparison system 116 can also utilize some or all features of other subsystems as described herein. The medical scan comparison system 116 can be operable to receive a medical scan via a network and can generate similar scan data. The similar scan data can include a subset of medical scans from a medical scan database and can be generated by performing an abnormality similarity function, such as medical scan similarity analysis function, to determine that a set of abnormalities included in the subset of medical scans compare favorably to an abnormality identified in the medical scan. At least one cross-sectional image can be selected from each medical scan of the subset of medical scans for display on a display device associated with a user of the medical scan comparison system in conjunction with the medical scan.

Figure 2A:
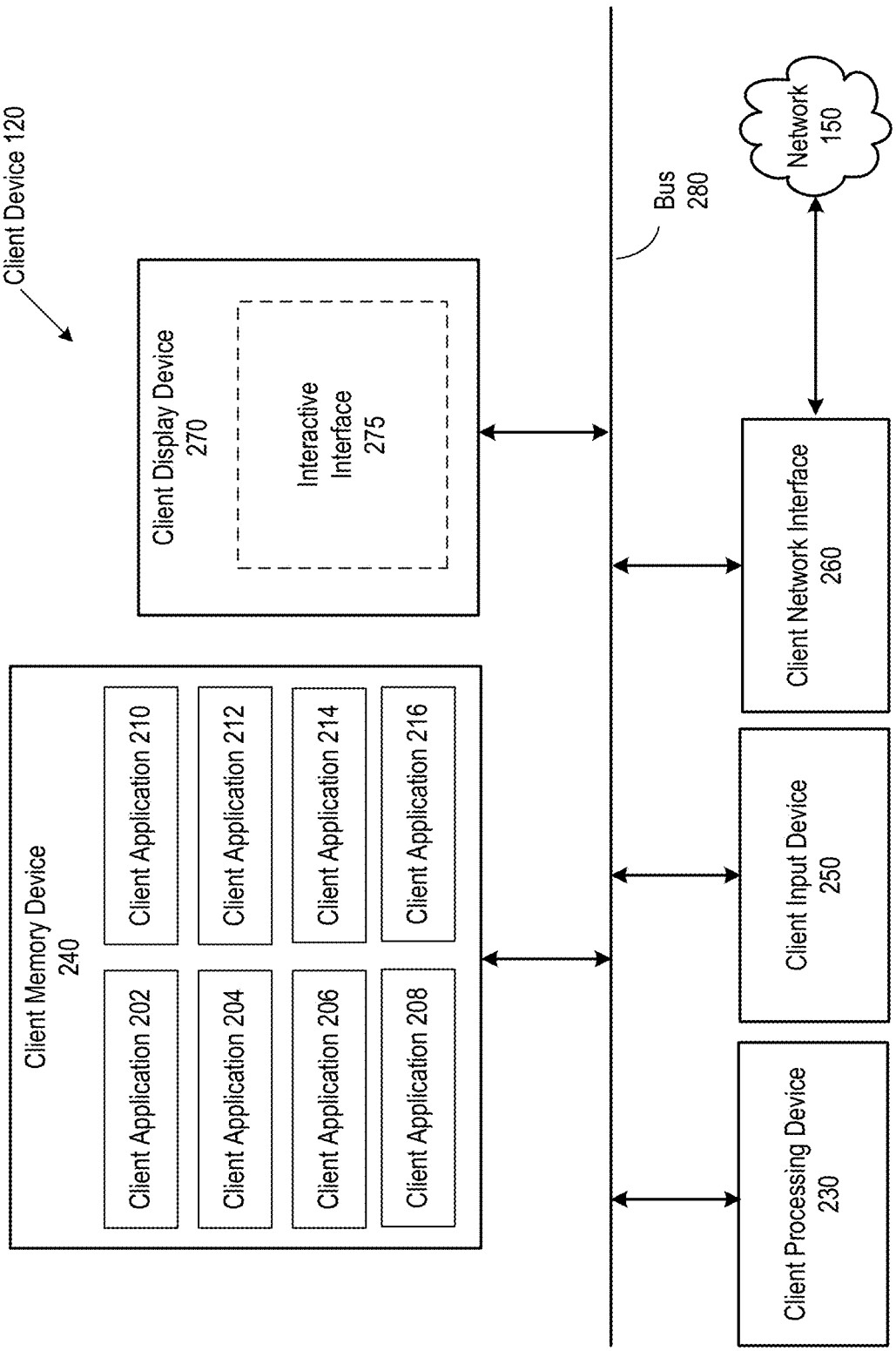
FIG. 2A is a schematic block diagram of a client device in accordance with various embodiments.

FIG. 2A presents an embodiment of client device 120. Each client device 120 can include one or more client processing devices 230, one or more client memory devices 240, one or more client input devices 250, one or more client network interfaces 260 operable to more support one or more communication links via the network 150 indirectly and/or directly, and/or one or more client display devices 270, connected via bus 280. Client applications 202, 204, 206, 208, 210, 212, 214, and/or 216 correspond to subsystems 102, 104, 106, 108, 110, 112, 114, and/or 116 of the medical scan processing system respectfully. Each client device 120 can receive the application data from the corresponding subsystem via network 150 by utilizing network interface 260, for storage in the one or more memory devices 240. In various embodiments, some or all client devices 120 can include a computing device associated with a radiologist, medical entity, or other user of one or more subsystems as described herein.

The one or more processing devices 230 can display interactive interface 275 on the one or more client display devices 270 in accordance with one or more of the client applications 202, 204, 206, 208, 210, 212, 214, and/or 216, for example, where a different interactive interface 275 is displayed for some or all of the client applications in accordance with the website presented by the corresponding subsystem 102, 104, 106, 108, 110, 112, 114 and/or 116. The user can provide input in response to menu data or other prompts presented by the interactive interface via the one or more client input devices 250, which can include a microphone, mouse, keyboard, touchscreen of display device 270 itself or other touchscreen, the user interface device of a smartphone or tablet, and/or other device allowing the user to interact with the interactive interface. The one or more processing devices 230 can process the input data and/or send raw or processed input data to the corresponding subsystem, and/or can receive and/or generate new data in response for presentation via the interactive interface 275 accordingly, by utilizing network interface 260 to communicate bidirectionally with one or more subsystems and/or databases of the medical scan processing system via network 150.

FIG. 2B presents an embodiment of a subsystem 101, which can be utilized in conjunction with subsystem 102, 104, 106, 108, 110, 112, 114 and/or 116. Each subsystem 101 can include one or more subsystem processing devices 235, one or more subsystem memory devices 245, and/or one or more subsystem network interfaces 265, connected via bus 285. The subsystem memory devices 245 can store executable instructions that, when executed by the one or more subsystem processing devices 235, facilitate performance of operations by the subsystem 101, as described for each subsystem herein.

Figure 3:
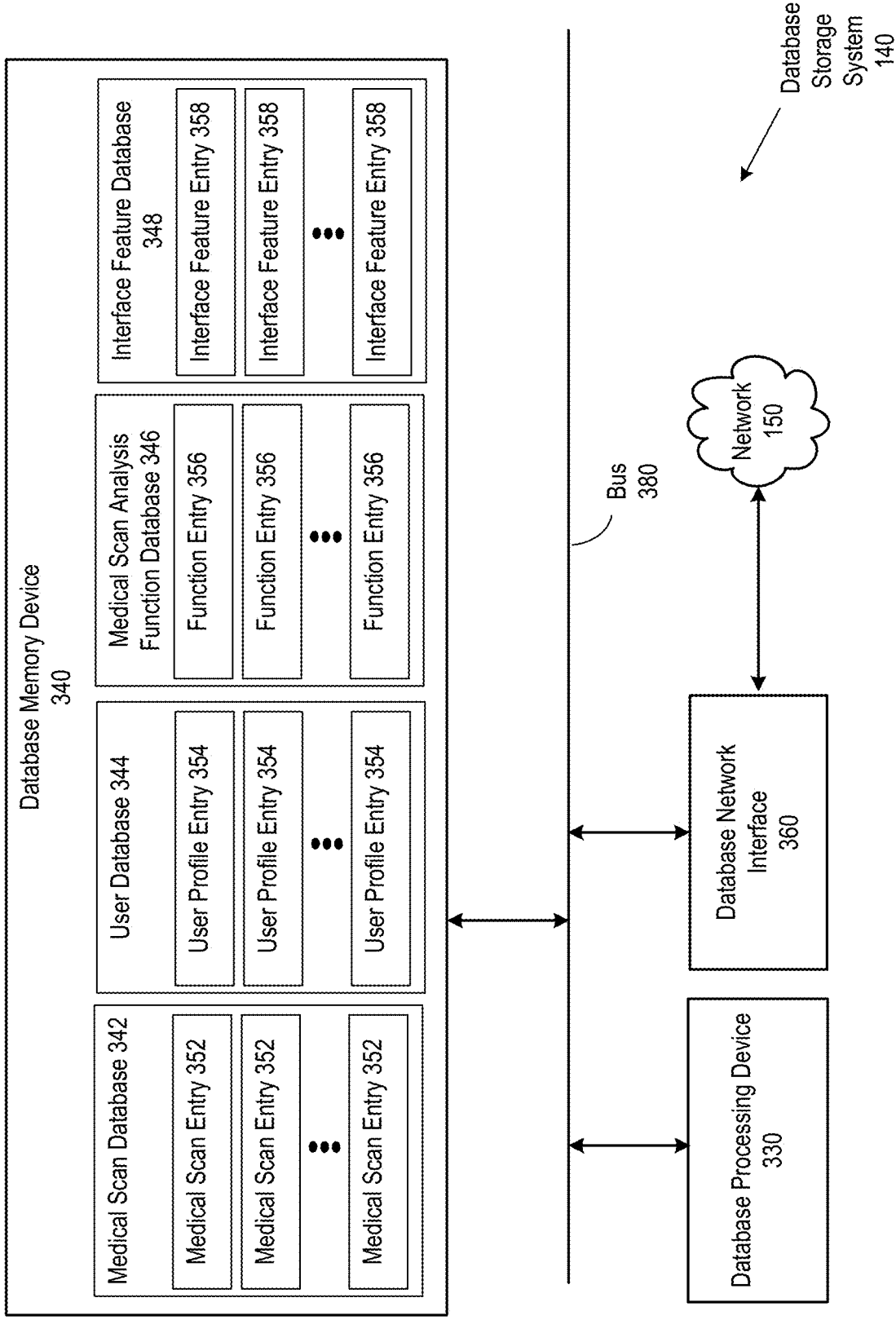
FIG. 3 is a schematic block diagram of a database storage system in accordance with various embodiments.

FIG. 3 presents an embodiment of the database storage system 140. Database storage system 140 can include at least one database processing device 330, at least one database memory device 340, and at least one database network interface 360, operable to more support one or more communication links via the network 150 indirectly and/or directly, all connected via bus 380. The database storage system 140 can store one or more databases the at least one memory 340, which can include a medical scan database 342 that includes a plurality medical scan entries 352, a user database 344 that includes a plurality of user profile entries 354, a medical scan analysis function database 346 that includes a plurality of medical scan analysis function entries 356, an interface feature database 348 can include a plurality of interface feature entries 358, and/or other databases that store data generated and/or utilized by the subsystems 101. Some or all of the databases 342, 344, 346 and/or 348 can consist of multiple databases, can be stored relationally or non-relationally, and can include different types of entries and different mappings than those described herein. A database entry can include an entry in a relational table or entry in a non-relational structure. Some or all of the data attributes of an entry 352, 354, 356, and/or 358 can refer to data included in the entry itself or that is otherwise mapped to an identifier included in the entry and can be retrieved from, added to, modified, or deleted from the database storage system 140 based on a given identifier of the entry. Some or all of the databases 342, 344, 346, and/or 348 can instead be stored locally by a corresponding subsystem, for example, if they are utilized by only one subsystem.

The processing device 330 can facilitate read/write requests received from subsystems and/or client devices via the network 150 based on read/write permissions for each database stored in the at least one memory device 340. Different subsystems can be assigned different read/write permissions for each database based on the functions of the subsystem, and different client devices 120 can be assigned different read/write permissions for each database. One or more client devices 120 can correspond to one or more administrators of one or more of the databases stored by the database storage system, and database administrator devices can manage one or more assigned databases, supervise assess and/or efficiency, edit permissions, or otherwise oversee database processes based on input to the client device via interactive interface 275.

Figure 4A:
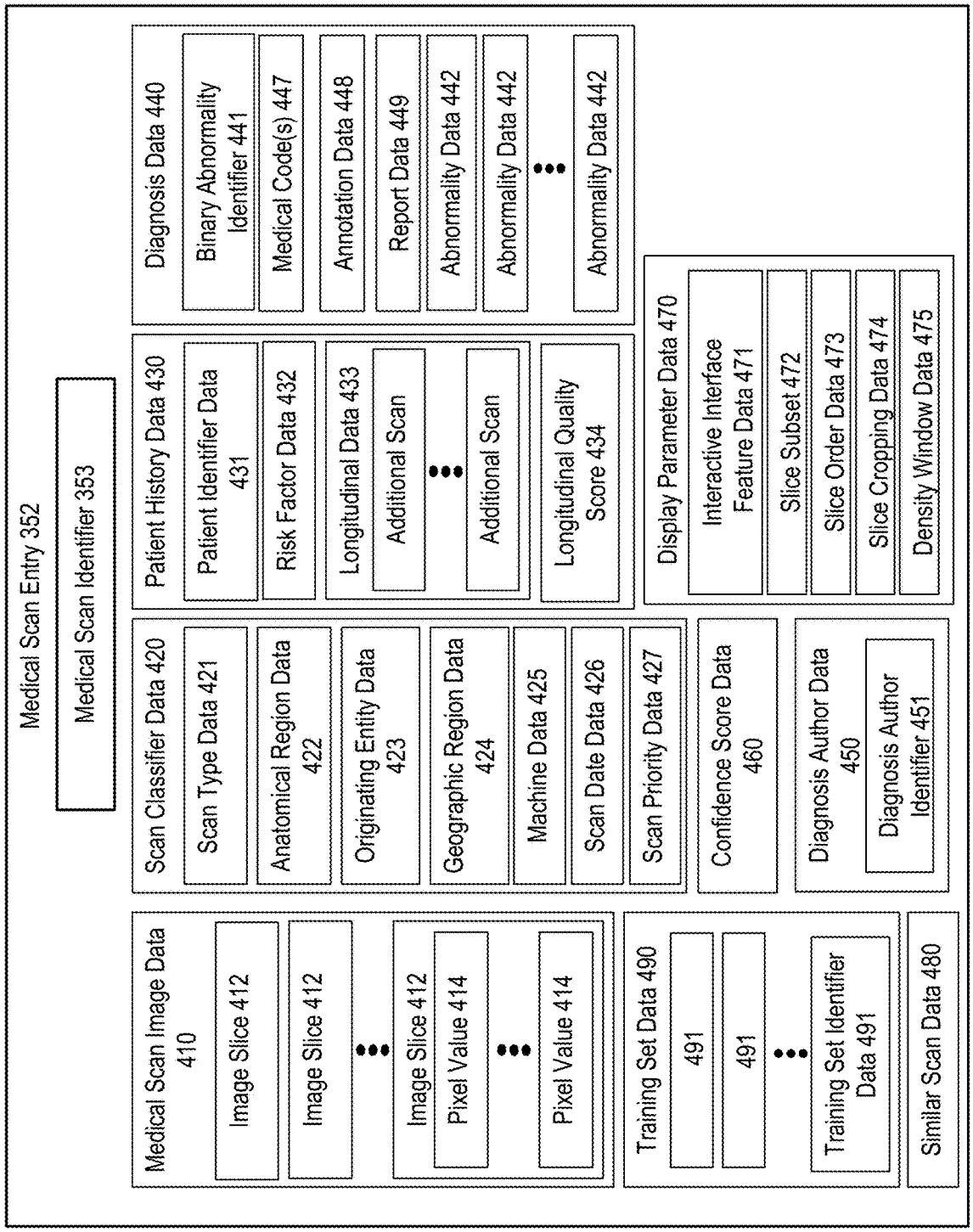
FIG. 4A is schematic block diagram of a medical scan entry in accordance with various embodiments.

FIG. 4A presents an embodiment of a medical scan entry 352, stored in medical scan database 342, included in metadata of a medical scan, and/or otherwise associated with a medical scan. A medical scan can include imaging data corresponding to a CT scan, x-ray, Mill, PET scan, Ultrasound, EEG, mammogram, or other type of radiological scan or medical scan taken of an anatomical region of a human body, animal, organism, or object and further can include metadata corresponding to the imaging data. Some or all of the medical scan entries can be formatted in accordance with a Digital Imaging and Communications in Medicine (DICOM) format or other standardized image format, and some or more of the fields of the medical scan entry 352 can be included in a DICOM header or other standardized header of the medical scan. Medical scans can be awaiting review or can have already been reviewed by one or more users or automatic processes and can include tentative diagnosis data automatically generated by a subsystem, generated based on user input, and/or generated from another source. Some medical scans can include final, known diagnosis data generated by a subsystem and/or generated based on user input, and/or generated from another source, and can included in training sets used to train processes used by one or more subsystems such as the medical scan image analysis system 112 and/or the medical scan natural language analysis system 114.

Some medical scans can include one or more abnormalities, which can be identified by a user or can be identified automatically. Abnormalities can include nodules, for example malignant nodules identified in a chest CT scan. Abnormalities can also include and/or be characterized by one or more abnormality pattern categories such as such as cardiomegaly, consolidation, effusion, emphysema, and/or fracture, for example identified in a chest x-ray. Abnormalities can also include any other unknown, malignant or benign feature of a medical scan identified as not normal. Some scans can contain zero abnormalities, and can be identified as normal scans. Some scans identified as normal scans can include identified abnormalities that are classified as benign, and include zero abnormalities classified as either unknown or malignant. Scans identified as normal scans may include abnormalities that were not detected by one or more subsystems and/or by an originating entity. Thus, some scans may be improperly identified as normal. Similarly, scans identified to include at least one abnormality may include at least one abnormality that was improperly detected as an abnormality by one or more subsystems and/or by an originating entity. Thus, some scans may be improperly identified as containing abnormalities.

Each medical scan entry 352 can be identified by its own medical scan identifier 353, and can include or otherwise map to medical scan image data 410, and metadata such as scan classifier data 420, patient history data 430, diagnosis data 440, annotation author data 450, confidence score data 460, display parameter data 470, similar scan data 480, training set data 490, and/or other data relating to the medical scan. Some or all of the data included in a medical scan entry 352 can be used to aid a user in generating or editing diagnosis data 440, for example, in conjunction with the medical scan assisted review system 102, the medical scan report labeling system 104, and/or the medical scan annotator system 106. Some or all of the data included in a medical scan entry 352 can be used to allow one or more subsystems 101, such as automated portions of the medical scan report labeling system 104 and/or the medical scan diagnosing system 108, to automatically generate and/or edit diagnosis data 440 or other data the medical scan. Some or all of the data included in a medical scan entry 352 can be used to train some or all medical scan analysis functions of the medical scan analysis function database 346 such as one or more medical scan image analysis functions, one or more medical scan natural language analysis functions, one or more medical scan similarity analysis functions, one or more medical report generator functions, and/or one or more medical report analysis functions, for example, in conjunction with the medical scan image analysis system 112, the medical scan natural language analysis system 114, and/or the medical scan comparison system 116.

The medical scan entries 352 and the associated data as described herein can also refer to data associated with a medical scan that is not stored by the medical scan database, for example, that is uploaded by a client device for direct transmission to a subsystem, data generated by a subsystem and used as input to another subsystem or transmitted directly to a client device, data stored by a Picture Archive and Communication System (PACS) communicating with the medical scan processing system 100, or other data associated with a medical scan that is received and or generated without being stored in the medical scan database 342. For example, some or all of the structure and data attributes described with respect to a medical scan entry 352 can also correspond to structure and/or data attribute of data objects or other data generated by and/or transmitted between subsystems and/or client devices that correspond to a medical scan. Herein, any of the data attributes described with respect to a medical scan entry 352 can also correspond to data extracted from a data object generated by a subsystem or client device or data otherwise received from a subsystem, client device, or other source via network 150 that corresponds to a medical scan.

The medical scan image data 410 can include one or more images corresponding to a medical scan. The medical scan image data 410 can include one or more image slices 412, for example, corresponding to a single x-ray image, a plurality of cross-sectional, tomographic images of a scan such as a CT scan, or any plurality of images taken from the same or different point at the same or different angles. The medical scan image data 410 can also indicate an ordering of the one or more image slices 412. Herein, a "medical scan" can refer a full scan of any type represented by medical scan image data 410. Herein, an "image slice" can refer to one of a plurality of cross-sectional images of the medical scan image data 410, one of a plurality of images taken from different angles of the medical scan image data 410, and/or the single image of the medical scan image data 410 that includes only one image. Furthermore "plurality of image slices" can refer to all of the images of the associated medical scan, and refers to only a single image if the medical scan image data 410 includes only one image. Each image slice 412 can include a plurality of pixel values 414 mapped to each pixel of the image slice. Each pixel value can correspond to a density value, such as a Hounsfield value or other measure of density. Pixel values can also correspond to a grayscale value, a RGB (Red-Green-Blue) or other color value, or other data stored by each pixel of an image slice 412.

Scan classifier data 420 can indicate classifying data of the medical scan. Scan classifier data can include scan type data 421, for example, indicating the modality of the scan. The scan classifier data can indicate that the scan is a CT scan, x-ray, Mill, PET scan, Ultrasound, EEG, mammogram, or other type of scan. Scan classifier data 420 can also include anatomical region data 422, indicating for example, the scan is a scan of the chest, head, right knee, or other anatomical region. Scan classifier data can also include originating entity data 423, indicating the hospital where the scan was taken and/or a user that uploaded the scan to the system. If the originating entity data corresponds to a user of one or more subsystems 101, the originating entity data can include a corresponding user profile identifier and/or include other data from the user profile entry 354 of the user. Scan classifier data 420 can include geographic region data 424, indicating a city, state, and/or country from which the scan originated, for example, based on the user data retrieved from the user database 344 based on the originating entity. Scan classifier data can also include machine data 425, which can include machine identifier data, machine model data, machine calibration data, and/or contrast agent data, for example based on imaging machine data retrieved from the user database 344 based on the originating entity data 423. The scan classifier data 420 can include scan date data 426 indicating when the scan was taken. The scan classifier data 420 can include scan priority data 427, which can indicate a priority score, ranking, number in a queue, or other priority data with regard to triaging and/or review. A priority score, ranking, or queue number of the scan priority data 427 can be generated by automatically by a subsystem based on the scan priority data 427, based on a severity of patient symptoms or other indicators in the risk factor data 432, based on a priority corresponding to the originating entity, based on previously generated diagnosis data 440 for the scan, and/or can be assigned by the originating entity and/or a user of the system.

The scan classifier data 420 can include other classifying data not pictured in FIG. 4A. For example, a set of scans can include medical scan image data 410 corresponding to different imaging planes. The scan classifier data can further include imaging plane data indicating one or more imaging planes corresponding to the image data. For example, the imaging plane data can indicate the scan corresponds to the axial plane, sagittal plane, or coronal plane. A single medical scan entry 352 can include medical scan image data 410 corresponding multiple planes, and each of these planes can be tagged appropriately in the image data. In other embodiments, medical scan image data 410 corresponding to each plane can be stored as separate medical scan entries 352, for example, with a common identifier indicating these entries belong to the same set of scans.

Alternatively or in addition, the scan classifier data 420 can include sequencing data. For example, a set of scans can include medical scan image data 410 corresponding to different sequences. The scan classifier data can further include sequencing data indicating one or more of a plurality of sequences of the image data corresponds to, for example, indicating whether an MRI scan corresponds to a T2 sequence, a T1 sequence, a T1 sequence with contrast, a diffusion sequence, a FLAIR sequence, or other MRI sequence. A single medical scan entry 352 can include medical scan image data 410 corresponding to multiple sequences, and each of these sequences can be tagged appropriately in the entry. In other embodiments, medical scan image data 410 corresponding to each sequence can be stored as separate medical scan entries 352, for example, with a common identifier indicating these entries belong to the same set of scans.

Alternatively or in addition, the scan classifier data 420 can include an image quality score. This score can be determined automatically by one or more subsystems 101, and/or can be manually assigned the medical scan. The image quality score can be based on a resolution of the image data 410, where higher resolution image data is assigned a more favorable image quality score than lower resolution image data. The image quality score can be based on whether the image data 410 corresponds to digitized image data received directly from the corresponding imaging machine, or corresponds to a hard copy of the image data that was later scanned in. In some embodiments, the image quality score can be based on a detected corruption, and/or detected external factor that determined to negatively affect the quality of the image data during the capturing of the medical scan and/or subsequent to the capturing of the medical scan. In some embodiments, the image quality score can be based on detected noise in the image data, where a medical scan with a higher level of detected noise can receive a less favorable image quality score than a medical scan with a lower level of detected noise. Medical scans with this determined corruption or external factor can receive a less favorable image quality score than medical scans with no detected corruption or external factor.

In some embodiments, the image quality score can be based on include machine data 425. In some embodiments, one or more subsystems can utilize the image quality score to flag medical scans with image quality scores that fall below an image quality threshold. The image quality threshold can be the same or different for different subsystems, medical scan modalities, and/or anatomical regions. For example, the medical scan image analysis system can automatically filter training sets based on selecting only medical scans with image quality scores that compare favorably to the image quality threshold. As another example, one or more subsystems can flag a particular imaging machine and/or hospital or other medical entity that have produced at least a threshold number and/or percentage of medical scan with image quality scores that compare unfavorably to the image quality threshold. As another example, a de-noising algorithm can be automatically utilized to dean the image data when the image quality score compares unfavorably to the image quality threshold. As another example, the medical scan image analysis system can select a particular medical image analysis function from a set of medical image analysis functions to utilize on a medical scan to generate inference data for the medical scan. Each of this set of medical image analysis function can be trained on different levels of image quality, and the selected image analysis function can be selected based on the determined image quality score falling within a range of image quality scores the image analysis function was trained on and/or is otherwise suitable for.

The patient history data 430 can include patient identifier data 431 which can include basic patient information such as name or an identifier that may be anonymized to protect the confidentiality of the patient, age, and/or gender. The patient identifier data 431 can also map to a patient entry in a separate patient database stored by the database storage system, or stored elsewhere. The patient history data can include patient risk factor data 432 which can include previous medical history, family medical history, smoking and/or drug habits, pack years corresponding to tobacco use, environmental exposures, patient symptoms, etc. The patient history data 430 can also include longitudinal data 433, which can identify one or more additional medical scans corresponding to the patient, for example, retrieved based on patient identifier data 431 or otherwise mapped to the patient identifier data 431. Some or all additional medical scans can be included in the medical scan database, and can be identified based on their corresponding identifiers medical scan identifiers 353. Some or all additional medical scans can be received from a different source and can otherwise be identified. Alternatively or in addition, the longitudinal data can simply include some or all relevant scan entry data of a medical scan entry 352 corresponding to the one or more additional medical scans. The additional medical scans can be the same type of scan or different types of scans. Some or all of the additional scans may correspond to past medical scans, and/or some or all of the additional scans may correspond to future medical scans. The longitudinal data 433 can also include data received and/or determined at a date after the scan such as final biopsy data, or some or all of the diagnosis data 440. The patient history data can also include a longitudinal quality score 434, which can be calculated automatically by a subsystem, for example, based on the number of additional medical scans, based on how many of the additional scans in the file were taken before and/or after the scan based on the scan date data 426 of the medical scan and the additional medical scans, based on a date range corresponding to the earliest scan and corresponding to the latest scan, based on the scan types data 421 these scans, and/or based on whether or not a biopsy or other final data is included. As used herein, a "high" longitudinal quality score refers to a scan having more favorable longitudinal data than that with a "low" longitudinal quality score.

Diagnosis data 440 can include data that indicates an automated diagnosis, a tentative diagnosis, and/or data that can otherwise be used to support medical diagnosis, triage, medical evaluation and/or other review by a medical professional or other user. The diagnosis data 440 of a medical scan can include a binary abnormality identifier 441 indicating whether the scan is normal or includes at least one abnormality. In some embodiments, the binary abnormality identifier 441 can be determined by comparing some or all of confidence score data 460 to a threshold, can be determined by comparing a probability value to a threshold, and/or can be determined by comparing another continuous or discrete value indicating a calculated likelihood that the scan contains one or more abnormalities to a threshold. In some embodiments, non-binary values, such as one or more continuous or discrete values indicating a likelihood that the scan contains one or more abnormalities, can be included in diagnosis data 440 in addition to, or instead of, binary abnormality identifier 441. One or abnormalities can be identified by the diagnosis data 440, and each identified abnormality can include its own set of abnormality annotation data 442. Alternatively, some or all of the diagnosis data 440 can indicate and/or describe multiple abnormalities, and thus will not be presented for each abnormality in the abnormality annotation data 442. For example, the report data 449 of the diagnosis data 440 can describe all identified abnormalities, and thus a single report can be included in the diagnosis.

Figure 4B:
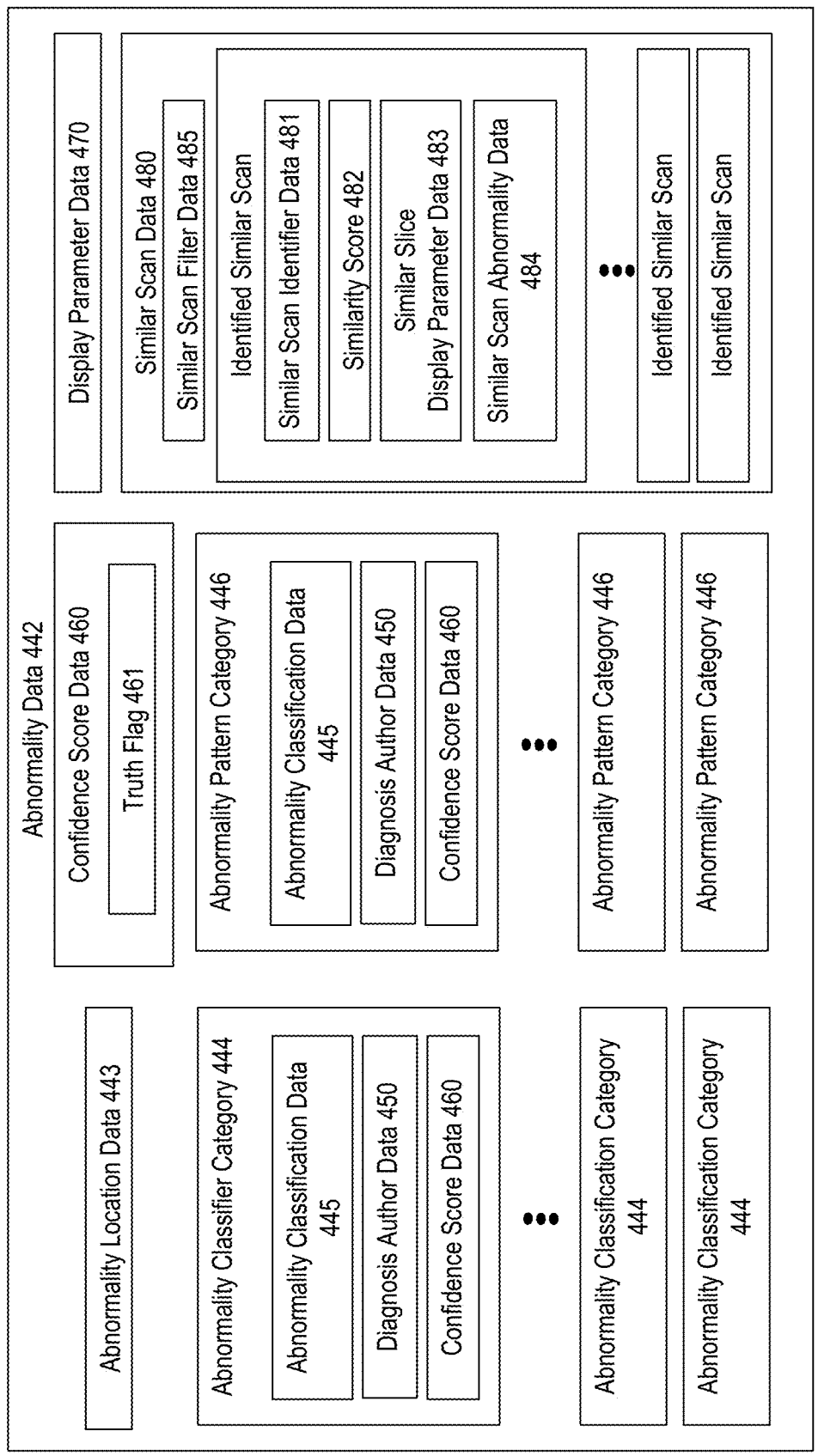
FIG. 4B is a schematic block diagram of abnormality data in accordance with various embodiments.

FIG. 4B presents an embodiment of the abnormality annotation data 442. The abnormality annotation data 442 for each abnormality can include abnormality location data 443, which can include an anatomical location and/or a location specific to pixels, image slices, coordinates or other location information identifying regions of the medical scan itself. The abnormality annotation data 442 can include abnormality classification data 445 which can include binary, quantitative, and/or descriptive data of the abnormality as a whole, or can correspond to one or more abnormality classifier categories 444, which can include size, volume, pre-post contrast, doubling time, calcification, components, smoothness, spiculation, lobulation, sphericity, internal structure, texture, or other categories that can classify and/or otherwise characterize an abnormality. Abnormality classifier categories 444 can be assigned a binary value, indicating whether or not such a category is present. For example, this binary value can be determined by comparing some or all of confidence score data 460 to a threshold, can be determined by comparing a probability value to a threshold, and/or can be determined by comparing another continuous or discrete value indicating a calculated likelihood that a corresponding abnormality classifier category 444 is present to a threshold, which can be the same or different threshold for each abnormality classifier category 444. In some embodiments, abnormality classifier categories 444 can be assigned one or more non-binary values, such as one or more continuous or discrete values indicating a likelihood that the corresponding classifier category 444 is present.

The abnormality classifier categories 444 can also include a malignancy category, and the abnormality classification data 445 can include a malignancy rating such as a Lung-RADS score, a Fleischner score, and/or one or more calculated values that indicate malignancy level, malignancy severity, and/or probability of malignancy. Alternatively or in addition, the malignancy category can be assigned a value of "yes", "no", or "maybe". The abnormality classifier categories 444 can also include abnormality pattern categories 446 such as cardiomegaly, consolidation, effusion, emphysema, and/or fracture, and the abnormality classification data 445 for each abnormality pattern category 446 can indicate whether or not each of the abnormality patterns is present.

The abnormality classifier categories can correspond to Response Evaluation Criteria in Solid Tumors (RECIST) eligibility and/or RECIST evaluation categories. For example, an abnormality classifier category 444 corresponding to RECIST eligibility can have corresponding abnormality classification data 445 indicating a binary value "yes" or "no", and/or can indicate if the abnormality is a "target lesion" and/or a "non-target lesion." As another example, an abnormality classifier category 444 corresponding to a RECIST evaluation category can be determined based on longitudinal data 433 and can have corresponding abnormality classification data 445 that includes one of the set of possible values "Complete Response", "Partial Response", "Stable Disease", or "Progressive Disease."

The diagnosis data 440 as a whole, and/or the abnormality annotation data 442 for each abnormality, can include custom codes or datatypes identifying the binary abnormality identifier 441, abnormality location data 443 and/or some or all of the abnormality classification data 445 of one or more abnormality classifier categories 444. Alternatively or in addition, some or all of the abnormality annotation data 442 for each abnormality and/or other diagnosis data 440 can be presented in a DICOM format or other standardized image annotation format, and/or can be extracted into custom datatypes based on abnormality annotation data originally presented in DICOM format. Alternatively or in addition, the diagnosis data 440 and/or the abnormality annotation data 442 for each abnormality can be presented as one or more medical codes 447 such as SNOMED codes, Current Procedure Technology (CPT) codes, ICD-9 codes, ICD-10 codes, or other standardized medical codes used to label or otherwise describe medical scans.

Alternatively or in addition, the diagnosis data 440 can include natural language text data 448 annotating or otherwise describing the medical scan as a whole, and/or the abnormality annotation data 442 can include natural language text data 448 annotating or otherwise describing each corresponding abnormality. In some embodiments, some or all of the diagnosis data 440 is presented only as natural language text data 448. In some embodiments, some or all of the diagnosis data 440 is automatically generated by one or more subsystems based on the natural language text data 448, for example, without utilizing the medical scan image data 410, for example, by utilizing one or more medical scan natural language analysis functions trained by the medical scan natural language analysis system 114. Alternatively or in addition, some embodiments, some or all of the natural language text data 448 is generated automatically based on other diagnosis data 440 such as abnormality annotation data 442, for example, by utilizing a medical scan natural language generating function trained by the medical scan natural language analysis system 114.

The diagnosis data can include report data 449 that includes at least one medical report, which can be formatted to include some or all of the medical codes 447, some or all of the natural language text data 448, other diagnosis data 440, full or cropped images slices formatted based on the display parameter data 470 and/or links thereto, full or cropped images slices or other data based on similar scans of the similar scan data 480 and/or links thereto, full or cropped images or other data based on patient history data 430 such as longitudinal data 433 and/or links thereto, and/or other data or links to data describing the medical scan and associated abnormalities. The diagnosis data 440 can also include finalized diagnosis data corresponding to future scans and/or future diagnosis for the patient, for example, biopsy data or other longitudinal data 433 determined subsequently after the scan. The medical report of report data 449 can be formatted based on specified formatting parameters such as font, text size, header data, bulleting or numbering type, margins, file type, preferences for including one or more full or cropped image slices 412, preferences for including similar medical scans, preferences for including additional medical scans, or other formatting to list natural language text data and/or image data, for example, based on preferences of a user indicated in the originating entity data 423 or other responsible user in the corresponding report formatting data.

Annotation author data 450 can be mapped to the diagnosis data for each abnormality, and/or mapped to the scan as a whole. This can include one or more annotation author identifiers 451, which can include one or more user profile identifiers of a user of the system, such as an individual medical professional, medical facility and/or medical entity that uses the system. Annotation author data 450 can be used to determine the usage data of a user profile entry 354. Annotation author data 450 can also include one or more medical scan analysis function identifiers 357 or other function identifier indicating one or more functions or other processes of a subsystem responsible for automatically generating and/or assisting a user in generating some or all of the diagnosis data, for example an identifier of a particular type and/or version of a medical scan image analysis functions that was used by the medical scan diagnosing system 108 used to generate part or all of the diagnosis data 440 and/or an interface feature identifier, indicating an one or more interface features presented to a user to facilitate entry of and/or reviewing of the diagnosis data 440. The annotation author data can also simply indicate, for one or more portions of the diagnosis data 440, if this portion was generated by a human or automatically generated by a subsystem of the medical scan processing system.

In some embodiments, if a medical scan was reviewed by multiple entities, multiple, separate diagnosis data entries 440 can be included in the medical scan entry 352, mapped to each diagnosis author in the annotation author data 450. This allows different versions of diagnosis data 440 received from multiple entities. For example, annotation author data of a particular medical scan could indicate that the annotation data was written by a doctor at medical entity A, and the medical code data was generated by user Y by utilizing the medical scan report labeling system 104, which was confirmed by expert user X. The annotation author data of another medical scan could indicate that the medical code was generated automatically by utilizing version 7 of the medical scan image analysis function relating to chest x-rays, and confirmed by expert user X. The annotation author data of another medical scan could indicate that the location and a first malignancy rating were generated automatically by utilizing version 7 of the medical scan image analysis function relating to chest x-rays, and that a second malignancy rating was entered by user Z. In some embodiments, one of the multiple diagnosis entries can include consensus annotation data, for example, generated automatically by a subsystem such as the medical scan annotating system 106 based on the multiple diagnosis data 440, based on confidence score data 460 of each of the multiple diagnosis data 440, and/or based on performance score data of a corresponding user, a medical scan analysis function, or an interface feature, identified in the annotation author data for each corresponding one of the multiple diagnosis data 440.

Confidence score data 460 can be mapped to some or all of the diagnosis data 440 for each abnormality, and/or for the scan as a whole. This can include an overall confidence score for the diagnosis, a confidence score for the binary indicator of whether or not the scan was normal, a confidence score for the location a detected abnormality, and/or confidence scores for some or all of the abnormality classifier data. This may be generated automatically by a subsystem, for example, based on the annotation author data and corresponding performance score of one or more identified users and/or subsystem attributes such as interactive interface types or medical scan image analysis functions indicated by the annotation author data. In the case where multiple diagnosis data entries 440 are included from different sources, confidence score data 460 can be computed for each entry and/or an overall confidence score, for example, corresponding to consensus diagnosis data, can be based on calculated distance or other error and/or discrepancies between the entries, and/or can be weighted on the confidence score data 460 of each entry. In various embodiments, the confidence score data 460 can include a truth flag 461 indicating the diagnosis data is considered as "known" or "truth", for example, flagged based on user input, flagged automatically based on the author data, and/or flagged automatically based on the calculated confidence score of the confidence score data exceeding a truth threshold. As used herein, a "high" confidence score refers to a greater degree or more favorable level of confidence than a "low" confidence score.

Display parameter data 470 can indicate parameters indicating an optimal or preferred display of the medical scan by an interactive interface 275 and/or formatted report for each abnormality and/or for the scan as a whole. Some or all of the display parameter data can have separate entries for each abnormality, for example, generated automatically by a subsystem 101 based on the abnormality annotation data 442. Display parameter data 470 can include interactive interface feature data 471, which can indicate one or more selected interface features associated with the display of abnormalities and/or display of the medical scan as a whole, and/or selected interface features associated with user interaction with a medical scan, for example, based on categorized interface feature performance score data and a category associated with the abnormality and/or with the medical scan itself. The display parameter data can include a slice subset 472, which can indicate a selected subset of the plurality of image slices that includes a single image slice 412 or multiple image slices 412 of the medical scan image data 410 for display by a user interface. The display parameter data 470 can include slice order data 473 that indicates a selected custom ordering and/or ranking for the slice subset 472, or for all of the slices 412 of the medical scan. The display parameter data 470 can include slice cropping data 474 corresponding to some or all of the slice subset 472, or all of the image slices 412 of the medical scan, and can indicating a selected custom cropped region of each image slice 412 for display, or the same selected custom cropped region for the slice subset 472 or for all slices 412. The display parameter data can include density window data 475, which can indicate a selected custom density window for display of the medical scan as a whole, a selected custom density window for the slice subset 472, and/or selected custom density windows for each of the image slices 412 of the slice subset 472, and/or for each image slice 412 of the medical scan. The density window data 475 can indicate a selected upper density value cut off and a selected lower density value cut off, and/or can include a selected deterministic function to map each density value of a pixel to a grayscale value based on the preferred density window. The interactive interface feature data 471, slice subset 472, slice order data 473, slice cropping data 474, and/or the density window data 475 can be selected via user input and/or generated automatically by one or more subsystems 101, for example, based on the abnormality annotation data 442 and/or based on performance score data of different interactive interface versions.

Similar scan data 480 can be mapped to each abnormality, or the scan as a whole, and can include similar scan identifier data 481 corresponding to one or more identified similar medical scans, for example, automatically identified by a subsystem 101, for example, by applying a similar scan identification step of the medical scan image analysis system 112 and/or applying medical scan similarity analysis function to some or all of the data stored in the medical scan entry of the medical scan, and/or to some or all corresponding data of other medical scans in the medical scan database. The similar scan data 480 can also correspond to medical scans received from another source. The stored similarity data can be used to present similar cases to users of the system and/or can be used to train medical scan image analysis functions or medical scan similarity analysis functions.

Each identified similar medical scan can have its own medical scan entry 352 in the medical scan database 342 with its own data, and the similar scan identifier data 481 can include the medical scan identifier 353 each similar medical scan. Each identified similar medical scan can be a scan of the same scan type or different scan type than medical scan.

The similar scan data 480 can include a similarity score 482 for each identified similar scan, for example, generated based on some or all of the data of the medical scan entry 352 for medical scan and based on some or all of the corresponding data of the medical scan entry 352 for the identified similar medical scan. For example, the similarity score 482 can be generated based on applying a medical scan similarity analysis function to the medical image scan data of medical scans and 402, to some or all of the abnormality annotation data of medical scans and 402, and/or to some or all of the patient history data 430 of medical scans and 402 such as risk factor data 432. As used herein, a "high" similarity score refers a higher level of similarity that a "low" similarity score.

The similar scan data 480 can include its own similar scan display parameter data 483, which can be determined based on some or all of the display parameter data 470 of the identified similar medical scan. Some or all of the similar scan display parameter data 483 can be generated automatically by a subsystem, for example, based on the display parameter data 470 of the identified similar medical scan, based on the abnormality annotation data 442 of the medical scan itself and/or based on display parameter data 470 of the medical scan itself. Thus, the similar scan display parameter data 483 can be the same or different than the display parameter data 470 mapped to the identified similar medical scan and/or can be the same or different than the display parameter data 470 of the medical scan itself. This can be utilized when displaying similar scans to a user via interactive interface 275 and/or can be utilized when generating report data 449 that includes similar scans, for example, in conjunction with the medical scan assisted review system 102.

The similar scan data 480 can include similar scan abnormality data 484, which can indicate one of a plurality of abnormalities of the identified similar medical scan and its corresponding abnormality annotation data 442. For example, the similarity scan abnormality data 484 can include an abnormality pair that indicates one of a plurality of abnormalities of the medical scan, and indicates one of a plurality of abnormalities of the identified similar medical scan, for example, that was identified as the similar abnormality.

The similar scan data 480 can include similar scan filter data 485. The similar scan filter data can be generated automatically by a subsystem, and can include a selected ordered or un-ordered subset of all identified similar scans of the similar scan data 480, and/or a ranking of all identified similar scans. For example, the subset can be selected and/or some or all identified similar scans can be ranked based on each similarity score 482, and/or based on other factors such as based on a longitudinal quality score 434 of each identified similar medical scan.

The training set data 490 can indicate one or more training sets that the medical scan belongs to. For example, the training set data can indicate one or more training set identifiers 491 indicating one or more medical scan analysis functions that utilized the medical scan in their training set, and/or indicating a particular version identifier 641 of the one or more medical scan analysis functions that utilized the medical scan in their training set. The training set data 490 can also indicate which portions of the medical scan entry were utilized by the training set, for example, based on model parameter data 623 of the corresponding medical scan analysis functions. For example, the training set data 490 can indicate that the medical scan image data 410 was included in the training set utilized to train version X of the chest x-ray medical scan image analysis function, or that the natural language text data 448 of this medical scan was used to train version Y of the natural language analysis function.

Figure 5A:
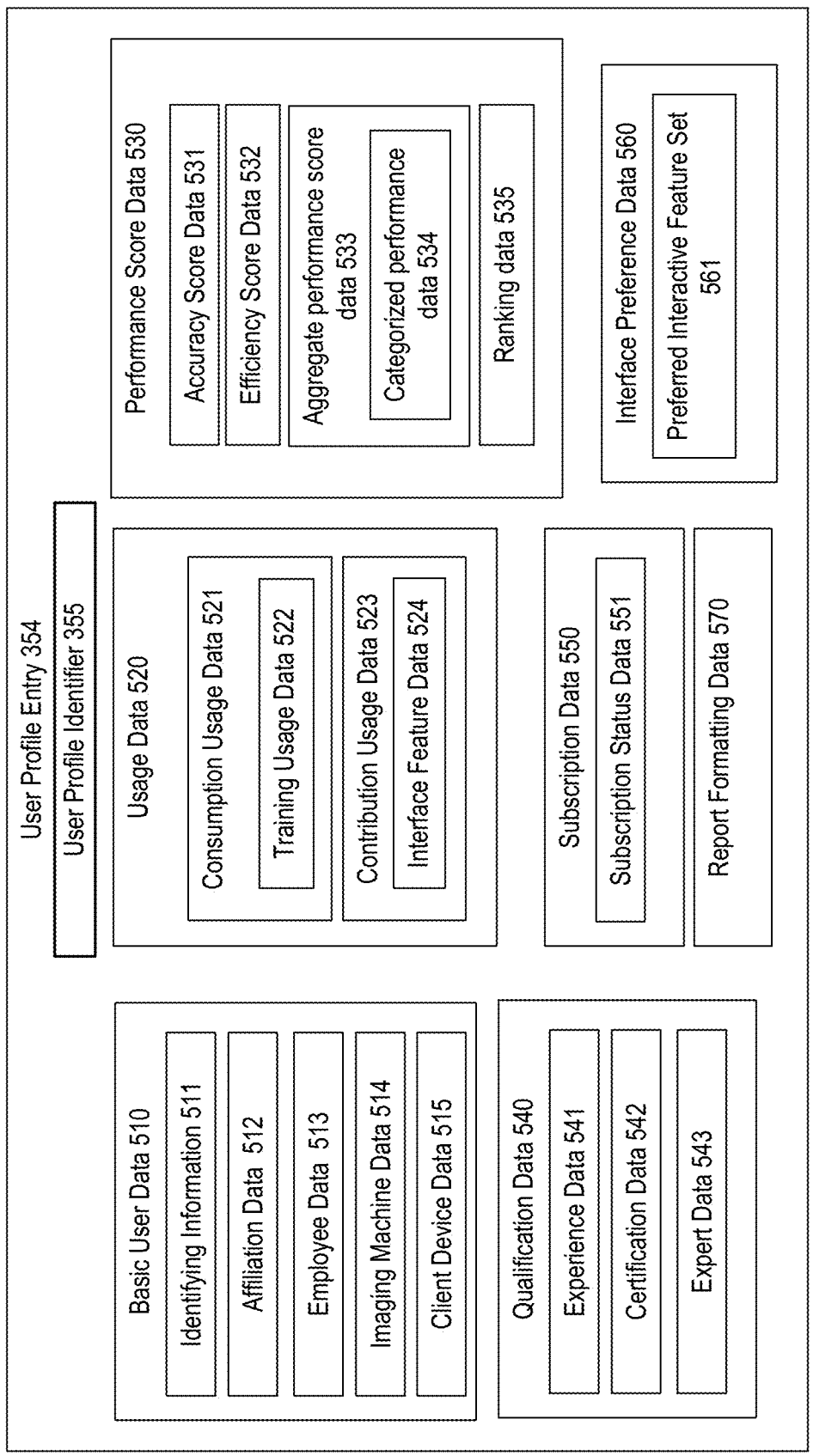
FIG. 5A is a schematic block diagram of a user profile entry in accordance with various embodiments.

FIG. 5A presents an embodiment of a user profile entry 354, stored in user database 344 or otherwise associated with a user. A user can correspond to a user of one or more of the subsystems such as a radiologist, doctor, medical professional, medical report labeler, administrator of one or more subsystems or databases, or other user that uses one or more subsystems 101. A user can also correspond to a medical entity such as a hospital, medical clinic, establishment that utilizes medical scans, establishment that employs one or more of the medical professionals described, an establishment associated with administering one or more subsystems, or other entity. A user can also correspond to a particular client device 120 or account that can be accessed one or more medical professionals or other employees at the same or different medical entities. Each user profile entry can have a corresponding user profile identifier 355.

A user profile entry 354 can include basic user data 510, which can include identifying information 511 corresponding to the user such as a name, contact information, account/login/password information, geographic location information such as geographic region data 424, and/or other basic information. Basic user data 510 can include affiliation data 512, which can list one or more medical entities or other establishments the user is affiliated with, for example, if the user corresponds to a single person such as a medical professional, or if the user corresponds to a hospital in a network of hospitals. The affiliation data 512 can include one or more corresponding user profile identifiers 355 and/or basic user data 510 if the corresponding affiliated medical entity or other establishment has its own entry in the user database. The user identifier data can include employee data 513 listing one or more employees, such as medical professionals with their own user profile entries 354, for example, if the user corresponds to a medical entity or supervising medical professional of other medical professional employees, and can list a user profile identifier 355 and/or basic user data 510 for each employee. The basic user data 510 can also include imaging machine data 514, which can include a list of machines affiliated with the user which can include machine identifiers, model information, calibration information, scan type information, or other data corresponding to each machine, for example, corresponding to the machine data 425. The user profile entry can include client device data 515, which can include identifiers for one or more client devices associated with the user, for example, allowing subsystems 101 to send data to a client device 120 corresponding to a selected user based on the client device data and/or to determine a user that data was received by determining the client device from which the data was received.

The user profile entry can include usage data 520 which can include identifying information for a plurality of usages by the user in conjunction with using one or more subsystems 101. This can include consumption usage data 521, which can include a listing of, or aggregate data associated with, usages of one or more subsystems by the user, for example, where the user is utilizing the subsystem as a service. For example, the consumption usage data 521 can correspond to each instance where diagnosis data was sent to the user for medical scans provided to the user in conjunction with the medical scan diagnosing system 108 and/or the medical scan assisted review system 102. Some or all of consumption usage data 521 can include training usage data 522, corresponding to usage in conjunction with a certification program or other user training provided by one or more subsystems. The training usage data 522 can correspond to each instance where diagnosis feedback data was provided by user for a medical scan with known diagnosis data, but diagnosis feedback data is not utilized by a subsystem to generate, edit, and/or confirm diagnosis data 440 of the medical scan, as it is instead utilized to train a user and/or determine performance data for a user.

Usage data 520 can include contribution usage data 523, which can include a listing of, or aggregate data associated with, usages of one or more subsystems 101 by the user, for example, where the user is generating and/or otherwise providing data and/or feedback that can is utilized by the subsystems, for example, to generate, edit, and/or confirm diagnosis data 440 and/or to otherwise populate, modify, or confirm portions of the medical scan database or other subsystem data. For example, the contribution usage data 523 can correspond to diagnosis feedback data received from user, used to generate, edit, and/or confirm diagnosis data. The contribution usage data 523 can include interactive interface feature data 524 corresponding to the interactive interface features utilized with respect to the contribution.

The consumption usage data 521 and/or the contribution usage data 523 can include medical scan entry 352 whose entries the user utilized and/or contributed to, can indicate one or more specific attributes of a medical scan entry 352 that a user utilized and/or contributed to, and/or a log of the user input generated by a client device of the user in conjunction with the data usage. The contribution usage data 523 can include the diagnosis data that the user may have generated and/or reviewed, for example, indicated by, mapped to, and/or used to generate the annotation author data 450 of corresponding medical scan entries 352. Some usages may correspond to both consumption usage of the consumption usage data 521 and contribution usage of the contribution usage data 523. The usage data 520 can also indicate one or more subsystems 101 that correspond to each consumption and/or contribution.

The user profile entry can include performance score data 530. This can include one or more performance scores generated based on the contribution usage data 523 and/or training usage data 522. The performance scores can include separate performance scores generated for every contribution in the contribution usage data 523 and/or training usage data 522 and/or generated for every training consumption usages corresponding to a training program. As used herein, a "high" performance score refers to a more favorable performance or rating than a "low" performance score.

The performance score data can include accuracy score data 531, which can be generated automatically by a subsystem for each contribution, for example, based on comparing diagnosis data received from a user to data to known truth data such as medical scans with a truth flag 461, for example, retrieved from the corresponding medical scan entry 352 and/or based on other data corresponding to the medical scan, for example, received from an expert user that later reviewed the contribution usage data of the user and/or generated automatically by a subsystem. The accuracy score data 531 can include an aggregate accuracy score generated automatically by a subsystem, for example, based on the accuracy data of multiple contributions by the user over time.

The performance data can also include efficiency score data 532 generated automatically by a subsystem for each contribution based on an amount of time taken to complete a contribution, for example, from a time the request for a contribution was sent to the client device to a time that the contribution was received from the client device, based on timing data received from the client device itself, and/or based on other factors. The efficiency score can include an aggregate efficiency score, which can be generated automatically by a subsystem based on the individual efficiency scores over time and/or based on determining a contribution completion rate, for example based on determining how many contributions were completed in a fixed time window.

Aggregate performance score data 533 can be generated automatically by a subsystem based on the aggregate efficiency and/or accuracy data. The aggregate performance data can include categorized performance data 534, for example, corresponding to different scan types, different anatomical regions, different subsystems, different interactive interface features and/or display parameters. The categorized performance data 534 can be determined automatically by a subsystem based on the scan type data 421 and/or anatomical region data 422 of the medical scan associated with each contribution, one or more subsystems 101 associated with each contribution, and/or interactive interface feature data 524 associated with each contribution. The aggregate performance data can also be based on performance score data 530 of individual employees if the user corresponds to a medical entity, for example, retrieved based on user profile identifiers 355 included in the employee data 513. The performance score data can also include ranking data 535, which can include an overall ranking or categorized rankings, for example, generated automatically by a subsystem or the database itself based on the aggregate performance data.

In some embodiments, aggregate data for each user can be further broken down based on scores for distinct scan categories, for example, based on the scan classifier data 420, for example, where a first aggregate data score is generated for a user "A" based on scores from all knee x-rays, and a second aggregate data score is generated for user A based on scores from all chest CT scans. Aggregate data for each user can be further based on scores for distinct diagnosis categories, where a first aggregate data score is generated for user A based on scores from all normal scans, and a second aggregate data score is generated for user A based on scores from all scans that contain an abnormality. This can be further broken down, where a first aggregate score is generated for user A based on all scores from scans that contain an abnormality of a first type and/or in a first anatomical location, and a second aggregate score is generated for A based on all scores from scans that contain an abnormality of a second type and/or in a second location. Aggregate data for each user can be further based on affiliation data, where a ranking is generated for a medical professional "B" based on scores from all medical professionals with the same affiliation data, and/or where a ranking is generated for a hospital "C" based on scores for all hospitals, all hospitals in the same geographical region, etc. Aggregate data for each user can be further based on scores for interface features, where a first aggregate data score is generated for user A based on scores using a first interface feature, and a second aggregate data score is generated for user A based on scores using a first interface feature.

The user profile entry can include qualification data 540. The qualification data can include experience data 541 such as education data, professional practice data, number of years practicing, awards received, etc. The qualification data 540 can also include certification data 542 corresponding to certifications earned based on contributions to one or more subsystems, for example, assigned to users automatically by a subsystem based on the performance score data 530 and/or based on a number of contributions in the contribution usage data 523 and/or training usage data 522. For example, the certifications can correspond to standard and/or recognized certifications to train medical professionals and/or incentivize medical professionals to use the system. The qualification data 540 can include expert data 543. The expert data 543 can include a binary expert identifier, which can be generated automatically by a subsystem based on experience data 541, certification data 542, and/or the performance score data 530, and can indicate whether the user is an expert user. The expert data 543 can include a plurality of categorized binary expert identifiers corresponding to a plurality of qualification categories corresponding to corresponding to scan types, anatomical regions, and/or the particular subsystems. The categorized binary expert identifiers can be generated automatically by a subsystem based on the categorized performance data 534 and/or the experience data 541. The categories be ranked by performance score in each category to indicate particular specialties. The expert data 543 can also include an expert ranking or categorized expert ranking with respect to all experts in the system.

The user profile entry can include subscription data 550, which can include a selected one of a plurality of subscription options that the user has subscribed to. For example, the subscription options can correspond to allowed usage of one or more subsystems, such as a number of times a user can utilize a subsystem in a month, and/or to a certification program, for example paid for by a user to receive training to earn a subsystem certification of certification data 542. The subscription data can include subscription expiration information, and/or billing information. The subscription data can also include subscription status data 551, which can for example indicate a number of remaining usages of a system and/or available credit information. For example, the remaining number of usages can decrease and/or available credit can decrease in response to usages that utilize one or more subsystems as a service, for example, indicated in the consumption usage data 521 and/or training usage data 522. In some embodiments, the remaining number of usages can increase and/or available credit can increase in response to usages that correspond to contributions, for example, based on the contribution usage data 523. An increase in credit can be variable, and can be based on a determined quality of each contribution, for example, based on the performance score data 530 corresponding to the contribution where a higher performance score corresponds to a higher increase in credit, based on scan priority data 427 of the medical scan where contributing to higher priority scans corresponds to a higher increase in credit, or based on other factors.

The user profile entry 354 can include interface preference data 560. The interface preference data can include a preferred interactive interface feature set 561, which can include one or more interactive interface feature identifiers and/or one or more interactive interface version identifiers of interface feature entries 358 and/or version identifiers of the interface features. Some or all of the interface features of the preferred interactive interface feature set 561 can correspond to display parameter data 470 of medical scans. The preferred interactive interface feature set 561 can include a single interactive feature identifier for one or more feature types and/or interface types, and/or can include a single interactive interface version identifier for one or more interface categories. The preferred interactive interface feature set 561 can include a ranking of multiple features for the same feature type and/or interface type. The ranked and/or unranked preferred interactive interface feature set 561 can be generated based on user input to an interactive interface of the client device to select and/or rank some or all of the interface features and/or versions. Some or all of the features and/or versions of the preferred interactive feature set can be selected and/or ranked automatically by a subsystem such as the medical scan interface evaluator system, for example based on interface feature performance score data and/or feature popularity data. Alternatively or in addition, the performance score data 530 can be utilized by a subsystem to automatically determine the preferred interactive feature set, for example, based on the scores in different feature-based categories of the categorized performance data 534.

The user profile entry 354 can include report formatting data 570, which can indicate report formatting preferences indicated by the user. This can include font, text size, header data, bulleting or numbering type, margins, file type, preferences for including one or more full or cropped image slices 412, preferences for including similar medical scans, preferences for including additional medical scans in reports, or other formatting preference to list natural language text data and/or image data corresponding to each abnormality. Some or all of the report formatting data 570 can be based on interface preference data 560. The report formatting data 570 can be used by one or more subsystems to automatically generate report data 449 of medical scans based on the preferences of the requesting user.

Figure 5B:
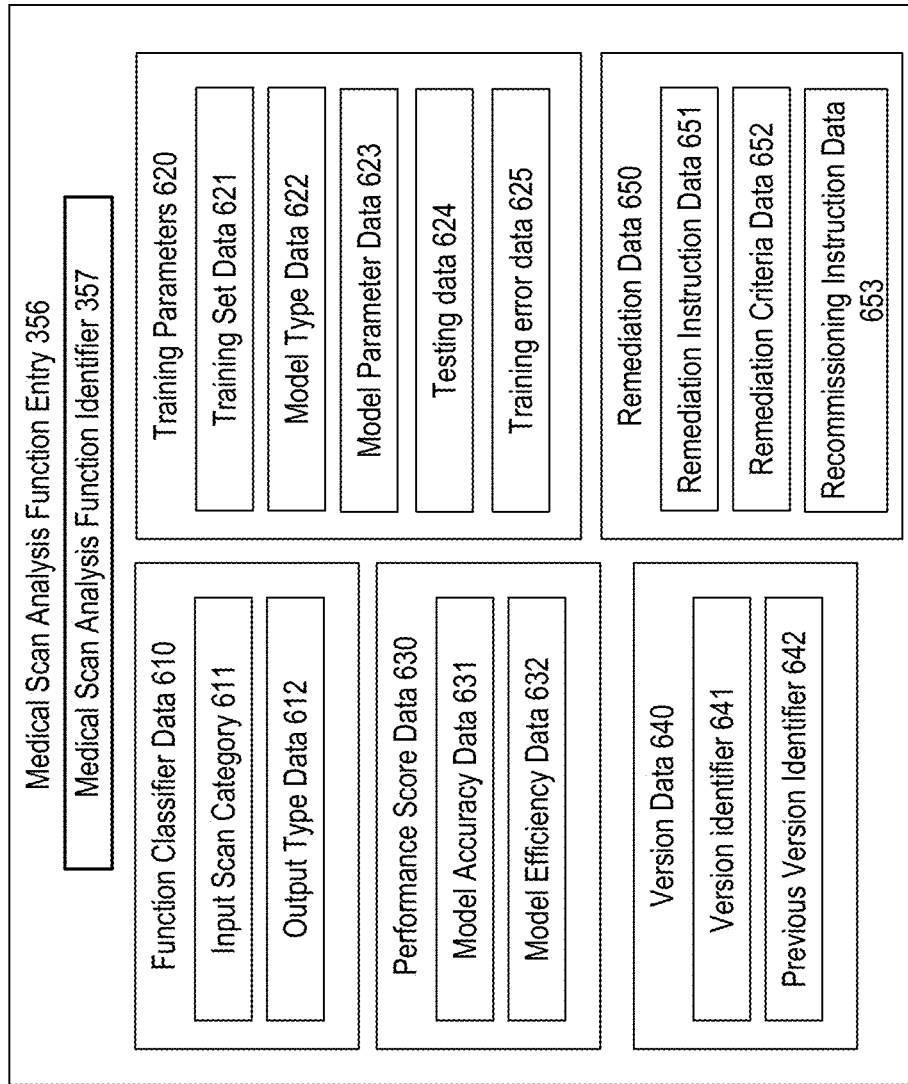
FIG. 5B is a schematic block diagram of a medical scan analysis function entry in accordance with various embodiments.

FIG. 5B presents an embodiment of a medical scan analysis function entry 356, stored in medical scan analysis function database 346 or otherwise associated with one of a plurality of medical scan analysis functions trained by and/or utilized by one or more subsystems 101. For example, a medical scan analysis function can include one or more medical scan image analysis functions trained by the medical scan image analysis system 112; one or more medical scan natural language analysis functions trained by the medical scan natural language analysis system 114; one or more medical scan similarity analysis function trained by the medical scan image analysis system 112, the medical scan natural language analysis system 114, and/or the medical scan comparison system 116; one or more medical report generator functions trained by the medical scan natural language analysis system 114 and/or the medical scan image analysis system 112, and/or the medical report analysis function trained by the medical scan natural language analysis system 114. Some or all of the medical scan analysis functions can correspond to medical scan inference functions of the medical scan diagnosing system 108, the de-identification function and/or the inference functions utilized by a medical picture archive integration system as discussed in conjunction with FIGS. 8A-8F, or other functions and/or processes described herein in conjunction with one or more subsystems 101. Each medical scan analysis function entry 356 can include a medical scan analysis function identifier 357.

Some or all medical scan analysis functions performed by one or more subsystem 101, stored in the medical scan analysis functions medical scan analysis function database 346, and/or otherwise described herein, can utilize, correspond to, and/or be based on artificial intelligence algorithms and/or techniques, and/or machine learning algorithms and/or techniques.

Some or all medical scan analysis functions discussed herein cannot be practically be trained by the human mind. Instead, such medical scan analysis functions and/or corresponding models can be trained based on applying artificial intelligence algorithms and/or techniques, and/or machine learning algorithms and/or techniques, to a training set of medical scans. Alternatively or in addition, training some or all medical scan analysis functions cannot be practically be trained by the human mind based upon: a great complexity of the resulting medical scan analysis function and/or corresponding model; a large size of the training set utilized to train the medical scan analysis function; the medical scan analysis taking an infeasibly long amount of time to train utilizing only pen and paper; and/or other reasons.

Some or all medical scan analysis functions discussed herein cannot be practically be performing by the human mind. Instead, such medical scan analysis functions can be performed utilizing artificial intelligence algorithms and/or techniques, and/or machine learning algorithms and/or techniques. Alternatively or in addition, such medical scan analysis functions can be performed utilizing a model trained utilizing artificial intelligence algorithms and/or techniques, and/or machine learning algorithms and/or techniques. Alternatively or in addition, performing some or all medical scan analysis functions cannot be practically be performed by the human mind based upon: a great complexity of the medical scan analysis function; an accuracy rate of detection, characterization, and/or measurement of abnormalities by the medical scan analysis function being more favorable than that of a human; a speed of detection, characterization, and/or measurement of abnormalities by the medical scan analysis function being more favorable than that of a human; the medical scan analysis function detecting a type of abnormality that cannot be discerned by a human; the medical scan analysis taking an infeasibly long amount of time to perform utilizing only pen and paper; and/or other reasons. and/or other reasons.

A medical scan analysis function entry 356 can include function classifier data 610. Function classifier data 610 can include input and output types corresponding to the function. For example the function classifier data can include input scan category 611 that indicates which types of scans can be used as input to the medical scan analysis function. For example, input scan category 611 can indicate that a medical scan analysis function is for chest CT scans from a particular hospital or other medical entity. The input scan category 611 can include one or more categories included in scan classifier data 420. In various embodiments, the input scan category 611 corresponds to the types of medical scans that were used to train the medical scan analysis function. Function classifier data 610 can also include output type data 612 that characterizes the type of output that will be produced by the function, for example, indicating that a medical scan analysis function is used to generate medical codes 447. The input scan category 611 can also include information identifying which subsystems 101 are responsible for running the medical scan analysis function.

A medical scan analysis function entry 356 can include training parameters 620. This can include training set data 621, which can include identifiers for the data used to train the medical scan analysis function, such as a set of medical scan identifiers 353 corresponding to the medical scans used to train the medical scan analysis function, a list of medical scan reports and corresponding medical codes used to train the medical scan analysis function, etc. Alternatively or in addition to identifying particular scans of the training set, the training set data 621 can identify training set criteria, such as necessary scan classifier data 420, necessary abnormality locations, classifiers, or other criteria corresponding to abnormality annotation data 442, necessary confidence score data 460, for example, indicating that only medical scans with diagnosis data 440 assigned a truth flag 461 or with confidence score data 460 otherwise comparing favorably to a training set confidence score threshold are included, a number of medical scans to be included and proportion data corresponding to different criteria, or other criteria used to populate a training set with data of medical scans. Training parameters 620 can include model type data 622 indicating one or more types of model, methods, and/or training functions used to determine the medical scan analysis function by utilizing the training set 621. Training parameters 620 can include model parameter data 623 that can include a set of features of the training data selected to train the medical scan analysis function, determined values for weights corresponding to selected input and output features, determined values for model parameters corresponding to the model itself, etc. The training parameter data can also include testing data 624, which can identify a test set of medical scans or other data used to test the medical scan analysis function. The test set can be a subset of training set 621, include completely separate data than training set 621, and/or overlap with training set 621. Alternatively or in addition, testing data 624 can include validation parameters such as a percentage of data that will be randomly or pseudo-randomly selected from the training set for testing, parameters characterizing a cross validation process, or other information regarding testing. Training parameters 620 can also include training error data 625 that indicates a training error associated with the medical scan analysis function, for example, based on applying cross validation indicated in testing data 624.

A medical scan analysis function entry 356 can include performance score data 630. Performance data can include model accuracy data 631, for example, generated and/or updated based on the accuracy of the function when performed on new data. For example, the model accuracy data 631 can include or be calculated based on the model error for determined for individual uses, for example, generated by comparing the output of the medical scan analysis function to corresponding data generated by user input to interactive interface 275 in conjunction with a subsystem 101 and/or generated by comparing the output of the medical scan analysis function to medical scans with a truth flag 461. The model accuracy data 631 can include aggregate model accuracy data computed based on model error of individual uses of the function over time. The performance score data 630 can also include model efficiency data 632, which can be generated based on how quickly the medical scan analysis function performs, how much memory is utilized by medical scan analysis function, or other efficiency data relating to the medical scan analysis function. Some or all of the performance score data 630 can be based on training error data 625 or other accuracy and/or efficiency data determined during training and/or validation. As used herein, a "high" performance score refers to a more favorable performance or rating than a "low" performance score.

A medical scan analysis function entry 356 can include version data 640. The version data can include a version identifier 641. The version data can indicate one or more previous version identifiers 642, which can map to version identifiers 641 stored in other medical scan analysis function entry 356 that correspond to previous versions of the function. Alternatively or in addition, the version data can indicate multiple versions of the same type based on function classifier data 610, can indicate the corresponding order and/or rank of the versions, and/or can indicate training parameters 620 associated with each version.

A medical scan analysis function entry 356 can include remediation data 650. Remediation data 650 can include remediation instruction data 651 which can indicate the steps in a remediation process indicating how a medical scan analysis function is taken out of commission and/or reverted to a previous version in the case that remediation is necessary. The version data 640 can further include remediation criteria data 652, which can include threshold data or other criteria used to automatically determine when remediation is necessary. For example, the remediation criteria data 652 can indicate that remediation is necessary at any time where the model accuracy data and/or the model efficiency data compares unfavorably to an indicated model accuracy threshold and/or indicated model efficiency threshold. The remediation data 650 can also include recommissioning instruction data 653, identifying required criteria for recommissioning a medical scan analysis function and/or updating a medical scan analysis function. The remediation data 650 can also include remediation history, indicating one or more instances that the medical scan analysis function was taken out of commission and/or was recommissioned.

Figure 6A:
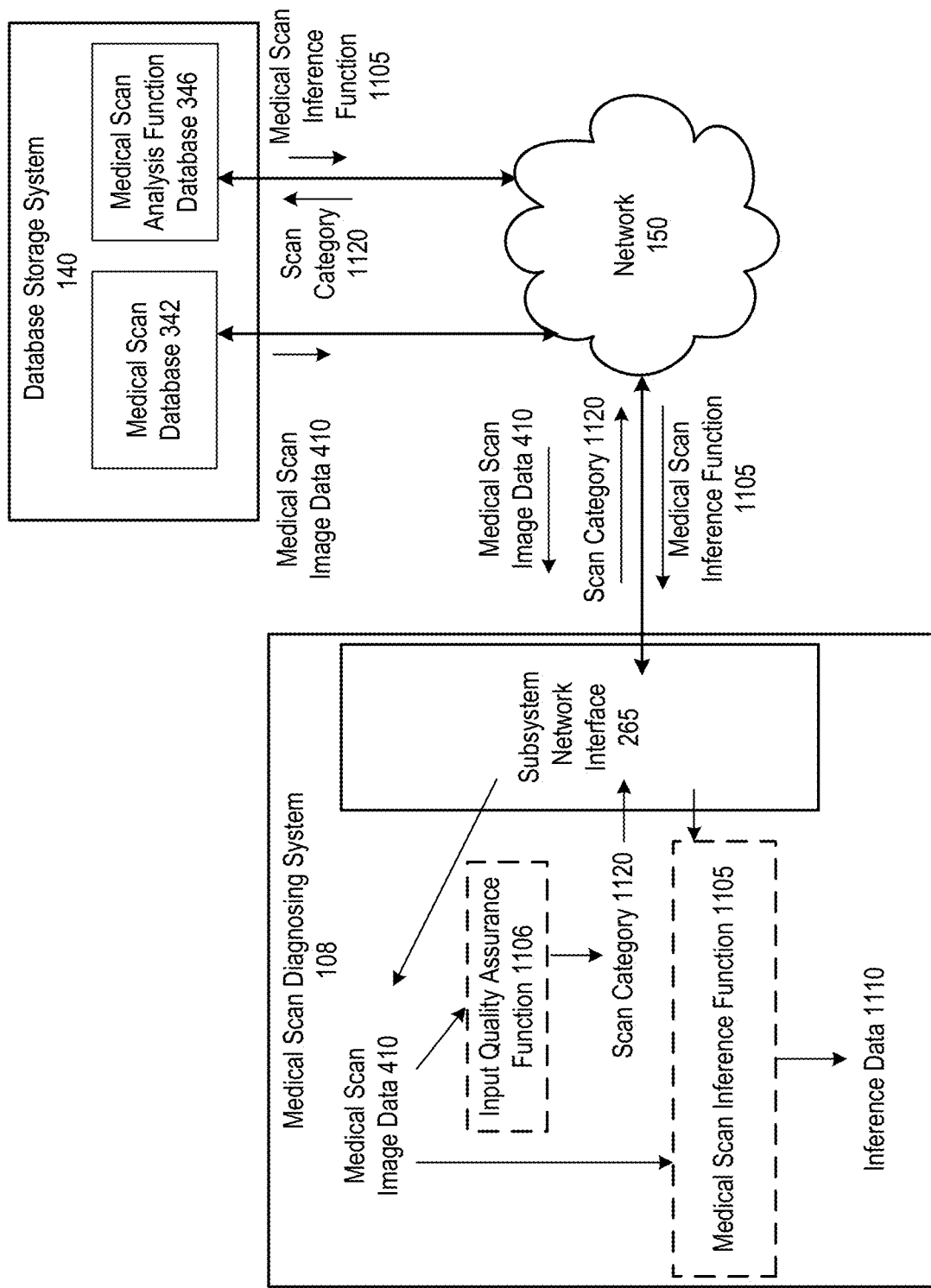
FIGS. 6A-6B are schematic block diagram of a medical scan diagnosing system in accordance with various embodiments.
Figure 6B:
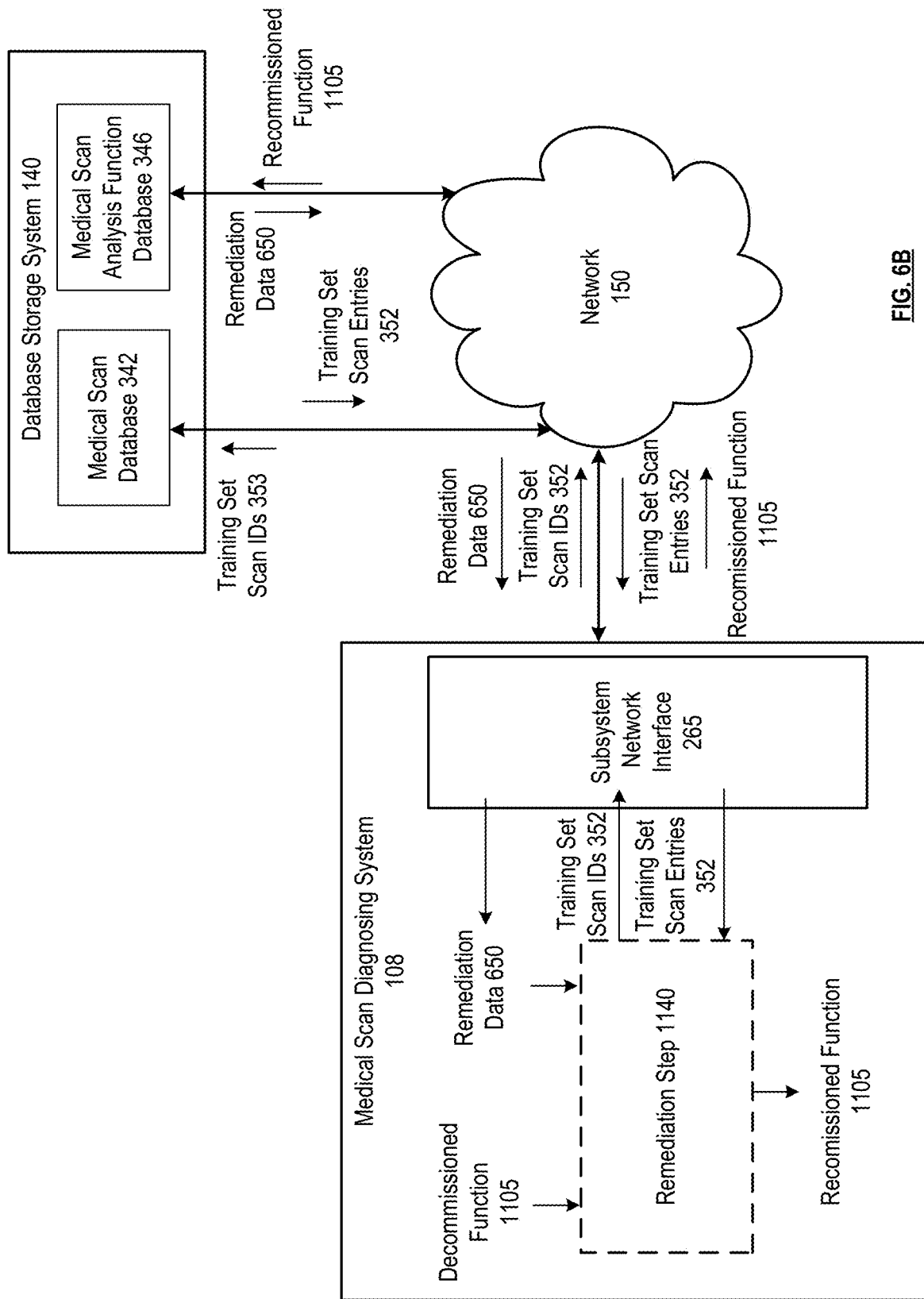

FIGS. 6A and 6B present an embodiment of a medical scan diagnosing system 108. The medical scan diagnosing system 108 can generate inference data 1110 for medical scans by utilizing a set of medical scan inference functions 1105, stored and run locally, stored and run by another subsystem 101, and/or stored in the medical scan analysis function database 346, where the function and/or parameters of the function can be retrieved from the database by the medical scan diagnosing system. For example, the set of medical scan inference function 1105 can include some or all medical scan analysis functions described here0in or other functions that generate inference data 1110 based on some or all data corresponding to a medical scan such as some or all data of a medical scan entry 352. Each medical scan inference function 1105 in the set can correspond to a scan category 1120, and can be trained on a set of medical scans that compare favorably to the scan category 1120. For example, each inference function can be trained on a set of medical scans of the one or more same scan classifier data 420, such as the same and/or similar scan types, same and/or similar anatomical regions locations, same and/or similar machine models, same and/or similar machine calibration, same and/or similar contrasting agent used, same and/or similar originating entity, same and/or similar geographical region, and/or other classifiers. Thus, the scan categories 1120 can correspond to one or more of a scan type, scan anatomical region data, hospital or other originating entity data, machine model data, machine calibration data, contrast agent data, geographic region data, and/or other scan classifying data 420. For example, a first medical scan inference function can be directed to characterizing knee x-rays, and a second medical scan inference function can be directed to chest CT scans. As another example, a first medical scan inference function can be directed to characterizing CT scans from a first hospital, and a second medical scan image analysis function can be directed to characterizing CT scans from a second hospital.

Training on these categorized sets separately can ensure each medical scan inference function 1105 is calibrated according to its scan category 1120, for example, allowing different inference functions to be calibrated on type specific, anatomical region specific, hospital specific, machine model specific, and/or region-specific tendencies and/or discrepancies. Some or all of the medical scan inference functions 1105 can be trained by the medical scan image analysis system and/or the medical scan natural language processing system, and/or some medical scan inference functions 1105 can utilize both image analysis and natural language analysis techniques to generate inference data 1110. For example, some or all of the inference functions can utilize image analysis of the medical scan image data 410 and/or natural language data extracted from abnormality annotation data 442 and/or report data 449 as input, and generate diagnosis data 440 such as medical codes 447 as output. Each medical scan inference function can utilize the same or different learning models to train on the same or different features of the medical scan data, with the same or different model parameters, for example indicated in the model type data 622 and model parameter data 623. Model type and/or parameters can be selected for a particular medical scan inference function based on particular characteristics of the one or more corresponding scan categories 1120, and some or all of the indicated in the model type data 622 and model parameter data 623 can be selected automatically by a subsystem during the training process based on the particular learned and/or otherwise determined characteristics of the one or more corresponding scan categories 1120.

As shown in FIG. 6A, the medical scan diagnosing system 108 can automatically select a medical scan for processing in response to receiving it from a medical entity via the network. Alternatively, the medical scan diagnosing system 108 can automatically retrieve a medical scan from the medical scan database that is selected based on a request received from a user for a particular scan and/or based on a queue of scans automatically ordered by the medical scan diagnosing system 108 or another subsystem based on scan priority data 427.

Once a medical scan to be processed is determined, the medical scan diagnosing system 108 can automatically select an inference function 1105 based on a determined scan category 1120 of the selected medical scan and based on corresponding inference function scan categories. The scan category 1120 of a scan can be determined based one some or all of the scan classifier data 420 and/or based on other metadata associated with the scan. This can include determining which one of the plurality of medical scan inference functions 1105 matches or otherwise compares favorably to the scan category 1120, for example, by comparing the scan category 1120 to the input scan category of the function classifier data 610.

Alternatively or in addition, the medical scan diagnosing system 108 can automatically determine which medical scan inference function 1105 is utilized based on an output preference that corresponding to a desired type of inference data 1110 that is outputted by an inference function 1105. The output preference designated by a user of the medical scan diagnosing system 108 and/or based on the function of a subsystem 101 utilizing the medical scan diagnosing system 108. For example, the set of inference functions 1105 can include inference functions that are utilized to indicate whether or not a medical scan is normal, to automatically identify at least one abnormality in the scan, to automatically characterize the at least one abnormality in the scan, to assign one or more medical codes to the scan, to generate natural language text data and/or a formatted report for the scan, and/or to automatically generate other diagnosis data such as some or all of diagnosis data 440 based on the medical scan. Alternatively or in addition, some inference functions can also be utilized to automatically generate confidence score data 460, display parameter data 470, and/or similar scan data 480. The medical scan diagnosing system 108 can compare the output preference to the output type data 612 of the medical scan inference function 1105 to determine the selected inference function 1105. For example, this can be used to decide between a first medical scan inference function that automatically generates medical codes and a second medical scan inference function that automatically generates natural language text for medical reports based on the desired type of inference data 1110.

Prior to performing the selected medical scan inference function 1105, the medical scan diagnosing system 108 can automatically perform an input quality assurance function 1106 to ensure the scan classifier data 420 or other metadata of the medical scan accurately classifies the medical scan such that the appropriate medical scan inference function 1105 of the appropriate scan category 1120 is selected. The input quality assurance function can be trained on, for example, medical scan image data 410 of plurality of previous medical scans with verified scan categories. Thus, the input quality assurance function 1106 can take medical scan image data 410 as input and can generate an inferred scan category as output. The inferred scan category can be compared to the scan category 1120 of the scan, and the input quality assurance function 1106 can determine whether or not the scan category 1120 is appropriate by determining whether the scan category 1120 compares favorably to the automatically generated inferred scan category. The input quality assurance function 1106 can also be utilized to reassign the generated inferred scan category to the scan category 1120 when the scan category 1120 compares favorably to the automatically generated inferred scan category. The input quality assurance function 1106 can also be utilized to assign the generated inferred scan category to the scan category 1120 for incoming medical scans that do not include any classifying data, and/or to add classifiers in scan classifier data 420 to medical scans missing one or more classifiers.

In various embodiments, upon utilizing the input quality assurance function 1106 to determine that the scan category 1120 determined by a scan classifier data 420 or other metadata is inaccurate, the medical scan diagnosing system 108 can transmit an alert and/or an automatically generated inferred scan category to the medical entity indicating that the scan is incorrectly classified in the scan classifier data 420 or other metadata. In some embodiments, the medical scan diagnosing system 108 can automatically update performance score data corresponding to the originating entity of the scan indicated in originating entity data 423, or another user or entity responsible for classifying the scan, for example, where a lower performance score is generated in response to determining that the scan was incorrectly classified and/or where a higher performance score is generated in response to determining that the scan was correctly classified.

In some embodiments, the medical scan diagnosing system 108 can transmit the medical scan and/or the automatically generated inferred scan category to a selected user. The user can be presented the medical scan image data 410 and/or other data of the medical scan via the interactive interface 275, for example, displayed in conjunction with the medical scan assisted review system 102. The interface can prompt the user to indicate the appropriate scan category 1120 and/or prompt the user to confirm and/or edit the inferred scan category, also presented to the user. For example, scan review data can be automatically generated to reflect the user generated and/or verified scan category 1120, This user indicated scan category 1120 can be utilized to select to the medical scan inference function 1105 and/or to update the scan classifier data 420 or other metadata accordingly. In some embodiments, for example, where the scan review data indicates that the selected user disagrees with the automatically generated inferred scan category created by the input quality assurance function 1106, the medical scan diagnosing system 108 can automatically update performance score data 630 of the input quality assurance function 1106 by generating a low performance score and/or determine to enter the remediation step 1140 for the input quality assurance function 1106.

The medical scan diagnosing system 108 can also automatically perform an output quality assurance step after a medical scan inference function 1105 has been performed on a medical scan to produce the inference data 1110, as illustrated in the embodiment presented in FIG. 6B. The output quality assurance step can be utilized to ensure that the selected medical scan inference function 1105 generated appropriate inference data 1110 based on expert feedback. The inference data 1110 generated by performing the selected medical scan inference function 1105 can be sent to a client device 120 of a selected expert user, such as an expert user in the user database selected based on categorized performance data and/or qualification data that corresponds to the scan category 1120 and/or the inference itself, for example, by selecting an expert user best suited to review an identified abnormality classifier category 444 and/or abnormality pattern category 446 in the inference data 1110 based on categorized performance data and/or qualification data of a corresponding user entry. The selected user can also correspond to a medical professional or other user employed at the originating entity and/or corresponding to the originating medical professional, indicated in the originating entity data 423.

FIG. 6B illustrates an embodiment of the medical scan diagnosing system 108 in conjunction with performing a remediation step 1140. The medical scan diagnosing system 108 can monitor the performance of the set of medical scan inference functions 1105, for example, based on evaluating inference accuracy data outputted by an inference data evaluation function and/or based monitoring on the performance score data 630 in the medical scan analysis function database, and can determine whether or not if the corresponding medical scan inference function 1105 is performing properly. This can include, for example, determining if a remediation step 1140 is necessary for a medical scan inference function 1105, for example, by comparing the performance score data 630 and/or inference accuracy data to remediation criteria data 652. Determining if a remediation step 1140 is necessary can also be based on receiving an indication from the expert user or another user that remediation is necessary for one or more identified medical scan inference functions 1105 and/or for all of the medical scan inference functions 1105.

In various embodiments, a remediation evaluation function is utilized to determine if a remediation step 1140 is necessary for medical scan inference function 1105. The remediation evaluation function can include determining that remediation is necessary when recent accuracy data and/or efficiency data of a particular medical scan inference function 1105 is below the normal performance level of the particular inference function. The remediation evaluation function can include determining that remediation is necessary when recent or overall accuracy data and/or efficiency data of a particular medical scan inference function 1105 is below a recent or overall average for all or similar medical scan inference functions 1105. The remediation evaluation function can include determining that remediation is necessary only after a threshold number of incorrect diagnoses are made. In various embodiments, multiple threshold number of incorrect diagnoses correspond to different diagnoses categories. For example, the threshold number of incorrect diagnoses for remediation can be higher for false negative diagnoses than false positive diagnoses. Similarly, categories corresponding to different diagnosis severities and/or rarities can have different thresholds, for example where a threshold number of more severe and/or more rare diagnoses that were inaccurate to necessitate remediation is lower than a threshold number of less severe and/or less rare diagnoses that were inaccurate.

The remediation step 1140 can include automatically updating an identified medical inference function 1105. This can include automatically retraining identified medical inference function 1105 on the same training set or on a new training set that includes new data, data with higher corresponding confidence scores, or data selected based on new training set criteria. The identified medical inference function 1105 can also be updated and/or changed based on the review data received from the client device. For example, the medical scan and expert feedback data can be added to the training set of the medical scan inference function 1105, and the medical scan inference function 1105 can be retrained on the updated training set. Alternatively or in addition, the expert user can identify additional parameters and/or rules in the expert feedback data based on the errors made by the inference function in generating the inference data 1110 for the medical scan, and these parameters and/or rules can be applied to update the medical scan inference function, for example, by updating the model type data 622 and/or model parameter data 623.

The remediation step 1140 can also include determining to split a scan category 1120 into two or more subcategories. Thus, two or more new medical scan inference functions 1105 can be created, where each new medical scan inference functions 1105 is trained on a corresponding training set that is a subset of the original training set and/or includes new medical scan data corresponding to the subcategory. This can allow medical scan inference functions 1105 to become more specialized and/or allow functions to utilize characteristics and/or discrepancies specific to the subcategory when generating inference data 1110. Similarly, a new scan category 1120 that was not previously represented by any of the medical scan inference functions 1105 can be added in the remediation step, and a new medical scan inference functions 1105 can be trained on a new set of medical scan data that corresponds to the new scan category 1120. Splitting a scan category and/or adding a scan category can be determined automatically by the medical scan diagnosing system 108 when performing the remediation step 1140, for example, based on performance score data 630. This can also be determined based on receiving instructions to split a category and/or add a new scan category from the expert user or other user of the system.

After a medical scan inference function 1105 is updated or created for the first time, the remediation step 1140 can further undergo a commissioning test, which can include rigorous testing of the medical scan inference function 1105 on a testing set, for example, based on the training parameters 620. For example, the commissioning test can be passed when the medical scan inference function 1105 generates a threshold number of correct inference data 1110 and/or the test can be passed if an overall or average discrepancy level between the inference data and the test data is below a set error threshold. The commissioning test can also evaluate efficiency, where the medical scan inference function 1105 only passes the commissioning test if it performs at or exceeds a threshold efficiency level. If the medical scan inference function 1105 fails the commissioning test, the model type and/or model parameters can be modified automatically or based on user input, and the medical scan inference function can be retested, continuing this process until the medical scan inference function 1105 passes the commissioning test.

The remediation step 1140 can include decommissioning the medical scan inference function 1105, for example, while the medical scan inference function is being retrained and/or is undergoing the commissioning test. Incoming scans to the medical scan diagnosing system 108 with a scan category 1120 corresponding to a decommissioned medical scan inference function 1105 can be sent directly to review by one or more users, for example, in conjunction with the medical scan annotator system 106. These user-reviewed medical scans and corresponding annotations can be included in an updated training set used to train the decommissioned medical scan inference function 1105 as part of the remediation step 1140. In some embodiments, previous versions of the plurality of medical scan image analysis functions can be stored in memory of the medical scan diagnosing system and/or can be determined based on the version data 640 of a medical scan inference function 1105. A previous version of a medical scan inference function 1105, such as most recent version or version with the highest performance score, can be utilized during the remediation step 1140 as an alternative to sending all medical scans to user review.

A medical scan inference function can also undergo the remediation step 1140 automatically in response to a hardware and/or software update on processing, memory, and/or other computing devices where the medical scan inference function 1105 is stored and/or performed. Different medical scan inference functions 1105 can be containerized on their own devices by utilizing a micro-service architecture, so hardware and/or software updates may only necessitate that one of the medical scan inference functions 1105 undergo the remediation step 1140 while the others remain unaffected. A medical scan inference function 1105 can also undergo the remediation step 1140 automatically in response to normal system boot-up, and/or periodically in fixed intervals. For example, in response to a scheduled or automatically detected hardware and/or software update, change, or issue, one or more medical scan inference functions 1105 affected by this hardware or software can be taken out of commission until they each pass the commissioning test. Such criteria can be indicated in the remediation criteria data 652.

The medical scan diagnosing system 108 can automatically manage usage data, subscription data, and/or billing data for the plurality of users corresponding to user usage of the system, for example, by utilizing, generating, and/or updating some or all of the subscription data of the user database. Users can pay for subscriptions to the system, which can include different subscription levels that can correspond to different costs. For example, a hospital can pay a monthly cost to automatically diagnose up to 100 medical scans per month. The hospital can choose to upgrade their subscription or pay per-scan costs for automatic diagnosing of additional scans received after the quota is reached and/or the medical scan diagnosing system 108 can automatically send medical scans received after the quota is reached to an expert user associated with the hospital. In various embodiments incentive programs can be used by the medical scan diagnosing system to encourage experts to review medical scans from different medical entities. For example, an expert can receive credit to their account and/or subscription upgrades for every medical scan reviewed, or after a threshold number of medical scans are reviewed. The incentive programs can include interactions by a user with other subsystems, for example, based on contributions made to medical scan entries via interaction with other subsystems.

Figure 7A:
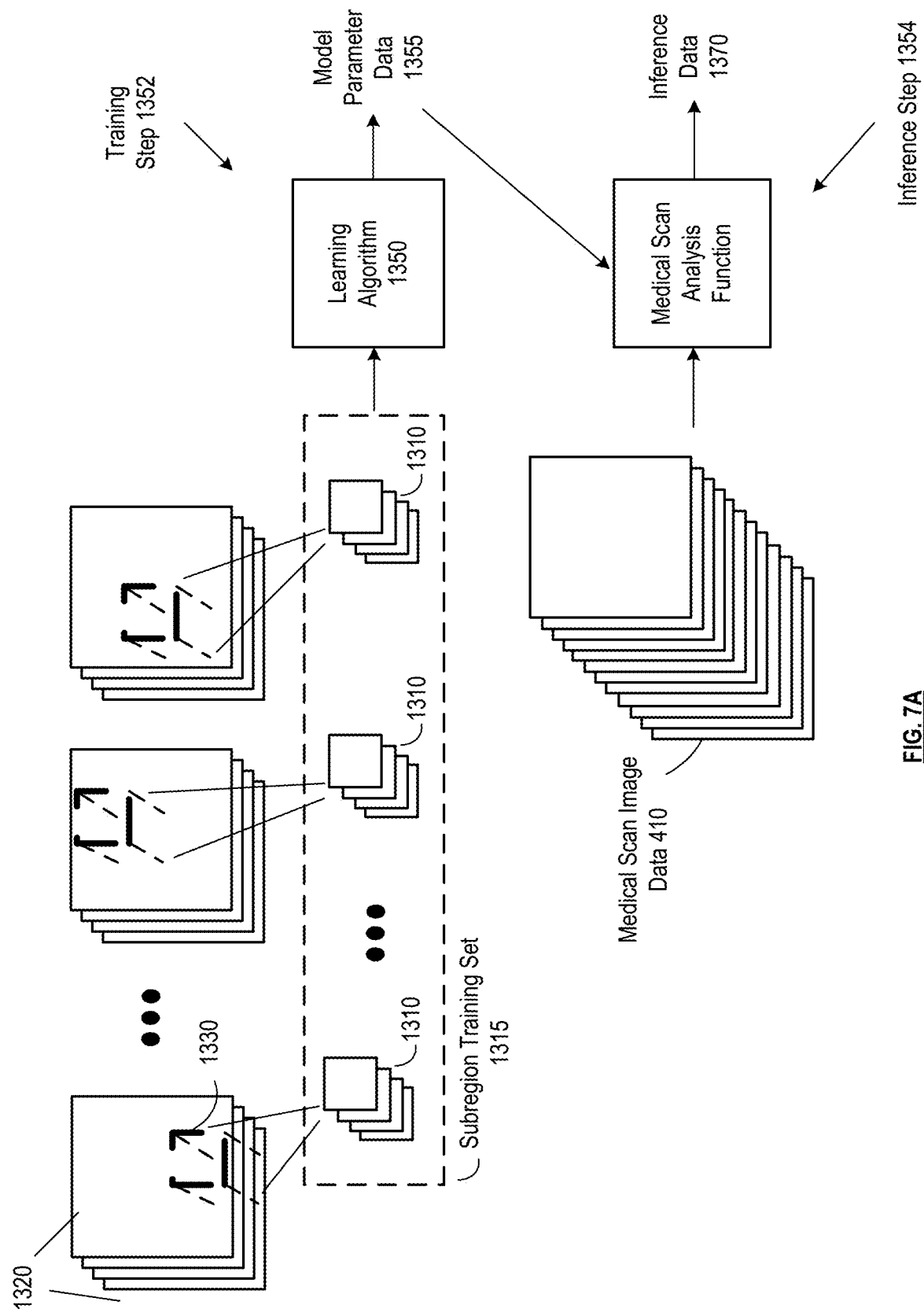
FIG. 7A is a flowchart representation of an inference step in accordance with various embodiments.

FIG. 7A presents an embodiment of a medical scan image analysis system 112. A training set of medical scans used to train one more medical scan image analysis functions can be received from one or more client devices via the network and/or can be retrieved from the medical scan database 342, for example, based on training set data 621 corresponding to medical scan image analysis functions. Training set criteria, for example, identified in training parameters 620 of the medical scan image analysis function, can be utilized to automatically identify and select medical scans to be included in the training set from a plurality of available medical scans. The training set criteria can be automatically generated based on, for example, previously learned criteria, and/or training set criteria can be received via the network, for example, from an administrator of the medical scan image analysis system. The training set criteria can include a minimum training set size. The training set criteria can include data integrity requirements for medical scans in the training set such as requiring that the medical scan is assigned a truth flag 461, requiring that performance score data for a hospital and/or medical professional associated with the medical scan compares favorably to a performance score threshold, requiring that the medical scan has been reviewed by at least a threshold number of medical professionals, requiring that the medical scan and/or a diagnosis corresponding to a patient file of the medical scan is older than a threshold elapsed time period, or based on other criteria intended to insure that the medical scans and associated data in the training set is reliable enough to be considered "truth" data. The training set criteria can include longitudinal requirements such the number of required subsequent medical scans for the patient, multiple required types of additional scans for the patient, and/or other patient file requirements.

The training set criteria can include quota and/or proportion requirements for one or more medical scan classification data. For example, the training set criteria can include meeting quota and/or proportion requirements for one or more scan types and/or human body location of scans, meeting quota or proportion requirements for a number of normal medical scans and a number of medicals scans with identified abnormalities, meeting quota and/or proportion requirements for a number of medical scans with abnormalities in certain locations and/or a number of medical scans with abnormalities that meet certain size, type, or other characteristics, meeting quota and/or proportion data for a number of medical scans with certain diagnosis or certain corresponding medical codes, and/or meeting other identified quota and/or proportion data relating to metadata, patient data, or other data associated with the medical scans.

In some embodiments, multiple training sets are created to generate corresponding medical scan image analysis functions, for example, corresponding to some or all of the set of medical scan inference functions 1105. Some or all training sets can be categorized based on some or all of the scan classifier data 420 as described in conjunction with the medical scan diagnosing system 108, where medical scans are included in a training set based on their scan classifier data 420 matching the scan category of the training set. In some embodiments, the input quality assurance function 1106 or another input check step can be performed on medical scans selected for each training set to confirm that their corresponding scan classifier data 420 is correct. In some embodiments, the input quality assurance function can correspond to its own medical scan image analysis function, trained by the medical scan image analysis system, where the input quality assurance function utilizes high level computer vision technology to determine a scan category 1120 and/or to confirm the scan classifier data 420 already assigned to the medical scan.

In some embodiments, the training set will be used to create a single neural network model, or other model corresponding to model type data 622 and/or model parameter data 623 of the medical scan image analysis function that can be trained on some or all of the medical scan classification data described above and/or other metadata, patient data, or other data associated with the medical scans. In other embodiments, a plurality of training sets will be created to generate a plurality of corresponding neural network models, where the multiple training sets are divided based on some or all of the medical scan classification data described above and/or other metadata, patient data, or other data associated with the medical scans. Each of the plurality of neural network models can be generated based on the same or different learning algorithm that utilizes the same or different features of the medical scans in the corresponding one of the plurality of training sets. The medical scan classifications selected to segregate the medical scans into multiple training sets can be received via the network, for example based on input to an administrator client device from an administrator. The medical scan classifications selected to segregate the medical scans can be automatically determined by the medical scan image analysis system, for example, where an unsupervised clustering algorithm is applied to the original training set to determine appropriate medical scan classifications based on the output of the unsupervised clustering algorithm.

In embodiments where the medical scan image analysis system is used in conjunction with the medical scan diagnosing system, each of the medical scan image analysis functions associated with each neural network model can correspond to one of the plurality of neural network models generated by the medical scan image analysis system. For example, each of the plurality of neural network models can be trained on a training set classified on scan type, scan human body location, hospital or other originating entity data, machine model data, machine calibration data, contrast agent data, geographic region data, and/or other scan classifying data as discussed in conjunction with the medical scan diagnosing system. In embodiments where the training set classifiers are learned, the medical scan diagnosing system can determine which of the medical scan image analysis functions should be applied based on the learned classifying criteria used to segregate the original training set.

A computer vision-based learning algorithm used to create each neural network model can include selecting a three-dimensional subregion 1310 for each medical scan in the training set. This three-dimensional subregion 1310 can correspond to a region that is "sampled" from the entire scan that may represent a small fraction of the entire scan. Recall that a medical scan can include a plurality of ordered cross-sectional image slices. Selecting a three-dimensional subregion 1310 can be accomplished by selecting a proper image slice subset 1320 of the plurality of cross-sectional image slices from each of the plurality of medical scans, and by further selecting a two-dimensional subregion 1330 from each of the selected subset of cross-sectional image slices of the each of the medical scans. In some embodiments, the selected image slices can include one or more non-consecutive image slices and thus a plurality of disconnected three-dimensional subregions will be created. In other embodiments, the selected proper subset of the plurality of image slices correspond to a set of consecutive image slices, as to ensure that a single, connected three-dimensional subregion is selected. In some embodiments, entire scans of the training set are used to train the neural network model. In such embodiment, as used herein, the three-dimensional subregion 1310 can refer to all of the medical scan image data 410 of a medical scan.

In some embodiments, a density windowing step can be applied to the full scan or the selected three-dimensional subregion. The density windowing step can include utilizing a selected upper density value cut off and/or a selected lower density value cut off, and masking pixels with higher values than the upper density value cut off and/or masking pixels with lower values than the lower density value cut off. The upper density value cut off and/or a selected lower density value cut off can be determined based on based on the range and/or distribution of density values included in the region that includes the abnormality, and/or based on the range and/or distribution of density values associated with the abnormality itself, based on user input to a subsystem, based on display parameter data associated with the medical scan or associated with medical scans of the same type, and/or can be learned in the training step. In some embodiments, a non-linear density windowing function can be applied to alter the pixel density values, for example, to stretch or compress contrast. In some embodiments, this density windowing step can be performed as a data augmenting step, to create additional training data for a medical scan in accordance with different density windows.

Having determined the subregion training set 1315 of three-dimensional subregions 1310 corresponding to the set of full medical scans in the training set, the medical scan image analysis system can complete a training step 1352 by performing a learning algorithm on the plurality of three-dimensional subregions to generate model parameter data 1355 of a corresponding learning model. The learning model can include one or more of a neural network, an artificial neural network, a convolutional neural network, a Bayesian model, a support vector machine model, a cluster analysis model, or other supervised or unsupervised learning model. The model parameter data 1355 can generated by performing the learning algorithm 1350, and the model parameter data 1355 can be utilized to determine the corresponding medical scan image analysis functions. For example, some or all of the model parameter data 1355 can be mapped to the medical scan analysis function in the model parameter data 623 or can otherwise define the medical scan analysis function.

The training step 1352 can include creating feature vectors for each three-dimensional subregion of the training set for use by the learning algorithm 1350 to generate the model parameter data 1355. The feature vectors can include the pixel data of the three-dimensional subregions such as density values and/or grayscale values of each pixel based on a determined density window. The feature vectors can also include other features as additional input features or desired output features, such as known abnormality data such as location and/or classification data, patient history data such as risk factor data or previous medical scans, diagnosis data, responsible medical entity data, scan machinery model or calibration data, contrast agent data, medical code data, annotation data that can include raw or processed natural language text data, scan type and/or anatomical region data, or other data associated with the image, such as some or all data of a medical scan entry 352. Features can be selected based on administrator instructions received via the network and/or can be determined based on determining a feature set that reduces error in classifying error, for example, by performing a cross-validation step on multiple models created using different feature sets. The feature vector can be split into an input feature vector and output feature vector. The input feature vector can include data that will be available in subsequent medical scan input, which can include for example, the three-dimensional sub-region pixel data and/or patient history data. The output feature vector can include data that will be inferred in in subsequent medical scan input and can include single output value, such as a binary value indicating whether or not the medical scan includes an abnormality or a value corresponding to one of a plurality of medical codes corresponding to the image. The output feature vector can also include multiple values which can include abnormality location and/or classification data, diagnosis data, or other output. The output feature vector can also include a determined upper density value cut off and/or lower density value cut off, for example, characterizing which pixel values were relevant to detecting and/or classifying an abnormality. Features included in the output feature vector can be selected to include features that are known in the training set, but may not be known in subsequent medical scans such as triaged scans to be diagnosed by the medical scan diagnosing system, and/or scans to be labeled by the medical scan report labeling system. The set of features in the input feature vector and output feature vector, as well as the importance of different features where each feature is assigned a corresponding weight, can also be designated in the model parameter data 1355.

Consider a medical scan image analysis function that utilizes a neural network. The neural network can include a plurality of layers, where each layer includes a plurality of neural nodes. Each node in one layer can have a connection to some or all nodes in the next layer, where each connection is defined by a weight value. Thus, the model parameter data 1355 can include a weight vector that includes weight values for every connection in the network. Alternatively or in addition, the model parameter data 1355 can include any vector or set of parameters associated with the neural network model, which can include an upper density value cut off and/or lower density value cut off used to mask some of the pixel data of an incoming image, kernel values, filter parameters, bias parameters, and/or parameters characterizing one or more of a plurality of convolution functions of the neural network model. The medical scan image analysis function can be utilized to produce the output vector as a function of the input feature vector and the model parameter data 1355 that characterizes the neural network model. In particular, the medical scan image analysis function can include performing a forward propagation step plurality of neural network layers to produce an inferred output vector based on the weight vector or other model parameter data 1355. Thus, the learning algorithm 1350 utilized in conjunction with a neural network model can include determining the model parameter data 1355 corresponding to the neural network model, for example, by populating the weight vector with optimal weights that best reduce output error.

In particular, determining the model parameter data 1355 can include utilizing a backpropagation strategy. The forward propagation algorithm can be performed on at least one input feature vector corresponding to at least one medical scan in the training set to propagate the at least one input feature vector through the plurality of neural network layers based on initial and/or default model parameter data 1355, such as an initial weight vector of initial weight values set by an administrator or chosen at random. The at least one output vector generated by performing the forward propagation algorithm on the at least one input feature vector can be compared to the corresponding at least one known output feature vector to determine an output error. Determining the output error can include, for example, computing a vector distance such as the Euclidian distance, or squared Euclidian distance, between the produced output vector and the known output vector, and/or determining an average output error such as an average Euclidian distance or squared Euclidian distance if multiple input feature vectors were employed. Next, gradient descent can be performed to determine an updated weight vector based on the output error or average output error. This gradient descent step can include computing partial derivatives for the error with respect to each weight, or other parameter in the model parameter data 1355, at each layer starting with the output layer. Chain rule can be utilized to iteratively compute the gradient with respect to each weight or parameter at each previous layer until all weight's gradients are computed. Next updated weights, or other parameters in the model parameter data 1355, are generated by updating each weight based on its corresponding calculated gradient. This process can be repeated on at least one input feature vector, which can include the same or different at least one feature vector used in the previous iteration, based on the updated weight vector and/or other updated parameters in the model parameter data 1355 to create a new updated weight vector and/or other new updated parameters in the model parameter data 1355. This process can continue to repeat until the output error converges, the output error is within a certain error threshold, or another criterion is reached to determine the most recently updated weight vector and/or other model parameter data 1355 is optimal or otherwise determined for selection.

The model parameter data 1355 can be determined by utilizing any other artificial intelligence algorithm and/or technique, and/or by utilizing any other machine learning algorithm and/or technique. In some or all embodiments, determining the model parameter data 1355 cannot be practically be performed by the human mind.

Figure 7B:
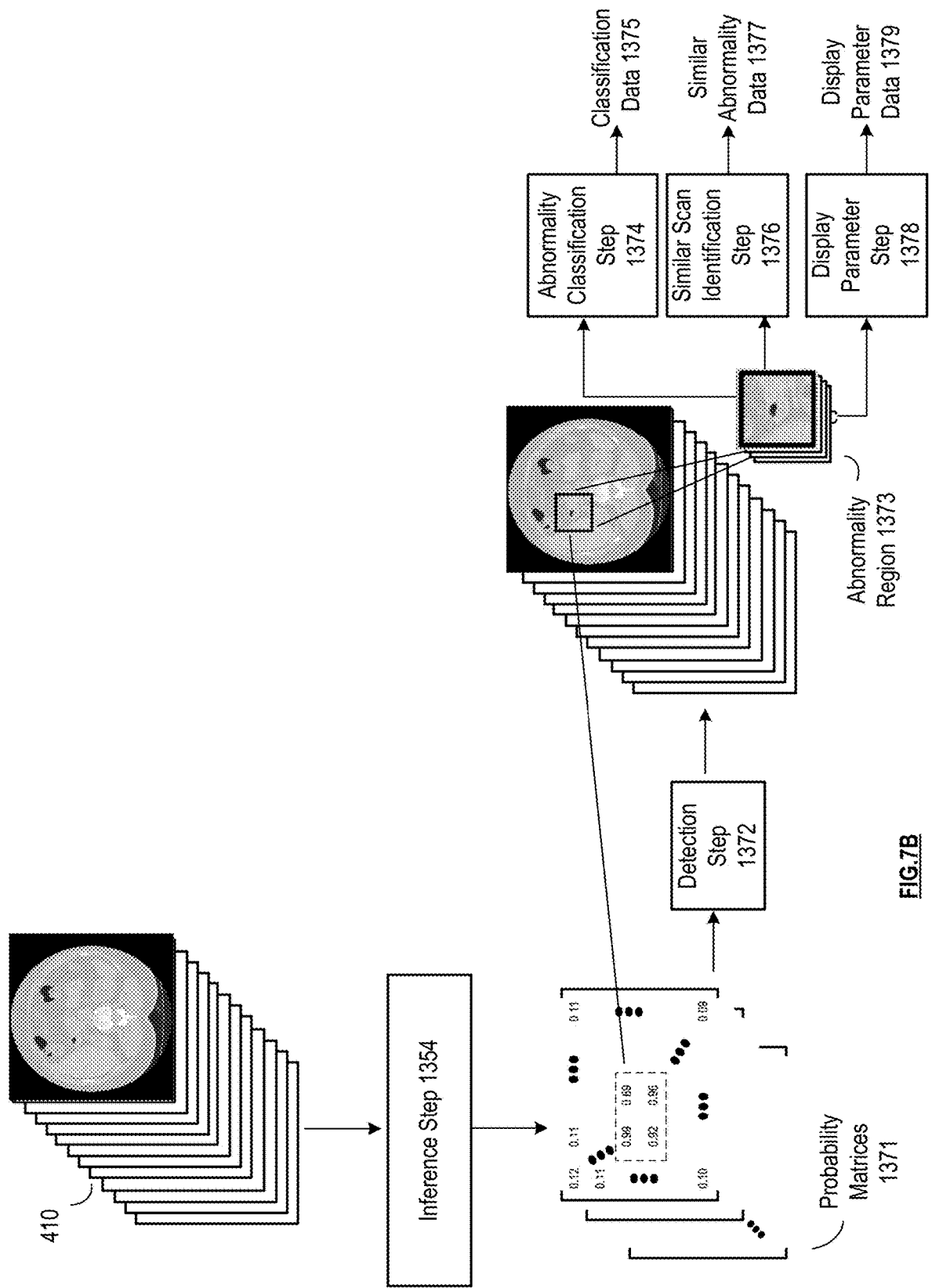
FIG. 7B is a flowchart representation of a detection step in accordance with various embodiments.

Having determined the medical scan neural network and its final other model parameter data 1355, an inference step 1354 can be performed on new medical scans to produce inference data 1370, such as inferred output vectors, as shown in FIG. 7B. The inference step can include performing the forward propagation algorithm to propagate an input feature vector through a plurality of neural network layers based on the final model parameter data 1355, such as the weight values of the final weight vector, to produce the inference data. This inference step 1354 can correspond to performing the medical scan image analysis function, as defined by the final model parameter data 1355, on new medical scans to generate the inference data 1370, for example, in conjunction with the medical scan diagnosing system 108 to generate inferred diagnosis data or other selected output data for triaged medical scans based on its corresponding the input feature vector.

The inference step 1354 can be performed utilizing any other artificial intelligence algorithm and/or technique, and/or any other machine learning algorithm and/or technique. In some or all embodiments, inference step 1354 and/or otherwise generating the inference data 1370 cannot be practically be performed by the human mind.

The inference step 1354 can include applying the density windowing step to new medical scans. Density window cut off values and/or a non-linear density windowing function that are learned can be automatically applied when performing the inference step. For example, if the training step 1352 was used to determine optimal upper density value cut off and/or lower density value cut off values to designate an optimal density window, the inference step 1354 can include masking pixels of incoming scans that fall outside of this determined density window before applying the forward propagation algorithm. As another example, if learned parameters of one or more convolutional functions correspond to the optimal upper density value cut off and/or lower density value cut off values, the density windowing step is inherently applied when the forward propagation algorithm is performed on the new medical scans.

In some embodiments where a medical scan analysis function is defined by model parameter data 1355 corresponding to a neutral network model, the neural network model can be a fully convolutional neural network. In such embodiments, only convolution functions are performed to propagate the input feature vector through the layers of the neural network in the forward propagation algorithm. This enables the medical scan image analysis functions to process input feature vectors of any size. For example, as discussed herein, the pixel data corresponding to the three-dimensional subregions is utilized input to the forward propagation algorithm when the training step 1352 is employed to populate the weight vector and/or other model parameter data 1355. However, when performing the forward propagation algorithm in the inference step 1354, the pixel data of full medical scans can be utilized as input, allowing the entire scan to be processed to detect and/or classify abnormalities, or otherwise generate the inference data 1370. This may be a preferred embodiment over other embodiments where new scans must also be sampled by selecting a three-dimensional subregions and/or other embodiments where the inference step requires "piecing together" inference data 1370 corresponding to multiple three-dimensional subregions processed separately.

The inferred output vector of the inference data 1370 can include a plurality of abnormality probabilities mapped to a pixel location of each of a plurality of cross-sectional image slices of the new medical scan. For example, the inferred output vector can indicate a set of probability matrices 1371, where each matrix in the set corresponds to one of the plurality of image slices of the medical scan, where each matrix is a size corresponding to the number of pixels in each image slice, where each cell of each matrix corresponds to a pixel of the corresponding image slice, whose value is the abnormality probability of the corresponding pixel.

A detection step 1372 can include determining if an abnormality is present in the medical scan based on the plurality of abnormality probabilities. Determining if an abnormality is present can include, for example, determining that a cluster of pixels in the same region of the medical scan correspond to high abnormality probabilities, for example, where a threshold proportion of abnormality probabilities must meet or exceed a threshold abnormality probability, where an average abnormality probability of pixels in the region must meet or exceed a threshold abnormality probability, where the region that includes the cluster of pixels must be at least a certain size, etc. Determining if an abnormality is present can also include calculating a confidence score based on the abnormality probabilities and/or other data corresponding to the medical scan such as patient history data. The location of the detected abnormality can be determined in the detection step 1372 based on the location of the pixels with the high abnormality probabilities. The detection step can further include determining an abnormality region 1373, such as a two-dimensional subregion on one or more image slices that includes some or all of the abnormality. The abnormality region 1373 determined in the detection step 1372 can be mapped to the medical scan to populate some or all of the abnormality location data 443 for use by one or more other subsystems 101 and/or client devices 120. Furthermore, determining whether or not an abnormality exists in the detection step 1372 can be used to populate some or all of the diagnosis data 440 of the medical scan, for example, to indicate that the scan is normal or contains an abnormality in the diagnosis data 440.

An abnormality classification step 1374 can be performed on a medical scan in response to determining an abnormality is present. Classification data 1375 corresponding to one or more classification categories such as abnormality size, volume, pre-post contract, doubling time, calcification, components, smoothness, texture, diagnosis data, one or more medical codes, a malignancy rating such as a Lung-RADS score, or other classifying data as described herein can be determined based on the detected abnormality. The classification data 1375 generated by the abnormality classification step 1374 can be mapped to the medical scan to populate some or all of the abnormality classification data 445 of the corresponding abnormality classifier categories 444 and/or abnormality pattern categories 446 and/or to determine one or more medical codes 447 of the medical scan. The abnormality classification step 1374 can include performing an abnormality classification function on the full medical scan, or the abnormality region 1373 determined in the detection step 1372. The abnormality classification function can be based on another model trained on abnormality data such as a support vector machine model, another neural network model, or any supervised classification model trained on medical scans, or portions of medical scans, that include known abnormality classifying data to generate inference data for some or all of the classification categories. For example, the abnormality classification function can include another medical scan analysis function. Classification data 1375 in each of a plurality of classification categories can also be assigned their own calculated confidence score, which can also be generated by utilizing the abnormality classification function. Output to the abnormality classification function can also include at least one identified similar medical scan and/or at least one identified similar cropped image, for example, based on the training data. The abnormality classification step can also be included in the inference step 1354, where the inferred output vector or other inference data 1370 of the medical scan image analysis function includes the classification data 1375.

The abnormality classification function can be trained on full medical scans and/or one or more cropped or full selected image slices from medical scans that contain an abnormality. For example, the abnormality classification function can be trained on a set of two-dimensional cropped slices that include abnormalities. The selected image slices and/or the cropped region in each selected image slice for each scan in the training set can be automatically selected based upon the known location of the abnormality. Input to the abnormality classification function can include the full medical scan, one or more selected full image slices, and/or one or more selected image slices cropped based on a selected region. Thus, the abnormality classification step can include automatically selecting one or more image slices that include the detected abnormality. The slice selection can include selecting the center slice in a set of consecutive slices that are determined to include the abnormality or selecting a slice that has the largest cross-section of the abnormality, or selecting one or more slices based on other criteria. The abnormality classification step can also include automatically generating one or more cropped two-dimensional images corresponding to the one or more of the selected image slices based on an automatically selected region that includes the abnormality.

Input to the abnormality classification function can also include other data associated with the medical scan, including patient history, risk factors, or other metadata. The abnormality classification step can also include determining some or all of the characteristics based on data of the medical scan itself. For example, the abnormality size and volume can be determined based on a number of pixels determined to be part of the detected abnormality. Other classifiers such as abnormality texture and/or smoothness can be determined by performing one or more other preprocessing functions on the image specifically designed to characterize such features. Such preprocessed characteristics can be included in the input to the abnormality classification function to the more difficult task of assigning a medical code or generating other diagnosis data. The training data can also be preprocessed to include such preprocessed features.

A similar scan identification step 1376 can also be performed on a medical scan with a detected abnormality and/or can be performed on the abnormality region 1373 determined in the detection step 1372. The similar scan identification step 1376 can include generating similar abnormality data 1377, for example, by identifying one or more similar medical scans or one or more similar cropped two-dimensional images from a database of medical scans and/or database of cropped two-dimensional images. Similar medical scans and/or cropped images can include medical scans or cropped images that are visually similar, medical scans or cropped images that have known abnormalities in a similar location to an inferred abnormality location of the given medical scan, medical scans that have known abnormalities with similar characteristics to inferred characteristics of an abnormality in the given scan, medical scans with similar patient history and/or similar risk factors, or some combination of these factors and/or other known and/or inferred factors. The similar abnormality data 1377 can be mapped to the medical scan to populate some or all of its corresponding similar scan data 480 for use by one or more other subsystems 101 and/or client devices 120.

The similar scans identification step 1376 can include performing a scan similarity algorithm, which can include generating a feature vector for the given medical scan and for medical scans in the set of medical scans, where the feature vector can be generated based on quantitative and/or category based visual features, inferred features, abnormality location and/or characteristics such as the predetermined size and/or volume, patient history and/or risk factor features, or other known or inferred features. A medical scan similarity analysis function can be applied to the feature vector of the given medical scan and one or more feature vectors of medical scans in the set. The medical scan similarity analysis function can include computing a similarity distance such as the Euclidian distance between the feature vectors, and assigning the similarity distance to the corresponding medical scan in the set. Similar medical scans can be identified based on determining one or more medical scans in the set with a smallest computed similarity distance, based on ranking medical scans in the set based on the computed similarity distances and identifying a designated number of top ranked medical scans, and/or based on determining if a similarity distance between the given medical scan and a medical scan in the set is smaller than a similarity threshold. Similar medical scans can also be identified based on determining medical scans in a database that mapped to a medical code that matches the medical code of the medical scan, or mapped to other matching classifying data. A set of identified similar medical scans can also be filtered based on other inputted or automatically generated criteria, where for example only medical scans with reliable diagnosis data or rich patient reports, medical scans with corresponding with longitudinal data in the patient file such as multiple subsequent scans taken at later dates, medical scans with patient data that corresponds to risk factors of the given patient, or other identified criteria, where only a subset of scans that compare favorably to the criteria are selected from the set and/or only a highest ranked single scan or subset of scans are selected from the set, where the ranking is automatically computed based on the criteria. Filtering the similar scans in this fashion can include calculating, or can be based on previously calculated, one or more scores as discussed herein. For example, the ranking can be based on a longitudinal quality score, such as the longitudinal quality score 434, which can be calculated for an identified medical scan based on a number of subsequent and/or previous scans for the patient. Alternatively or in addition, the ranking can be based on a confidence score associated with diagnosis data of the scan, such as confidence score data 460, based on performance score data associated with a user or medical entity associated with the scan, based on an amount of patient history data or data in the medical scan entry 352, or other quality factors. The identified similar medical scans can be filtered based on ranking the scans based on their quality score and/or based on comparing their quality score to a quality score threshold. In some embodiments, a longitudinal threshold must be reached, and only scans that compare favorably to the longitudinal threshold will be selected. For example, only scans with at least three scans on file for the patient and final biopsy data will be included.

In some embodiments, the similarity algorithm can be utilized in addition to or instead of the trained abnormality classification function to determine some or all of the inferred classification data 1375 of the medical scan, based on the classification data such as abnormality classification data 445 or other diagnosis data 440 mapped to one or more of the identified similar scans. In other embodiments, the similarity algorithm is merely used to identify similar scans for review by medical professionals to aid in review, diagnosis, and/or generating medical reports for the medical image.

A display parameter step 1378 can be performed based on the detection and/or classification of the abnormality. The display parameter step can include generating display parameter data 1379, which can include parameters that can be used by an interactive interface to best display each abnormality. The same or different display parameters can be generated for each abnormality. The display parameter data generated in the display parameter step 1378 can be mapped to the medical scan to populate some or all of its corresponding display parameter data 470 for use by one or more other subsystems 101 and/or client devices 120.

Performing the display parameter step 1378 can include selecting one or more image slices that include the abnormality by determining the one or more image slices that include the abnormality and/or determining one or more image slices that has a most optimal two-dimensional view of the abnormality, for example by selecting the center slice in a set of consecutive slices that are determined to include the abnormality, selecting a slice that has the largest cross-section of the abnormality, selecting a slice that includes a two-dimensional image of the abnormality that is most similar to a selected most similar two-dimensional-image, selecting the slice that was used as input to the abnormality classification step and/or similar scan identification step, or based on other criteria. This can also include automatically cropping one or more selected image slices based on an identified region that includes the abnormality. This can also select an ideal Hounsfield window that best displays the abnormality. This can also include selecting other display parameters based on data generated by the medical scan interface evaluating system and based on the medical scan.

Detection step 1372, abnormality classification step 1374, similar scans identification step 1376, and/or display parameter step 1378 can be performed by utilizing at least one artificial intelligence algorithm and/or technique, and/or by utilizing at least one machine learning algorithm and/or technique. In some or all embodiments, performing detection step 1372, abnormality classification step 1374, similar scans identification step 1376, and/or display parameter step 1378 cannot be practically be performed by the human mind.

FIGS. 8A-8F illustrate embodiments of a medical picture archive integration system 2600. The medical picture archive integration system 2600 can provide integration support for a medical picture archive system 2620, such as a PACS that stores medical scans. The medical picture archive integration system 2600 can utilize model parameters received from a central server system 2640 via a network 2630 to perform an inference function on de-identified medical scans of medical scans received from the medical picture archive system 2620. The annotation data produced by performing the inference function can be transmitted back to the medical picture archive system. Furthermore, the annotation data and/or de-identified medical scans can be sent to the central server system 2640, and the central server system can train on this information to produce new and/or updated model parameters for transmission back to the medical picture archive integration system 2600 for use on subsequently received medical scans.

In various embodiments, medical picture archive integration system 2600 includes a de-identification system that includes a first memory designated for protected health information (PHI), operable to perform a de-identification function on a DICOM image, received from a medical picture archive system, to identify at least one patient identifier and generate a de-identified medical scan that does not include the at least one patient identifier. The medical picture archive integration system further includes a de-identified image storage system that stores the de-identified medical scan in a second memory that is separate from the first memory, and an annotating system, operable to utilize model parameters received from a central server to perform an inference function on the de-identified medical scan, retrieved from the second memory to generate annotation data for transmission to the medical picture archive system as an annotated DICOM file.

The first memory and the second memory can be implemented by utilizing separate storage systems: the first memory can be implemented by a first storage system designated for PHI storage, and the second memory can be implemented by a second storage system designated for storage of de-identified data. The first storage system can be protected from access by the annotating system, while the second storage system can be accessible by the annotating system. The medical picture archive integration system 2600 can be operable to perform the de-identification function on data in first storage system to generate de-identified data. The de-identified data can then be stored in the second storage system for access by the annotating system. The first and second storage systems can be physically separate, each utilizing at least one of their own, separate memory devices. Alternatively, the first and second storage systems can be virtually separate, where data is stored in separate virtual memory locations on the same set of memory devices. Firewalls, virtual machines, and/or other protected containerization can be utilized to enforce the separation of data in each storage system, to protect the first storage system from access by the annotating system and/or from other unauthorized access, and/or to ensure that only data of the first storage system that has been properly de-identified through application of the de-identification function can be stored in the second storage system.

Figure 8A:
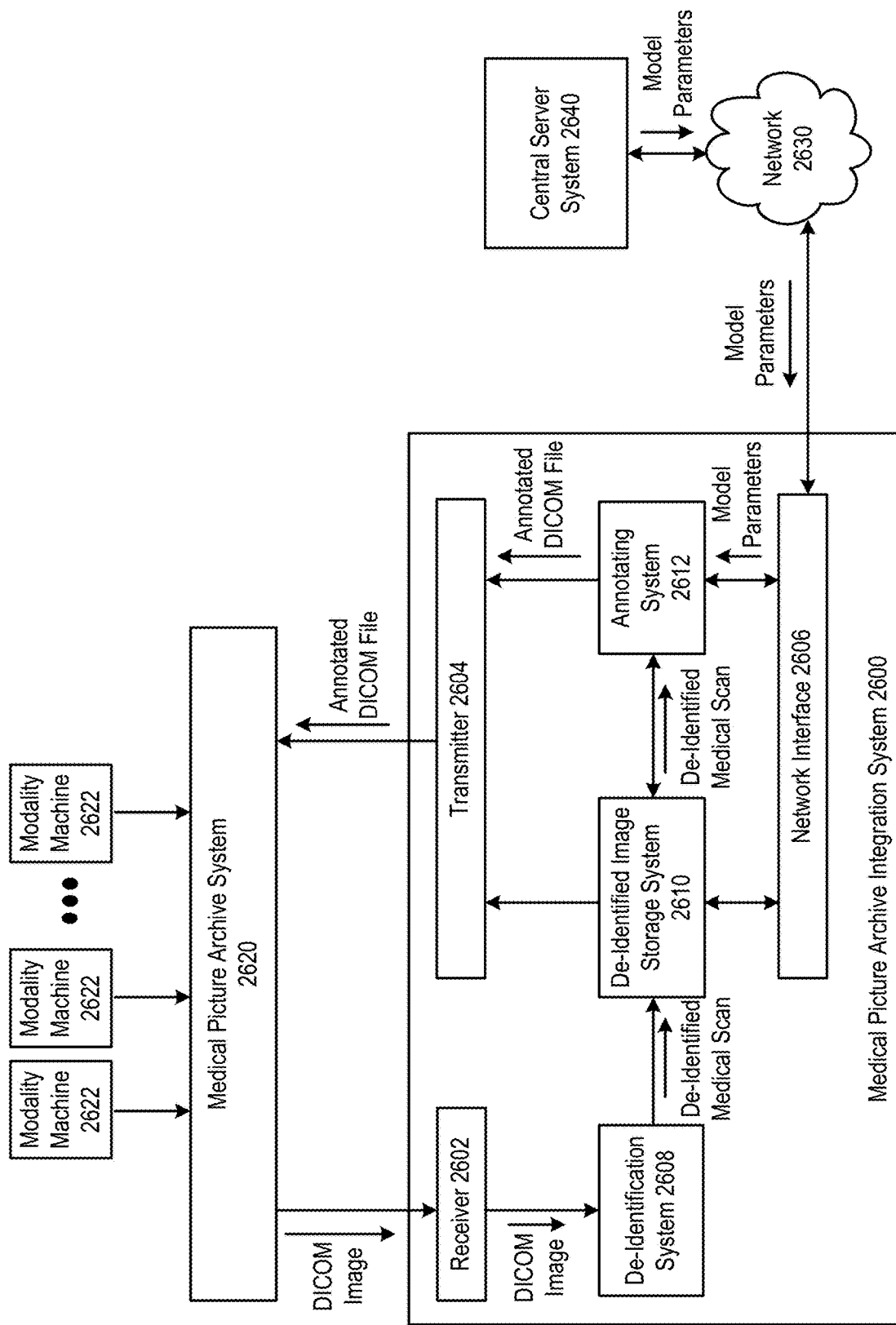
FIGS. 8A-8F are schematic block diagrams of a medical picture archive integration system in accordance with various embodiments.

As shown in FIG. 8A, the medical picture archive system 2620 can receive image data from a plurality of modality machines 2622, such as CT machines, MIll machines, x-ray machines, and/or other medical imaging machines that produce medical scans. The medical picture archive system 2620 can store this image data in a DICOM image format and/or can store the image data in a plurality of medical scan entries 352 as described in conjunction with some or all of the attributes described in conjunction with FIGS. 4A and 4B. While "DICOM image" will be used herein to refer to medical scans stored by the medical picture archive system 2620, the medical picture archive integration system 2600 can provide integration support for medical picture archive systems 2620 that store medical scans in other formats.

The medical picture archive integration system 2600 can include a receiver 2602 and a transmitter 2604, operable to transmit and receive data from the medical picture archive system 2620, respectively. For example, the receiver 2602 and transmitter 2604 can be configured to receive and transmit data, respectively, in accordance with a DICOM communication protocol and/or another communication protocol recognized by the medical picture archive system 2620. The receiver can receive DICOM images from the medical picture archive system 2620. The transmitter 2604 can send annotated DICOM files to the medical picture archive system 2620.

DICOM images received via receiver 2602 can be sent directly to a de-identification system 2608. The de-identification system 2608 can be operable to perform a de-identification function on the first DICOM image to identify at least one patient identifier in the DICOM image, and to generate a de-identified medical scan that does not include the identified at least one patient identifier. As used herein, a patient identifier can include any patient identifying data in the image data, header, and/or metadata of a medical scan, such as a patient ID number or other unique patient identifier, an accession number, a service-object pair (SOP) instance unique identifier (UID) field, scan date and/or time that can be used to determine the identity of the patient that was scanned at that date and/or time, and/or other private data corresponding to the patient, doctor, or hospital. In some embodiments, the de-identified medical scan is still in a DICOM image format. For example, a duplicate DICOM image that does not include the patient identifiers can be generated, and/or the original DICOM image can be altered such that the patient identifiers of the new DICOM image are masked, obfuscated, removed, replaced with a custom fiducial, and/or otherwise anonymized. In other embodiments, the de-identified medical scan is formatted in accordance with a different image format and/or different data format that does not include the identifying information. In some embodiments, other private information, for example, associated with a particular doctor or other medical professional, can be identified and anonymized as well.

Some patient identifying information can be included in a DICOM header of the DICOM image, for example, in designated fields for patient identifiers. These corresponding fields can be anonymized within the corresponding DICOM header field. Other patient identifying information can be included in the image itself, such as in medical scan image data 410. For example, the image data can include a patient name or other identifier that was handwritten on a hard copy of the image before the image was digitized. As another example, a hospital administered armband or other visual patient information in the vicinity of the patient may have been captured in the image itself. A computer vision model can detect the presence of these identifiers for anonymization, for example, where a new DICOM image includes a fiducial image that covers the identifying portion of the original DICOM image. In some embodiments, patient information identified in the DICOM header can be utilized to detect corresponding patient information in the image itself. For example, a patient name extracted from the DICOM header before anonymization can be used to search for the patient name in the image and/or to detect a location of the image that includes the patient name. In some embodiments, the de-identification system 2608 is implemented by the de-identification system discussed in conjunction with FIGS. 10A, 10B and 11, and/or utilizes functions and/or operations discussed in conjunction with FIGS. 10A, 10B and 11.

The de-identified medical scan can be stored in de-identified image storage system 2610 and the annotating system 2612 can access the de-identified medical scan from the de-identified image storage system 2610 for processing. The de-identified storage system can archive a plurality of de-identified DICOM images and/or can serve as temporary storage for the de-identified medical scan until processing of the de-identified medical scan by the annotating system 2612 is complete. The annotating system 2612 can generate annotation data by performing an inference function on the de-identified medical scan, utilizing the model parameters received from the central server system 2640. The annotation data can correspond to some or all of the diagnosis data 440 as discussed in conjunction with FIGS. 4A and 4B. In come embodiments, the annotating system 2612 can utilize the model parameters to perform inference step 1354, the detection step 1372, the abnormality classification step 1374, the similar scan identification step 1376, and/or the display parameter step 1378 of the medical scan image analysis system 112, as discussed in conjunction with FIG. 7B, on de-identified medical scans received from the medical picture archive system 2620.

In some embodiments, model parameters for a plurality of inference functions can be received from the central server system 2640, for example, where each inference function corresponds to one of a set of different scan categories. Each scan category can correspond to a unique combination of one or a plurality of scan modalities, one of a plurality of anatomical regions, and/or other scan classifier data 420. For example, a first inference function can be trained on and intended for de-identified medical scans corresponding chest CT scans, and a second inference function can be trained on and intended for de-identified medical scans corresponding to head MRI scans. The annotating system can select one of the set of inference functions based on determining the scan category of the DICOM image, indicated in the de-identified medical scan, and selecting the inference function that corresponds to the determined scan category.

To ensure that scans received from the medical picture archive system 2620 match the set of scan categories for which the annotating system is operable to perform a corresponding inference function, the transmitter can transmit requests, such as DICOM queries, indicating image type parameters such as parameters corresponding to scan classifier data 420, for example indicating one or more scan modalities, one or more anatomical regions, and/or other parameters. For example, the request can indicate that all incoming scans that match the set of scan categories corresponding to a set of inference functions the annotating system 2612 for which the annotating system has obtained model parameters from the central server system 2640 and is operable to perform.

Once the annotation data is generated by performing the selected inference function, the annotating system 2612 can generate an annotated DICOM file for transmission to the medical picture archive system 2620 for storage. The annotated DICOM file can include some or all of the fields of the diagnosis data 440 and/or abnormality annotation data 442 of FIGS. 4A and 4B. The annotated DICOM file can include scan overlay data, providing location data of an identified abnormality and/or display data that can be used in conjunction with the original DICOM image to indicate the abnormality visually in the DICOM image and/or to otherwise visually present the annotation data, for example, for use with the medical scan assisted review system 102. For example, a DICOM presentation state file can be generated to indicate the location of an abnormality identified in the de-identified medical scan. The DICOM presentation state file can include an identifier of the original DICOM image, for example, in metadata of the DICOM presentation state file, to link the annotation data to the original DICOM image. In other embodiments, a full, duplicate DICOM image is generated that includes the annotation data with an identifier linking this duplicate annotated DICOM image to the original DICOM image.

The identifier linking the annotated DICOM file to the original DICOM image can be extracted from the original DICOM file by the de-identification system 2608, thus enabling the medical picture archive system 2620 to link the annotated DICOM file to the original DICOM image in its storage. For example, the de-identified medical scan can include an identifier that links the de-identified medical scan to the original DICOM file, but does not link the de-identified medical scan to a patient identifier or other private data.

In some embodiments, generating the annotated DICOM file includes altering one or more fields of the original DICOM header. For example, standardized header formatting function parameters can be received from the central server system and can be utilized by the annotating system to alter the original DICOM header to match a standardized DICOM header format. The standardized header formatting function can be trained in a similar fashion to other medical scan analysis functions discussed herein and/or can be characterized by some or all fields of a medical scan analysis function entry 356. The annotating system can perform the standardized header formatting function on a de-identified medical scan to generate a new, standardized DICOM header for the medical scan to be sent back to the medical picture archive system 2620 in the annotated DICOM file and/or to replace the header of the original DICOM file. The standardized header formatting function can be run in addition to other inference functions utilized to generate annotation data. In other embodiments, the medical picture archive integration system 2600 is implemented primarily for header standardization for medical scans stored by the medical picture archive system 2620. In such embodiments, only the standardized header formatting function is performed on the de-identified data to generate a modified DICOM header for the original DICOM image, but the de-identified medical scan is not annotated.

In some embodiments of header standardization, the annotation system can store a set of acceptable, standardized entries for some or all of the DICOM header fields, and can select one of the set of acceptable, standardized entries in populating one or more fields of the new DICOM header for the annotated DICOM file. For example, each of the set of scan categories determined by the annotating system can correspond to a standardized entry of one or more fields of the DICOM header. The new DICOM header can thus be populated based on the determined scan category.

In some embodiments, each of the set of standardized entries can be mapped to a set of related, non-standardized entries, such as entries in a different order, commonly misspelled entries, or other similar entries that do not follow a standardized format. For example, one of the set of acceptable, standardized entries for a field corresponding to a scan category can include "Chest CT", which can be mapped to a set of similar, non-standardized entries which can include "CT chest", "computerized topography CT", and/or other entries that are not standardized. In such embodiments, the annotating system can determine the original DICOM header is one of the similar non-standardized entries, and can select the mapped, standardized entry as the entry for the modified DICOM header. In other embodiments, the image data itself and/or or other header data can be utilized by the annotation system to determine a standardized field. For example, an input quality assurance function 1106 can be trained by the central server system and sent to the annotating system to determine one or more appropriate scan classifier fields, or one or more other DICOM header fields, based on the image data or other data of the de-identified medical scan. One or more standardized labels can be assigned to corresponding fields of the modified DICOM header based on the one or more fields determined by the input quality assurance function.

In some embodiments, the DICOM header is modified based on the annotation data generated in performing the inference function. In particular, a DICOM priority header field can be generated and/or modified automatically based on the severity and/or time-sensitivity of the abnormalities detected in performing the inference function. For example, a DICOM priority header field can be changed from a low priority to a high priority in response to annotation data indicating a brain bleed in the de-identified medical scan of a DICOM image corresponding to a head CT scan, and a new DICOM header that includes the high priority DICOM priority header field can be sent back to the medical picture archive system 2620 to replace or otherwise be mapped to the original DICOM image of the head CT scan.

In various embodiments, the medical picture archive system 2620 is disconnected from network 2630, for example, to comply with requirements regarding Protected Health Information (PHI), such as patient identifiers and other private patient information included in the DICOM images and/or otherwise stored by the medical picture archive system 2620. The medical picture archive integration system 2600 can enable processing of DICOM images while still protecting private patient information by first de-identifying DICOM data by utilizing de-identification system 2608. The de-identification system 2608 can utilize designated processors and memory of the medical picture archive integration system, for example, designated for PHI. The de-identification system 2608 can be decoupled from the network 2630 to prevent the DICOM images that still include patient identifiers from being accessed via the network 2630. For example, as shown in FIG. 8A, the de-identification system 2608 is not connected to network interface 2606. Furthermore, only the de-identification system 2608 has access to the original DICOM files received from the medical picture archive system 2620 via receiver 2602. The de-identified image storage system 2610 and annotating system 2612, as they are connected to network 2630 via network interface 2606, only store and have access to the de-identified medical scan produced by the de-identification system 2608.

Figure 8B:
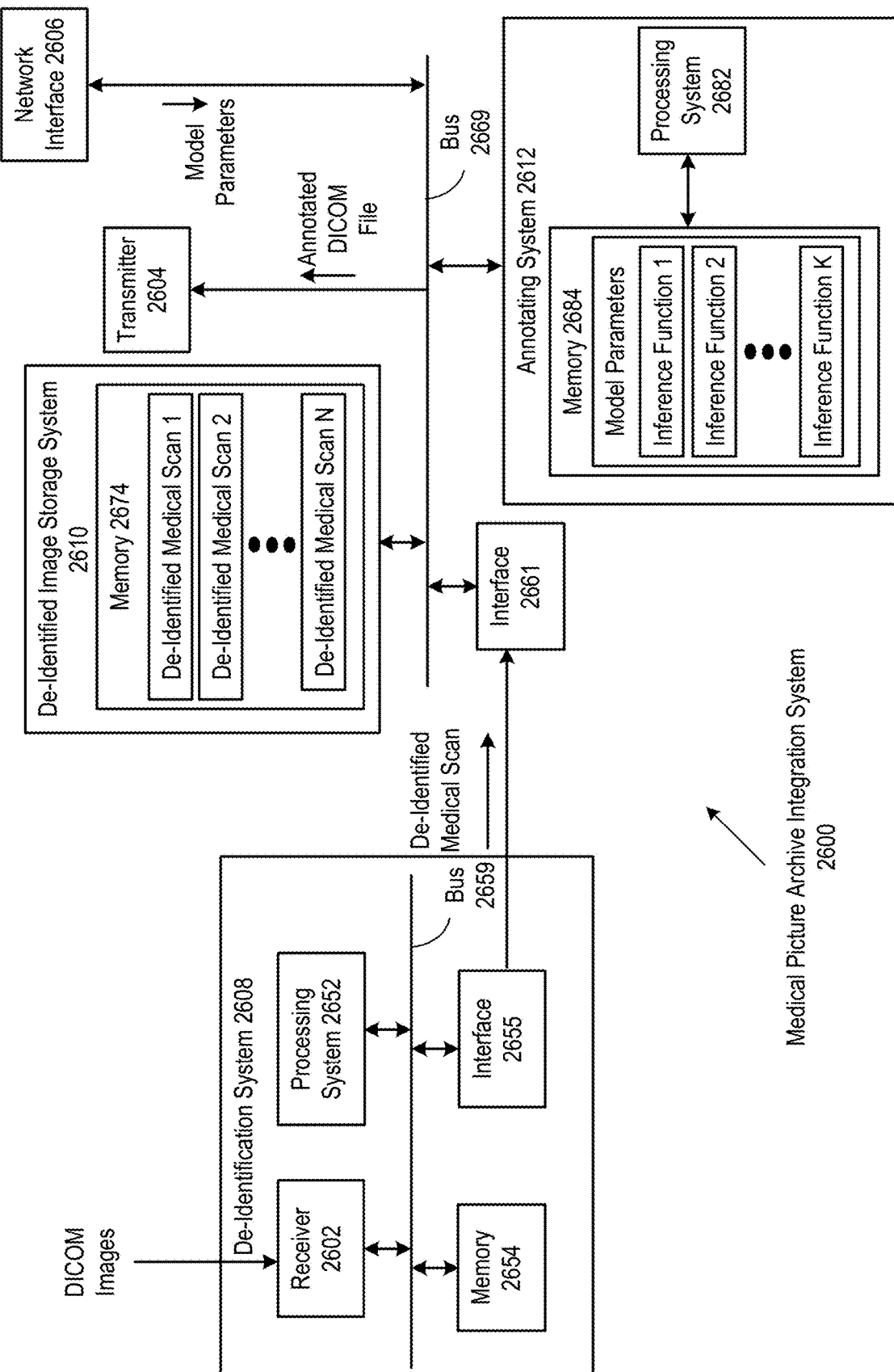

This containerization that separates the de-identification system 2608 from the de-identified image storage system 2610 and the annotating system 2612 is further illustrated in FIG. 8B, which presents an embodiment of the medical picture archive integration system 2600. The de-identification system 2608 can include its own designated memory 2654 and processing system 2652, connected to receiver 2602 via bus 2659. For example, this memory 2654 and processing system 2652 can be designated for PHI, and can adhere to requirements for handling PHI. The memory 2654 can store executable instructions that, when executed by the processing system 2652, enable the de-identification system to perform the de-identification function on DICOM images received via receiver 2602 of the de-identification system. The incoming DICOM images can be temporarily stored in memory 2654 for processing, and patient identifiers detected in performing the de-identification function can be temporarily stored in memory 2654 to undergo anonymization. Interface 2655 can transmit the de-identified medical scan to interface 2661 for use by the de-identified image storage system 2610 and the annotating system 2612. Interface 2655 can be protected from transmitting original DICOM files and can be designated for transmission of de-identified medical scan only.

Bus 2669 connects interface 2661, as well as transmitter 2604 and network interface 2606, to the de-identified image storage system 2610 and the annotating system 2612. The de-identified image storage system 2610 and annotating system 2612 can utilize separate processors and memory, or can utilize shared processors and/or memory. For example, the de-identified image storage system 2610 can serve as temporary memory of the annotating system 2612 as de-identified images are received and processed to generate annotation data.

As depicted in FIG. 8B, the de-identified image storage system 2610 can include memory 2674 that can temporarily store incoming de-identified medical scans as it undergoes processing by the annotating system 2612 and/or can archive a plurality of de-identified medical scans corresponding to a plurality of DICOM images received by the medical picture archive integration system 2600. The annotating system 2612 can include a memory 2684 that stores executable instructions that, when executed by processing system 2682, cause the annotating system 2612 perform a first inference function on de-identified medical scan to generate annotation data by utilizing the model parameters received via interface 2606, and to generate an annotated DICOM file based on the annotation data for transmission via transmitter 2604. The model parameters can be stored in memory 2684, and can include model parameters for a plurality of inference functions, for example, corresponding to a set of different scan categories.

The medical picture archive integration system can be an onsite system, installed at a first geographic site, such as a hospital or other medical entity that is affiliated with the medical picture archive system 2620. The hospital or other medical entity can further be responsible for the PHI of the de-identification system, for example, where the memory 2654 and processing system 2652 are owned by, maintained by, and/or otherwise affiliated with the hospital or other medical entity. The central server system 2640 can be located at a second, separate geographic site that is not affiliated with the hospital or other medical entity and/or at a separate geographic site that is not affiliated with the medical picture archive system 2620. The central server system 2640 can be a server configured to be outside the network firewall and/or out outside the physical security of the hospital or other medical entity or otherwise not covered by the particular administrative, physical and technical safeguards of the hospital or other medical entity.

Figure 8C:
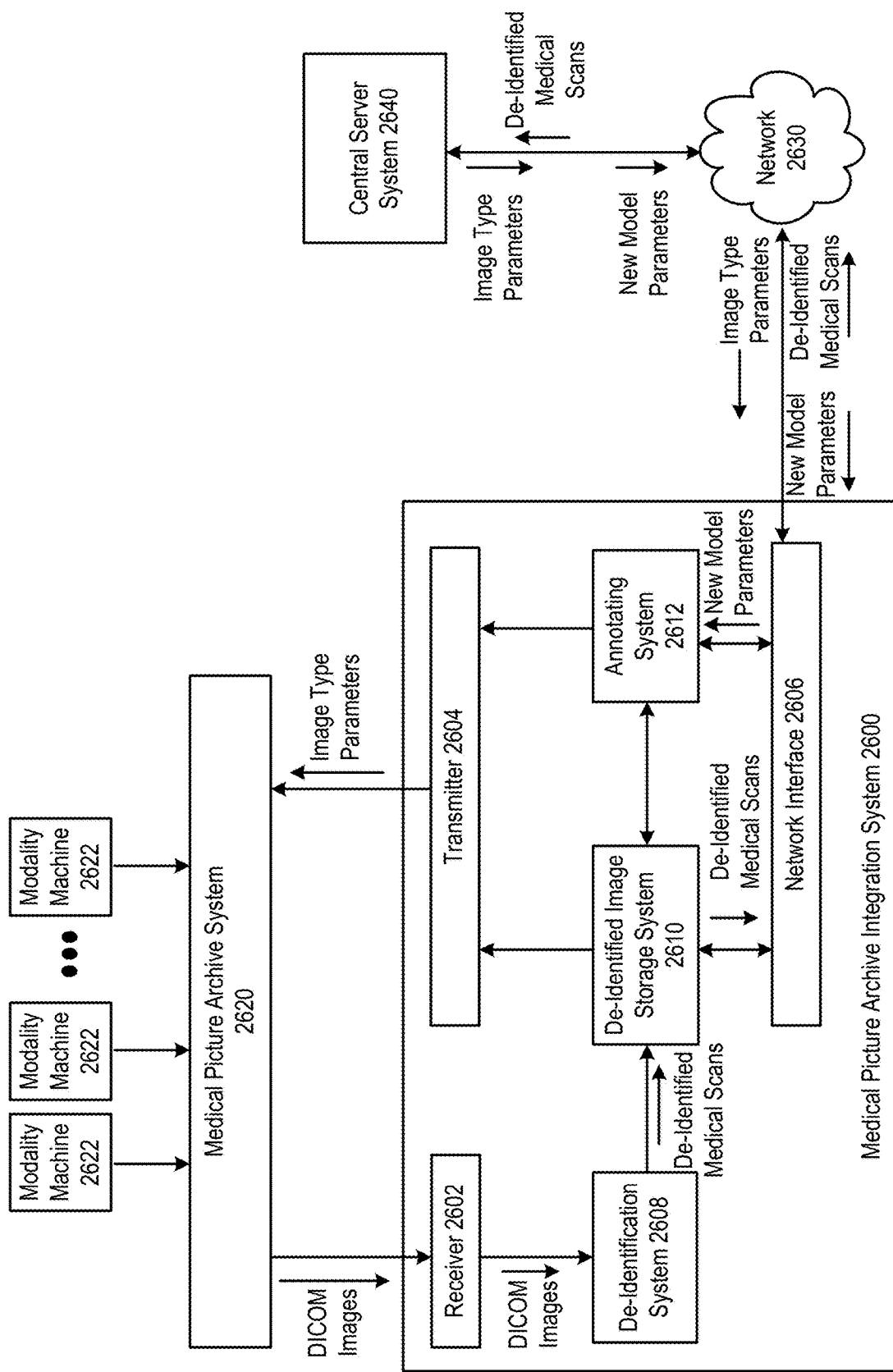

FIG. 8C further illustrates how model parameters can be updated over time to improve existing inference functions and/or to add new inference functions, for example corresponding to new scan categories. In particular, the some or all of the de-identified medical scans generated by the de-identification system 2608 can be transmitted back to the central server system, and the central server system 2640 can train on this data to improve existing models by producing updated model parameters of an existing inference function and/or to generate new models, for example, corresponding to new scan categories, by producing new model parameters for new inference functions. For example, the central server system 2640 can produce updated and/or new model parameters by performing the training step 1352 of the medical scan image analysis system 112, as discussed in conjunction with FIG. 7A, on a plurality of de-identified medical scans received from the medical picture archive integration system 2600.

The image type parameters can be determined by the central server system to dictate characteristics of the set of de-identified medical scans to be received to train and/or retrain the model. For example, the image type parameters can correspond to one or more scan categories, can indicate scan classifier data 420, can indicate one or more scan modalities, one or more anatomical regions, a date range, and/or other parameters. The image type parameters can be determined by the central server system based on training parameters 620 determined for the corresponding inference function to be trained, and/or based on characteristics of a new and/or existing scan category corresponding to the inference function to be trained. The image type parameters can be sent to the medical picture archive integration system 2600, and a request such as a DICOM query can be sent to the medical picture archive system 2620, via transmitter 2604, that indicates the image type parameters. For example, the processing system 2682 can be utilized to generate the DICOM query based on the image type parameters received from the central server system 2640. The medical picture archive system can automatically transmit one or more DICOM images to the medical picture archive integration system in response to determining that the one or more DICOM images compares favorably to the image type parameters. The DICOM images received in response can be de-identified by the de-identification system 2608. In some embodiments, the de-identified medical scans can be transmitted directly to the central server system 2640, for example, without generating annotation data.

The central server system can generate the new and/or updated model parameters by training on the received set of de-identified medical scans, and can transmit the new and/or updated model parameters to the de-identified storage system. If the model parameters correspond to a new inference function for a new scan category, the medical picture archive integration system 2600 can generate a request, such as a DICOM query, for transmission to the medical picture archive system indicating that incoming scans corresponding to image type parameters corresponding to the new scan category be sent to the medical picture archive integration system. The annotating system can update the set of inference functions to include the new inference function, and the annotating system can select the new inference function from the set of inference functions for subsequently generated de-identified medical scans by the de-identification system by determining each of these de-identified medical scans indicate the corresponding DICOM image corresponds to the new scan category. The new model parameters can be utilized to perform the new inference function on each of these de-identified medical scans to generate corresponding annotation data, and an annotated DICOM file corresponding to each of these de-identified medical scans can be generated for transmission to the medical picture archive system via the transmitter.

In some embodiments, the central server system 2640 receives a plurality of de-identified medical scans from a plurality of medical picture archive integration system 2600, for example, each installed at a plurality of different hospitals or other medical entities, via the network 2630. The central server system can generate training sets by integrating de-identified medical scans from some or all of the plurality of medical picture archive integration systems 2600 to train one or more inference functions and generate model parameters. The plurality of medical picture archive integration systems 2600 can utilize the same set of inference functions or different sets of inference functions. In some embodiments, the set of inference functions utilized by the each of the plurality of medical picture archive systems 2620 are trained on different sets of training data. For example, the different sets of training data can correspond to the set of de-identified medical scans received from the corresponding medical picture archive integration system 2600.

In some embodiments, the medical scan diagnosing system 108 can be utilized to implement the annotating system 2612, where the corresponding subsystem processing device 235 and subsystem memory device 245 of the medical scan diagnosing system 108 are utilized to implement the processing system 2682 and the memory 2684, respectively. Rather than receiving the medical scans via the network 150 as discussed in conjunction with FIG. 6A, the medical scan diagnosing system 108 can perform a selected medical scan inference function 1105 on an incoming de-identified medical scan generated by the de-identification system 2608 and/or retrieved from the de-identified image storage system 2610. Memory 2684 can store the set of medical scan inference functions 1105, each corresponding to a scan category 1120, where the inference function is selected from the set based on determining the scan category of the de-identified medical scan and selecting the corresponding inference function. The processing system 2682 can perform the selected inference function 1105 to generate the inference data 1110, which can be further utilized by the annotating system 2612 to generate the annotated DICOM file for transmission back to the medical picture archive system

2620. New medical scan inference functions 1105 can be added to the set when corresponding model parameters are received from the central server system. The remediation step 1140 can be performed locally by the annotating system 2612 and/or can be performed by the central server system 2640 by utilizing one or more de-identified medical scans and corresponding annotation data sent to the central server system 2640. Updated model parameters can be generated by the central server system 2640 and sent to the medical picture archive integration system 2600 as a result of performing the remediation step 1140.

The central server system 2640 can be implemented by utilizing one or more of the medical scan subsystems 101, such as the medical scan image analysis system 112 and/or the medical scan diagnosing system 108, to produce model parameters for one or more inference functions. The central server system can store or otherwise communicate with a medical scan database 342 that includes the de-identified medical scans and/or annotation data received from one or more medical picture archive integration systems 2600. Some or all entries of the medical scan database 342 can be utilized to as training data to produce model parameters for one or more inference functions. These entries of the medical scan database 342 can be utilized by other subsystems 101 as discussed herein. For example, other subsystems 101 can utilize the central server system 2640 to fetch medical scans and/or corresponding annotation data that meet specified criteria. The central server system 2640 can query the medical picture archive integration system 2600 based on this criteria, and can receive de-identified medical scans and/or annotation data in response. This can be sent to the requesting subsystem 101 directly and/or can be added to the medical scan database 342 or another database of the database storage system 140 for access by the requesting subsystem 101.

Alternatively or in addition, the central server system 2640 can store or otherwise communicate with a user database 344 storing user profile entries corresponding to each of a plurality of medical entities that each utilize a corresponding one of a plurality of medical picture archive integration systems 2600. For example, basic user data corresponding to the medical entity can be stored as basic user data, a number of scans or other consumption information indicating usage of one or more inference functions by corresponding medical picture archive integration system can be stored as consumption usage data, and/or a number of scans or other contribution information indicating de-identified scans sent to the central server system as training data can be stored as contribution usage data. The user profile entry can also include inference function data, for example, with a list of model parameters or function identifiers, such as medical scan analysis function identifiers 357, of inference functions currently utilized by the corresponding medical picture archive integration system 2600. These entries of the user database 344 can be utilized by other subsystems 101 as discussed herein.

Alternatively or in addition, the central server system 2640 can store or otherwise communicate with a medical scan analysis function database 346 to store model parameters, training data, or other information for one or more inference functions as medical scan analysis function entries 356. In some embodiments, model parameter data 623 can indicate the model parameters and function classifier data 610 can indicate the scan category of inference function entries. In some embodiments, the medical scan analysis function entry 356 can further include usage identifying information indicating a medical picture archive integration system identifier, medical entity identifier, and/or otherwise indicating which medical archive integration systems and/or medical entities have received the corresponding model parameters to utilize the inference function corresponding to the medical scan analysis function entry 356. These entries of the medical scan analysis function database 346 can be utilized by other subsystems 101 as discussed herein.

In some embodiments, the de-identification function is a medical scan analysis function, for example, with a corresponding medical scan analysis function entry 356 in the medical scan analysis function database 346. In some embodiments, the de-identification function is trained by the central server system 2640. For example, the central server system 2640 can send de-identification function parameters to the medical picture archive integration system 2600 for use by the de-identification system 2608. In embodiments with a plurality of medical picture archive integration systems 2600, each of the plurality of medical picture archive integration systems 2600 can utilize the same or different de-identification functions. In some embodiments, the de-identification function utilized by the each of the plurality of medical picture archive integration systems 2600 are trained on different sets of training data. For example, the different sets of training data can correspond to each different set of de-identified medical scans received from each corresponding medical picture archive integration system 2600.

Figure 8D:
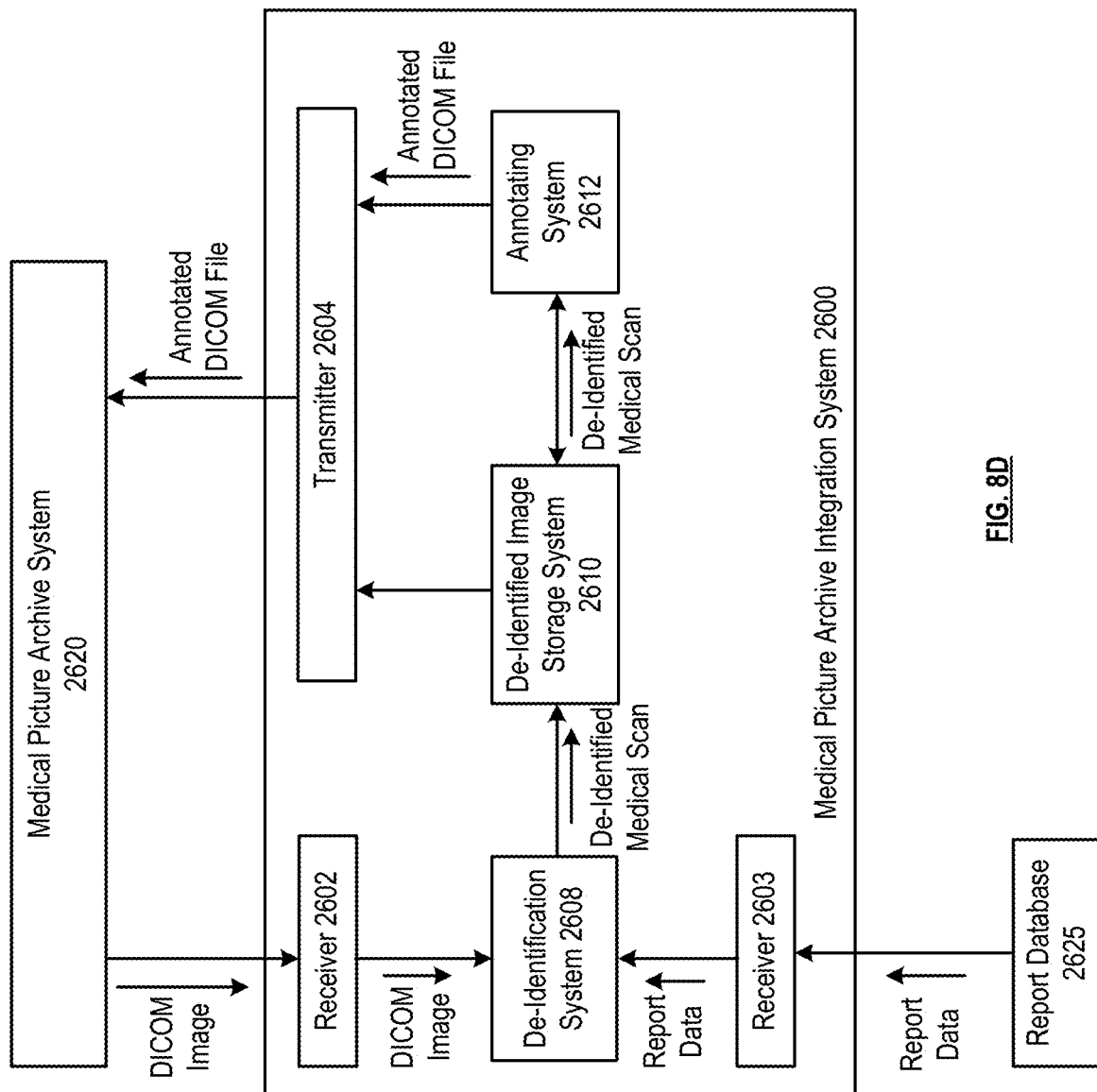
Figure 8E:
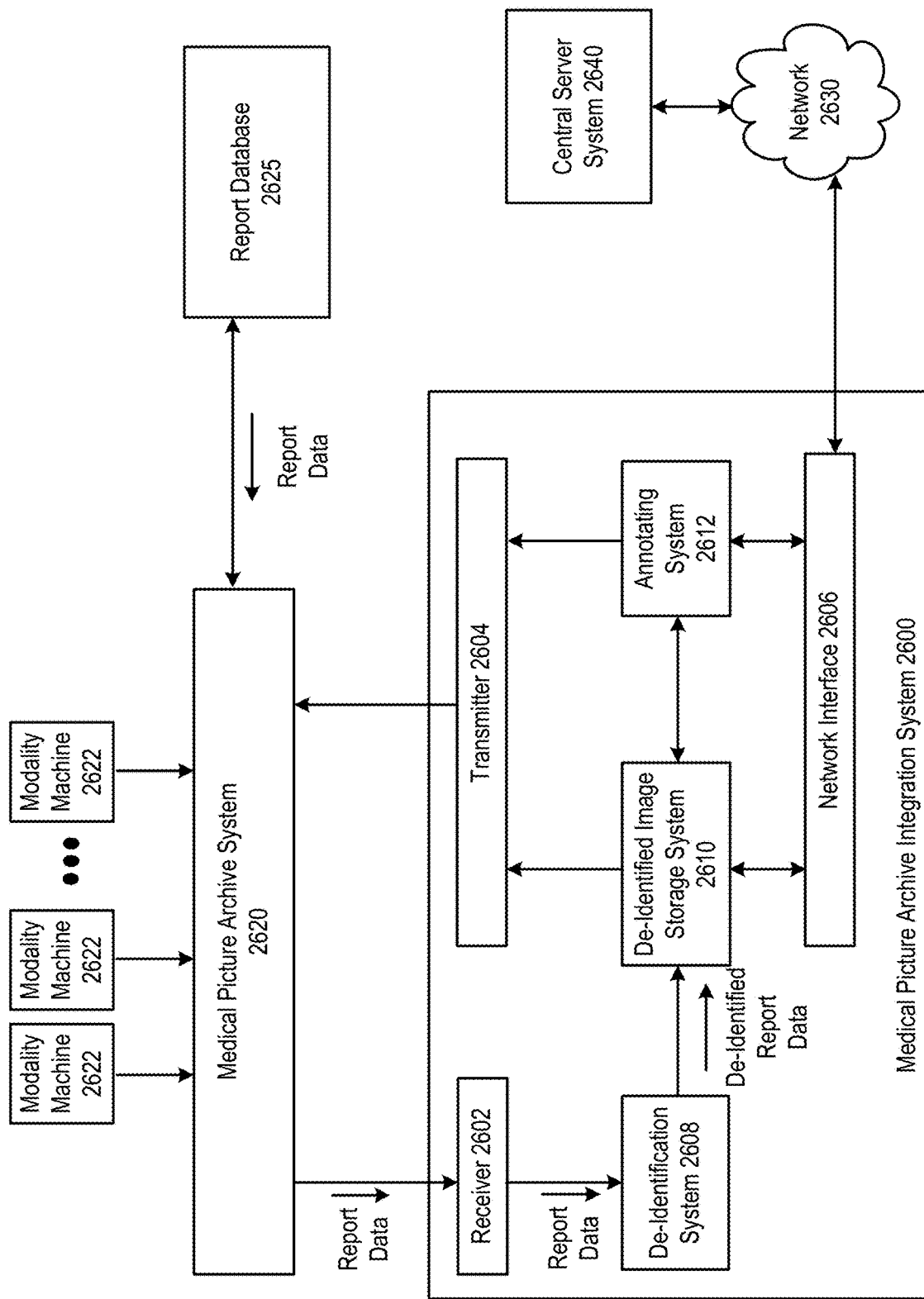
Figure 8F:
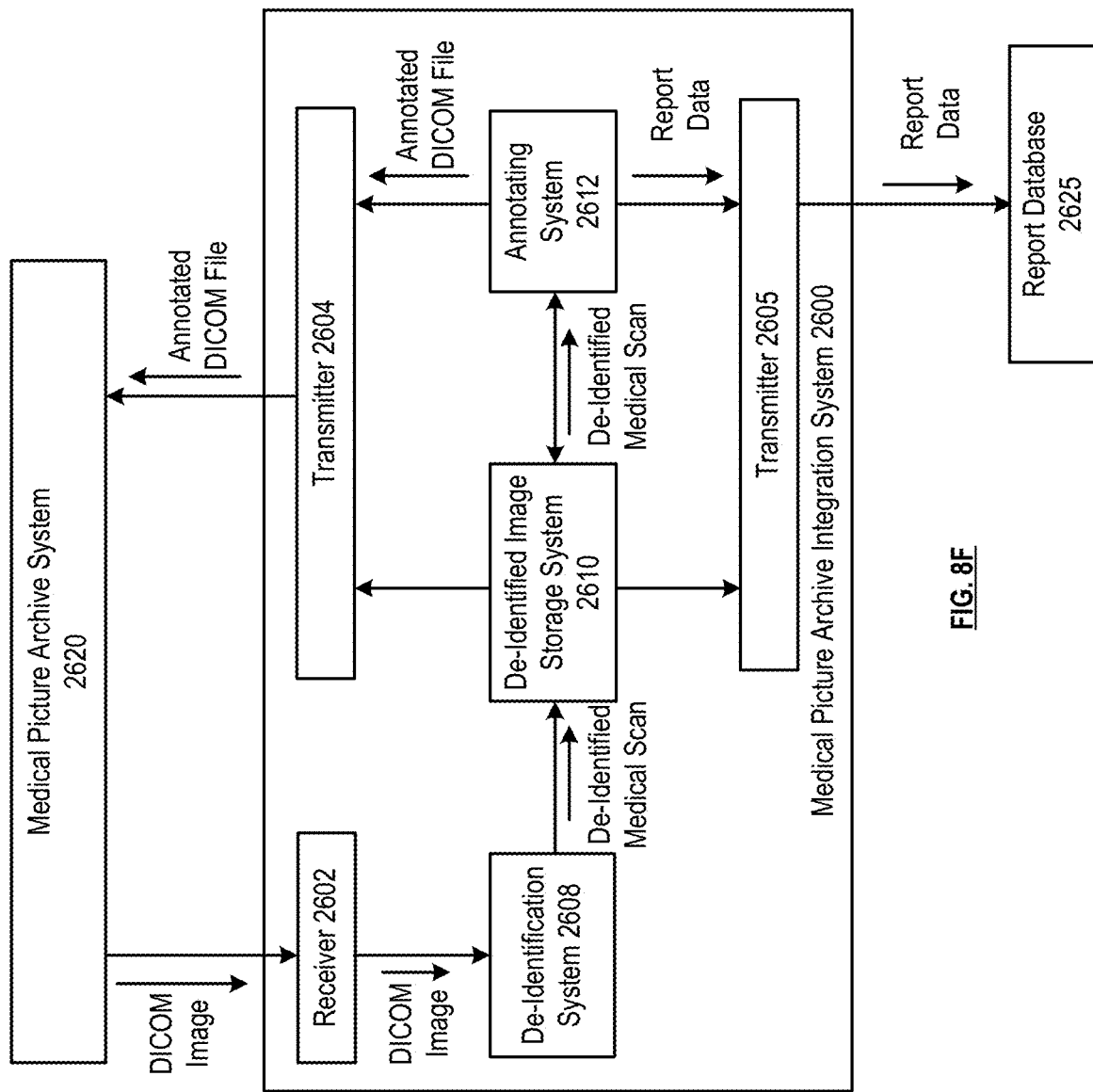

In some embodiments, as illustrated in FIGS. 8D-8F, the medical picture archive integration system 2600 can further communicate with a report database 2625, such as a Radiology Information System (RIS), that includes a plurality of medical reports corresponding to the DICOM images stored by the medical picture archive system 2620.

As shown in FIG. 8D, the medical picture archive integration system 2600 can further include a receiver 2603 that receives report data, corresponding to the DICOM image, from report database 2625. The report database 2625 can be affiliated with the medical picture archive system 2620 and can store report data corresponding to DICOM images stored in the medical picture archive system. The report data of report database 2625 can include PHI, and the report database 2625 can thus be disconnected from network 2630.

The report data can include natural language text, for example, generated by a radiologist that reviewed the corresponding DICOM image. The report data can be used to generate the de-identified medical scan, for example, where the de-identification system 2608 performs a natural language analysis function on the report data to identify patient identifying text in the report data. The de-identification system 2608 can utilize this patient identifying text to detect matching patient identifiers in the DICOM image to identify the patient identifiers of the DICOM image and generate the de-identified medical scan. In some embodiments, the report data can be de-identified by obfuscating, hashing, removing, replacing with a fiducial, or otherwise anonymizing the identified patient identifying text to generate de-identified report data.

The de-identified report data can be utilized by the annotating system 2612, for example, in conjunction with the DICOM image, to generate the annotation data. For example, the annotating system 2612 can perform a natural language analysis function on the de-identified natural language text of the report data to generate some or all of the annotation data. In some embodiments, the de-identified report data is sent to the central server system, for example, to be used as training data for inference functions, for natural language analysis functions, for other medical scan analysis functions, and/or for use by at least one other subsystem 101.

For example, other subsystems 101 can utilize the central server system 2640 to fetch medical reports that correspond to particular medical scans or otherwise meet specified criteria. The central server system 2640 can query the medical picture archive integration system 2600 based on this criteria, and can receive de-identified medical reports in response. This can be sent to the requesting subsystem 101 directly, can be added to the medical scan database 342, a de-identified report database, or another database of the database storage system 140 for access by the requesting subsystem 101.

In some embodiments the medical picture archive integration system 2600 can query the report database 2625 for the report data corresponding to a received DICOM image by utilizing a common identifier extracted from the DICOM image.

In some embodiments, the report data can correspond to a plurality of DICOM images. For example, the report data can include natural language text describing a plurality of medical scans of a patient that can include multiple sequences, multiple modalities, and/or multiple medical scans taken over time. In such embodiments, the patient identifying text and/or annotation data detected in the report data can also be applied to de-identify and/or generate annotation data for the plurality of DICOM images it describes. In such embodiments, the medical picture archive integration system 2600 can query the medical picture archive system 2620 for one or more additional DICOM images corresponding to the report data, and de-identified data and annotation data for these additional DICOM images can be generated accordingly by utilizing the report data.

In some embodiments, as shown in FIG. 8E, the medical picture archive system 2620 communicates with the report database 2625. The medical picture archive system 2620 can request the report data corresponding to the DICOM image from the report database 2625, and can transmit the report data to the medical picture archive integration system 2600 via a DICOM communication protocol for receipt via receiver 2602. The medical picture archive system 2620 can query the report database 2625 for the report data, utilizing a common identifier extracted from the corresponding DICOM image, in response to determining to send the corresponding DICOM image to the medical picture archive integration system 2600.

FIG. 8F presents an embodiment where report data is generated by the annotating system 2612 and is transmitted, via a transmitter 2605, to the report database 2625, for example via a DICOM communication protocol or other protocol recognized by the report database 2625. In other embodiments, the report data is instead transmitted via transmitter 2604 to the medical picture archive system 2620, and the medical picture archive system 2620 transmits the report data to the report database 2625.

The report data can be generated by the annotating system 2612 as output of performing the inference function on the de-identified medical scan. The report data can include natural language text data 448 generated automatically based on other diagnosis data 440 such as abnormality annotation data 442 determined by performing the inference function, for example, by utilizing a medical scan natural language generating function trained by the medical scan natural language analysis system 114. The report data can be generated instead of, or in addition to, the annotated DICOM file.

Figure 9:
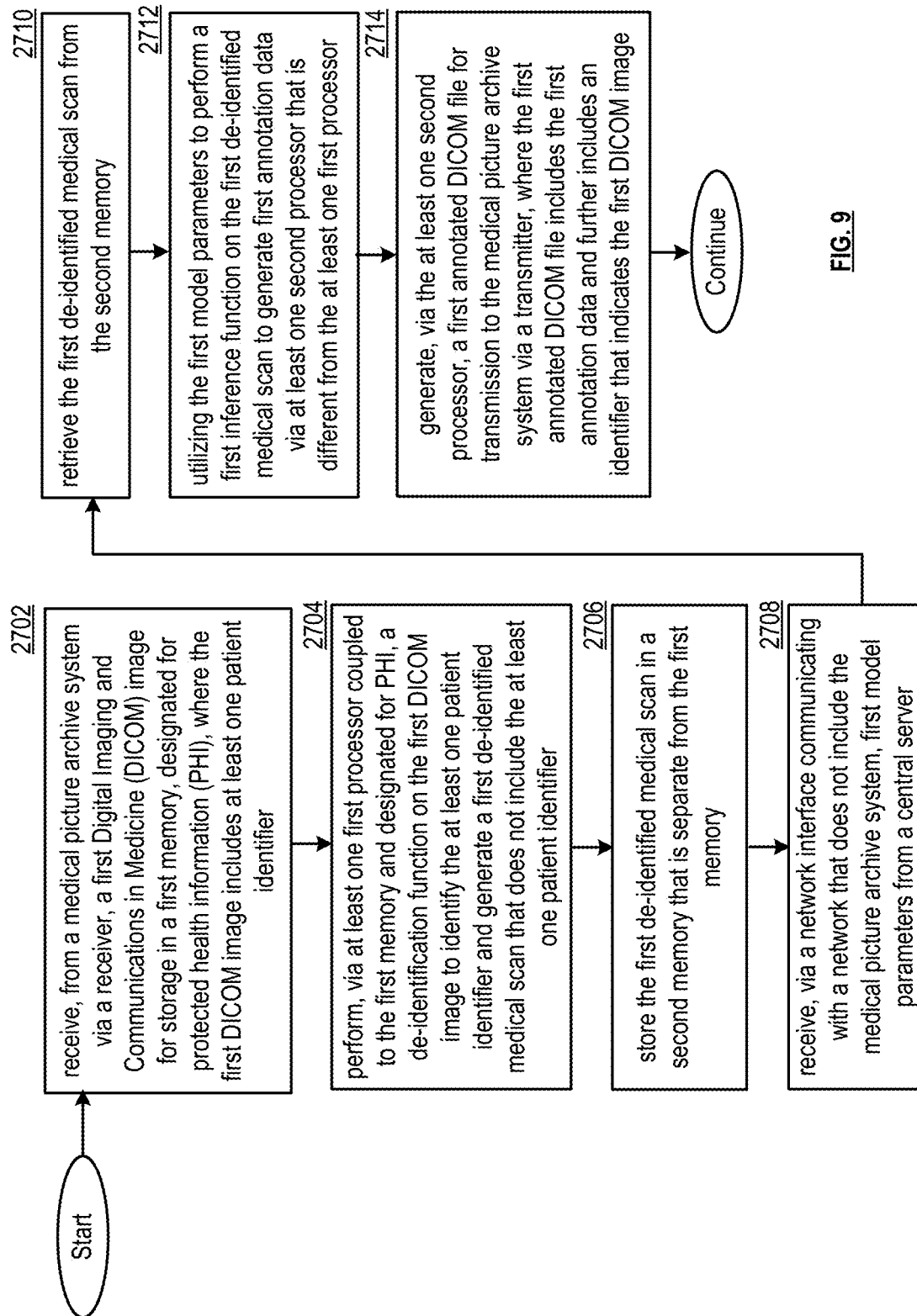
FIG. 9 is a flowchart representation of a method for execution by a medical picture archive integration system in accordance with various embodiments.

FIG. 9 presents a flowchart illustrating a method for execution by a medical picture archive integration system 2600 that includes a first memory and a second memory that store executional instructions that, when executed by at least one first processor and at least one second processor, respectfully, cause the medical picture archive integration system to perform the steps below. In various embodiments, the first memory and at least one first processor is implemented by utilizing, respectfully, the memory 2654 and processing system 2652 of FIG. 8B. In various embodiments, the second memory is implemented by utilizing the memory 2674 and/or the memory 2684 of FIG. 8B. In various embodiments, the at least one second processor is implemented by utilizing the processing system 2682 of FIG. 8B.

Step 2702 includes receiving, from a medical picture archive system via a receiver, a first DICOM image for storage in the first memory, designated for PHI, where the first DICOM image includes at least one patient identifier. Step 2704 includes performing, via at least one first processor coupled to the first memory and designated for PHI, a de-identification function on the first DICOM image to identify the at least one patient identifier and generate a first de-identified medical scan that does not include the at least one patient identifier. Step 2706 includes storing the first de-identified medical scan in a second memory that is separate from the first memory. Step 2708 includes receiving, via a network interface communicating with a network that does not include the medical picture archive system, first model parameters from a central server. Step 2710 includes retrieving the first de-identified medical scan from the second memory. Step 2712 includes utilizing the first model parameters to perform a first inference function on the first de-identified medical scan to generate first annotation data via at least one second processor that is different from the at least one first processor. Step 2714 includes generating, via the at least one second processor, a first annotated DICOM file for transmission to the medical picture archive system via a transmitter, where the first annotated DICOM file includes the first annotation data and further includes an identifier that indicates the first DICOM image. In various embodiments, the first annotated DICOM file is a DICOM presentation state file.

In various embodiments, the second memory further includes operational instructions that, when executed by the at least one second processor, further cause the medical picture archive integration system to retrieve a second de-identified medical scan from the de-identified image storage system, where the second de-identified medical scan was generated by the at least one first processor by performing the de-identification function on a second DICOM image received from the medical picture archive system. The updated model parameters are utilized to perform the first inference function on the second de-identified medical scan to generate second annotation data. A second annotated DICOM file is generated for transmission to the medical picture archive system via the transmitter, where the second annotated DICOM file includes the second annotation data and further includes an identifier that indicates the second DICOM image.

In various embodiments, the second memory stores a plurality of de-identified medical scans generated by the at least one first processor by performing the de-identification function on a corresponding plurality of DICOM images received from the medical picture archive system via the receiver. The plurality of de-identified medical scans is transmitted to the central server via the network interface, and the central server generates the first model parameters by performing a training function on training data that includes the plurality of de-identified medical scans.

In various embodiments, the central server generates the first model parameters by performing a training function on training data that includes a plurality of de-identified medical scans received from a plurality of medical picture archive integration systems via the network. Each of the plurality of medical picture archive integration systems communicates bidirectionally with a corresponding one of a plurality of medical picture archive systems, and the plurality of de-identified medical scans corresponds to a plurality of DICOM images stored by the plurality of medical picture archive integration systems.

In various embodiments, the first de-identified medical scan indicates a scan category of the first DICOM image. The second memory further stores operational instructions that, when executed by the at least one second processor, further cause the medical picture archive integration system to select the first inference function from a set of inference functions based on the scan category. The set of inference functions corresponds to a set of unique scan categories that includes the scan category. In various embodiments, each unique scan category of the set of unique scan categories is characterized by one of a plurality of modalities and one of a plurality of anatomical regions.

In various embodiments, the first memory further stores operational instructions that, when executed by the at least one first processor, further cause the medical picture archive integration system to receive a plurality of DICOM image data from the medical picture archive system via the receiver for storage in the first memory in response to a query transmitted to the medical picture archive system via the transmitter. The query is generated by the medical picture archive integration system in response to a request indicating a new scan category received from the central server via the network. The new scan category is not included in the set of unique scan categories, and the plurality of DICOM image data corresponds to the new scan category. The de-identification function is performed on the plurality of DICOM image data to generate a plurality of de-identified medical scans for transmission to the central server via the network.

The second memory further stores operational instructions that, when executed by the at least one second processor, further cause the medical picture archive integration system to receive second model parameters from the central server via the network for a new inference function corresponding to the new scan category. The set of inference functions is updated to include the new inference function. The second de-identified medical scan is retrieved from the first memory, where the second de-identified medical scan was generated by the at least one first processor by performing the de-identification function on a second DICOM image received from the medical picture archive system. The new inference function is selected from the set of inference functions by determining the second de-identified medical scan indicates the second DICOM image corresponds to the new scan category. The second model parameters are utilized to perform the new inference function on the second de-identified medical scan to generate second annotation data. A second annotated DICOM file is generated for transmission to the medical picture archive system via the transmitter, where the second annotated DICOM file includes the second annotation data and further includes an identifier that indicates the second DICOM image.

In various embodiments, the medical picture archive integration system generates parameter data for transmission to the medical picture archive system that indicates the set of unique scan categories. The medical picture archive system automatically transmits the first DICOM image to the medical picture archive integration system in response to determining that the first DICOM image compares favorably to one of the set of unique scan categories.

In various embodiments, the second memory further stores operational instructions that, when executed by the at least one second processor, cause the medical picture archive integration system to generate a natural language report data is based on the first annotation data and to transmit, via a second transmitter, the natural language report data to a report database associated with the medical picture archive integration system, where the natural language report data includes an identifier corresponding to the first DICOM image.

In various embodiments, the first memory further stores operational instructions that, when executed by the at least one first processor, cause the medical picture archive integration system to receive, via a second receiver, a natural language report corresponding to the first DICOM image from the report database. A set of patient identifying text included in the natural language report are identified. Performing the de-identification function on the first DICOM image includes searching the first DICOM image for the set of patient identifying text to identify the at least one patient identifier.

In various embodiments, the first memory is managed by a medical entity associated with the medical picture archive system. The medical picture archive integration system is located at a first geographic site corresponding to the medical entity, and the central server is located at a second geographic site. In various embodiments, the first memory is decoupled from the network to prevent the first DICOM image that includes the at least one patient identifier from being communicated via the network. In various embodiments, the medical picture archive system is a Picture Archive and Communication System (PACS) server, and the first DICOM image is received in response to a query sent to the medical picture archive system by the transmitter in accordance with a DICOM communication protocol.

Figure 10A:
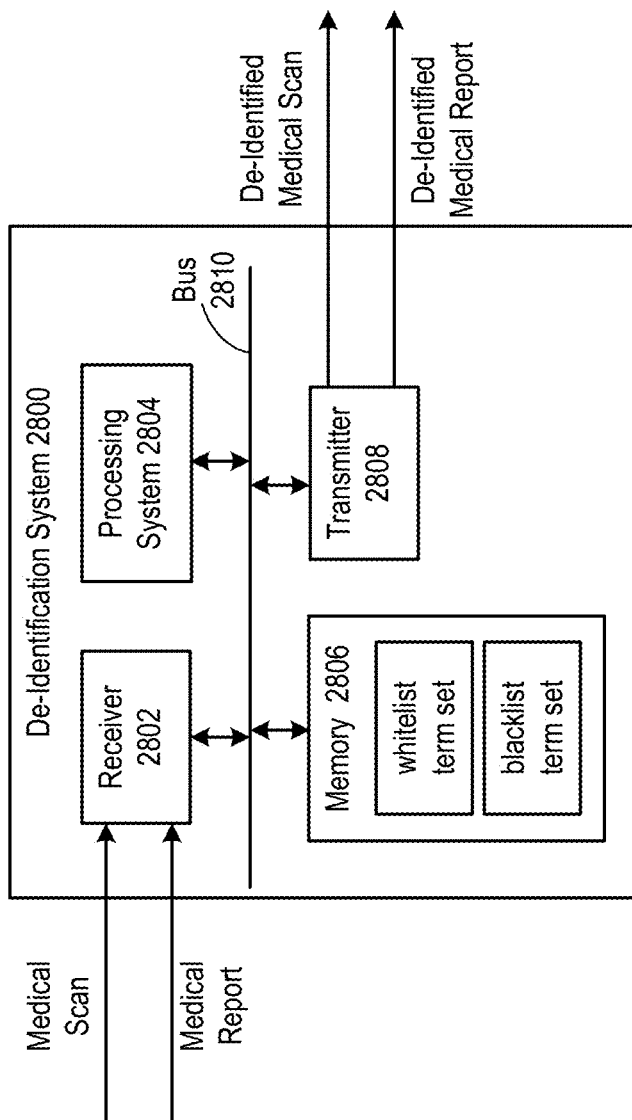
FIG. 10A is a schematic block diagram of a de-identification system in accordance with various embodiments.

FIG. 10A presents an embodiment of a de-identification system 2800. The de-identification system 2800 can be utilized to implement the de-identification system 2608 of FIGS. 8A-8F. In some embodiments, the de-identification system 2800 can be utilized by other subsystems to de-identify image data, medical report data, private fields of medical scan entries 352 such as patient identifier data 431, and/or other private fields stored in databases of the database memory device 340.

The de-identification system can be operable to receive, from at least one first entity, a medical scan and a medical report corresponding to the medical scan. A set of patient identifiers can be identified in a subset of fields of a header of the medical scan. A header anonymization function can be performed on each of the set of patient identifiers to generate a corresponding set of anonymized fields. A de-identified medical scan can be generated by replacing the subset of fields of the header of the medical scan with the corresponding set of anonymized fields.

A subset of patient identifiers of the set of patient identifiers can be identified in the medical report by searching text of the medical report for the set of patient identifiers. A text anonymization function can be performed on the subset of patient identifiers to generate corresponding anonymized placeholder text for each of the subset of patient identifiers. A de-identified medical report can be generated by replacing each of the subset of patient identifiers with the corresponding anonymized placeholder text. The de-identified medical scan and the de-identified medical report can be transmitted to a second entity via a network.

As shown in FIG. 10A, the de-identification system 2800 can include at least one receiver 2802 operable to receive medical scans, such as medical scans in a DICOM image format. The at least one receiver 2802 is further operable to receive medical reports, such as report data 449 or other reports containing natural language text diagnosing, describing, or otherwise associated the medical scans received by the de-identification system. The medical scans and report data can be received from the same or different entity, and can be received by the same or different receiver 2802 in accordance with the same or different communication protocol. For example, the medical scans can be received from the medical picture archive system 2620 of FIGS. 8A-8F and the report data can be received from the report database 2625 of FIGS. 8D-8F. In such embodiments, the receiver 2802 can be utilized to implement the receiver 2602 of FIG. 8B.

The de-identification system 2800 can further include a processing system 2804 that includes at least one processor, and a memory 2806. The memory 2806 can store operational instructions that, when executed by the processing system, cause the de-identification system to perform at least one patient identifier detection function on the received medical scan and/or the medical report to identify a set of patient identifiers in the medical scan and/or the medical report. The operational instructions, when executed by the processing system, can further cause the de-identification system to perform an anonymization function on the medical scan and/or the medical report to generate a de-identified medical scan and/or a de-identified medical report that do not include the set of patient identifiers found in performing the at least one patient identifier detection function. Generating the de-identified medical scan can include generating a de-identified header and generating de-identified image data, where the de-identified medical scan includes both the de-identified header and the de-identified image data. The memory 2806 can be isolated from Internet connectivity, and can be designated for PHI.

The de-identification system 2800 can further include at least one transmitter 2808, operable to transmit the de-identified medical scan and de-identified medical report. The de-identified medical scan and de-identified medical report can be transmitted back to the same entity from which they were received, respectively, and/or can be transmitted to a separate entity. For example, the at least one transmitter can transmit the de-identified medical scan to the de-identified image storage system 2610 of FIGS. 8A-8F and/or can transmit the de-identified medical scan to central server system 2640 via network 2630 of FIGS. 8A-8F. In such embodiments, the transmitter 2808 can be utilized to implement the interface 2655 of FIG. 8B. The receiver 2802, processing system 2804, memory 2806, and/or transmitter 2808 can be connected via bus 2810.

Some or all of the at least one patient identifier detection function and/or at least one anonymization function as discussed herein can be trained and/or implemented by one or subsystems 101 in the same fashion as other medical scan analysis functions discussed herein, can be stored in medical scan analysis function database 346 of FIG. 3, and/or can otherwise be characterized by some or all fields of a medical scan analysis function entry 356 of FIG. 5.

The de-identification system 2800 can perform separate patient identifier detection functions on the header of a medical report and/or medical scan, on the text data of the medical report, and/or on the image data of the medical scan, such as text extracted from the image data of the medical scan. Performance of each of these functions generates an output of its own set of identified patient identifiers. Combining these sets of patient identifiers yields a blacklist term set. A second pass of the header of a medical report and/or medical scan, on the text data of the medical report, and/or on the image data of the medical scan that utilizes this blacklist term set can catch any terms that were missed by the respective patient identifier detection function, and thus, the outputs of these multiple identification processes can support each other. For example, some of the data in the headers will be in a structured form and can thus be easier to reliably identify. This can be exploited and used to further anonymize these identifiers when they appear in free text header fields, report data, and/or in the image data of the medical scan. Meanwhile, unstructured text in free text header fields, report data, and/or image data of the medical scan likely includes pertinent clinical information to be preserved in the anonymization process, for example, so it can be leveraged by at least one subsystems 101 and/or so it can be leveraged in training at least one medical scan analysis function.

At least one first patient identifier detection function can include extracting the data in a subset of fields of a DICOM header, or another header or other metadata of the medical scan and/or medical report with a known type that corresponds to patient identifying data. For example, this patient identifying subset of fields can include a name field, a patient ID number field or other unique patient identifier field, a date field, a time field, an age field, an accession number field, SOP instance UID, and/or other fields that could be utilized to identify the patient and/or contain private information. A non-identifying subset of fields of the header can include hospital identifiers, machine model identifiers, and/or some or all fields of medical scan entry 352 that do not correspond to patient identifying data. The patient identifying subset of fields and the non-identifying subset of fields can be mutually exclusive and collectively exhaustive with respect to the header. The at least one patient identifier function can include generating a first set of patient identifiers by ignoring the non-identifying subset of fields and extracting the entries of the patient identifying subset of fields only. This first set of patient identifiers can be anonymized to generate a de-identified header as discussed herein.

In some embodiments, at least one second patient identifier detection function can be performed on the report data of the medical report. The at least one second patient identifier detection function can include identifying patient identifying text in the report data by performing a natural language analysis function, for example, trained by the medical scan natural language analysis system 114. For example, the at least one second patient identifier detection function can leverage the known structure of the medical report and/or context of the medical report. A second set of patient identifiers corresponding to the patient identifying text can be determined, and the second set of patient identifiers can be anonymized to generate a de-identified medical report. In some embodiments, a de-identified medical report includes clinical information, for example, because the portion of the original medical report that includes the clinical information was deemed to be free of patient identifying text and/or because the portion of the original medical report that includes the clinical information was determined to include pertinent information to be preserved.

In some embodiments, the medical report includes image data corresponding to freehand or typed text. For example the medical report can correspond to a digitized scan of original freehand text written by a radiologist or other medical professional. In such embodiments, the patient identifier detection function can first extract the text from the freehand text in the image data to generate text data before the at least one second patient identifier detection function is performed on the text of the medical report to generate the second set of patient identifiers.

In some embodiments, the at least one second patient identifier detection function can similarly be utilized to identify patient identifying text in free text fields and/or unstructured text fields of a DICOM header and/or other metadata of the medical scan and/or medical report data by performing a natural language analysis function, for example, trained by the medical scan natural language analysis system 114. A third set of patient identifiers corresponding to this patient identifying text of the free text and/or unstructured header fields can be determined, and the third set of patient identifiers can be anonymized to generate de-identified free text header field and/or unstructured header fields. In some embodiments, a de-identified free text header field and/or unstructured header field includes clinical information, for example, because the portion of the original corresponding header field that includes the clinical information was deemed to be free of patient identifying text and/or because the portion of the original corresponding header field that includes the clinical information was determined to include pertinent information to be preserved.

Patient identifiers can also be included in the image data of the medical scan itself. For example, freehand text corresponding to a patient name written on a hard copy of the medical scan before digitizing can be included in the image data, as discussed in conjunction with FIG. 10B. Other patient identifiers, such as information included on a patient wristband or other identifying information located on or within the vicinity of the patient may have been captured when the medical scan was taken, and can thus be included in the image. At least one third patient identifier detection function can include extracting text from the image data and/or detecting non-text identifiers in the image data by performing a medical scan image analysis function, for example, trained by the medical scan image analysis system 112. For example, detected text that corresponds to an image location known to include patient identifiers, detected text that corresponds to a format of a patient identifier, and/or or detected text or other image data determined to correspond to a patient identifier can be identified. The at least one third patient identifier detection function can further include identifying patient identifying text in the text extracted from the image data by performing the at least one second patient identifier detection function and/or by performing a natural language analysis function. A fourth set of patient identifiers corresponding to patient identifying text or other patient identifiers detected in the image data of the medical scan can be determined, and the fourth set of patient identifiers can be anonymized in the image data to generate de-identified image data of the medical scan as described herein. In particular, the fourth set of patient identifiers can be detected in a set of regions of image data of the medical scan, and the set of regions of the image data can be anonymized.

In some embodiments, only a subset of the patient identifier detection functions described herein are performed to generate respective sets of patient identifiers for anonymization. In some embodiments, additional patient identifier detection functions can be performed on the medical scan and/or medical report to determine additional respective sets of patient identifiers for anonymization. The sets of patient identifiers outputted by performing each patient identifier detection function can have a null or non-null intersection. The sets of patient identifiers outputted by performing each patient identifier function can have null or non-null set differences.

Cases where the sets of patient identifiers have non-null set differences can indicate that a patient identifier detected by one function may have been missed by another function. The combined set of patient identifiers, for example, generated as the union of the sets of sets of patient identifiers outputted by performing each patient identifier function, can be used to build a blacklist term set, for example, stored in memory 2806. The blacklist term set can designate the final set of terms to be anonymized. A second pass of header data, medical scans, medical reports, and/or any free text extracted from the header data, the medical scan, and/or the medical report can be performed by utilizing the blacklist term set to flag terms for anonymization that were not caught in performing the respective at least one patient identifier detection function. For example, performing the second pass can include identifying at least one patient identifier of the blacklist term set in the header, medical report, and/or image data of the medical scan. This can include by searching corresponding extracted text of the header, medical report, and/or image data for terms included in blacklist term set and/or by determining if each term in the extracted text is included in the blacklist term set.

In some embodiments, at least one patient identifier is not detected until the second pass is performed. Consider an example where a free text field of a DICOM header included a patient name that was not detected in performing a respective patient identifier detection function on the free text field of the DICOM header. However, the patient name was successfully identified in the text of the medical report in performing a patient identifier detection function on the medical report. This patient name is added to the blacklist term list, and is detected in a second pass of the free text field of the DICOM header. In response to detection in the second pass, the patient name of the free text field of the DICOM header can be anonymized accordingly to generate a de-identified free text field. Consider a further example where the patient name is included in the image data of the medical scan, but was not detected in performing a respective patient identifier detection function on the free text field of the DICOM header. In the second pass, this patient name can be detected in at least one region of image data of the medical scan by searching the image data for the blacklist term set.

In some embodiments, performing some or all of the patient identifier detection functions includes identifying a set of non-identifying terms, such as the non-identifying subset of fields of the header. In particular, the non-identifying terms can include terms identified as clinical information and/or other terms determined to be preserved. The combined set of non-identifying terms, for example, generated as the union of the sets of sets of non-identifying outputted by performing each patient identifier function, can be used to build a whitelist term set, for example, stored in memory 2806. Performing the second pass can further include identifying at least one non-identifying term of the whitelist term set in the header, medical report, and/or image data of the medical scan, and determining not to anonymize, or to otherwise ignore, the non-identifying term.

In various embodiments, some or all terms of the whitelist term set can be removed from the blacklist term set. In particular, at least one term previously identified as a patient identifier in performing one or more patient identifier detection functions is determined to be ignored and not anonymized in response to determining the term is included in the whitelist term set. This can help ensure that clinically important information is not anonymized, and is thus preserved in the de-identified medical scan and de-identified medical report.

In some embodiments, the second pass can be performed after each of the patient identifier detection functions are performed. For example, performing the anonymization function can include performing this second pass by utilizing the blacklist term set to determine the final set of terms to be anonymized. New portions of text in header fields, not previously detected in generating the first set of patient identifiers or the third set of patient identifiers, can be flagged for anonymization by determining these new portions of text correspond to terms of the blacklist term set. New portions of text the medical report, not previously detected in generating in the second set of patient identifiers, can be flagged for anonymization by determining these new portions of text correspond to terms of the blacklist term set. New regions of the image data of the medical scan, not previously detected in generating the fourth set of patient identifiers, can be flagged for anonymization by determining these new portions of text correspond to terms of the blacklist term set.

In some embodiments, the blacklist term set is built as each patient identifier detection function is performed, and performance of subsequent patient identifier detection functions includes utilizing the current blacklist term set. For example, performing the second patient identifier detection function can include identifying a first subset of the blacklist term set in the medical report by searching the text of the medical report for the blacklist term set and/or by determining if each term in the text of the medical report is included in the blacklist term set. Performing the second patient identifier detection function can further include identifying at least one term in the medical report that is included in the whitelist term set, and determining to ignore the term in response. The first subset can be anonymized to generate the de-identified medical report as discussed herein. New patient identifiers not already found can be appended to the blacklist term set, and the updated blacklist term set can be applied to perform a second search of the header and/or image data of the medical scan, and at least one of the new patient identifiers can be identified in the header in the second search of the header and/or in the image data in a second search of the image data. These newly identified patient identifiers in the header and/or image data are anonymized in generating the de-identified medical scan.

As another example, a second subset of the blacklist term set can be detected in a set of regions of image data of the medical scan by performing the medical scan image analysis function on image data of the medical scan, where the image analysis function includes searching the image data for the set of patient identifiers. For example, the medical scan image analysis function can include searching the image data for text, and the second subset can include detected text that matches one or more terms of the blacklist term set. In some embodiments, detected text that matches one or more terms of the whitelist term set can be ignored. The second subset can be anonymized to generate de-identified image data as discussed herein. New patient identifiers that are detected can be appended to the blacklist term set, and the updated blacklist term set can be applied to perform a second search of the header and/or metadata of the medical scan, and/or can be applied to perform a second search of the medical report. At least one of the new patient identifiers can be identified in the header as a result of performing the second search of the header and/or at least one of the new patient identifiers can be identified medical report as a result of performing the second search of the medical report. These newly identified patient identifiers can be anonymized in the header along with the originally identified blacklist term set in generating the de-identified header, and/or can be anonymized in the medical report along with the originally identified first subset in generating the de-identified medical report.

In some embodiments, the memory 2806 further stores a global blacklist, for example, that includes a vast set of known patient identifying terms. In some embodiments, the global blacklist is also utilized by at least one patient identifier detection function and/or in performing the second pass to determine patient identifying terms for anonymization. In some embodiments, the blacklist term set generated for a particular medical scan and corresponding medical report can be appended to the global blacklist for use in performing the second pass and/or in detecting patient identifiers in subsequently received medical scans and/or medical reports.

Alternatively or in addition, the memory 2806 can further store a global whitelist, for example, that includes a vast set of terms that can be ignored. In particular, the global whitelist can include clinical terms and/or other terms that are deemed beneficial to preserve that do not correspond to patient identifying information. In some embodiments, the global whitelist is utilized by at least one patient identifier detection function and/or in performing the second pass to determine terms to ignore in the header, image data, and/or medical report. In some embodiments, the whitelist term set generated for a particular medical scan and corresponding medical report can be appended to the global whitelist for use in performing the second pass and/or in ignoring terms in subsequently received medical scans and/or medical reports.

Alternatively or in addition, the memory 2806 can further store a global graylist, for example, that includes ambiguous terms that could be patient identifying terms in some contexts, but non-identifying terms in other contexts. For example, "Parkinson" could correspond to patient identifying data if part of a patient name such as "John Parkinson", but could correspond to non-patient identifying data meant to be ignored and preserved in the de-identified medical report and/or de-identified medical scan if part of a diagnosis term such as "Parkinson's disease." In some embodiments, the global graylist is also utilized in performing the second pass and/or in performing at least one patient identifier detection function to determine that a term is included in the graylist, and to further determine whether the term should be added to the blacklist term set for anonymization or whitelist term set to be ignored by leveraging context of accompanying text, by leveraging known data types of a header field from which the term was extracted, by leveraging known structure of the term, by leveraging known data types of a location of the image data from which the term was extracted, and/or by leveraging other contextual information. In some embodiments, the graylist term set can be updated based on blacklist and/or whitelist term sets for a particular medical scan and corresponding medical report.

In some embodiments, the at least one anonymization function includes a fiducial replacement function. For example, some or all of the blacklist term set can be replaced with a corresponding, global fiducial in the header, report data, and/or image data. In some embodiments, the global fiducial can be selected from a set of global fiducials based on a type of the corresponding patient identifier. Each patient identifier detected in the header and/or medical report can be replaced with a corresponding one of the set of global text fiducials. Each patient identifiers detected in the image data can be replaced with a corresponding one of the set of global image fiducials. For example, one or more global image fiducials can overlay pixels of regions of the image data that include the identifying patient data, to obfuscate the identifying patient data in the de-identified image data.

The global text fiducials and/or global image fiducials can be recognizable by inference functions and/or training functions, for example, where the global text fiducials and global image fiducials are ignored when processed in a training step to train an inference function and/or are ignored in an inference step when processed by an inference function. Furthermore, the global text fiducials and/or global image fiducials can be recognizable by a human viewing the header, medical report, and/or image data. For example, a radiologist or other medical professional, upon viewing a header, medical report, and/or image data, can clearly identify the location of a patient identifier that was replaced by the fiducial and/or can identify the type of patient identifier that was replaced by the fiducial.

As an example, the name "John Smith" can be replaced in a header and/or medical report with the text "% PATIENT NAME %", where the text "% PATIENT NAME %" is a global fiducial for name types of the header and/or the text of medical reports. The training step and/or inference step of medical scan natural language analysis functions can recognize and ignore text that matches "% PATIENT NAME %" automatically.

Figure 10B:
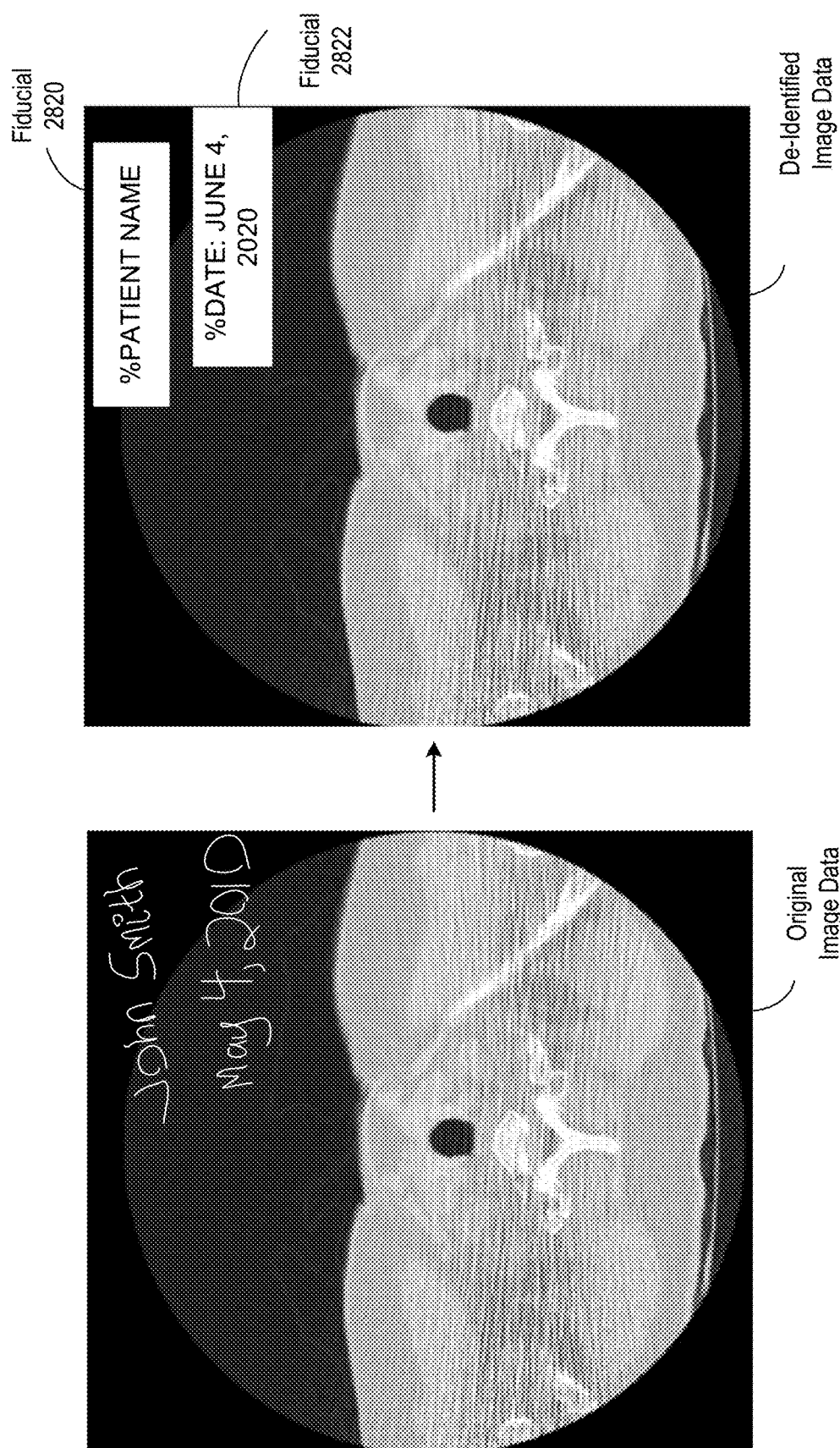
FIG. 10B is an illustration of an example of anonymizing patient identifiers in image data of a medical scan in accordance with various embodiments.

FIG. 10B illustrates an example of anonymizing patient identifiers in image data of a medical scan. In this example, the name "John Smith" and the date "May 4, 2010" is detected as freehand text in the original image data of a medical scan. The regions of the image data that include the patient identifiers can each be replaced by global fiducial in the shape of a rectangular bar, or any other shape. As shown in FIG. 10B, a first region corresponding to the location of "John Smith" in the original image data is replaced by fiducial 2820 in the de-identified image data, and a second region corresponding to the location of "May 4, 2010" in the original image data is replaced by fiducial 2822 in the de-identified image data. The size, shape, and/or location of each global visual fiducial can be automatically determined based on the size, shape, and/or location of the region that includes the patient identifier to minimize the amount of the image data that is obfuscated, while still ensuring the entirety of the text is covered. While not depicted in FIG. 10B, the fiducial can be of a particular color, for example, where pixels of the particular color are automatically recognized by the training step and/or inference step of medical scan image analysis functions to indicate that the corresponding region be ignored, and/or where the particular color is not included in the original medical scan and/or is known to not be included in any medical scans. The fiducial can include text recognizable to human inspection such as "% PATIENT NAME" and "% DATE" as depicted in FIG. 10B, and/or can include a QR code, logo, or other unique symbol recognizable to human inspection and/or automatically recognizable by the training step and/or inference step of medical scan image analysis functions to indicate that the corresponding region be ignored.

In some embodiments, other anonymization functions can be performed on different ones of the patient identifying subset of fields to generate the de-identified header, de-identified report data, and/or de-identified image data. For example, based on the type of identifying data of each field of the header, different types of header anonymization functions and/or text anonymization functions can be selected and utilized on the header fields, text of the report, and/or text extracted from the image data. A set of anonymization functions can include a shift function, for example, utilized to offset a date, time or other temporal data by a determined amount to preserve absolute time difference and/or to preserve relative order over multiple medical scans and/or medical reports of a single patient. FIG. 10B depicts an example where the shift function is performed on the date detected in the image data to generate fiducial 2822, where the determined amount is 10 years and 1 month. The determined amount can be determined by the de-identification system randomly and/or pseudo-randomly for each patient and/or for each medical scan and corresponding medical report, ensuring the original date cannot be recovered by utilizing a known offset. In various embodiments, other medical scans and/or medical reports are fetched for the same patient by utilizing a patient ID number or other unique patient identifier of the header. These medial scans and reports can be anonymized as well, where the dates and/or times detected in these medical scans and/or medical reports offset by the same determined amount, randomized or pseudo-randomized for particular patient ID number, for example, based on performing a hash function on the patient ID number.

The set of anonymization functions can include at least one hash function, for example utilized to hash a unique patient ID such as a patient ID number, accession number, and/or SOP instance UID of the header and/or text. In some embodiments, the hashed SOP instance UID, accession number, and/or patient ID number are prepended with a unique identifier, stored in a database of the memory 2806 and/or shared with the entities to which the de-identified medical scans and/or medical reports are transmitted, so that de-identified medical scans and their corresponding de-identified medical reports can be linked and retrieved retroactively. Similarly, longitudinal data can be preserved as multiple medical scans and/or medical reports of the same patient will be assigned the same hashed patient ID.

The set of anonymization functions can further include at least one manipulator function for some types of patient identifiers. Some values of header fields and/or report text that would normally not be considered private information can be considered identifying patient data if they correspond to an outlier value or other rare value that could then be utilized to identify the corresponding patient from a very small subset of possible options. For example, a patient age over 89 could be utilized to determine the identity of the patient, for example, if there are very few patients over the age of 89. To prevent such cases, in response to determining that a patient identifier corresponds to an outlier value and/or in response to determining that a patient identifier compares unfavorably to a normal-range threshold value, the patient identifier can be capped at the normal-range threshold value or can otherwise be manipulated. For example, a normal-range threshold value corresponding to age can be set at 89, and generating a de-identified patient age can include capping patient ages that are higher than 89 at 89 and/or can include keeping the same value for patient ages that are less than or equal to 89.

In some embodiments, the de-identified header data is utilized to replace the corresponding first subset of patient identifiers detected in the medical report with text of the de-identified header fields. In other embodiments, a set of text anonymization functions includes a global text fiducial replacement function, shift function, a hash function, and/or manipulator functions that anonymize the corresponding types of patient identifiers in the medical report separately.

In some embodiments where the image data of a medical scan includes an anatomical region corresponding to a patient's head, the image data may include an identifying facial structure and/or facial features that could be utilized to determine the patient's identity. For example, a database of facial images, mapped to a corresponding plurality of people including the patient, could be searched and a facial recognition function could be utilized to identify the patient in the database. Thus, facial structure included in the image data can be considered patient identifying data.

To prevent this problem and maintain patient privacy, the de-identification system can further be implemented to perform facial obfuscation for facial structure detected in medical scans. At least one region of the image data that includes identifying facial structure can be determined by utilizing a medical image analysis function. For example, the medical image analysis function can include a facial detection function that determines the regions of the image data that include identifying facial structure based on searching the image data for pixels with a density value that corresponds to facial skin, facial bone structure, or other density of an anatomical mass type that corresponds to identifying facial structure, and the facial obfuscation function can be performed on the identified pixels. Alternatively or in addition, the facial detection function can determine the region based on identifying at least one shape in the image data that corresponds to a facial structure.

The image obfuscation function can include a facial structure obfuscation function performed on the medical scan to generate de-identified image data that does not include identifying facial structure. For example, the facial structure obfuscation function can mask, scramble, replace with a fiducial, or otherwise obfuscate the pixels of the region identified by the facial detection function. In some embodiments, the facial structure obfuscation function can perform a one-way function on the region that preserves abnormalities of the corresponding portions of the image, such as nose fractures or facial skin legions, while still obfuscating the identifying facial structure such that the patient is not identifiable. For example, the pixels of the identifying facial structure can be altered such that they converge towards a fixed, generic facial structure. In some embodiments, a plurality of facial structure image data of a plurality of patients can be utilized to generate the generic facial structure, for example, corresponding to an average or other combination of the plurality of faces. For example, the pixels of the generic facial structure can be averaged with, superimposed upon, or otherwise combined with the pixels of the region of the image data identified by the facial detection function in generating the de-identified image data.

In some embodiments, a hash function can be performed on an average of the generic facial structure and the identified facial structure of the image data so that the generic facial structure cannot be utilized in conjunction with the resulting data of the de-identified image data to reproduce the original, identifying facial structure. In such embodiments, the hash function can alter the pixel values while still preserving abnormalities. In some embodiments, a plurality of random, generic facial structures can be generated by utilizing the plurality of facial structure image data, for example, where each if the plurality of facial structure image data are assigned a random or pseudo-random weight in an averaging function utilized to create the generic facial structure, where a new, random or pseudo-random set of weights are generated each time the facial structure obfuscation function is utilized to create a new, generic facial structure to be averaged with the identified facial structure in creating the de-identified image data to ensure the original identifying facial structure cannot be extracted from the resulting de-identified image data.

While facial obfuscation is described herein, similar techniques can be applied in a similar fashion to other anatomical regions that are determined to include patient identifiers and/or to other anatomical regions that can be utilized to extract patient identifying information if not anonymized.

In some embodiments, the at least one receiver 2802 is included in at least one transceiver, for example, enabling bidirectional communication between the medical picture archive system 2620 and/or the report database 2625. In such embodiments, the de-identification system 2800 can generate queries to the medical picture archive system 2620 and/or the report database 2625 for particular medical scans and/or medical reports, respectively. In particular, if the medical scan and medical report are stored and/or managed by separate memories and/or separate entities, they may not be received at the same time. However, a linking identifier, such as DICOM identifiers in headers or metadata of the medical scan and/or medical report, such accession number, patient ID number, SOP instance UID, or other linking identifier that maps the medical scan to the medical report can be utilized to fetch a medical report corresponding to a received medical scan and/or to fetch a medical scan corresponding to a received medical report via a query sent utilizing the at least one transceiver. For example, in response to receiving the medical scan from the medical picture archive system 2620, the de-identification system can extract a linking identifier from a DICOM header of the medical scan, and can query the report database 2625 for the corresponding medical report by indicating the linking identifier in the query. Conversely, in response to receiving the medical report from the report database 2625, the de-identification system can extract the linking identifier from a header, metadata, and/or text body of the medical report, and can query the medical picture archive system 2620 for the corresponding medical scan by indicating the linking identifier in the query. In some embodiments, a mapping of de-identified medical scans to original medical scans, and/or a mapping of de-identified medical reports to original medical reports can be stored in memory 2806. In some embodiments, linking identifiers such as patient ID numbers can be utilized to fetch additional medical scans, additional medical reports, or other longitudinal data corresponding to the same patient.

FIG. 11 presents a flowchart illustrating a method for execution by a de-identification system 2800 that stores executional instructions that, when executed by at least one processor, cause the de-identification to perform the steps below.

Step 2902 includes receiving from a first entity, via a receiver, a first medical scan and a medical report corresponding to the medical scan. Step 2904 includes identifying a set of patient identifiers in a subset of fields of a first header of the first medical scan. Step 2906 includes performing a header anonymization function on each of the set of patient identifiers to generate a corresponding set of anonymized fields. Step 2908 includes generating a first de-identified medical scan by replacing the subset of fields of the first header of the first medical scan with the corresponding set of anonymized fields. Step 2910 includes identifying a first subset of patient identifiers of the set of patient identifiers in the medical report by searching text of the medical report for the set of patient identifiers. Step 2912 includes performing a text anonymization function on the first subset of patient identifiers to generate corresponding anonymized placeholder text for each of the first subset of patient identifiers. Step 2914 includes generating a de-identified medical report by replacing each of the first subset of patient identifiers with the corresponding anonymized placeholder text. Step 2916 includes transmitting, via a transmitter, the de-identified first medical scan and the de-identified medical report to a second entity via a network.

In various embodiments, the medical scan is received from a Picture Archive and Communication System (PACS), where the medical report is received from a Radiology Information System (RIS), and where the first de-identified medical scan and the de-identified medical report are transmitted to a central server that is not affiliated with the PACS or the RIS. In various embodiments, first medical scan and the medical report are stored in a first memory for processing. The first memory is decoupled from the network to prevent the set of patient identifiers from being communicated via the network. The first de-identified medical scan and the de-identified medical report are stored in a second memory that is separate from the first memory. The first de-identified medical scan and the de-identified medical report are fetched from the second memory for transmission to the second entity.

In various embodiments, the header anonymization function performed on each of the set of patient identifiers is selected from a plurality of header anonymization functions based on one of a plurality of identifier types of the corresponding one of the subset of fields. In various embodiments, the plurality of identifier types includes a date type. A shift function corresponding to the date type is performed on a first date of the first header to generate the first de-identified medical scan, where the shift function includes offsetting the first date by a determined amount. A second medical scan is received, via the receiver, that includes a second header. A unique patient ID of the first header matches a unique patient ID of the second header. The shift function is performed on a second date of the second header by offsetting the second date by the determined amount to generate a second de-identified medical scan. The second de-identified medical scan is transmitted to the second entity via the network.

In various embodiments, the plurality of identifier types includes a unique patient ID type. A hash function corresponding the unique patient ID type is performed on the unique patient ID of the first header to generate the first de-identified medical scan. The hash function is performed on the unique patient ID of the second header to generate the second de-identified medical scan. An anonymized unique patient ID field of the first de-identified medical scan matches an anonymized unique patient ID field of the second de-identified medical scan as a result of the unique patient ID of the first header matching the unique patient ID of the second header.

In various embodiments, the plurality of identifier types includes a linking identifier type that maps the medical scan to the medical report. A hash function corresponding to the linking identifier type is performed on a linking identifier of the first header to generate a hashed linking identifier. A linking identifier field of the first de-identified medical scan includes the hashed linking identifier. Performing the text anonymization function on the first subset of patient identifiers includes determining one of the first subset of patient identifiers corresponds to linking identifier text and performing the hash function on the one of the first subset of patient identifiers to generate the hashed linking identifier, where the de-identified medical report includes the hashed linking identifier.

In various embodiments, a second subset of patient identifiers of the set of patient identifiers is identified in a set of regions of image data of the medical scan by performing an image analysis function on image data of the medical scan. The image analysis function includes searching the image data for the set of patient identifiers. An identifier type is determined for each of the second subset of patient identifiers. One of a plurality of image fiducials is selected for each of the second subset of patient identifiers based on the identifier type. De-identified image data is generated, where a set of regions of the de-identified image data, corresponding to the set of regions of the image data, includes the one of the plurality of image fiducials to obfuscate each of the second subset of patient identifiers. Generating the first de-identified medical scan further includes replacing the image data of the medical scan with the de-identified image data.

In various embodiments, a new patient identifier is identified in the medical report by performing a natural language analysis function on the medical report, where new patient identifier is not included in the set of patient identifiers. The set of patient identifiers is updated to include the new patient identifier prior to searching the image data of the medical scan for the set of patient identifiers, and the second subset of patient identifiers includes the new patient identifier.

In various embodiments, the memory further stores a global identifier blacklist. The natural language analysis function includes searching the medical report for a plurality of terms included in the global identifier blacklist to identify the new patient identifier. In various embodiments, the de-identification system determines that the global identifier blacklist does not include one of the set of patient identifiers, and the global identifier blacklist is updated to include the one of the set of patient identifiers.

In various embodiments, performing the image analysis function further includes identifying a new patient identifier in the image data, where new patient identifier is not included in the set of patient identifiers. Identifying text is extracted from a region of the image data corresponding to the new patient identifier. The new patient identifier is identified in the medical report by searching text of the medical report for the identifying text. The text anonymization function is performed on new patient identifier to generate anonymized placeholder text for the new patient identifier. Generating the de-identified medical report further includes replacing the identifying text with the anonymized placeholder text for the new patient identifier.

In various embodiments, generating the de-identified image data further includes detecting an identifying facial structure in the image data of the medical scan. Generating the de-identified image data includes performing a facial structure obfuscation function on the image data, and where the de-identified image data does not include the identifying facial structure.

FIG. 12A illustrates an embodiment of a lesion tracking system 3002. The lesion tracking system 3002 can receive multiple scans or other longitudinal of the same patient to track changes in one or more lesions detected in the multiple scans over time. In particular, the lesion size, shape, diameter, and/or volume, and/or other characteristics of the lesion such as other abnormality classification data 445 can be determined for each scan, and the changes in these features over time can be measured and tracked. For example, lesions can be determined to shrink, grow, or disappear over subsequent medical scans, and/or new lesions can be detected to appear over subsequent medical scans. Performing such calculations automatically by utilizing the lesion tracking system 3002 can generate more precise measurements than those generated by a radiologist's visual inspection of one or more medical scans. These automated measurements can thus be used to more accurately determine or predict if a patient's condition is bettering or worsening, to more accurately determine or predict if a patient is responding well or poorly to treatment, and/or to otherwise aid in diagnosing a patient's condition.

As shown in FIG. 12A, lesion tracking system 3002 can communicate bi-directionally, via network 150, with the medical scan database 342 and/or other databases of the database storage system 140, with one or more client devices 120, and/or, while not shown in FIG. 12A, one or more subsystems 101 of FIG. 1. In some embodiments, the lesion tracking system 3002 is an additional subsystem 101 of the medical scan processing system 100, implemented by utilizing the subsystem memory device 245, subsystem processing device 235, and/or subsystem network interface 265 of FIG. 2A. In some embodiments, some or all of the lesion tracking system 3002 is implemented by utilizing other subsystems 101 and/or is operable to perform functions or other operations described in conjunction with one or more other subsystems 101.

The lesion tracking system 3002 can be operable to receive, via subsystem network interface 265 or another receiver, a first medical scan that is associated with a first unique patient ID and a first scan date. The lesion tracking system 3002 can also receive a second medical scan that is associated with the first unique patient ID and a second scan date that is different from the first scan date. The first medical scan can include a first plurality of image slices, and the second medical scan can include a second plurality of image slices. As shown in FIG. 12A, the first medical scan and second medical scan can be received as medical scan entries 3005 and 3006, respectively. The medical scan entries can be received from the medical scan database 342, and each entry can include some or all fields of medical scan entries 352 as described in conjunction with FIG. 4A. For example, the unique patient ID can be indicated in the patient identifier data 431 and/or the scan date can be indicated in the scan date data 426. In some embodiments, more than two medical scans of the patient can be received for processing. In some embodiments, medical scan entry 3006 can be received as longitudinal data 433 of medical scan entry 3005 and/or an identifier of medical scan entry 3006 can be determined from longitudinal data 433 of medical scan entry 3005, which can be utilized by the lesion tracking system to fetch medical scan entry 3006 from the medical scan database 342. Medical scan entries 3005 and 3006 can correspond to the same or different scan categories, and can, for example, correspond to the same or different modality.

A lesion detection function 3020 can be performed to detect at least one lesion in medical scan entries 3005 and 3006. In some embodiments, the lesion detection function 3020 is performed on image data 410 on medical scan entries 3005 and 3006 to determine an anatomical location of the lesion, to determine a subset of image slices that contains the lesion for each medical scan, to determine abnormality location data 443 corresponding to the lesion, and/or to otherwise determine the location of the lesion in the image data. For example, as depicted in FIG. 12A, image slice subset 3030 can correspond to the subset of slices that include the detected lesion in image data 410 of medical scan entry 3005, and image slice subset 3031 can correspond to the subset of slices that include the detected lesion in image data 410 of medical scan entry 3006.

In some embodiments, the lesion detection function 3020 is implemented by utilizing a medical scan analysis function, for example, trained by the medical scan image analysis system 112. In such embodiments, the lesion detection function can correspond to the inference step 1354 and/or the detection step 1372 described in conjunction with FIG. 7B, to determine abnormality region 1373. In some embodiments, the lesion is detected in an image slice of the image data 410, A density value, density range and/or other pixel value of pixels determined to correspond to the lesion in the image slice is determined. This density value, density range and/or other pixel value is compared to the value corresponding pixels in neighboring image slices, or pixels within proximity of coordinate values determined to contain the lesion in the image slice. For example, the neighboring image slices can include one or more image slices before or after the image slice in the sequential slice ordering of the image data. If the pixel values compare favorably, this can be utilized to determine that the lesion is included in these neighboring slices and/or to determine which pixels of the neighboring image slices include the lesion. This process can continue for subsequent neighboring image slices to determine the remainder of the image slice subset 3030, continuing until no more neighboring image slices are determined to include the lesion. Thus, the image slice subset 3030 can correspond to a consecutive subset of image slices with respect to the sequential ordering of the image slices of the image data 410.

In some embodiments, the lesion detection function 3020 is first performed on medical scan entry 3005, and the anatomical location and/or subset of image slices is utilized to detect the lesion in medical scan entry 3006, for example, to ensure the same lesion is detected in both medical scan entries and/or to expedite processing of medical scan entry 3006. For example, performing the lesion detection function on medical scan entry 3006 can include searching only a subset of image slices of the medical scan entry 3006 corresponding to and/or neighboring the image slice subset 3030; searching an anatomical region determined in processing medical scan entry 3005 for the lesion; and/or searching only a subset of pixels of some or all image slices corresponding to and/or in proximity to the anatomical region, and/or pixels of the image slice subset 3030 determined to include the lesion. In some embodiments, the lesion detection function includes performing an abnormality similarity function or other medical scan similarity analysis function trained by and/or performed by the medical scan comparison system 116, where a similarity score for lesions detected in medical scan entry 3005 and 3006 is compared to a threshold, and is utilized to determine that the detected in medical scan entry 3006 is the same lesion as that detected in 3005 when the similarity score compares favorably to a threshold.

Once the lesion is detected, the image slice subset 3030, anatomical region data, pixel coordinates corresponding to the detected lesion, and/or other abnormality location data 443 corresponding to the lesion can be utilized as input to one or more lesion measurement functions 3045. In some embodiments, the lesion detection function 3020 is not performed by the lesion tracking system 3002. Instead, abnormality location data 443 that indicates the subset of the image slice subset 3030 and/or 3031, anatomical region data, pixel coordinates corresponding to the detected lesion, and/or other location data can be received from the medical scan database 342 and/or another subsystem 101 for use as input to the lesion measurement function 3045.

The one or more lesion measurement functions 3045 can include a lesion diameter measurement function, as shown in FIG. 12B, to determine diameter measurement 3022 for a lesion 3010 detected in the image data 410 of medical scan entry 3005 and/or to determine a diameter measurement 3024 for the lesion 3010 detected in image data 410 of medical scan entry 3006.

For a lesion 3010 detected in the image data of medical scan entry 3005, the lesion diameter measurement function can include performing a lesion diameter calculation on each of the image slice subset 3030 to generate a set of diameter measurements. Generating the lesion diameter measurement for the lesion of medical scan entry 3005 can include selecting a maximum of the set of diameter measurements. The lesion diameter measurement can correspond to a segment connecting a first point and a second point of a perimeter of the lesion in one of the image slice subset 3030. In some embodiments, the segment is oblique to an x-axis of the one of the image slice subset. In some embodiments, performing the lesion diameter measurement function can include determining a set of pixels of some or all of the subset of image slices that correspond to the perimeter of the first lesion in the one of the first subset of image slices. A set of segment lengths corresponding to a distance between each of a plurality of pairs of pixels can be calculated, for example, where the plurality of pairs of pixels includes every combination of selecting two of the set of pixels. The lesion diameter measurement can be determined by selecting a maximum of the set of segment lengths.

The diameter measurement 3024 corresponding to the diameter of the lesion 3010 in the image data of medical scan entry 3006 can be calculated in the same or different fashion. The diameter measurement 3024 can correspond to a segment on the same image slice index or different image slice index of the image slice that includes the diameter measurement 3022 for medical scan entry 3005. For example, the image slice containing the diameter of the lesion may change depending on how the lesion changed shape over time. Similarly, the axis along which the diameter falls relative to a coordinate system of the image slices can be different for diameter measurements 3022 and 3024, as shown in FIG. 12B.

In some embodiments, the diameter measurement can be measured across multiple slices, for example, based upon the three-dimensional structure of the lesion. For example, segment lengths for a plurality of pairs of pixels corresponding to the three-dimensional surface of the lesion across some or all of the image slice subset 3030 can be utilized to compute the diameter measurement 3022. In particular, a slice thickness can be determined, for example, based on metadata of the medical scan entry 3005 and/or based on the modality of the medical scan entry 3005, and can be used in computing the segment lengths for each of the plurality of pairs. The maximum segment length can be utilized as the diameter measurement 3022.

In some embodiments, the one or more lesion measurement functions 3045 can include a lesion area measurement function. For example, based on pixels in each of the subset of image slices determined to be included in the lesion, an area can be computed. In particular, a fixed pixel area corresponding to the true area represented by each individual pixel can be determined, for example, in the medical scan entry metadata and/or based on the modality of the medical scan. This pixel area can be multiplied by the number of pixels determined to be included in the lesion to calculate a lesion area for each image slice in the image slice subset.

Furthermore, this calculated set of areas can be utilized to calculate a volume approximation of the lesion by performing a lesion measurement functions 3045 corresponding to a lesion volume measurement function. Performing the lesion volume measurement function can include performing a Riemann sum calculation on the set of lesion area measurements, where a uniform partition width of the Riemann sum is determined based on the determined slice thickness of the image slices in the image data. For example, every pair of consecutive image slices of the image slice subset 3030 can correspond to one of a plurality of trapezoidal areas. Performing the performing the lesion volume calculation can include performing a summation of the plurality of trapezoidal areas. Each of the plurality of trapezoidal areas can be calculated by multiplying the slice thickness by half of the sum of a first base and a second base, where a value of the first base is equal to a first one of the set of lesion area measurements corresponding to a first one of a corresponding pair of consecutive image slices, and where a value of the second base is equal to a second one of the of the set of lesion area measurements corresponding to a second one of the corresponding pair of consecutive image slices.

FIG. 12C illustrates an example of performing the lesion volume measurement function. Image slice subset 3030 is determined from the image data 410 based on the detection of lesion 3010, and includes slice indexes 0-10. The lesion area of lesion 3010 can be calculated for each image slice, as illustrated in the discrete plot 3032 of slice index vs lesion area. Plot 3032 can be utilized to determine volume as the area under the curve of plot 3034 to perform a trapezoidal Riemann sum approximation of lesion volume, where the x-axis measures cross-sectional distance, or width, from slice 0. This can be determined by multiplying the slice index of the x-axis of plot 3032 by the slice thickness to determine the x-value of each of the coordinates plotted in plot 3032. A continuous curve of lesion area can be approximated by connecting discrete points of plot 3032 to create the curve of plot 3032. While linear segments are shown to connect the discrete points in FIG. 12C, any curve fitting function can be utilized to generate the area curve. In this example, calculating the area under the curve to approximate volume can correspond to a trapezoidal Riemann sum approximation, but other Riemann sum approximations, other integral approximation functions, and/or other volume approximation techniques can be utilized to approximate volume based on the discrete areas of plot 3032.

One or more of the lesion measurement functions 3045 can be medical scan analysis functions, for example, trained by and/or performed by the medical scan image analysis system 112 and/or trained and/or performed in the same fashion as other medical scan analysis functions described herein. In some embodiments, the lesion measurement function is implemented by utilizing the abnormality classification step 1374 to generate classification data 1375 that includes the lesion measurement data 3040 and/or 3041.

The lesion measurements can be compared by performing a lesion measurement change function 3050 on the lesion measurement data 3040 and 3041. The lesion measurement change function 3050 can include computing difference of corresponding measurement values, such as a difference in diameter and/or a difference in volume of the lesion. The lesion measurement function can also calculate a Euclidean distance of vectors that include a set of measurements in lesion measurement data 3040 and 3041. The lesion measurement change function 3050 can be a medical scan analysis function, such as a medical scan comparison function, trained by and/or performed by the medical scan image analysis system 112, trained by and/or performed by the medical scan comparison system 116, and/or trained and/or performed in the same fashion as other medical scan analysis functions described herein.

In some embodiments, the lesion measurement function 3045 is not performed by the lesion tracking system 3002. Instead, abnormality classification data 445 corresponding to one or more measurement categories 444 can include lesion measurement data 3040 and/or 3041, and can be received from the medical scan database 342 and/or another subsystem 101 for use as input to the lesion measurement change function 3050.

The lesion measurement change data 3055 can be transmitted via subsystem network interface 265 and/or via another transmitter, for transmission to one or more client devices 120 for display via a display device. For example, the lesion measurement change data can be displayed as text and/or can be displayed visually in conjunction with the image data 410 of medical scan entries 3005 and/or 3006 by utilizing the medical scan assisted review system 102. For example, the measurement data can be displayed as state change data of abnormalities detected in longitudinal data as described in conjunction with the of the medical scan assisted review system 102. Alternatively or in addition, the lesion measurement change data 3055 can be sent to one or more other subsystems for processing, for example, to be utilized as training data by one or more medical scan analysis functions trained by medical scan image analysis system 112. Alternatively or in addition, the lesion measurement change data 3055 can be sent to the medical scan database for storage, for example, as part of the longitudinal data 433 for medical scan entry 3005 and/or 3006. Alternatively or in addition, the lesion measurement data 3040 and/or 3041 can be sent to the medical scan database for storage, for example, as part of abnormality classification data 445 for medical scan entry 3005 and/or 3006, respectively, corresponding to abnormality classifier categories 444 corresponding to a diameter category, an area category, a volume category, or other measurement category.

In some embodiments, a set of three or more medical scans of the same patient are received, and the lesion measurement change data is calculated for consecutive ones of the set of three or more medical scans with respect to scan data. In some embodiments, lesion measurement change data is also calculated for some or all of every possible pair of the medical scans in the set of three or more medical scans.

FIG. 12D illustrates an example of an interface 3080, which can be displayed on a display device of client device 120. The interface can present a selected image slice of each image slice subset 3030 and 3031. A region detected to include the lesion can be overlaid on the image slice as annotation data, and/or other annotation data can be displayed to indicate the lesion. In some embodiments, the diameter measurement data can be displayed visually for medical scan entries 3005 and/or 3006. For example, the image slice of image slice subset 3030 and/or 3031 determined to include the largest diameter can be automatically presented, and a segment connecting the corresponding first pixel and second pixel determined to correspond to endpoints of the diameter can be automatically overlaid on the displayed image slice. In some embodiments, a solid or semi-transparent outline and/or shading of the pixels determined to include the lesion in an image slice of medical scan entry 3005 can be overlaid upon the corresponding pixel coordinates in the display of the corresponding image slice of medical scan entry 3006 by the interface, for example, to visually depict how much the lesion has shrunk, grown, or otherwise changed shape and/or position. In some embodiments, some or all of the lesion measurement data and/or lesion measurement change data is displayed as text in conjunction with the image data. In some embodiments, a three-dimensional rendering of the lesion, generated based on the lesion volume measurement data, can be displayed in accordance with a three-dimensional visualization interface.

In some embodiments, other classification data can be generated based on a diameter measurement, area measurement, and/or volume measurement of the lesion measurement data. For example, the lesion diameter data can be utilized to determine RECIST eligibility data and/or can be utilized to determine whether or not the lesion corresponds to a target lesion or non-target lesion. The lesion change measurement data can be utilized to determine RECIST evaluation data based on the change in the lesion in a more recent scan when compared to a prior scan. In particular, the lesion change measurement data can be utilized to indicate if the lesion is "Complete Response", "Partial Response", "Stable Disease", or "Progressive Disease". In cases where three or more scans are evaluated for a patient, the RECIST evaluation data can reflect changes over time. In some embodiments, a plurality of lesions are detected, measured and tracked in the medical scan entries 3005 and 3006. RECIST eligibility data and/or RECIST evaluation data can be generated for each the plurality of lesions, and/or RECIST evaluation data and/or diagnosis data can be generated based on assessing the plurality of lesions as a whole.

RECIST eligibility data and/or evaluation data can be transmitted to the client device for display via the display device, can be transmitted to the medical scan database for storage in a corresponding medical scan entry as abnormality annotation data 442 and/or as longitudinal data 433, and/or can be transmitted to other subsystems 101, for example, as part of a training set to train a medical scan analysis function. Other standardized medical assessment scores characterizing the lesion, such as a Lung-RADS assessment score, can be generated automatically based on the measurement data.

The medical scan entries 3005 and 3006 can be received at the same time or different times for processing. For example, as medical scan entries 3005 and 3006 correspond to different scan dates, they can be sent to the medical scan lesion tracking system for processing as scans are taken for the patient. In some embodiments, only medical scan entry 3005 is received, and lesion measurement data is calculated for medical scan entry 3005. This can be sent to the client device 120 and/or can be sent to the medical scan database 342 for storage as abnormality annotation data 442 or other data of the medical scan entry 3005. Later, medical scan entry 3006 can be received, and lesion location data and/or lesion measurement data 3040 corresponding to the lesion in medical scan entry 3005 can be fetched from the database in response to generate the lesion measurement change data 3055. The lesion location and/or measurement data of the lesion in medical scan entry 3005 can also be utilized to aid in detecting the lesion in medical scan entry 3006, to aid in generating lesion measurement data for the lesion in medical scan entry 3006.

In some embodiments, the data generated by the lesion tracking system 3002 can be utilized to train a longitudinal lesion model. The longitudinal lesion model can be generated by the lesion tracking model, and/or output of the lesion tracking model can be sent to another subsystem, such as the medical scan image analysis system. For example, a training step 1352 can be performed on a plurality of sets of longitudinal data, where each set of longitudinal data corresponds to a patient and includes the lesion measurement data, the lesion measurement change data, the classification data such as RECIST eligibility data, RECIST evaluation data, and/or Lung-RADS assessment data determined for a corresponding plurality of medical scans entries of the patient. Each of the plurality of sets of longitudinal data can include other fields of the corresponding plurality of medical scan entries of the patient, such as the image data, diagnosis data, patient history, and/or other relevant fields of one or more medical scan entries of the corresponding patient.

The longitudinal lesion model can be utilized to perform an inference function on subsequent medical scans, such as a single medical scan entry of a new patient or a set of medical scan entries of a new patient. The inference function can be performed by the lesion tracking system 3002, by the medical scan image analysis system 112, and/or by another subsystem 101. The inference function corresponding to the longitudinal lesion model can be a medical scan analysis function, and can be trained and/or performed as discussed herein with regards to medical scan analysis function.

By performing the inference function on one or more medical scans of a patient, lesion change prediction data can be generated for at least one lesion detected in the one or more medical scans. For example, the lesion change prediction data can include a lesion growth factor or a lesion shrinkage factor. Alternatively or in addition, the inference function can generate other inference data, such as other assessment and/or prediction data. This can include inference data that assesses lesion growth and/or shrinkage in the set of medical scans, that assesses and/or predicts changes in the severity of the patient's condition, that diagnoses the new patient, that includes determined treatment steps for the new patient, that determines whether the new patient is responding favorably or unfavorably to treatment, and/or that otherwise assesses and/or predicts the new patient's current condition and/or future condition. Some or all of the inference data generated by performing the inference function can be determined based on assessing the size and/or characteristics of detected lesions, and/or based on predicting the change in size or change in characteristics of detected lesions.

In some embodiments, performing the inference function includes performing the lesion measurement function on the one or more medical scans of the new patient and/or includes performing the lesion measurement change function on the one or more medical scans of the new patient. The lesion measurement data and/or lesion measurement change data generated for the new patient can be input to the inference function in addition to or instead of the one or more medical scans entries themselves.

The lesion change prediction data or other inference data can be transmitted to a client device for display on a display device via an interface, for example, in conjunction with the one or more medical scans of the new patient. Presenting the lesion change prediction data can include overlaying a predicted diameter, area, and/or volume change of the lesion, for example, by displaying a solid or semi-transparent outline and/or shading of the pixels in accordance with a predicted future size, a predicted future shape, and/or predicted future location of the lesion in at least one image slice of the one or more new medical scan entries, to visually depict how much the lesion is predicted to shrink, grow, or otherwise change shape and/or position. In some embodiments, a predicted future three-dimensional rendering of the lesion can be displayed in accordance with a three-dimensional visualization interface.

In some embodiments, the inference function can generate a set of lesion change prediction data corresponding to a set of different projected time spans. For example, lesion change prediction data can be generated for one year, two years, and three years in the future, and the prediction data for each projected time span can be sent to the client device for display. In some embodiments, the interface can prompt the user to select one of the set of different projected time spans, and the prediction data for the selected one of the projected time spans will be displayed accordingly. To enable this capability, the longitudinal lesion model can be trained on sets of longitudinal data with medical scans of varying time spans, and the relative time between dates of medical scans and/or dates of other data in a set of longitudinal data can be utilized in performing the training step.

In some embodiments, before execution of the inference function on the one or more medical scans of the new patient, a user interacting with the interface displayed by the display device can select a projected time span from a discrete set of options, and/or can enter any projected time span. The inference function can be performed by utilizing the selected projected time span received from the client device, and prediction data can reflect this selected projected time span from the current date and/or from a date of the most recent scan in the one or more medical scans for the new patient. For example, if the selected projected time span is 18 months, the inference data can include a lesion growth factor, a lesion shrinkage factor, and/or other prediction data projected for 18 months in the future.

In some embodiments, medical scan entry 3005 and/or medical scan entry 3006 already have associated measurement data. Human assessment data, such as human measurement data corresponding to a radiologist measurement or other human measurement of the lesion, can be included in the medical scan entry and/or can be received in conjunction with the medical scan entry. For example, a human diameter measurement can be included in the human assessment data of a medical scan corresponding to a radiologist's documentation of the diameter based on visual inspection of the image data of the medical scan. This human assessment data can correspond to abnormality annotation data 442 with annotation author data 450 corresponding to the radiologist or other human that took the measurement. This annotation author data 450 can correspond to an identifier of the radiologist or other human in a corresponding user profile entry 354 the user database 344. The human assessment data can also include abnormality classification data 445, such as RECIST eligibility data, RECIST evaluation data, a Lung-RADS assessment score, or other abnormality classification data 445 discussed herein.

Performing one or more of the lesion measurement functions on the medical scan entry 3005 and/or 3006 can be further utilized to measure the accuracy of the human assessment data taken by a radiologist. For example, a radiologist may have measured a diameter incorrectly by failing to measure the distance between two points of the perimeter of the lesion properly, by identifying a wrong segment on an image slice as being the maximum segment connecting perimeter points of the lesion, by identifying a maximum segment in an image slice when a different image slice includes a portion of the lesion with a larger maximum segment, by considering pixels of an image slice that are not part of the lesion or do not correspond to the perimeter of the lesion when determining the diameter, by failing to consider a true diameter that connects two points along the surface of a three-dimensional representation of the lesion where the two points are on different image slices of the medical scan, by mischaracterizing the scan and taking a measurement for a lesion that is not actually a lesion, by mischaracterizing the scan and failing to take a measurement for a lesion based on a determination that the lesion did not exist or based on a determination that the lesion does not meet criteria such as RECIST criteria, by characterizing a lesion as a target lesion or non-target lesion improperly, by characterizing a lesion or the medical scan as "Complete Response", "Partial Response", "Stable Disease", or "Progressive Disease" improperly, by determining abnormality classification data 445 incorrectly, by otherwise measuring and/or characterizing the lesion improperly, and/or by otherwise measuring and/or characterizing a change in the lesion across multiple medical scans of the patient improperly.

The accuracy of human assessment data can be determined by generating automated assessment data. The automated assessment data can be generated by performing the lesion detection function, by performing the one or more lesion measurement functions, and/or by classifying the lesion, for example, by performing abnormality classification step 1374. The lesion location determined in the detection data, the lesion diameter, area and/or volume determined in the lesion measurement data, and/or abnormality classification data 445 for one or more abnormality classifier categories 444 can be compared to corresponding portions of the human assessment data by performing a similarity function, by computing a difference in values, by determining whether or not the values match or otherwise compare favorably, and/or by computing a Euclidean distance between feature vectors of the human assessment data and the automated assessment data.

The difference between some or all of the human assessment data and the automated assessment data can be compared to a threshold to determine if the human assessment data is correct or incorrect. The difference between some or all of the human assessment data and the automated assessment data can also correspond to accuracy data such as an accuracy score, and the accuracy score can be assigned to the corresponding radiologist or other human. For example, the accuracy score can be mapped to the radiologist in the corresponding user profile entry 354 of the user database 344. The accuracy score can also be transmitted to a client device for display via the display device. Accuracy scores that compare unfavorably to a threshold can be utilized to automatically flag radiologists or other humans that recorded an incorrect measurement or characterization of a lesion, and/or are consistently recording incorrect measurements or characterizations of lesions.

FIG. 13A presents a retroactive discrepancy flagging system 3100. The retroactive discrepancy flagging system 3100 can be utilized to flag medical scans based on the result of performing an automated, retroactive review of a set of selected medical scans. Retroactive discrepancy notifications can be generated that provide retrospective insights regarding potential errors made by medical professionals in reviewing a medical scan and/or generating a medical report. The retroactive discrepancy flagging system 3100 improves the technology of viewing tools and review systems, by automatically determining and flagging potential errors for further review.

In various embodiments, sets of one or more medical scans, each corresponding to one of a set of patients and/or one of a set of studies, can be selected for retroactive review. These selected medical scans and their corresponding medical reports can be retrieved in response. Automated assessment data can be generated for each of the one or more medical scans by performing an inference function on the medical scan by utilizing a computer vision model trained on a plurality of medical scans. Human assessment data, corresponding to diagnosis or findings made by a radiologist or other human in conjunction with viewing the one or more medical scans, can be generated based on findings extracted from the corresponding medical report. A consensus function can be performed by comparing the automated assessment data and the human assessment data, and the retroactive discrepancy flagging system can determine whether the comparison is favorable or unfavorable. When the result of the consensus function indicates that the comparison is unfavorable, the corresponding one or more medical scans can be flagged in retroactive discrepancy notifications that can be transmitted to a client device for display and used, for example, for peer-review or other review and correction of the medical report, in generating updated performance data for medical professions that can be evaluated by healthcare management for training, education, performance reviews, for manual billing correction, etc. Furthermore, retroactive discrepancy notifications can be sent for review by another automated subsystem 101 and used, for example, to automatically generate updated billing data to bill for missed diagnoses, to determine error factors and other trends associated with particular medical professionals, institutions, viewing tools and specific interface functions, medical conditions, etc., and/or other subsystems 101 that perform other functions in either a semi-automated or fully automated fashion.

As used herein "review", contemplates peer-review of retrospective discrepancy notifications by a medical professional other than the medical professional that authored the particular medical report, re-review of retrospective discrepancy notifications by a medical professional that authored the particular medical report, semi-automated review of retrospective discrepancy notifications by another subsystem 101 that includes feedback from a medical professional, and further fully automated review of retrospective discrepancy notifications by another subsystem 101 without feedback from a medical professional.

As shown in FIG. 13A, the retroactive discrepancy flagging system 3100 can communicate bi-directionally, via network 150, with the medical scan database 342, with a medical report database 392, with user database 344, and/or with other databases of the database storage system 140, with one or more client devices 120, and/or, while not shown in FIG. 13A, with one or more subsystems 101 of FIG. 1. In some embodiments, the medical report database can be implemented by utilizing report database 2625. In some embodiments, medical reports are instead retrieved as report data 449 from the medical scan database 342, and/or the medical report database 392 contains entries corresponding to report data 449 of corresponding medical scan entries of the medical scan database 342.

In various embodiments, the retroactive discrepancy flagging system 3100 is implemented via at least one processor; and a memory that stores operational instructions that, when executed by the at least one processor, cause the retroactive discrepancy flagging system to receive, via a network interface such as subsystem network interface 265, a medical scan and a medical report corresponding to the medical scan that was written by a medical professional/user in conjunction with review of the medical scan. The retroactive discrepancy flagging system also operates to generate automated assessment data by performing an inference function 3110 on the first medical scan utilizing a computer vision model trained on a plurality of medical scans; generates human assessment data by performing an extraction function 3120 on the medical report; and further generates consensus data by performing a consensus function 3195 on the automated assessment data and the human assessment data. Performing the consensus function 3195 can include comparing the automated assessment data to the human assessment data. The retroactive discrepancy flagging system 3100 also operates to determine if the consensus data indicates the automated assessment data compares favorably or unfavorably to the first human assessment data, i.e. they match or they do not match. A retroactive discrepancy notification is generated in response to determining that the consensus data indicates the automated assessment data compares unfavorably to the human assessment data.

In various embodiments, the retroactive discrepancy notification includes at least one image associated with the medical scan and retroactive discrepancy data that indicates at least one discrepancy between the automated assessment data and the human assessment data. For example, the retroactive discrepancy notification can include an identification of the medical scan, an identification of a particular subset of images and/or image portions in the medical scan that include the discrepancy and/or a plurality of medical conditions that are determined to be either present of absent, based on either the automated assessment data or the human assessment data. The retroactive discrepancy notification can also include or indicate the medical report and an identification of the medical professional that generated the medical report, as well as information pertaining to the nature of the discrepancy. For example, the retroactive discrepancy notification can indicate that the automated assessment data indicated the presence of a particular abnormality or other medical condition while the human assessment data did not or vice versa. The particular, an abnormality or other medical condition can be identified, for example, by including a corresponding medical code, medical term and or other abnormality classification data in the retroactive discrepancy notification. In addition or in the alternative, the retroactive discrepancy notification can provide other information regarding the generation of the medical report such as the time of day the report was generated, the number of medical reports generated by the user in a review session that included the subject medical report, the progress through the review session at the time the report was generated, a preliminary diagnosis and/or a request for review by the user by another medical professional, the type of PACS viewer or other user interface that was used by the user to generate the report, and/or other data or metadata derived from the medical report or medical scan.

The retroactive discrepancy flagging system 3100 also operates to transmit, via the network interface such as subsystem network interface 265, the retroactive discrepancy notification via the network 150 to the client device 120 and/or to other subsystems 101. Consider an example where the retroactive discrepancy notification is sent to client device 120 for peer review. The retroactive discrepancy data can also include a prompt to update the human assessment data for display via an interactive user interface of the client device. In this fashion, the peer reviewer or other user of the client device 120 can respond to the prompt by either correcting the human assessment data or the automated assessment data and, if necessary, to generate discrepancy correction data that can be sent to the database storage system that can be used to correct the medical report. In particular, the client device 120 generates, in response to user interaction with the interactive user interface and in response to the prompt, the discrepancy correction data that indicates the correction or that provides a complete corrected medical report.

In various embodiments, the retroactive discrepancy flagging system 3100 is an additional subsystem 101 of the medical scan processing system 100, implemented by utilizing the subsystem memory device 245, subsystem processing device 235, and/or subsystem network interface 265 of FIG. 2B. In some embodiments, the retroactive discrepancy flagging system 3100 utilizes, or otherwise communicates with, the central server system 2640. For example, some or all of the databases of the database storage system 140 are populated with de-identified data generated by the medical picture archive integration system 2600. The retroactive discrepancy flagging system 3100 can receive de-identified medical scans, annotation data, and/or reports directly from the medical picture archive integration system 2600. For example, the retroactive discrepancy flagging system 3100 can request de-identified medical scans, annotation data, and/or reports that match requested criteria. In some embodiments, some or all of the retroactive discrepancy flagging system 3100 is implemented by utilizing other subsystems 101 and/or is operable to perform functions or other operations described in conjunction with one or more other subsystems 101.

The retroactive discrepancy flagging system 3100 can retroactively select one or more medical scans for review. The one or more medical scans can be selected randomly, pseudo-randomly, as part of a non-random/systematic audit, can be selected based on selected criteria, can be selected based on a peer-review schedule, can be selected based on a determined proportion of medical scans to review, can be determined based on a selected frequency or rate of medical scans to review within a time frame. Further, such an audit can be a non-random audit associated with the particular medical professional triggered by the identification of one or more prior errors associated with one or more prior retrospective discrepancy notifications or otherwise based on a number of medical scans, such as more than a threshold number, that have previously been flagged for review, can be otherwise selected based on prior review results, can be selected in response to identifying repeated or systematic or cognitive errors associated with a particular PACS viewing system, user, and/or institution, can be selected based on the presence or absence of a particular medical condition and/or can be selected based on other factors. This selection can include selecting the number of medical scans for review; selecting medical scans for review that correspond to a selected medical scan type, modality and/or a selected anatomical region; selecting medical scans for review where a selected medical professional authored or otherwise generated the corresponding annotation data, diagnosis data, and/or report data; selecting medical scans for review associated with a selected medical institution; selecting medical scans for review associated with a selected geographic region; selected selecting medical scans for review associated with a selected diagnosis type; selecting medical scans for review associated with patients that meet selected patient history or patient demographic criteria; selected selecting medical scans for review based on other selection criteria and/or otherwise selecting medical scans based on received criteria and/or criteria automatically determined by the retroactive discrepancy flagging system 3100. Some or all of the selection criteria can be received via user input to a user interface, via the network, and/or via one or more other subsystems 101.

The selection criteria and/or identifiers for selected medical scans, medical reports, medical professionals, medical institutions, and/or patients can be utilized to by the retroactive discrepancy flagging system 3100 to fetch the selected medical scans and/or corresponding medical reports from database system 140. In various embodiments, the medical scans and/or corresponding medical reports can be retrieved from a medical picture archive system and/or a report database. In some embodiments, the medical scans and/or corresponding medical reports can be de-identified prior to review, for example, by utilizing the medical picture archive integration system 2600.

Upon receiving the medical scan and/or the medical report, human assessment data can be generated by applying an extraction function 3120 to the medical report. In some embodiments, only medical scans are received, and extraction function 3120 is applied to metadata of the medical scan or other human-generated findings included along with image data of the medical scan. The human assessment data can correspond to the human assessment data discussed in conjunction with the lesion tracking system 3002, can correspond to annotation data generated by a medical professional, can correspond to measurements made by a medical professional of lesions or other abnormalities detected by the medical professional, can correspond to a classification made by the medical professional of one or more abnormalities or other medical conditions detected by the medical professional, can correspond to a diagnosis made by the medical professional, and/or can correspond to other measurements or findings in the medical scan, determined by a human. The extraction function can be utilized to extract the human assessment data from metadata of the medical scan, from fields of the medical scan entry 352 such as from diagnosis data 440, and/or from the text, metadata, or other fields of the medical report. In some embodiments, performing the extraction function 3120 can include performing a medical scan natural language analysis function and/or inference function. For example, the medical scan natural language analysis function can be performed on text corresponding to the findings made by the medical professional, such as text of the medical report.

Automated assessment data is generated by performing at least one inference function 3110 on the medical scan. In some embodiments, the inference function 3110 can be performed on the image data of medical scans alone. In other embodiments, the inference function 3110 can utilize other pertinent data in addition to the image data, such as patient history or other data of the medical scan entry 342, to generate the automated assessment data. The inference function 3110 can utilize a computer vision model, for example, trained by medical scan image analysis system 112 on a plurality of medical scans as discussed herein. Performing the inference function 3110 can include performing one or more lesion measurement functions discussed herein to generate measurement data, and/or the automated assessment data can correspond to the automated assessment data discussed in conjunction with the lesion tracking system 3002. Performing the inference function 3110 can include performing any medical scan analysis function and/or inference function discussed herein to generate automated assessment data that corresponds to automatically generated annotation data, diagnosis data, abnormality detection data, and/or abnormality classification data associated with an abnormality or other medical condition.

Consensus function 3195 can be performed on the human assessment data and the automated assessment data to generate consensus data. One or more types of fields and/or values of the automated assessment data can correspond to one or more same types of fields and/or values of the human assessment data to enable comparison of the human assessment data and the automated assessment data. Performing the consensus function can include measuring a disagreement between the automated assessment data and the human assessment data and determining whether the measured disagreement compares favorably or unfavorably to a disagreement threshold. For example, measuring the disagreement can include performing a similarity function, can include computing a difference in values or logical results (e.g. yes versus no, a condition is present versus a condition is not present, a scan is normal versus a scan is abnormal, etc.), can include determining whether or not the values or logical results match or otherwise compare favorably, and/or by computing a Euclidean distance between feature vectors of the human assessment data and the automated assessment data. When the measured disagreement compares unfavorably to the disagreement threshold, the comparison is determined to be unfavorable, and when the measured disagreement compares favorably to the disagreement threshold, the comparison is determined to be favorable. The disagreement threshold can be set or predetermined to permit no level of disagreement or can be set or predetermined to permit some modest level of disagreement. Medical scans yielding an unfavorable comparison in performing the consensus function can be flagged for generation of a corresponding retroactive discrepancy notification.

In various embodiments, retroactive review/audit of entire studies is conducted. The retroactive discrepancy flagging system can retrieve a plurality of sets of longitudinal data for review, where each set of longitudinal data corresponds to one of a set of patients. The retroactive discrepancy flagging system can extract the human assessment data for each set of longitudinal data, can generate automated assessment data for each set of longitudinal data, and can compare this human assessment data to the automated assessment data for each set of longitudinal data. The longitudinal data corresponding to a patient can be is reviewed, for example, as discussed in conjunction with the lesion tracking system 3002. The human assessment data can correspond to human measurement of one or more lesions and/or human classification of one or more lesions. The automated assessment data can be generated by performing the one or more lesion measurement functions and/or by classifying the lesion by performing abnormality classification step 1374 as discussed herein. The consensus function can be performed, and when the human assessment data and the automated assessment data of a set of longitudinal data yield an unfavorable comparison, the entire study can be flagged for generation of a corresponding retroactive discrepancy notification.

Medical scans or entire studies flagged for review/audit can be indicated in a notification transmitted, for example, to at least one client device 120, for display by a display device of the client device. In some embodiments, a notification is transmitted indicating the result of the consensus function for all retroactively reviewed scans, and thus both favorable and unfavorable results of the consensus function are indicated in one or more notifications for display by a display device of the client device. In other embodiments, notifications only indicate medial scans that are flagged for review.

In some embodiments, the automated assessment data and/or the human assessment data are included in the retroactive discrepancy notification and can be displayed by the display device of the client device 120 via an interactive user interface. In such embodiments, an administrator or other human can view the discrepancy between the automated assessment data and the human assessment data, for example, via the interactive user interface of the display device displaying the automated assessment data the human assessment data. In some embodiments, the medical scan and/or set of longitudinal data is also sent to the client device 120, and the human assessment data and/or automated assessment data is presented in conjunction with the medical scan and/or the set of longitudinal data. For example, annotation data, diagnosis data, lesion measurements, and/or other data of the human assessment data and/or the automated assessment data is presented, for example, overlaying one or more displayed image slices of the medical scan, where the findings of the human assessment data are distinguished from the findings of the automated assessment data. In some embodiments, the disagreement measured in performing the consensus function are visually displayed, overlaying one or more displayed image slices of the medical scan. In the case where lesion measurement differences are used to generate the consensus data, the lesion measurement of the human assessment data and the automated assessment data can be displayed, and/or a highlighted area or line segments overlaying the image representing the measured disagreement in human versus automated measurements can be displayed in conjunction with the one or more displayed image slices.

In some embodiments, one or more medical professionals can be automatically flagged themselves if they authored, wrote, generated, oversaw, and/or are otherwise responsible for or associated with the annotation data, diagnosis data, and/or medical report utilized to generate human assessment data of a medical scan or study that is flagged for peer-review. As used herein, one or more one or more medical professionals that "authored the human assessment data" indicates that the medical professional authored, wrote, generated, oversaw, and/or is otherwise responsible for or associated with the annotation data, diagnosis data, and/or medical report utilized by the retroactive discrepancy flagging system 3100 to generate the corresponding human assessment data. A medical professional that authored the human assessment data of a medical scan or study flagged for review can be determined based on the annotation author data 450 associated with the medical scan.

In some embodiments, a medical professional is only flagged once a threshold number or proportion of medical scans for which the medical professional authored the human assessment data are flagged for generation of a corresponding retroactive discrepancy notification. In some embodiments, a medical professional is only flagged when the disagreement measurement exceeds a second disagreement threshold, which can be higher or lower than the disagreement threshold utilized to flag the medical scan itself for review, and can be different for different medical professionals. For example, the second disagreement threshold can be based on the performance score data of the medical professional, where a more favorable accuracy score yields a less strict second disagreement threshold than a less favorable accuracy score. As another example, the second disagreement threshold can be a function of the number, proportion, or frequency of medical scans for which the medical professional authored the human assessment data that were previously flagged for peer-review. For example, the second disagreement threshold can be stricter for a medical professional that authored human assessment data for a higher number, proportion, or frequency of medical scans flagged for peer-review than that for a medical professional that authored that authored human assessment data for a lower number, proportion, or frequency of medical scans flagged for review. As another example, the second disagreement threshold can be a function of the magnitude of the disagreement measured for one or more medical scans for which the medical professional authored the human assessment data. For example, the second disagreement threshold can be stricter for a medical professional that authored human assessment data with greater disagreement measured from the corresponding automated assessment data than that for a medical professional that authored human assessment data with lower disagreement measured from the corresponding automated assessment. In some embodiments, the medical professional is only flagged when human assessment data authored by the medical professional for at least a threshold number, proportion, or frequency of medical scans for which the medical professional authored the human assessment data yields a measured disagreement that compares unfavorably to the second disagreement threshold.

Once a medical professional is flagged, a notification can be transmitted to the client device 120 for display via a display device can be generated indicating the flagged medical professional. Alternatively or in addition, once a medical professional is flagged, credentials and/or performance of the medical professional stored in a user database is updated. For example, the performance score data 530 of a user profile entry 354 of user database 344 corresponding to a flagged medical professional can be updated as a result of the medical professional being flagged. Alternatively or in addition, use of other subsystems 101 by flagged medical professionals can be suspended for or terminated, for example, where flagged medical professionals are not permitted to generate annotation data, diagnosis data, or report data, for example, by using the medical scan assisted review system 102, or otherwise are not permitted to generate to generate annotation data, diagnosis data, or report data to be mapped to additional medical scans for a fixed or indefinite period of time. Alternatively or in addition, peer-review is automatically initiated for some or all additional medical scans or studies for which a flagged medical professional authored the corresponding annotation data, diagnosis data, and/or report data.

In some embodiments, once a medical professional is flagged, some or all additional medical scans or studies for which the medical professional authored the corresponding annotation data, diagnosis data, and/or report data can be fetched automatically by the retroactive discrepancy flagging system 3100 for retroactive review, where human assessment data and automated assessment data is generated for these fetched scans to determine if some or all these fetched medical scans associated with the flagged medical professional also require review. In these cases, a stricter disagreement threshold can be selected in performing the consensus function on these additional medical scans, in response to determining the medical professional is flagged. The stricter disagreement threshold can be a function of the number, proportion, or frequency of medical scans for which the medical professional authored the human assessment data that were flagged for review. For example, the magnitude of the differential from an original disagreement threshold to the stricter disagreement threshold can be an increasing function of the number, proportion, or frequency of medical scans, for which the medical professional authored the human assessment data, that were flagged for review.

The stricter disagreement threshold can be a function of the magnitude of the disagreement measured for one or more medical scans for which the medical professional authored the human assessment data. For example, the magnitude of the differential from an original disagreement threshold to the stricter disagreement threshold can be an increasing function of the magnitude of the measured disagreement for one or more flagged medical scans for which the medical professional authored the human assessment data.

In some embodiments, the performance score data 530 of a user profile entry 354 for a medical professional of user database 344, or other database tracking accuracy of the medical professionals, is updated in response to retroactively reviewing medical scans for which the human assessment data was authored by the medical professional, even if the medical professional themselves have not been flagged. For example, user profile entries for medical professionals with zero or a low number of corresponding medical scans flagged for review can reflect this favorable performance of the medical professional. As another example, medical professionals with corresponding disagreement measurements that are consistently near zero or otherwise well-below the disagreement threshold can have user profile entries that reflect this high accuracy, with very favorable performance scores. Meanwhile, medical professionals with corresponding disagreement measurements that are consistently barely-below the disagreement threshold can have user profile entries that reflect this acceptable, but not exceptional, accuracy, with acceptable but less favorable performance scores.

The performance score data can indicate the number of times the medical professional has authored human assessment data for scans flagged for review, can indicate the frequency or proportion of medical scans for which the medical professional has authored the human assessment data that have been flagged for review, and/or can indicate the value of the disagreement measured in performing the consensus function on one or more medical scans for which the medical professional authored the human assessment data. The accuracy data 531 can be updated for each retroactively reviewed scan corresponding the medical professional, and/or can be updated only for each scan corresponding to the medical professional that is flagged for review. In some embodiments, the accuracy data can be computed and updated based on the average disagreement measured for some or all retroactively reviewed medical scans for which the medical professional authored the human assessment data. In some embodiments, the accuracy data 531 can be updated to a more favorable value in response to the human assessment data of a medical scan comparing favorably to the automated assessment data, and/or can be updated to a less favorable value in response to the human assessment data of a medical scan comparing unfavorably to the automated assessment data. In some embodiments, the accuracy data 531 can be updated as a function of the magnitude of the disagreement measured. For example, the magnitude of the differential from a first accuracy value to an updated, less favorable value, can be an increasing function of the measured disagreement for one or more flagged medical scans for which the medical professional authored the human assessment data. In some embodiments, the accuracy data 531 can be updated as a function of the number of flagged medical scans for which the medical professional authored the human assessment data. For example, the value of the differential from a first accuracy value to an updated, less favorable value, can be an increasing function of the number, proportion, or frequency of medical scans for which the medical professional authored the human assessment data, that were flagged for peer-review. In some embodiments, the disagreement threshold utilized in performing the consensus function for any medical scan can be a function the accuracy data, or other performance score data, of the medical professional that authored the human assessment data.

Furthermore, medical institutions or entities such as hospitals that employ, train, or otherwise are associated with the medical professionals that authored the human assessment data can be flagged and tracked in the same fashion as discussed with regards to the medical professionals themselves, for example, where medical institutions are flagged based on a number, proportion, or frequency of medical scans authored by medical professionals associated with the medical institution that are flagged for review, based on the magnitude of disagreement of medical scans authored by medical professionals associated with the medical institution, and/or based on a number, proportion, or frequency of flagged medical professionals associated with the medical institution. In response to a medical institution being flagged, the medical institution can similarly have access to subsystems 101 suspended or terminated, can similarly have review automatically initiated some or all other medical scans associated with the medical institution, can similarly have a user profile entry associated with the medical institution updated accordingly, and/or the retroactive discrepancy flagging system can similarly automatically fetch some or all other medical scans associated with the medical institution for retroactive review by the retroactive discrepancy flagging system, utilizing the same disagreement threshold or a stricter disagreement threshold.

Furthermore, the retroactive discrepancy flagging system 3100 can track trends across medical scans, medical professionals, and/or medical institutions in the retroactive review and/or in flagging medical scans, medical professionals, and/or medical institutions. For example, the retroactive discrepancy flagging system can determine trends that correlate to higher or lower number, proportion, or frequency of flagged medical scans, medical professionals, and/or medical institutions and/or can determine trends that that correlate to higher or lower magnitude of disagreement measurement. For example, the retroactive discrepancy flagging system can track these trends across types of medical scans, anatomical regions of medical scans, particular attributes of patient history, different geographic regions, qualifications or backgrounds of medical professionals and/or medical institutions, and/or other attributes mapped to medical scans or medical professionals, for example, in medical scan entries 352 or user profile entries 354. For example, the retroactive discrepancy flagging system can identify a geographic region where a particular scan type is flagged for review more frequently. As another example, the retroactive discrepancy flagging system can identify qualifications of medical professionals that correlate to very low disagreement measurements and/or medical scans generated by particular model of imaging machine that correlates to very low disagreement measurements. Trends that are identified as statistically significant or otherwise compare favorably to a significance threshold can be transmitted as a notification for display by a display device of a client device. Trends that are identified as statistically significant can also be used to automatically adjust disagreement thresholds for subsequently received scans that are reviewed retroactively that match the criteria of the trend. For example, in response to identifying the geographic region where a particular scan type is flagged for review more frequently, the disagreement threshold for subsequently received scans from this geographic region that match the particular scan type can be updated to a stricter disagreement threshold, to ensure that these scans are reviewed with more scrutiny. As another example, in response to identifying the particular model of imaging machine that correlates to very low disagreement measurements, the disagreement threshold for subsequently received scans generated by this particular model of imaging machine can be updated to a less strict disagreement threshold. Furthermore, in response to determining a trend that correlates to higher number, proportion, or frequency of disagreement, the retroactive discrepancy flagging system can automatically fetch additional medical scans corresponding to the criteria of the trend for retroactive review and/or automatically initiate peer-review on additional medical scans corresponding to the criteria of the trend.

In some embodiments, trends that correlates to higher number, proportion, or frequency of disagreement can be utilized to generate, update and/or standardize review standards across a medical institution, across multiple medical institutions, and/or across multiple geographic regions, for example, where the standardized review standards indicate a number and/or frequency of scans to be peer-reviewed that can be the same or different for different criteria, and/or where the review standards indicate selection criteria in randomly or deterministically selecting scans for review.

In some embodiments, once retroactive review of a medical scan is complete and the medical scan is flagged for generation of a corresponding retroactive discrepancy notification, the retroactive discrepancy flagging system 3100, can also automatically initiate and/or facilitate a peer-review process. Initiation and/or facilitation of the peer-review process can utilize other subsystems 101 discussed herein, such as the medical scan annotating system 106 and/or medical scan assisted review system 102, to facilitate review of the flagged medical scans by other medical professionals, to determine a final consensus based on the human assessment data received from multiple medical professionals that reviewed the data, and/or to update medical reports or final diagnosis of medical scans based on the final consensus.

This initiation of the peer-review process can include determining time sensitivity, severity, and/or rarity of the one or more medical scans, for example, based on inference data generated in performing the inference function. Alternatively or in addition, initiation of the peer-review process can include determining if one medical professionals, or a selected number of medical professionals, should review the one or more medical scans. This can be used to determine qualification, performance, or expertise criteria for medical professionals that will review the one or more medical scans. For example, more severe medical scans can necessitate review by medical professionals with higher qualifications and/or performance scores, and/or rarer scans can necessitate review by a greater number of medical professionals. Based on these determinations, one or more medical professionals can be selected to peer-review the flagged medical scans, for example, based on the desired number of medical professionals for peer-review and/or based on the qualification criteria, expertise criteria, time sensitivity, severity, and/or rarity. For example, medical professionals that meet the desired criteria can be selected from user database 344, based on performance score data and/or qualification data of the user entries comparing favorably to the desired criteria.

The retroactive discrepancy flagging system 3100 and/or one or more other subsystems 101 can facilitate transmission of the one or more medical scans to client devices associated with the one or more new medical professionals selected to conduct the peer-review, and/or can facilitate queuing of the one or more medical scans for review by the new medical professionals. Review of the one or more medical scans by the new medical professionals can be facilitated, for example, by utilizing the medical scan assisted review system 102. In some embodiments, the human assessment data and/or automated assessment data generated in the retroactive review are transmitted to the selected medical professional and are displayed by the display device to assist the new medical professional in conducting the peer-review of the medical scan. In other embodiments, a blind peer-review is performed without knowledge of the human assessment data and/or automated assessment data.

Annotation data, diagnosis data, report data, or other data indicating findings made by the new medical professionals in their peer-review of the one or more medical scans can then be received by the retroactive discrepancy flagging system 3100 and/or one or more other subsystems 101 that includes the new medical professional's findings. In some embodiments, the peer-review system performs the same or different extraction function to generate new human assessment data corresponding to the received annotation data, diagnosis data, report data, and or other data of the peer-review.

The retroactive discrepancy flagging system 3100 and/or one or more other subsystems 101 can then perform the same or different consensus function on the original human assessment data and new human assessment data received from one or more medical professionals. Furthermore, the same or different consensus function can be performed on the automated assessment data and the new human assessment data received from one or more medical professionals. This can include first computing an average consensus between new human assessment data received from multiple medical professionals, and then performing the consensus function on this average consensus of the new human assessment data and the original human assessment data, and/or performing the consensus function on the average consensus of the new human assessment data and the automated assessment data. The average consensus can be computed as a weighted average, for example, where medical professionals with more favorable qualifications and/or performance scores are weighted higher in determining the average consensus. Furthermore, in performing the consensus function, the average consensus can be weighted higher than the original human assessment data, for example, where the relative weight of average consensus of the new human assessment data to the original human assessment data, or to the automated assessment data, can be an increasing function of the number of medical professionals that contributed. As another example, the relative weight of average consensus of the new human assessment data to the original human assessment data, or to the automated assessment data, is a decreasing function of the measured disagreement amongst the plurality new human assessment data.

The result of the peer-review can then be evaluated based on the result of the consensus function, and the result can be transmitted as a notification to the client device for display on the display device. Determining the result of the peer-review can include determining that the original human assessment data stands, for example, in response to determining it compares favorably to the new human assessment data. In response to determining the original human assessment data stands, the retroactive discrepancy flagging system can reverse or correct any action previously taken in response to flagging the medical scan, for example, where the medical scan and/or a corresponding medical professional or medical institution is unflagged, where the medical scan has the original medical report and/or other diagnosis data restored, and/or where the corresponding medical professional or medical institution has a previous performance score restored.

Alternatively or in addition, determining the result of the peer-review can include determining the original human assessment data can is overturned, and can further include determining the new assessment data and/or the automated assessment data stands, for example, when the original human assessment data compares unfavorably to the new assessment data, and/or when the new human assessment data compares favorably to the automated assessment data. In response to determining the new assessment data and/or the automated assessment data stands, updated annotation data, diagnosis data, and/or report data can be automatically generated to reflect the new assessment data and/or the automated assessment data, and the updated annotation data, diagnosis data, and/or report data can be mapped to the medical scan, for example, in an update to the medical scan database 142 and/or in a transmission to a client device.

Alternatively or in addition, determining the result of the peer-review can include determining the results are inconclusive and/or that further peer-review is required, for example, when the original human assessment data compares unfavorably to the new assessment data, when the new human assessment data compares unfavorably to the automated assessment data, and/or when the disagreement amongst the new assessment data received from multiple medical professionals exceeds a threshold. In response, some or all of these steps of initiating and facilitating this peer-review process can repeat, where new medical professionals are identified to provide additional human assessment data for the inconclusive medical scan. Alternatively or in addition, the retroactive discrepancy flagging system can initiate remediation of the inference function utilized to generate the automated assessment data in response to the original human assessment data comparing unfavorably to the new assessment data, the new human assessment data comparing unfavorably to the automated assessment data, and/or the disagreement amongst the new assessment data received from multiple medical professionals exceeding a threshold. For example, the remediation step 1140 can be initiated for the inference function.

FIGS. 13B-13D are illustrations 3102-1, 3102-2 and 3102-3 of example interfaces displayed by a display device of a client device 120 in accordance with various embodiments. In each illustration an annotated medical scan 3104 is presented along with retroactive discrepancy data that indicates at least one discrepancy between the automated assessment data and the human assessment data.

In various embodiments, retroactive discrepancy notifications are used to present discrepancies between automated model findings and radiologist findings in a 2-column format for a single scan or multiple scans, enabling human review and/or correction of model findings and/or NLP report processing as needed to correct any mischaracterized discrepancies. The rows presented can correspond to types of abnormalities, where each cell indicates whether or not the abnormality was detected by the model and/or included in the report. This can aid in reviewing which particular types of abnormalities led to discrepancy. Consider an example where, for cardiomegaly, column 1 and column 2 both say not present, but for pneumothorax, column 1 says present, and column 2 says not present.

This format also can be used to indicate discrepancy in detected abnormality type, even when both the model and radiologist both indicated the scan was abnormal. Consider an example where, for a cardiomegaly row, cell for column 1 says present and cell for column 2 says not present, but for pneumothorax row, cell for column 1 says not present, and cell for column 2 says present. In this case, both the model and radiologist indicate scan is abnormal, but for different reasons, so a discrepancy still exists. In various embodiments, types of abnormalities with discrepancies can be sorted to the top, and/or abnormalities without discrepancies can be filtered out or sorted to the bottom.

Such an interactive user interface can also be used to display results in a 2-column format for a stream of scans. Each row can correspond a single medical scan in the set, where each cell indicates whether the scan was labeled as global normal/abnormal by the model/in the report, and/or can indicate whether ANY discrepancy between the report and model exists (e.g. both labeling as abnormal but for different reasons, as discussed above).

Scans with discrepancies can be visually indicated in their respective row, showing disagreement between the automated model and radiologist, for example cell for column 1 says NORMAL, cell for column 2 says ABNORMAL, or entire row is highlighted in bold or a different color such as red to indicate the discrepancy. In a further example, a row is highlighted and/or discrepancy abnormalities that were/ weren't detected in the scan row are listed in each cell (i.e. cell for column 1 says "cardiomegaly: YES, pneumothorax: NO" and cell for column 2 says "cardiomegaly: NO, pneumothorax: YES". In various embodiments, the reviewer can click/interact with row via an interactive user interface of a PACS viewer or other viewing tool to view the scan/ corresponding report, or view the entire 2 column format for the individual scan with the abnormality type rows.

In various embodiments, scans with discrepancies can be listed at the top and/or the list can be filtered to only include scans with discrepancies. The reviewer can view any scan and corresponding report (for example, to confirm whether a discrepancy was appropriate), and can actively confirm or change any of the findings. For example, the reviewer can change the model finding of cardiomegaly from YES to NO, or can check a box confirming the YES was appropriate, after viewing the medical scan and confirming whether or not cardiomegaly was present. Similarly, the reviewer can change the report finding of cardiomegaly from NO to YES, or can check a box confirming the NO was appropriate, after viewing the report and determining whether the label extracted via NLP was appropriate or not. This process can be used to confirm whether or not the discrepancy actually exists or was due to either image model error in processing the scan or NLP error in processing the report. View of the corresponding report can include displaying highlighted portions of the report that agree/disagree with the model output. The discrepancy correction data indicating the final list of scans with discrepancies (as it stands or after human review) can be used in retrospective insights, for example, in identifying cognitive factors or systematic factors in errors generated by particular medical professionals or over a wide set of medical professionals, for educating radiologists based on their error trends as will be discussed further in conjunction with FIGS. 15A-B and 16A-C and/or for retroactively correcting billings to add billing codes as will be discussed further in conjunction with FIGS. 14A-D and 14F.

Turning first to FIG. 13B, the retroactive discrepancy data 3106-1 is presented in a 2-column format that indicates that a discrepancy has been flagged between the automated model labeled "system" and a report by a particular user "XABC". In particular, the user XABC indicated that the scan was normal while the system identified the presence of pneumothorax. The retroactive discrepancy data 3106-1 includes a prompt to update the human assessment data for display via an interactive user interface of the client device. In this fashion, the peer reviewer or other user of the client device 120 can respond to the prompt to correct the human assessment data of user XABC, if necessary, to generate discrepancy correction data that can be sent to the database storage system that can be used to correct the medical report. This process is reflected in the retroactive discrepancy data 3106-2 of FIG. 13C.

In FIG. 13D, the discrepancy data 3106-D indicates that, while the system and user XABC both indicate that an abnormality is present, the user XABC indicated that the presence of cardiomegaly and no pneumothorax, the system identified the presence of pneumothorax and no presence of cardiomegaly. As before, the peer reviewer or other user of the client device 120 can respond to the prompt to correct the human assessment data of user XABC, if necessary, to generate discrepancy correction data that can be sent to the database storage system that can be used to correct the medical report. It should be noted that the discrepancy correction data can include a fully corrected medical report, merely an indication of the correction to be linked or appended to an existing medical report and/or associated medical scan, any of the information included in the retroactive discrepancy notification or some other subset or combination thereof.

FIG. 13E presents a flowchart illustrating a method. In particular, a method is presented for use in conjunction with a retroactive discrepancy flagging system and/or with one or more other functions and features described herein. Step 3202 includes receiving, via a network interface, a first medical scan and a first medical report corresponding to the first medical scan, wherein the first medical report was written by a first medical professional in conjunction with review of the first medical scan. Step 3204 includes generating first automated assessment data by performing a first inference function on the first medical scan by utilizing a computer vision model trained on a plurality of medical scans. Step 3206 includes generating first human assessment data by performing an extraction function on the first medical report. Step 3208 includes generating first consensus data by performing a consensus function on the first automated assessment data and the first human assessment data, wherein performing the consensus function includes comparing the first automated assessment data to the first human assessment data. Step 3210 includes transmitting, via the network interface, a first retroactive discrepancy notification, wherein the first retroactive discrepancy notification indicates the first medical scan is flagged in response to determining the first consensus data indicates the automated assessment data compares unfavorably to the first human assessment data.

In various embodiments, the retroactive discrepancy flagging system 3100 is further operable to receive, via a receiver, a second medical scan that includes annotation data, where the annotation data was generated by a first medical professional in conjunction with review of the first medical scan. Second automated assessment data is generated by performing the first inference function on the second medical scan by utilizing the computer vision model. Second human assessment data is generated by performing a second extraction function on the annotation data. Second consensus data is generated by performing the consensus function on the second automated assessment data and the second human assessment data. A retroactive discrepancy notification is transmitted, via a transmitter, to a client device for display via a display device, where the retroactive discrepancy notification indicates the second medical scan is flagged in response to determining the second consensus data indicates the second automated assessment data compares unfavorably to the second human assessment data.

FIGS. 14A and 14B are a schematic block diagrams of a system that includes a retroactive discrepancy flagging system 3100 and medical billing verification system (MBV) system 4000 in accordance with various embodiments. In particular, this system includes several common elements from FIG. 13A that are referred to by common reference numerals. As shown in FIG. 14A, the discrepancy correction data is sent to medical billing verification (MBV) system 4000 for review and possible generation of updated billing information. The medical billing verification system 4000 improves the technology of medical billing platforms by automatically determining and reporting billing codes that had never been recorded based on abnormalities that are later detected by the retroactive discrepancy flagging system and submit billing verification data for further review by a user of client device 120 as shown in FIG. 14B. In other examples, the medical billing verification system 4000 operated directly on automatically generated retroactive discrepancy notifications to determine and report billing codes that had never been recorded and automatically generate updated billing data as will be discussed later in conjunction with FIG. 14E.

In various embodiments, the retroactive discrepancy flagging system 3100 and medical billing verification system 4000 cooperate to: identify scans with abnormalities that were never reported, generate billing codes for these unreported abnormalities automatically; and also generate billing codes for ALL abnormalities to confirm that the other, reported abnormalities were indeed billed; and determine if these billing codes were not already reported for the corresponding scan (e.g. in case the radiologist report did not include the abnormality but the abnormality was billed anyways). Billing verification data is generated to indicate such under billings that are optionally verified by client device 120 and used as a basis for generating updated billing data. While the retroactive discrepancy flagging system 3100 and the medical billing verification system 4000 are shown as separate entities in communication via network 150, the retroactive discrepancy flagging system 3100 and the medical billing verification system 4000 can otherwise be implemented via a single processing system such as a subsystem 101 of FIG. 2B.

As previously discussed, the one or more medical scans can be selected randomly, pseudo-randomly, as part of a non-random/systematic audit, can be selected based on selected criteria, can be selected based on a peer-review or other review schedule, can be selected based on a determined proportion of medical scans to review, can be determined based on a selected frequency or rate of medical scans to review within a time frame, can be selected based on medical scans that have previously been flagged for review, can be selected based on prior review results, can be selected in response to identifying repeated or systematic errors associated with a particular PACS viewing system, user, and/or institution, can be selected based on the presence or absence of a particular medical condition and/or can be selected based on other factors. This selection can include selecting the number of medical scans for review; selecting medical scans for review that correspond to a selected medical scan type and/or a selected anatomical region; selecting medical scans for review where a selected medical professional authored or otherwise generated the corresponding annotation data, diagnosis data, and/or report data; selecting medical scans for peer-review associated with a selected medical institution; selecting medical scans for review associated with a selected geographic region; selected selecting medical scans for review associated with a selected diagnosis type; selecting medical scans for review associated with patients that meet selected patient history or patient demographic criteria; and/or otherwise selecting medical scans based on received criteria and/or criteria automatically determined by the retroactive discrepancy flagging system 3100. Some or all of the selection criteria can be received via user input to a user interface, via the network, and/or via one or more other subsystems 101.

The medical billing verification system 4000, shown in FIG. 14B, is configured to: receive the discrepancy correction data; determine at least one medical code corresponding to a medical condition indicated by the discrepancy correction data; receive actual billing data from a medical billing system 4010; compare the at least one medical code to the actual billing data to determine whether or not the at least one medical code compares favorably to (e.g. is present in) or unfavorably to (e.g. is not present in) the actual billing data; generate billing verification data when the at least one medical code compares unfavorably to the actual billing data; and transmit the billing verification data to the client device 120.

In various embodiments, the billing verification data includes a prompt to update the actual billing data for display via the interactive user interface of the client device 120. The billing verification data can also indicate a medical condition that was present in the medical scan or medical report that was billed in the actual billing data corresponding to the billing report. The billing verification data can optionally include any of the other information included in the retroactive discrepancy notification and/or the discrepancy correction data. In operation, the client device 120 generates, in response to user interaction with the interactive user interface and in response to the prompt, updated billing data for transmission to a medical billing system 4010.

In various embodiments, the medical condition can be indicated in the billing verification data via an annotated medical scan, image or portion thereof, via one or more medical terms, and/or via one or more medical codes. In addition, the billing verification data can also include an indication of the medical professional that generated the original medical report, a proposed billing code to be added, portions or all of the retroactive discrepancy data, portions or all of the retroactive discrepancy data and/or other metadata associated with the corresponding medical report, medical scan and/or actual billing data.

In addition to identifying missing billing codes in actual billing, the medical billing verification system 4000 can automatically review medical reports and also determine a rate to be billed for a procedure indicated in each of the medical reports, and/or retroactively review medical reports to determine if a discrepancy exists between a rate that should have been billed for a procedure indicated in each of the medical reports and a rate that was actually billed. This can be determined based on determining medical codes that map to billing rates, where the medical codes are determined based on medical conditions indicated by the discrepancy correction data. The discrepancy between actual billing rates and billing rates indicated by the medical codes can also be utilized to determine whether the report accurately reflects the procedure that was actually performed. This can further be utilized to determine whether a procedure that was actually performed was appropriate, given findings extracted from the medical report, given findings extracted from a medical scan that corresponds to the medical report, and/or given other files or patient history corresponding to the patient. Analysis of billing rates, performed procedures, and/or diagnoses indicated in medical codes collected over time can be utilized to generate risk stratification data, which can include categorized aggregate statistics and analysis of risk for categories sorted by patient demographic, patient history, procedures, diagnosis, biopsy data, or other information.

Existing systems can be improved by this automatic determination and/or verification of billing rates by the medical billing verification system 4000. For example, this means of billing verification ensures that medical procedures are billed accurately, which can proactively prevent resources and time required to correct human billing errors. This retroactive review by the medical billing verification system 4000 of report accuracy and/or appropriateness of medical procedures performed also improves existing systems by providing quality assurance and by retroactively correcting inaccurate reports. Furthermore, this generation of categorized risk stratification data by the medical billing verification system 4000 improves existing systems by allowing risk to be quantified appropriately, for example, by health insurance entities, based on automatic, aggregate analysis of standardized information represented by the medical codes.

As shown in FIGS. 14A-14B, the medical billing verification system 4000 can communicate bi-directionally with network 150 via subsystem network interface 265, and with the medical scan database 342, a report database 4044, and/or other databases of the database storage system 140. In some embodiments, the medical billing verification system 4000 is an additional subsystem 101 of the medical scan processing system 100, implemented by utilizing the subsystem memory device 245, subsystem processing device 235, and/or subsystem network interface 265 of FIG. 2B. The medical scan database 342 can correspond to a PACS server and/or medical picture archive system 2620. The report database 4044 can correspond to a RIS and/or report database 2625. In some embodiments, medical reports received from the report database corresponds to report data 449. Report data 449 can be retrieved directly from the medical scan database 342 instead of or in addition the report database 4044.

The medical billing verification system 4000 can further communicate bi-directionally with a medical billing system 4010, which can include at least one processor and memory, and can be associated with an entity that is responsible for recording and/or facilitating medical billing. This communication can be facilitated via network 150, and/or via a different wired and/or wireless connection. The medical billing system 4010 include and/or utilize a database of billing records, which can be an additional database of database storage system 140. The database of billing records can include billing information for individual procedures and/or individual patients. These records can include rates billed, payments received, and/or outstanding payments. The medical billing system 4010 can facilitate communicating billing data with a medical entity such as a hospital, or a payment processing entity, that conducts sending of bills to patients and/or collecting of payment from patients. The medical billing system 4010 can process payment electronically by sending and/or receiving payments via communication with a client device 120 that utilizes a secure payment system. In some embodiments, the medical billing system 4010 is only responsible for storage of billing records, and these billing records are used by one or more other entities to process payments. In some embodiments, the medical billing system 4010 can be implemented by, or can otherwise communicate with, the central server 2640 and/or another subsystem 101.

The medical billing verification system 4000 can further communicate bi-directionally with at least one client device 120. The at least one client device 120 can be associated with an administrator of the medical billing verification system 4000, a user associated with the medical billing system 4010, and/or a patient associated with a medical report and/or billing data that was reviewed and/or needs to be rectified.

In some embodiments, the medical billing verification system 4000 is implemented by utilizing, or otherwise communicates with, the central server 2640. For example, some or all of the databases of the database storage system 140 are populated with de-identified data generated by the medical picture archive integration system 2600. In some embodiments, the medical billing verification system 4000 can receive de-identified medical scans, annotation data, and/or reports directly from the medical picture archive integration system 2600. For example, the medical billing verification system 4000 can request de-identified medical scans, annotation data, and/or reports that match requested criteria. In some embodiments, some or all of the medical billing verification system 4000 is implemented by utilizing other subsystems 101 and/or is operable to perform functions or other operations described in conjunction with one or more other subsystems 101. In particular, the medical billing verification system 4000 can be implemented by utilizing medical scan report labeling system 104.

In operation, the medical billing verification system 4000 can receive the discrepancy correction data from the network 150 via the subsystem network interface 265. While not expressly shown, the corresponding medical report can optionally be received from the report database 4044. A billing data generator function 4050 can be performed on the discrepancy correction data and/or medical report to generate automatically determined billing data. This auto-determined billing data can be determined based on one or more medical codes and/or medical condition terms corresponding to the discrepancy correction data and/or the medical report. These medical codes and/or medical condition terms can be indicated directly in the discrepancy correction data and/or the medical report, for example, in a header of the discrepancy correction data and/or the metadata of the medical report. Similarly, these medical codes and/or medical condition terms can be indicated directly in the discrepancy correction data and/or the, for example, in a header of the medical report or metadata of the medical report. The medical codes can correspond to some or all of medical codes 447, and can include CPT codes, ICD-10 codes, or other medical codes 447 discussed herein. The medical condition terms can correspond to a medical scan alias database that correlates different and possible alternative terminologies to corresponding medical codes.

In some embodiments, a first step of the billing data generator function 4050 includes generating the at least one medical code. In particular, the one or more medical codes can be determined by the billing data generator function 4050 utilizing a known mapping of medical terms to medical codes, such as using the medical scan alias database. The one or more medical codes can be determined in response to receiving the discrepancy correction data, where identified terms are extracted from the discrepancy correction data as medical condition term data that indicates abnormalities or other medical conditions that were the subject of the discrepancy. In addition, all other medical terms that describe abnormalities and/or medical conditions identified as being present in the corresponding medical report can detected automatically by performing by analyzing the medical report itself as received by the subsystem network interface 265 via a medical report analysis function trained by the medical scan natural language analysis system 114 and can be included in identified medical condition term data. The automatically identified other medical terms can also be mapped to the medical codes by utilizing the medical scan alias database.

The medical codes can be billing codes or other medical codes that indicate a procedure performed on the patient, a medical condition present in the medical report and/or a medical condition identified via the retroactive discrepancy flagging system 3100. For example, the medical codes can indicate one or more medical scans captured for the patient, where these medical scans correspond to one or more medical scans described by the medical report. The medical reports can indicate other procedures performed on the patient, for example, as a result of a diagnosis determined based on medical scans that have already been captured. The medical report can indicate any billable procedures and/or conditions that are independent of any medical scans. Thus, some medical reports may not have any associated medical scans in the medical scan database.

Some or all medical codes can directly indicate or otherwise be mapped to a billing code, billing rate, and/or can indicate an amount to be billed. In particular, medical codes that correspond to a procedure or condition that can have a corresponding, deterministic billing code and/or billing rate. A plurality of medical codes can indicate a total billing rate/amount based on a sum of billing rates/rate for each of the plurality of medical codes. In some embodiments, one or more medical codes can indicate a billing deduction and/or discount, and the total billing rate/amount can include applying a deduction indicated in one or more medical codes. A mapping of medical codes to billing rates/amount can be utilized to determine a total billing rate/amount in the automatically determined billing data. The auto-determined billing data can indicate a single billing code and/or billing rate/amount and/or a plurality of billing codes and/or billing rates/amounts for separate procedures. In some embodiments, the auto-determined billing data can indicate a billing due date and/or can otherwise indicate the date since the procedure occurred, based on a date of the procedure extracted from text of the report and/or a date of the report itself. In some embodiments, the billing rate changes over time, and the billing rate can further be determined based on the date of the procedure extracted from the report.

The mapping of medical codes to billing codes and/or billing rates/amounts can be the same or different for different hospitals, different medical entities, different geographic regions, etc. In some embodiments, different medical billing verification systems 4000 are utilized for different medical entities and/or different billing schemes. Alternatively, the same medical billing verification system 4000 can utilize multiple mapping of medical codes to billing codes and/or billing rates/amounts for multiple billing schemes, and can select which mapping will be used based on a medical entity, geographic region, and/or other indication of what billing scheme to use extracted from text or metadata of the medical report and/or identified based on the source of the medical report.

The medical billing verification system 4000 can store one or more mappings of medical codes to billing codes and/or billing rates/amounts in memory and/or can access a separate database or memory system that stores the one or more mappings via the network. A user can input and/or update billing information stored in one or more mappings based on user input to a user interface displayed on a display device of a corresponding client device 120. Alternatively, the medical billing verification system 4000 can automatically determine the mapping of medical codes to billing codes and/or billing rates/amounts based on past billing records and/or based on other information that indicates the billing rates.

In some embodiments, a single medical code is not sufficient to deterministically select the corresponding billing rate. In such embodiments, pairs or groupings of medical codes, for example, that all describe billable costs and/or otherwise describe different aspects of a single procedure, can be utilized to determine the billing rate for the procedure. The mapping can include a mapping of sets of medial codes to a billing rate, where the sets can include one or more medical codes. One or more subsets of the medical codes for a medical report can be determined to be included in the mapping and can each be utilized to determine corresponding billing rates.

The automatically determined billing data can be compared to actual billing data for the one or more procedures corresponding to the medical report. The actual billing data can be retrieved from the medical billing system 4010. Alternatively, the actual billing data can be sent to the medical billing verification system from a client device associated with payment of the billing amount, such as a client device associated with processing a payment of the actual billing amount and/or a client device of a patient and/or insurance company that electronically paid the actual billing amount. Alternatively, the actual billing data can be retrieved from an entry of the medical scan database and/or an entry of the report database, for example, where a medical scan entry and/or medical report entry indicates an amount that was billed for capturing the medical scan or an amount that was billed for another corresponding procedure.

The actual billing data can indicate the actual amount that was billed, can indicate when the amount was billed, can indicate whether the amount has been paid, can indicate when the amount was paid, and/or can indicate whether payment is overdue. The actual billing data can reflect a total billing amount before insurance is applied, and/or can indicate a subtotal billed to an insurance company and a subtotal billed to the patient. The actual billing data can be requested from any of these sources via a request transmitted via the network 150, where the request includes an identifier of the medical report, an identifier of the patient, medical codes extracted from the medical report indicating the procedure performed, a date of the procedure extracted from the medical report, an identifier of a billing extracted from the medical report, and/or other information that is utilized to fetch the corresponding actual billing data. The actual billing data can be fetched locally, for example, if the medical billing system 4010 is included in memory of the medical billing verification system 4000.

In various embodiments, a comparison function 4070 can be performed on the auto-determined billing data and the actual billing data. As previously discussed, the comparison function 4070 operates to determine to determine whether or not the medical/billing code(s) from the auto-determines billing data compares favorably to (e.g. is present in) or unfavorably to (e.g. is not present in) the actual billing data. Furthermore, performing the comparison function 4070 can include determining whether or not an amount of the auto-determined billing data and an amount of the actual billing data is equal, for example, by performing a subtraction on the two amounts. Performing the comparison function 4070 can include comparing a plurality of line item amounts of the auto-determined billing data to a plurality of line item amounts of the actual billing data and determining whether each line item amount is matches, whether or not the totals match, and/or whether the same number of line item amounts are included.

Billing verification data can indicate a result of the comparison, and can be transmitted to at least one client device 120 for display via a display device to a user of the client device, such as an administrator of the system, an administrator of the medical billing system 4010, a user associated with an insurance company responsible for some or all of the payment, and/or a patient associated with the medical report and the billing. Alternatively or in addition, the billing verification data can be sent to the medical billing system 4010, for example, indicating discrepancies to be corrected and/or indicating that the actual billing data has been verified to be correct. A corresponding entry for the actual billing data in the medical billing system 4010 can be corrected and/or otherwise updated based on the billing verification data received from the medical billing verification system 4000.

In some embodiments, billing verification data is only transmitted to the at least one client device 120 and/or to the medical billing system 4010 when a discrepancy is detected, where the billing verification data is not transmitted when the auto-determined billing data compares favorably to the actual billing data. Alternatively, the billing verification data can be sent regardless of outcome, and can indicate whether or not the auto-determined billing data compared favorably to the actual billing data, for example, where a favorable comparison corresponds to the auto-determined billing data matching the actual billing data exactly. The billing verification data can indicate that the auto-determined billing data indicates a total amount that is less than a total amount of the actual billing data. The discrepancy can be indicated, and a total refund amount or multiple line item refund amounts owed back to the patient and/or insurance company can be determined based on the discrepancy. If the patient and/or insurance company has not yet paid, the discrepancy can be simply be deducted from a total indicated in the actual billing data to correct the actual billing data accordingly. The billing verification data can indicate that the auto-determined billing data indicates a total amount that is more than a total amount of the actual billing data. The discrepancy can be indicated, and a total additional amount or multiple line item additional amounts billed to the patient and/or insurance company can be determined based on the discrepancy. Alternatively, such additional amounts can be billed to a medical professional, medical entity, and/or insurance company responsible for the medical report, ensuring that the patient is not billed an additional amount that was not initially quoted and/or ensuring that the patient is not penalized with additional, unexpected fees due to a mistake by the medical professional, medical entity, and/or insurance company.

The actual billing data can indicate one or more corresponding procedures that were billed for in the actual billing data. The one or more corresponding procedures can be indicated in the same or different medical code format as discussed to extract medical codes from the medical report to generate the billing data. In some embodiments, line item text or unstructured text accompanies the actual billing data to indicate the one or more corresponding procedures, and the medical codes can be determined automatically from the line item text or unstructured text, for example, by identifying medical terms by utilizing a medical report natural language analysis function and by utilizing the medical label alias database 3920. The medical codes determined in the actual billing data can be compared to the medical codes extracted from the medical report in performing the comparison function 4070, for example, where a discrepancy in the medical codes indicates improper billing. Such a discrepancy can be included in the billing verification data, for example, to providing an explanation for the billing discrepancy by indicating the medical codes do not match.

FIGS. 14C-14D are illustrations of example interfaces 4102-1 and 4102-2 displayed by a display device of a client device, such as client device 120, in accordance with various embodiments. In particular, an annotated medical scan 4104 is presented along with other billing verification data 4106-2. In the example shown, the billing verification data indicates that pneumothorax was presented but not billed. The user is prompted in FIG. 14C to add a corresponding medical/billing code to the billing. In FIG. 14D, the user has interacted with the interactive user interface to indicate that "YES" the medical/billing code should be added. In response, the client device 120 can automatically generate the updated billing data and transmits it to medical billing system 4010.

FIG. 14E is a schematic block diagram of a medical billing verification system in accordance with various embodiments. In particular, similar elements presented in conjunction with FIG. 14B are referred to by common reference numerals. While much of the prior discussions have focused on automatically generated retroactive discrepancy notifications and automatically generation of billing verification data that is subsequently reviewed by a user of client device 120 before generating updated billing data, in the example shown, the medical billing verification system 4000 can operate directly on the retroactive discrepancy notifications, determine and report medical/billing codes that had never been recorded and automatically generate updated billing data. In effect, the billing updates generated by the comparison function can be treated as truth, and the actual billing data is automatically corrected by generating updated billing data accordingly.

For example, the medical billing verification system can operate to: receive a retrospective discrepancy notification via the subsystem network interface 265; determine, via the billing data generator function 4050 at least one medical code corresponding to a medical condition indicated by the retroactive discrepancy notification; receive, via the subsystem network interface 265, actual billing data corresponding to the medical report from a medical billing system; compare, via the comparison function 4070, the at least one medical code to the actual billing data; generate, via the comparison function 4070, updated billing data when the at least one medical code compares unfavorably to the actual billing data; and transmit, via the subsystem network interface 265, the updated billing data to the medical billing system.

While the updated billing data is treated as truth, in various embodiments, a quality assurance process can be performed on this automatic billing process, where a random proper subset of updated billing data is sent to a client device 120 for review via a display device to ensure the auto-determined billing data was generated properly. In some embodiments, the auto-determined billing data is transmitted and displayed in conjunction with the medical report and/or medical scan utilized to generate the auto-determined billing data. The medical codes extracted from the medical report and/or medical scan can also be transmitted, and the identifying key terms and/or other information utilized to select the medical codes can be indicated in a transmission to the client device for display, allowing the user to determine where the medical billing verification system erred in making the selection of medical codes and/or billing rates. The user can input correction information via an interactive interface for transmission back to the medical billing verification system 4000 based on errors identified in generating the auto-determined billing data. The user can override mappings in the medical label alias database 3920 and/or in the mapping of medical codes to billing rates. The user can send the billing data generator function 4050 into remission and can retrain the medical report natural language analysis function and/or the billing data generator function 4050 itself based on new training data.

In other examples of medical billing verification system 4000, the auto-determined billing data itself is treated as truth and is always utilized as the updated billing data. In such cases, the auto-determined billing data does not need to be compared to actual billing data at all, and can be sent to the medical billing system 4010 for storage as the updated billing data. The auto-determined billing data can replace corresponding, existing actual billing data, or can correspond to a new entry for the actual billing data. In particular, the medical billing verification system 4000 can be exclusively utilized to generate all of the actual billing data automatically by utilizing the billing data generator function 4050. This can eliminate the need for a user to manually input billing data and can proactively prevent error in billing by eliminating a separate entity that generates actual billing records.

FIG. 14F presents a flowchart illustrating a method in accordance with various embodiments. In particular, a method is presented for use in conjunction with a medical billing verification system and/or with one or more other functions and features described herein. Step 4202 includes receiving retrospective discrepancy notification. Step 4204 includes determining, via the billing data generator function 4050 at least one medical code corresponding to a medical condition indicated by the retroactive discrepancy notification. Step 4206 includes receiving actual billing data corresponding to the medical report from a medical billing system. Step 4208 includes comparing the at least one medical code to the actual billing data. Step 4210 includes generating updated billing data when the at least one medical code compares unfavorably to the actual billing data. Step 4212 includes transmitting the updated billing data to the medical billing system.

FIG. 15A is a schematic block diagram of a factor detection system in accordance with various embodiments. In particular, a factor detection system 4300 is presented in a system that includes several similar elements presented in FIG. 14E that are referred to by common reference numerals. In addition, a medical administration system 4325 in bidirectional communication with network 150 is also included. The factor detection system 4300 is configured to generate factor data, based on a plurality of retroactive discrepancy notifications from the retroactive discrepancy flagging system 3100. The factor data identifies one or more factors, that contribute to errors associated with the either a particular medical professional, a selected subset of medical professionals, an entire set of medical professionals, a PACS viewer or other viewing tool or interface feature thereof, a medical institution, or other entity. For example, factor detection system 4300 can analyze the retroactive discrepancy notifications over time to evaluate and identify trends in the mistakes in reviewing medical scans made by radiologists or other medical professionals and further to identify systematic factors, cognitive factors and/or other factors that appear to lead these errors. This improves the technology of viewing and analysis tools and systems by assisting, in a fully automated way, the identification of errors and bias that can be used to help to prevent future errors.

In various embodiments, the retrospective discrepancy flagging system 3100 can identify a set of medical scans reviewed by a particular radiologist and corresponding medical reports, including the scans that were identified as having a discrepancy with either model generated output or an audit generated by other reviewers. A non-random audit can be automatically performed by the retrospective discrepancy flagging system 3100 on scans/reports that utilizes model output to determine scans with discrepancies based on, for example, retrospective discrepancy notification, and/or a random audit can be performed automatically to gather scans for a particular radiologist and determine their error rate based on their scans with discrepancies detected in the non-random audit. For example, radiologists can be flagged for this process only if their error rate (determined from random audit) exceeds a threshold. The set of medical scans/reports can be selected for audit randomly, pseudo-randomly, as part of a non-random/systematic audit, can be selected based on selected criteria, can be selected based on a peer-review schedule, can be selected based on a determined proportion of medical scans to review, can be determined based on a selected frequency or rate of medical scans to review within a time frame. Further, such an audit can be a non-random audit associated with the particular medical professional triggered by the identification of one or more prior errors associated with one or more prior retrospective discrepancy notifications or otherwise based on a number of medical scans, such as more than a threshold number, that have previously been flagged for review, can be otherwise selected based on prior review results, can be selected in response to identifying repeated or systematic or cognitive errors associated with a particular PACS viewing system, user, and/or institution, can be selected based on the presence or absence of a particular medical condition and/or can be selected based on other factors. This selection can include selecting the number of medical scans for review; selecting medical scans for review that correspond to a selected medical scan type, modality and/or a selected anatomical region; selecting medical scans for review where a selected medical professional authored or otherwise generated the corresponding annotation data, diagnosis data, and/or report data; selecting medical scans for review associated with a selected medical institution; selecting medical scans for review associated with a selected geographic region; selected selecting medical scans for review associated with a selected diagnosis type; selecting medical scans for review associated with patients that meet selected patient history or patient demographic criteria; selected selecting medical scans for review based on other selection criteria and/or otherwise selecting medical scans based on received criteria and/or criteria automatically determined by the retroactive discrepancy flagging system 3100. The factor detection system 4300 can evaluate trends identified this set of medical scans (for example, based on information presented in the metadata of each scan/report or extracted from output of a model performed on each scan/report and further based on retrospective discrepancies notifications corresponding to some subset of the total medical scans/reports in the audit) to determine particular systematic factors and/or cognitive factors that motivate the errors.

Identifying systematic and cognitive factors can include considering the report/referral sent to the radiologist to the radiologist's review, determining a proportion of all errors made by a radiologist that meet the trend criteria and comparing to a threshold, and/or determining if this trend criteria was present in less than a proportion of all correctly reviewed scans and comparing this proportion to a threshold—e.g., a trend of "the radiologist makes most of his errors after 5 pm" is not valid as a systematic error if the radiologist reviews every scan after 5 pm. Identifying a factor could include comparing trends detected across all radiologists in this process, and detecting common trends correlated to errors and/or non-errors across all radiologists (e.g. scans with errors across many radiologists correspond to a significant proportion of the scans reviewed by these radiologists after 5 pm—this could imply causation or otherwise indicate that post 5 pm review is a common trend across many radiologists that can be directly searched for in the future). Identifying a factor can include linking the factor to a particular type of scan/body part/abnormality (e.g. framing bias is predominant for radiologist X when presented with scans that include cardiomegaly).

Identified factors can be presented to hospitals/medical entities for review of their radiologists, to PACS tool makers or interface developers (if there are predominant trends in a particular tool causing systematic errors), and/or to radiologists to guide improvement in reviews (as will be discussed in FIGS. 16A-C). Identified factors can be processed and analyzed over all radiologists/radiologists at particular hospitals/radiologists in particular geographic regions/radiologists in particular fields of study/etc. to determine if there are predominant systematic factors and/or cognitive factors across the same hospital/geographic region/field of study/etc.

In some embodiments, the factor detection system 4300 is an additional subsystem 101 of the medical scan processing system 100, is configured to bidirectionally communicate with the network 150 and further operates by utilizing the subsystem memory device 245, subsystem processing device 235, and/or subsystem network interface 265 of FIG. 2B. While shown separately from the retroactive discrepancy flagging system 3100, in other examples, these two systems can be implemented together in a single platform with at least one processor and a memory that stores operational instructions to perform both functions.

As previously discussed, the retroactive discrepancy notifications can include an identification of a medical scan, an identification of a particular subset of images and/or image portions in the medical scan that include the discrepancy. The retroactive discrepancy notification can also include or indicate the medical report and an identification the medical professional that generated the medical report, as well as information pertaining the nature of the discrepancy. For example, the retroactive discrepancy notification can indicate that the automated assessment data indicated the presence of a particular abnormality while the human assessment data did not or vice versa. The particular anomaly or other condition can be identified, for example, by including a corresponding medical code, medical condition term and or other abnormality classification data in the retroactive discrepancy notification. In addition or in the alternative, the retroactive discrepancy notification can provide other information regarding the generation of the medical report such as the time of day the report was generated, the number of medical reports generated by the user in a review session that included the subject medical report, the progress through the review session at the time the report was generated, a preliminary diagnosis and/or request for review by the user by another medical professional, the type of PACS viewer or other user interface that was used by the user to generate the report, and/or other data or metadata derived from the medical report or medical scan.

The systematic factor identifier 4350 and the cognitive factor identifier 4370 can operate via an inference function, via a statistical analysis, hypothesis test, clustering algorithm, generate-and-test algorithm, search-based algorithm, a convolutional neural network, stacking neural network, a generative adversarial network, and/or other machine learning algorithm that operated based on data from retrospective discrepancy notifications and optionally other medical reports without errors to generate factor data that indicates one or more systematic, cognitive or other factors that correlate to the particular discrepancies or other errors presented by the retrospective discrepancy notifications.

In various embodiments, the systematic factors identified can indicate errors that occur more frequently for reviews associated with using a particular one of plurality of PACS viewers and/or other viewing tools and/or using a particular interface feature of a viewing tool. In further examples, a systemic error can be identified for reviews at a particular time a day such as early morning, mid-morning, immediately before or after lunch time, mid-afternoon, dinnertime, and or late at night when a dip in attention span could occur. In further examples, a systemic error can be identified based on a number of prior reviews in a reviewing session of a particular medical professional, for example, after 100 consecutive reviews or after a particular duration of the reviewing session, e.g., after two consecutive hours.

In various embodiments, the cognitive factors identified can indicate errors that occur more frequently for reviews associated with an anchoring bias factor where the medical professional depends too heavily on an initial piece of information offered, such as a prior diagnosis, preliminary diagnosis or review request from a referring physician or other medical professional, e.g. check for possible kidney stones. The cognitive factors identified can indicate errors that occur more frequently for reviews associated with a framing bias factor where the medical professional decides on options based on whether the options are presented with positive or negative connotations, e.g. a bias against the diagnosis of a very severe condition. The cognitive factors identified can indicate errors that occur more frequently for reviews associated with a satisfaction of search factor or a satisfaction of report factor where the reviewer stops looking for abnormalities after one or more abnormalities are already found. The cognitive factors identified can indicate errors that occur more frequently for reviews associated with a tunnel vision factor that indicates, for example, a cognitive confirmation bias, hindsight bias, and/or outcome bias.

In various embodiments, the systematic factor identifier 4350 and the cognitive factor identifier 4370 operate to track trends across medical scans, medical professionals, and/or medical institutions in the retroactive review and/or in flagging medical scans, medical professionals, and/or medical institutions. For example, the factor detection system 4300 can determine trends that correlate to a higher number, proportion, or frequency of medical scans flagged via retrospective discrepancy notifications. For example, the factor detection system 4300 can track these trends across types of medical scans, anatomical regions of medical scans, particular attributes of patient history, different geographic regions, qualifications or backgrounds of medical professionals and/or medical institutions, and/or other attributes mapped to medical scans or medical professionals, for example, in medical scan entries 352 or user profile entries 354. For example, the factor detection system 4300 can identify a geographic region where a particular scan type or modality is flagged for review more frequently.

As another example, the factor detection system 4300 can identify factors such as the qualifications of medical professionals that correlate to a higher number, proportion, or frequency of medical scans flagged via retrospective discrepancy notifications. Trends that are identified as statistically significant or otherwise compare favorably to a significance threshold can be transmitted as factor data for review via users of the medical administration system 4325. In various embodiments, the medical administration system can be a subsystem 101 as presented in conjunction with FIG. 2B and furthermore can be coupled to a client device 120 for review of the factor data via an interactive user interface for purposes of oversight, management, administration and/or maintenance of a medical institution, medical staff, a PACS viewer or other viewing tool, and other purposes.

FIG. 15B presents a flowchart illustrating a method in accordance with various embodiments. In particular, a method is presented for use in conjunction with a medical billing verification system and/or with one or more other functions and features described herein. Step 4402 includes auditing a plurality of medical reports and an associated plurality of medical scans to generate a plurality of retrospective discrepancy notifications that indicate inconsistencies between human assessment data and automated assessment data. Step 4404 includes generating factor data, based on the plurality retroactive discrepancy notifications, that identifies one or more factors that contribute to errors associated with a plurality of medical professionals.

FIG. 16A is a schematic block diagram of a factor detection system in accordance with various embodiments. In particular, a factor detection system 4300 is presented in a system that includes several similar elements presented in FIG. 14E that are referred to by common reference numerals. In various embodiments, the factor detection system 4300 is further configured to transmit the factor data to a client device 120 running a PACS viewer or other viewing tool associated with a medical professional. In response, one or more prompts are selected based on the cognitive factors and/or systematic factors identified for the radiologist in the factor data are presented to the radiologist during their review of a scan. In particular, the client device 120 is configured to generates prompts, via an interactive user interface of the viewing tool, based on the factor or factors that contribute to the errors associated with the medical professional.

For example, based on the cognitive factors and/or systematic factors identified in the factor data for a particular radiologist, that radiologist can presented with prompts during their subsequent reviews of scans, that serve as educational tools/reminders for the radiologists with the goal of preventing future errors and lowering the radiologists error rate. This improves the technology of viewing tools by assisting, in a fully automated way, the review of such scans and helping to prevent future errors. In various embodiments, the factor data indicates one or more conditions, and the prompts are in triggered by an occurrence of one or more conditions. The factor data can also indicate one or more lockout conditions, and in response the viewing tool of the client device 120 locks out the medical professional in response to an occurrence of these one or more conditions.

FIG. 16B is an illustration of an example interface 4502-2 of a viewing tool displayed by a display device of a client device 120 in accordance with various embodiments. In the example shown, a medical scan 4504 has been annotated to highlight and indicate the presence of a pneumothorax. The text annotation presented in text box 4506-2 makes the same indication. In this example, the factor data indicates an anchoring bias of the user XABC. Furthermore, the scan metadata indicates that the referring physician was asked to check for pneumothorax, the condition noted by the user A system prompt indicates, "abnormality noted, remember to check for other conditions!" in an attempt to prompt the user to, for example, check for the presence of a lung nodule or other condition in the scan.

Other examples of prompts can include, "remember to search the whole study" for an identified cognitive factor such as tunnel vision, anchoring bias, completion of report, or completion of search bias identified for a particular radiologist. This can be triggered, for example, in response to a condition where, for example, only some slices of an MRI are reviewed, or when an annotation only addresses a medical condition from review request from a consulting physician, e.g. check for possible kidney stones. Examples of prompts can include, "this is an early time for you to review a scan—how about a cup of coffee?" in response to an early morning condition and a systematic factor indicating higher than normal errors during this timeframe. Examples of prompts can include, "how about a quick tutorial before you try to use this PACS tool?" in response a systematic factor indicating higher than normal errors when using the viewing tool the user has selected. In various embodiments, the radiologist may be required to interact with the prompt itself (confirm acknowledgement of the prompt) before they are allowed to review the scan.

In other cases, a "system lockout" can occur if the current conditions meet a known systematic factor. For example, if a radiologist makes frequent errors after 5 pm, the viewing tool will not allow them to review scans (or particular types of scans) if the current time is after 5 pm (or will require an override by a supervisor/different medical professional). In a further example, a radiologist can be looked out from using a particular viewing tool or interface feature if such use has correlated to a higher number, proportion or frequency of detected discrepancies.

In some cases, information can be presented differently based on systematic/cognitive factors. For example, a radiologist may be presented with the scan first and may be asked to begin annotating the scan before being allowed to view the report/referral/symptoms sent by a clinician (if the radiologist has tendencies of anchoring bias). As another example, interface features of the viewing tool may be presented differently based on systematic factors indicating the radiologist struggles to use particular tools correctly. As another example, the operating point, such as the operating point along a receiver operating characteristic curve or other setting that relates to the probability of type I and type II errors used to detect and display abnormalities for user review, can be set differently for different radiologists based on their cognitive factors (i.e. more sensitive to show more possible abnormalities if the radiologist tends to have satisfaction of search cognitive factors) and/or at different times of day (i.e. more sensitive after 5 pm to make sure the radiologist checks everything if they tend to miss abnormalities after 5 pm).

FIG. 16C presents a flowchart illustrating a method in accordance with various embodiments. In particular, a method is presented for use in conjunction with a medical billing verification system and/or with one or more other functions and features described herein. Step 4602 includes auditing a plurality of medical reports and an associated plurality of medical scans to generate a plurality of retrospective discrepancy notifications that indicate inconsistencies between human assessment data and automated assessment data. Step 4606 includes generating factor data, based on the plurality retroactive discrepancy notifications, that identifies one or more factors that contribute to errors associated with the first medical professional. Step 4608 includes transmitting the factor data to a client device associated with the first medical professional, and wherein the client device generates prompts, via an interactive user interface of the client device, based on the one or more factors that contribute to the errors associated with the first medical professional.

FIGS. 17A-17U present embodiments where medical reports are analyzed during a predetermined staging duration or other fixed-length time frame, after being created and prior to final transmission to a report database. A medical report analysis system 5100 can receive medical reports after being created and prior to being sent to a report database. The medical report analysis system can generate report analysis data by performing a report processing function and/or can generate correction requirement notification data based on the report analysis data. The medical report analysis system can transmit the generate correction requirement notification data to a client device associated with a medical professional that created the report, can display the correction requirement notification data to the medical professional via a display device, and/or can otherwise facilitate communication of the correction requirement notification data to the medical professional.

This generation of report analysis data, generation of correction requirement notification data, and communication of the correction requirement notification data can be accomplished by the medical report analysis system prior to elapsing of the predetermined staging duration, for example, to ensure the medical professional is notified of required and/or recommended corrections prior to the medical report being transmitted to the report database for long term storage and/or prior to otherwise being formally submitted. This allows the medical professional to edit their medical report accordingly based on the correction requirement notification data and/or to optionally perform additional procedural actions as indicated in the correction requirement notification data, prior to formal transmission of the medical report. Meanwhile, medical reports that do not require correction have no notification communicated and are automatically submitted once the predetermined staging duration elapses.

Some or all of the functionality described in conjunction with FIGS. 17A-17U improves the technology of medical imaging by improving the quality of medical reports that are generated based on review of medical images. This improved quality of medical reports can further improve the technology of medical imaging by rendering larger and/or more accurate training data derived from medical images and corresponding medical reports generated via corrections prompted by the medical report analysis system 5100, which can induce more effective medical scan analysis function and/or inference functions, for example, trained and/or utilized by one or more other subsystems 101 and/or stored in medical scan analysis function database 346 as discussed previously. This functionality improves the technology of medical imaging by increasing medical professionals' awareness of report requirements and/or errors they are prone to in generating their medical reports, which can improve the quality of their future reports and/or increase the efficiency by which they generate their reports. This functionality improves the technology of medical imaging by increasing the efficiency that medical professionals such as radiologists can review medical images, which can in turn improve the technology of medical triage and/or medical treatment as more patients' conditions can be diagnosed with increased speed and/or increased accuracy. This functionality can improve the technology of clinical medicine by ensuring that all required analyses and/or procedural actions are performed for a given medical image based on relevant findings and/or as required by medical institutions, and/or by ensuring all analyses and/or procedural actions are billed appropriately. This functionality can also improve the accuracy and/or integrity of medical billing by ensuring that procedures are accounted for in medical reports, are billed accurately, are billed in compliance with requirements put in place by insurance companies and/or medical institutions, are justified by statements provided by medical professionals, and/or do not have discrepancies with a record of medical billing. This functionality can also improve the efficiency that errors in medical reports that could result in billing discrepancies are rectified based on detecting these errors and facilitating appropriate edits more quickly and prior to formal submission.

This functionality facilitates at least these improvements via processes that cannot be practically performed by the human mind. For example, the human mind is not equipped to rapidly ensure that each of a vast set of requirements are always met for every report that is generated. In particular, as this analysis must be performed within a fixed-time frame that may be less than or equal to four minutes, the human mind is not equipped to determine with consistent accuracy whether each of a vast set of requirements are met for a given medical report. Furthermore, as this analysis may be required for a great number of reports received from many different users concurrently, the human mind is further not equipped to perform this analysis for many reports, such as hundreds of reports, at the same time. For example, the human mind cannot accurately determine all required corrections for multiple reports within a same, short time frame, such as a time frame less than or equal to four minutes.

In some embodiments, the medical report analysis system 5100 facilitates at least these improvements via processes that are performed via at least one artificial intelligence algorithm and/or technique, and/or that are performed via at least one machine learning algorithm and/or technique. For example, the report processing function performed by the medical report analysis system can utilize a model, such as a natural language processing model, that was trained via at least one artificial intelligence algorithm and/or technique, and/or via at least one machine learning algorithm and/or technique. As another example, the report processing function performed by the medical report analysis system can include a natural language processing function that utilizes at least one artificial intelligence algorithm and/or technique, and/or that utilizes at least one machine learning algorithm and/or technique. The report processing function performed by the medical report analysis system can utilize one or more medical report analysis functions, for example, via communication with and/or integration with the medical scan natural language analysis system 114.

FIG. 17A illustrates an embodiment of a staging module 5110. The staging module can be implemented via at least one processor and/or memory. The staging module 5110 can be implemented as an additional subsystem 101 and/or can be integrated within one or more other subsystems 101 described herein. The staging module 5110 can be alternatively or additionally communicate with and/or be integrated within the medical picture archive system 2620 and/or the report database 2625. The staging module 5110 can be alternatively or additionally implemented via a third-party service that is separate from the medical report analysis system 5100 and/or the medical scan processing system 100, and/or that communicates with the medical report analysis system 5100 and/or the medical scan processing system 100 via network 150.

The staging module 5110 can receive medical reports from one or more client devices 120 corresponding to one or more medical professionals for "staging" during a predetermined staging duration 5114 between a creation time and a submission time. The staging module 5110 can facilitate staging of a medical report by: receiving the medical report from a client device; initiating the predetermined staging duration 5114 for the medical report based on receiving the medical report; temporarily storing the medical report in a memory module 5112 of the staging module 5110 for at least the predetermined staging duration 5114; formatting the medical report for storage via the medical report database 392 based on standardized formatting associated with the medical report database 392 and/or a communication protocol associated with the medical report database 392; generating metadata for the medical report and/or linking the medical report to a corresponding medical image stored in the medical scan database 342 and/or stored in the medical picture archive system 2620; sending the medical report to a medical report database 392 for long term storage when the predetermined staging duration 5114 elapses; and/or deleting the medical report from the memory module 5112 after the medical report is confirmed to be stored in a medical report database 392. The medical report database 392 can optionally be implemented as report database 2625 of FIGS. 8D-8F as a as a Radiology Information System (RIS), as report database 4044 of FIGS. 14B, 14E, 15A, and/or 16A, and/or as another report database that stores medical reports and/or enables future access of completed medical reports over time.

In some embodiments, the predetermined staging duration 5114 can be brief, such as a time frame that does not last longer than an hour, yet is still long enough, such as longer than a minute, to provide enough time for a medical professional to edit and/or recall their medical report prior to formal submission. For example, the predetermined staging duration 5114 is equal to and/or is approximately equal to four minutes. The predetermined staging duration 5114 can correspond to any other length of time. The predetermined staging duration 5114 can be the same and/or approximately the same for all medical reports. This fixed, predetermined staging duration 5114 can be public knowledge and/or can be known to medical professionals that create medical reports. Alternatively, in other embodiments, the staging duration is not fixed and/or is not predetermined, and can be different for some or all different medical reports.

The initiating the predetermined staging duration 5114 for a given medical report can be in accordance with a creation time, which can correspond to a time that the medical report is created. A memory module 5112 implemented by at least one memory of the staging module 5110 can store medical reports in conjunction with their corresponding creation times, such as a timestamp that the medical reports were created. A report database upload module 5121 can determine submission times for medical reports that are received and stored in memory module 5112 based on their respective creation times and based on a predetermined staging duration 5114. For example, the report database upload module 5121 transmits each given medical report to the medical report database 392 four minutes after their creation time. The report database upload module 5121 otherwise transmits each given medical report to the medical report database 392 once a time period dictated by the predetermined staging duration 5114 from the given medical report's creation time elapses.

As used herein, creation of a medical report corresponds to completion of a medical report by a medical professional, signing of a completed medical report by a medical professional, and/or receiving of a completed medical report from a client device associated with the medical professional. For example, the creation time of a medical report is established based on a time that the medical report was received from a client device 120, for example, in accordance with a medical professional submitting a drafted medical report that is generated via interaction with their client device 120. As another example, the creation time of a medical report is established based on a time that a digital signature and/or indication that the medical report be submitted received from a client device 120, for example, in accordance with a medical professional submitting a drafted medical report that is generated via interaction with their client device 120. For example, the medical professional previously typed some or all of their medical report via a keyboard associated with their client device 120 and/or previously dictated some or all of their medical report via a microphone associated with their client device 120. The medical professional can facilitate the creation of their medical report by facilitating sending the medical report to the staging module 5110 based on completing their medical report, for example, by interacting with a user interface displayed by a display device of their client device to, and/or by dictating instructions via a microphone of their client device to: denote completion of their medical report; to send their medical report to the staging module 5110, or to otherwise create their medical report.

The medical professional can create a given medical report to describe a particular patient and/or one or more medical images in a study. For example, the one or more medical images in the study are displayed to the medical professional via the same or different client device 120 utilized to by the medical professional to create their medical report. The medical report can be created to describe and/or indicate measurements of abnormalities and/or findings detected by the medical professional via review of a corresponding medical scan and/or to describe features included in the medical scan. The medical report can optionally be created to indicate detection, characterization, and/or measurement of abnormalities based on abnormality data automatically generated via performance of at least one inference function and/or at least one medical scan analysis function performed upon image data of the corresponding medical scan, for example, in conjunction with one or more other subsystems 101. For example, the medical professional utilizes the medical scan assisted review system 102 to generate the medical report. The medical report can optionally include some or all natural language text of report data 449 for a corresponding medical scan.

In some cases, the medical professional can treat the report creation process as formally submitting their medical report based on completing their medical report, and can interact with their client device to denote formal submission of their medical report. For example, the medical professional does not intend to further edit their medical report upon their creation of the medical report via submission and/or sending to the staging module 5110 based on deeming their report as complete and ready for long term storage in the medical report database 392. However, rather than the medical report being sent directly to medical report database 392, the medical report is nonetheless still staged via staging module 5110 for the staging duration. For example, the staging module 5110 functions to help ensure the report database 392 is not bombarded with new reports from a large number of users at a given time by streamlining the storage of many reports across many users creating reports at same or similar times.

Alternatively or in addition, the staging module 5110 functions to allow medical professionals a brief opportunity to correct any inadvertent errors they may become aware of after submitting their medical report. For example, the medical professional can elect to recall and/or edit their medical report so long as the predetermined staging duration 5114 for the medical report has not elapsed and/or so long as the medical report has otherwise not yet been sent to the report database 392. This can include editing a created medical report to render an updated medical report pending transmission to the medical report database that includes at least one edit, so long as the edits were initiated and/or completed prior to the elapsing of the predetermined staging duration. For example, the medical profession creates and sends edits to the created medical report stored in the memory module 5112 prior to elapsing of the predetermined staging duration 5114, where the staging module 5110 generates and stores an updated medical report from the created medical report based on the received edits. Alternatively or in addition, the medical professional can generate an updated medical report to replace a created medical report via their client device based on edits to their created medical report via their client device, and can send the updated medical report to the staging module to replace the previously created medical report prior to the elapsing of the predetermined staging duration. For example, a medical professional initiates edits, denotes edits are complete, elects to recall a medical report from staging, and/or elects to replace a currently staged medical report with an updated version of the medical report by interacting with a user interface displayed by a display device of their client device to denote these edits and/or instructions, and/or by dictating instructions via a microphone of their client device to denote these edits and/or instructions.

During staging via staging module 5110, other medical professionals and/or other users may not be permitted to review and/or access these medical reports via staging module 5110 as they have not yet been formally submitted. For example, medical reports are only accessible to other users and/or other subsystems 101 as discussed herein once stored in the medical report database 392, for example, via access to the medical report database 392 and not to the staging module 5110.

Edits to medical reports and/or updated medical reports may not be permitted once the predetermined staging duration elapses and/or once the medical report is submitted. For example, edits accomplished prior to the elapsing of the predetermined staging duration are not stored as new and/or different versions. Instead the medical report submitted to the medical report database 392 that reflect any edits accomplished during staging is considered the "original" medical report, where a version of the medical report prior to these edits is not preserved and/or stored in the medical report database 392. On the contrary, if edits are performed after staging and once the medical report is already stored in the medical report database 392, more formal addendums and/or a different amending process may be required to facilitate edits. Alternatively or in addition, edits performed after staging may result in separate addendum documents and/or separate report versions stored in the medical report database 392 along with the "original" medical report.

Thus, it can be preferred to correct any errors in medical reports via edits during staging rather than via edits after staging, as the editing process can be less tedious to the medical professional during staging and/or can ensure no errors are permanently documented in the medical report database 392. However, as the predetermined staging duration can be relatively short, such as only four minutes long, it can be difficult for a medical professional to catch and/or edit all errors in their report during this short time frame, and to consistently correct all errors across all reports they generate over time. Furthermore, as the medical professional may have deemed the medical report complete upon their creation of the medical report, they may believe their medical report is already error free, where additional edits are not attempted.

Rather than inducing the taxing task of manually searching for all possible problems requiring correction prior to submission, and/or rather than expecting medical professionals to detect and resolve all possible problems during such as short time frame themselves, a medical report analysis system 5100 can be implemented to automatically detect any problems with the medical report as illustrated in FIGS. 17B-17D. As the medical report analysis system 5100 can be implemented utilizing at least one computer to perform one or more sophisticated natural language processing functions, an exhaustive check for errors based on an extensive set of report requirements can be accomplished despite the short time frame. This can improve the technology of medical imaging by increasing the accuracy of reports generated by medical professional and increasing the efficiency that necessary edits to medical reports are created. This can alternatively or additionally improve the technology of medical imaging by increasing the efficiency that medical professionals generate medical reports based on at least partial reliance on the medical report analysis system 5100 to catch problems with their medical reports, rather than spending extensive periods of additional time to check for all of these problems themselves.

In various embodiments, the medical report analysis system 5100 is an additional subsystem 101 of the medical scan processing system 100, implemented by utilizing the subsystem memory device 245, subsystem processing device 235, and/or subsystem network interface 265 of FIG. 2B. In some embodiments, the medical report analysis system 5100 utilizes, or otherwise communicates with, the central server system 2640. In some embodiments, some or all of the medical report analysis system 5100 is implemented by utilizing other subsystems 101 and/or is operable to perform functions or other operations described in conjunction with one or more other subsystems 101.

FIGS. 17B and 17C illustrate an example functionality of a medical report analysis system 5100 for an example medical report A. First, an initial version of medical report A, denoted A.v1, is created based on client device 120 sending the medical report to the staging module 5110 and/or based on the medical professional otherwise electronically signing and/or denoting completion of the medical report. Based on medical report A.v1 being created, the medical report analysis system 5100 can receive the medical report A.v1 for processing.

For example, the medical report A.v1 is received from the staging module 5110 via network 150 in response to the medical report being created and/or being received by the staging module 5110 for staging. In such embodiments, the staging module 5110 can be configured to automatically transmit medical reports to the medical report analysis system 5100 as they are received.

As another example, the medical report analysis system 5100 is integrated within the staging module 5110 via processing and/or memory resources of the staging module 5110 and/or via processing and/or memory resources accessible by the staging module 5110 via network 150, and the staging module implements the medical report analysis system 5100 upon its staged records automatically during the predetermined staging duration. In such embodiments, the medical report A.v1 is received based on the staging module 5110 receiving the medical report and/or storing the medical report. For example, the medical report is accessed directly from memory module 5112.

As another example, the medical report A.v1 is received from the client device 120 via network 150 in response to the medical report being created and/or being received by the staging module 5110 for staging. In such embodiments, the client device 120 can be configured to automatically transmit medical reports to the medical report analysis system 5100 when they are created and/or in addition to being sent to staging module 5110 for staging.

As another example, the medical report analysis system 5100 is integrated within client device 120 via processing and/or memory resources of the client device 120 and/or via processing and/or memory resources accessible by the client device 120 via network 150. The client device 120 can implement its medical report analysis system 5100 automatically upon creating medical reports, for example, upon sending medical reports to the staging module 5110 and prior to elapsing of the predetermined staging duration. In such embodiments, different client devices 120 corresponding to different medical professionals can implement their own medical report analysis system 5100, where each medical report analysis system 5100 processes only medical reports generated by the corresponding medical professional. In such embodiments, the medical report A.v1 can be received based on the medical report being created, based on the medical professional indicating the medical report is complete, and/or based on the medical report being sent to the staging module 5110 for staging. Alternatively, the medical report analysis system 5100 can optionally be implemented prior to the medical report being sent for staging, for example, based on the medical professional indicating the medical report is complete or based on the medical professional electing to utilize the medical report analysis system 5100 to check a medical report for errors and/or necessary corrections prior to sending to staging module for staging.

Once a given medical report is received, a report processing function 5120 can be performed to generate report analysis data 5122. The report processing function 5120 can utilize one or more functions stored via medical scan analysis function database 346. Alternatively or in addition, the report processing function 5120 can be trained by and/or can be performed utilizing the medical scan natural language analysis system 114.

Performing the report processing function 5120 can include extracting text from the medical report corresponding to pathology labels, terms describing procedural actions, and/or other medical terms from the report. Performing the report processing function 5120 can include mapping the extracted pathology labels, terms describing procedural actions, medical terms, and/or other text to one or more words included in the report to a corresponding one or more medical codes 447 and/or to one or more billing codes. Performing the report processing function can include performing a natural language processing algorithm, Performing the report processing function 5120 can include generating the report analysis data 5122 to indicate, based on text extracted from the report: content of the report; description of one or more corresponding medical scans; one or more medical conditions indicated in the report: location, characterization, and/or measurements of one or more abnormalities indicated in the report; diagnosis information for the corresponding patient; one or more procedural actions and/or follow up actions that are indicated in the report to have been already performed; one or more procedural actions and/or follow up actions that are recommended in the report to be performed; one or more statements indicating reasoning for a particular finding and/or diagnosis; one or more statements indicating purpose and/or justification for performing a particular procedural action; and/or other information.

Performing the report processing function 5120 can include generating the report analysis data 5122 to indicate one or more required corrections to the medical report based on extracted and/or determined content of the medical report. In some cases, the required corrections can optionally indicate one or more procedural actions required by the medical professional prior to submitting the report alternatively or in addition to required edits to the report itself.

Performing the report processing function 5120 can include comparing the extracted pathology labels, terms describing procedural actions, medical terms, mapped medical codes and/or billing codes, and/or other text to a set of report requirements, as described in further detail in conjunction with FIGS. 17I-17M, to identify one or more report requirements that are not met, one or more required corrections to the medical report and/or one or more required procedural actions to be performed.

Performing the report processing function 5120 can include comparing extracted pathology labels, terms describing procedural actions, medical terms, mapped medical codes and/or billing codes, and/or other text to inference data generated for a corresponding medical scan as described in further detail in conjunction with FIG. 17R, to identify one or more discrepancies with the medical scan, one or more required corrections to the medical report and/or one or more required procedural actions to be performed.

Performing the report processing function 5120 can include comparing extracted pathology labels, terms describing procedural actions, medical terms, mapped medical codes and/or billing codes, and/or other text to metadata of the corresponding study that is retrieved from the medical picture archive system 2620, as described in further detail in conjunction with FIG. 17W, to identify one or more discrepancies with the metadata one or more required corrections to the medical report and/or one or more required procedural actions to be performed. Performing the report processing function 5120 can include identifying one or more typographical errors in the medical report.

Performing the report processing function 5120 can include determining whether any other discrepancies exist between extracted pathology labels, terms describing procedural actions, medical terms, mapped medical codes and/or billing codes determined for medical report and other information stored by database storage system 140 or another database system; medical picture archive system 2620 such as a PACS; medical billing system 4010 of FIG. 14B or another a billing database; a database of procedural actions performed by medical professionals; and/or other memory accessible by medical report analysis system 5100. For example, performing the report processing function 5120 can include comparing extracted pathology labels, terms describing procedural actions, medical terms, mapped medical codes and/or billing codes, and/or other text to a set of procedural actions determined to have been actually performed by the medical professional for a corresponding patient and/or study, and/or determining whether there are any discrepancies between the set of procedural actions and the extracted pathology labels, terms describing procedural actions, medical terms, mapped medical codes and/or billing codes, and/or other text. As another example performing the report processing function 5120 can include comparing extracted pathology labels, terms describing procedural actions, medical terms, mapped medical codes and/or billing codes, and/or other text to a set of billing codes billed for a corresponding patient and/or study, and/or determining whether there are any discrepancies between the set of billing codes and the extracted pathology labels, terms describing procedural actions, medical terms, mapped medical codes and/or billing codes, and/or other text.

Performing the report processing function 5120 can include performing: extraction function 3120 of FIG. 13A and/or billing data generator function 4050. For example, the medical report analysis system 5100 is implemented to perform some or all features and/or functionality of the retroactive discrepancy flagging system 3100 and/or the medical billing verification system 4000. In some cases, the inference function 3110 is performed upon corresponding medical scans to generate automated assessment data, and consensus function 3195 is performed to identify errors requiring correction.

Performing the report processing function 5120 can include generating and/or accessing factor data generated by factor detection system 4300 and utilizing the factor data to identify common problems. For example, performing the report processing function 5120 includes searching for common errors before less common errors, as indicated by the factor data. This can improve the speed of identifying the most likely errors, which can help ensure that errors are identified prior to the medical scan being formally submitted.

The report analysis data 5122 generated via performance of the report processing function 5120 can be utilized by a correction requirement notification data generator 5130 to generate correction requirement notification data 5132 to be communicated to the medical professional that created the medical report. In particular, the correction requirement notification data generator 5130 can utilize at least one processor and/or at least one memory of the medical report analysis system 5100 to generate correction requirement notification data 5132 indicating at least one correction indicated by the report analysis data 5122, based on: one or more errors and/or discrepancies detected in the medical report as indicated in the report analysis data 5122; one or more required corrections to the medical report to resolve detected errors as indicated in the report analysis data 5122; one or more required procedural actions to be performed prior to completion of the report as indicated in the report analysis data 5122; and/or one or more other problems requiring correction.

The correction requirement notification data 5132 can include text and/or one or more words indicating: detected errors in medical report A.v1; instructions for correction of the detected errors in medical report A.v1; instructions to perform additional procedural actions and/or to include description of these procedural actions in medical report A.v1; suggested and/or required edits to be incorporated into the medical report A.v1; and/or a new, updated version of the medical report that includes the suggested and/or required edits medical report A.v1, such as a proposed medical report A.v2, and/or other information indicating how edits be accomplished by the medical professional.

The medical report analysis system 5100 can facilitate communication of the correction requirement notification data 5132 to the medical professional based on determining notification routing information for the correction requirement notification data 5132 based on: an identifier of the medical professional, an identifier of the client device 120, account information for a messaging account accessible by the medical professional via the client device 120, a contact directory lookup to a contact directory stored in memory accessible by the medical report analysis system 5100 based on identifying information of the medical professional; accessing the medical professional's contact information via user profile entry 354 in user database 344; accessing a preferred means of notifying the medical professional of correction requirement notification data 5132 that was configured by the medical professional and/or that was determined automatically based on historical response time of the medical professional; and/or other means of determining how to communicate the correction requirement notification data 5132 to the medical professional. Some or all identifying and/or contact information can be automatically extracted from the medical report and/or can be received from the staging module 5110 in conjunction with receiving the medical report.

The medical report analysis system 5100 can facilitate communication of the correction requirement notification data 5132 to the medical professional by transmitting the correction requirement notification data 5132 to the same client device 120 utilized to generate the medical report A.v1 as illustrated in FIG. 17B. For example, a display device of the client device 120 displays the correction requirement notification data 5132 to the medical professional. As another example, speakers of the client device 120 dictate the correction requirement notification data 5132 to the medical professional. In embodiments where the medical report analysis system 5100 is integrated within client device 120, communication of the correction requirement notification data 5132 to the medical professional can include simply displaying the correction requirement notification data 5132 via the display device of the client device 120 and/or dictating the correction requirement notification data 5132 via the speakers of the client device 120.

The correction requirement notification data generator 5130 can facilitate communication of the correction requirement notification data 5132 to the medical professional by transmitting the correction requirement notification data 5132 to another client device 120.2 that is different from the client device 120.1 utilized to generate the medical report A.v1 as illustrated in FIG. 17C. For example, the medical professional utilized a laptop, desktop computer, and/or dictation device to generate the medical report, to send the medical report to the staging module 5110 and/or the medical report analysis system 5100, and/or to review image data a corresponding medical scan in conjunction with generating the medical report, for example, via at least one display device of the client device 120.1, via at least one keyboard of the client device 120.1 and/or via at least one speaker of the client device 120.1. Meanwhile, the correction requirement notification data 5132 is communicated to the medical professional via a cellular device, a telephone, a mobile device, a different device that can access the messaging platform utilized to send correction requirement notification data 5132, and/or another device implemented as client device 120.2 that is distinct from client device 120.1. As a particular example, the medical professional receives the correction requirement notification data 5132 via a text message sent to their cellular device via a cellular network by utilizing a cellular phone number associated with the medical professional. As another particular example, the medical professional receives the correction requirement notification data 5132 via a phone call by utilizing a phone number associated with the medical professional, where the correction requirement notification data 5132 is dictated to the medical professional via speakers of a telephone and/or cellular device implementing the client device 120.2.

Communicating correction requirement notification data 5132 to all respective medical professionals using the medical report analysis system 5100 via text message or phone call can be ideal in embodiments where substantial proportion of all users and/or all medical professionals are determined to be more responsive to and/or have a faster response to text messages or phone calls over other means of communication, such as emails and/or messages sent via other messaging platforms. For example, any medical professional using the system receives correction requirement notification data 5132 for their medical reports via text message or phone call automatically. In other embodiments, another fastest and/or other most effective means of communicating the medical professionals can be selected based on a substantial proportion of all users and/or all medical professionals being determined to be more responsive to and/or have a faster response to the another means of communicating.

In some embodiments, different medical professionals receive correction requirement notification data 5132 for their medical reports via different means of communication. For example, the particular medical professional in the example of FIG. 17C receives a text message based on configuring the correction requirement notification data 5132 to be sent via text message for their medical reports in an account accessible by and/or associated with the medical report analysis system 5100, while the particular medical professional in the example of FIG. 17B receives a message via an email account accessible via the computer utilized to generate the report based on configuring the correction requirement notification data 5132 to be sent via email. Communicating the correction requirement notification data 5132 to a particular medical professional via a particular means of communication can be automatically determined to be optimal based on the particular medical professional being determined to be more responsive to and/or have a faster response to the particular means of communication over other means of communication, for example, based on historical response times of the medical professional to notifications sent to the medical professional via various means.

The generation of report analysis data 5122; generation of correction requirement notification data 5132; and/or the communication of the correction requirement notification data 5132 can all occur prior to the elapsing of the predetermined staging duration to ensure that appropriate edits can be made to the medical report A.v1 prior to being formally submitted. For example, the generation of report analysis data 5122; generation of correction requirement notification data 5132; and/or the communication of the correction requirement notification data 5132 can be guaranteed to occur prior to the elapsing of a fixed-length time frame for all medical reports and/or for at least a threshold percentage of medical reports, where the fixed-length time frame induced by the medical report analysis system 5100 is equal to, less than by at least a threshold buffer timespan, and/or based on the predetermined staging duration induced by the staging module 5110.

For example, the medical report analysis system 5100 determines the fixed-length time frame based on receiving the predetermined staging duration from the staging module 5110, accessing the predetermined staging duration in memory, and/or the predetermined staging duration being known and/or public. The fixed-length time frame can commence from a known and/or estimated creation time 5113 of a given medical report and/or can be set based on a projected and/or estimated submission time of the given medical report by the staging module. For example, the creation time 5113 of each given medical report and/or projected submission time is received from the staging module 5110 in conjunction with the given medical report and/or is accessed in memory module 5112. The fixed-length time frame can alternatively commence from a time the medical report is received by the medical report analysis system 5100.

The threshold buffer timespan can be determined based on: a communication lag for the medical report analysis system 5100 receiving the medical report from the staging module 5110 and/or from the client device 120; a communication lag for transmitting the receiving the correction requirement notification data 5132 from the medical report analysis system 5100 to the client device 120; a communication lag for transmitting, from the client device 120 to the staging module 5110, an instruction to recall and/or edit a staged medical report; a communication lag for transmitting, from the medical report analysis system 5100 to the staging module 5110, an instruction to recall and/or edit a staged medical report; an average, expected, and/or maximum amount of time for a medical professional to request recalling and/or editing a medical report after client device 120 receives and/or displays the correction requirement notification data 5132; and/or another buffer to ensure that the medical professional has sufficient time to receive the communication and/or to recall and/or edit the medical report accordingly. For example, the fixed-length time frame is configured to be three minutes based on the predetermined staging duration being known to be four minutes and further based on determining a one minute threshold buffer timespan is sufficient to ensure a medical professional will have enough time to receive the notification and act accordingly in most or all cases.

The timely completion of these steps within the determined fixed-length time frame for each given medical report can be based on: selecting an algorithm, configuring parameters, and/or otherwise configuring the report processing function 5120 to be completed within the fixed-length time frame; configuring a speed and/or type of one or more processing devices and/or one or more memory devices utilized by the medical report analysis system 5100 to perform the report processing function 5120 and/or to implement correction requirement notification data generator 5130; configuring a level of parallelism for execution of the report processing function 5120 and/or a number of parallelized processing resources to execute the report processing function 5120 upon all reports based on the fixed-length time frame, based on processing speed of the parallelized processing resources, based on complexity of the report processing function 5120, based on a length of the given report and/or based on a number or requirements in the set of requirements; configuring a level of parallelism for execution of the report processing function 5120 and/or a number of parallelized processing resources to execute the report processing function 5120 upon a given report based on a length of the given report; selecting a number of subsets of the set of requirements to be checked for the medical report in parallel based on the fixed-length time frame and/or based on a number or requirements in the set of requirements; selecting a serial ordering for checking some or all the set of requirements for all medical reports based on a probability of the requirement not being met that is calculated and/or otherwise determined based on the factor data of FIGS. 15A-16C; selecting a serial ordering for checking some or all the set of requirements for each given medical report based on a probability of the requirement not being met that is calculated and/or otherwise determined based on performance score data 530 of the corresponding medical professional's user profile entry 354 and/or historical report analysis data generated for a plurality of prior medical reports created by the medical professional for same or different patients and/or studies; selecting one or more means of communicating correction requirement notification data 5132 from a set of options based on: transmission speed of each of the set of options; selecting one or more means of communicating correction requirement notification data 5132 for each given medical report from a set of options, for example, that includes cellular text message, email, phone call, one or more different client devices 120 corresponding to the medical professional that can receive the notification, sending the notification to a different assistant or different physician, one or more different communication networks, and/or one or more different messaging platforms, based on current network performance for each of the set of options, a configured preference of one of the set of options by the medical professional that created the given medical report, and/or historical response times tracked for the medical professional that created the given medical report for communications received via different ones of the set of options; generating report analysis data 5122 for each of a set of multiple medical reports with overlapping fixed-length time frames serially in accordance with an ordering of their creation times and/or in the order that they are received for processing; generating report analysis data 5122 for some or all of a set of multiple medical reports with overlapping fixed-length time frames in parallel via a set of parallelized processing resources of the medical report analysis system 5100; automatically ceasing performance of the report processing function 5120 prior to completing checking of all of a set of report requirements in response to detecting a first error in the medical report; and/or other configurations and/or optimizations that are standard across all medical reports received over time and/or that are configured for each medical report individually based on characteristics determined for each given medical report, each corresponding medical professional, the current load of the medical report analysis system, current state of system communication resources, and/or other information.

In some cases, the medical report analysis system 5100 determines that it will not complete generation of the report analysis data in time to ensure that correction requirement data 5132 is communicated prior to elapsing of the fixed-length time frame. In such cases, the medical report analysis system 5100 can automatically notify the corresponding medical professional of the delay, enabling the medical professional to recall the medical report, pull and/or the medical report for editing, and/or otherwise delay and/or cancel the formal submission of the medical report by the staging module 5110 accordingly. Alternatively or in addition, the medical report analysis system 5100 can automatically recall the medical report, pull and/or the medical report for editing, and/or otherwise delay and/or cancel the formal submission of the medical report by the staging module 5110 itself. For example, the medical report analysis system 5100 can automatically open the medical report for editing via sending a request to the staging module 5110 to pause a countdown timer associated with the predetermined staging duration by the staging module, and can end the editing once generation of the report analysis data has completed and/or once the corresponding correction requirement notification data 5132 is transmitted. As another example, the medical report analysis system 5100 can automatically recall the medical report, and can re-create the same medical report to restart the countdown timer associated with the predetermined staging duration once generation of the report analysis data has completed and/or once the corresponding correction requirement notification data 5132 is transmitted.

Because the correction requirement notification data 5132 is communicated to the medical professional prior to the elapsing of the predetermined staging duration, the medical professional can generate a new, updated medical report A.v2 based on the communicated correction requirement notification data 5132. This can include editing medical report A.v1 via interaction with the same or different client device 120 that was utilized to generated medical report A.v1 to render an updated medical report A.v2; opening staged medical report A.v1 for edits via a request sent by the same or different client device 120 to staging module 5110 and editing medical report A.v1 stored in staging module 5110 accordingly; approving one or more edits included in correction requirement notification data 5132 for inclusion in medical report A.v1 to render an updated medical report A.v2 via interaction with the same or different client device 120; approving or editing a proposed medical report A.v2 included in the correction requirement notification data 5132 via interaction with the same or different client device 120; and/or otherwise generating updated medical report A.v2 based on communicated correction requirement notification data 5132 that includes at least one edit to and/or change from medical report A.v1. For example, the medical professional types and/or dictates the edits via interaction with client device 120 for transmission to staging module 5110 prior to elapsing of the predetermined staging duration of medical report A.v1. As a particular example, the medical professional types and/or dictates the edits via interaction with client device 120 to generate and create medical report A.v2 to replace medical report A.v1 via sending medical report A.v2 to staging module 5110 prior to elapsing of the predetermined staging duration of medical report A.v1.

Thus, as medical report A.v2 replaced medical report A.v1 in staging prior to medical report A.v1 being sent to the medical report database 392, the staging module 5110 ultimately formally submits medical report A.v2, and not medical report A.v1. In particular, staging module 5110 can submit medical report A.v2 by sending medical report A.v2 to medical report database 392 for storage and future access by one or more medical professionals and/or by one or more other subsystem 101 as discussed previously. Staging module 5110 can submit medical report A.v2 based on the predetermined staging duration for medical report A.v2 elapsing. Note that the predetermined staging duration for medical report A.v2 may have been extended and/or reset from the predetermined staging duration for medical report A.v1 based on medical report A.v1 being edited and/or replaced by medical report A.v2. Such embodiments are discussed in further detail in conjunction with FIGS. 17G-17H.

In some embodiments, any edits or revisions, such as medical report A.v2, are also sent to medical report analysis system 5100 for processing. For example, medical report analysis data 5122 can be again generated to ensure the revised medical report A.v2 indeed corrected all errors and did not introduce new errors. Correction requirement notification data 5132 can similarly be generated based on medical report analysis data 5122 to indicate any maintained and/or new errors for correction, and is new correction requirement notification data 5132 can again be submitted to the medical professional. This can prompt another iteration of revision, and the process can continue until the most recently revised version of the medical report has no required corrections, where this most recently revised version of the medical report is ultimately submitted by staging module 5110 based on all edits to prior revisions being completed in a timely fashion and/or being completed prior to elapsing of the corresponding predetermined staging duration.

In some embodiments, the medical professional can elect to ignore one or more corrections indicated in the correction requirement notification data 5132. For example, the correction requirements can be implemented as recommendations and/or suggestions that are not always applicable, and the medical professional can deem that these recommendations and/or suggestions are not necessary for their medical report. In such cases, the medical professional can elect to ignore some or all edits indicated in the correction requirement notification data 5132, where the medical professional does not perform all suggested edits and/or foregoes any editing of their medical report. For example, the medical professional receives the correction requirement notification data 5132, determines not to edit medical report A.v1, and medical report A.v1 is thus submitted upon elapsing of the corresponding predetermined staging duration. In some embodiments, the medical professional can respond to the correction requirement notification data 5132 indicating whether any correction requirements were incorrect and/or not necessary, where this response is sent to and received by the medical report analysis system 5100. For example, the medical report analysis system 5100 automatically updates the report processing function 5120 and/or updates at least one requirement utilized to generate the report analysis data based on this feedback from the medical professional.

FIG. 17D illustrates an embodiment where a medical report B.v1 is similarly processed by medical report analysis system 5100 prior to elapsing of the predetermined staging duration, but is determined to require no correction. The medical report analysis system 5100 can generate report analysis data 5122 as discussed previously, and can determine no corrections are required based on the report analysis data 5122. For example, the correction requirement notification data generator 5130 is not implemented based on the report analysis data 5122 indicating no corrections required for medical report B.v1. In particular, the medical report analysis system can forego generation and facilitate communication of a notification to the medical professional in cases where the medical reports contain no issues. Medical report B.v1 is thus not edited, and the original version of medical report B.v1 is thus submitted by the staging module when the predetermined staging duration elapses.

This foregoing of notifications for reports not requiring correction can be preferred, as it enables medical professionals to proceed with normal submission of medical reports in most cases, where they are only interrupted with notifications when corrections are necessary, which can ensure they do not undergo alarm fatigue via notifications sent with every medical report creation and can thus ensure received notifications are treated seriously and induce necessary edits promptly.

Alternatively, the medical report analysis system 5100 can similarly generate and facilitate communication of correction requirement notification data 5132 indicating no corrections are required to the medical professional in cases where the medical reports contain no issues. This can be useful in easing the medical professional that all medical reports are being checked for errors by the medical report analysis system. In some embodiments, these notifications indicating no corrections are required are communicated to the medical professional via different, less urgent means than correction requirement notification data 5132 indicating corrections are required. In some embodiments, these notifications indicating no corrections are required are sent to a different location than the correction requirement notification data 5132 indicating corrections are required. For example, correction requirement notification data for all medical reports can be sent for storage in a log of correction requirement notification data, stored in at least one memory such as a database of database storage system 140 or another memory location accessible by a client device 120 of the medical professional. In such embodiments, medical professionals and/or other administrators can view the log data at their leisure to ensure that all medical reports are being processed in a timely fashion and/or that their report analysis data is catching all errors correctly.

FIGS. 17E-17H illustrate example timelines illustrating the functionality of medical report analysis system 5100 for relative to the predetermined staging duration. In particular, FIG. 17E illustrates an example timeline 5140 corresponding to the medical report analysis system 5100 processing medical report A.v1 as discussed in conjunction with FIGS. 17B and 17C. A creation time 5113 occurs based on medical report A.v1 being received by the staging module, dictating the projected submission time 5115 based on the predetermined staging duration, such as four minutes after the creation time 5113.

Following the creation time 5113 and prior to the submission time 5115, the medical report analysis system 5100 generates the medical report analysis data 5122 for medical report A.v1, generates the correction requirement notification data 5132 for medical report A.v1 to indicate required corrections indicated by the medical report analysis data 5122, and transmits or otherwise facilitates communication of the correction requirement notification data 5132 to the medical professional.

These steps can be performed by the medical report analysis system 5100 in accordance with a deadline 5118 imposed by a fixed-length time frame 5119 as discussed previously. The fixed-length time frame 5119 can be equal the predetermined staging duration in length, or can be optionally shorter than the predetermined staging duration in length as illustrated in FIG. 17E. The fixed-length time frame 5119 can begin at the creation time and/or at a time the medical report is received by the medical report analysis system 5100. The fixed-length time frame 5119 can thus induce a deadline 5118 by which these steps performed by the medical report analysis system 5100 are guaranteed to be complete and/or are projected to be complete with a probability that compares favorably to a predetermined and/or configured completion probability threshold. For example, the medical report analysis system 5100 is configured to complete the steps prior to the deadline 5118 for some or all medical reports via one or more of the mechanisms discussed previously.

In this example, the deadline 5118 for completion of these steps by the medical is prior to the submission time based on the fixed-length time frame being shorter than the predetermined staging duration, for example, to account for a buffer timespan for the medical professional to initiate and/or complete the required edits. Alternatively, the deadline 5118 for completion of these steps can be the same as the submission time based on the fixed-length time frame being equal to the predetermined staging duration.

After the radiologist receives the correction requirement notification data 5132, the radiologist can receive the correction requirement notification data 5132 and can edit the report accordingly, where ultimately edits that render medical report A.v2 are received by the staging module prior to the projected submission time 5115. At the projected submission time 5115, the medical report A.v2 is transmitted to the report database. Alternatively, the projected submission time 5115 is adjusted based on medical report A.v1 being edited, as discussed in further detail in conjunction with FIGS. 17G and 17H.

FIG. 17F illustrates an example timeline 5140 corresponding to the medical report analysis system 5100 processing medical report B.v1 as discussed in conjunction with FIG. 17D. A creation time 5116 occurs based on medical report B.v1 being received by the staging module, dictating the projected submission time 5117 based on the predetermined staging duration, such as four minutes after the creation time 5116. Following the creation time 5116 and prior to the submission time 5117, the medical report analysis data 5122 for medical report B.v1 can be generated. Again, the processing of the medical report B.v1 by the medical report analysis system 5100 is performed in accordance with a deadline 5118 determined for the medical report B.v1 based on the fixed-length time frame 5119. However, as the medical report analysis data 5122 indicates no errors, no correction requirement notification data 5132 need be generated or communicated. As no edits are received during staging based on no corrections being required, at the projected submission time 5115, the medical report B.v1 is transmitted to the report database.

In some embodiments, the predetermined staging durations and/or the fixed-length time frames for different medical reports processed by the medical report analysis system 5100 can be overlapping. For example, the creation time for medical report B.v1 occurs prior to submission time of medical report A.V2. As a particular example, the creation time for medical report B.v1 occurs shortly after the creation time of medical report A.v1 and prior to generation of report analysis data 5122, for example, based on medical report A.v1 and B.v1 being created by different medical professionals at similar times. The medical report analysis system 5100 can prioritize and/or order multiple received medical reports for processing by processing the medical reports based on ordering of their creation times, submission times, and/or deadlines, where the medical report with the earliest creation time 5113, earliest projected submission time 5115, and/or earliest deadline 5118 is processed first. The medical report analysis system 5100 can process multiple received medical reports in parallel to ensure deadlines 5118 are met for multiple medical reports with similar deadlines 5118. For example, medical report A.v1 is processed in parallel, simultaneously with processing of medical report B.v1, for example, where a first parallel processing resource processes medical report A.v1 independently from and in parallel with processing of medical report B.v1 via a second parallel processing resource, based on medical report A.v1 and medical report B.v1 having similar creation times, similar submission times, similar deadlines, overlapping predetermined staging durations, and/or overlapping fixed-length time frames.

FIG. 17G illustrates another example timeline 5140 corresponding to the medical report analysis system 5100 processing medical report A.v2 as discussed in conjunction with FIG. 17B and FIG. 17C, illustrating how the predetermined staging duration can be paused for editing in some embodiments. In particular, the total duration of the predetermined staging duration is divided into a first predetermined staging duration sub-portion 5114.1 and a second predetermined staging duration sub-portion 5114.2, separated by a pause window. The pause window can commence, ending the first predetermined staging duration sub-portion 5114.1 and/or otherwise pausing a countdown timer associated with the elapsing of the predetermined staging duration, based on initiation of editing the medical report A.v1 and/or opening the medical report A.v1 for edits via access to medical report A.v1 in staging module 5110. The pause window can end, continuing elapsing of the predetermined staging duration by starting the second predetermined staging duration sub-portion 5114.2 and/or otherwise resuming a countdown timer associated with the elapsing of the predetermined staging duration, once edits are complete, rendering medical report A.v2. This resetting of the predetermined staging duration can be ideal in ensuring that all desired edits to a medical report can be completed prior to the medical report being automatically submitted.

FIG. 17H illustrates another example timeline 5140 corresponding to the medical report analysis system 5100 processing medical report A.v2 as discussed in conjunction with FIG. 17B and FIG. 17C, illustrating how the predetermined staging duration can be reset when revisions are commenced or completed in some embodiments. The original version of the medical report A.v1 has a first predetermined staging duration, with a projected submission time 5115.1 dictated based on its creation time. Once a new medical report version A.v2 is created to replace medical report A.v1, a new corresponding predetermined staging duration can commence for this newly created version of the report with creation time 5113.2 and submission time 5115.2. The predetermined staging duration can have a fixed length as discussed previously, and thus the predetermined staging durations for medical report A.v1 and medical report A.v2 can each have same lengths with different start and end times. The medical report version A.v2 is not submitted until the elapsing of its predetermined staging duration at submission time 5115.2. The medical report version A.v1 is not submitted at its projected submission time 5115.1 based on the medical report version A.v2 being created to replace medical report version A.v1 prior to this projected submission time 5115.1. This resetting of the predetermined staging duration can be ideal in ensuring that: new versions of medical reports are staged for a sufficient amount of time, new versions of medical reports similarly have enough time for subsequent edits, and/or new versions of medical reports can be processed by the medical report analysis system 5100 prior to submission.

FIG. 17I illustrates an embodiment of the medical report analysis system 5100 that utilizes a report requirement set 5160 to generate report analysis data 5122 for incoming reports. Some or all features and/or functionality of the medical report analysis system 5100 of FIG. 17I can be utilized to implement the medical report analysis system 5100 of FIGS. 17B, 17C, and/or 17D, and/or any other embodiment of the medical report analysis system 5100 described herein.

A report requirement set 5160 that includes a set of one or more requirements 5107.1-5107.R can be determined by the medical report analysis system 5100. For example, the medical report analysis system 5100 determined the report requirement set 5160 based on: the report requirement set 5160 being received by the medical report analysis system 5100 via network 150; the report requirement set 5160 being stored in at least one that is accessed by the medical report analysis system 5100; the report requirement set 5160 being configured via user input to a graphical user interface; the report requirement set 5160 automatically generating the report requirement set 5160, for example, based on at least one medical report received from the medical report database 392; and/or based on another type of determination.

Some or all of the requirements 5107 in the report requirement set 5160 can be generated based on criteria defined by at least one insurance provider, for example relating to which conditions warrant gathering more diagnostic information via procedural actions and/or follow-up procedures, and/or what statements and/or findings are required to appear in medical reports to justify performance and/or billing of procedural actions and/or follow-up procedures. Some or all of the report requirement set 5160 can be generated based on criteria and/or recommendations defined by a medical institution, a medical society, and/or a medical standard, such as criteria and/or recommendations defined by the American College of Radiology, the British Thoracic Society, the Fleischner Society, and/or any other society that publishes recommendations and/or other criteria for reviewing medical scans, for generating medical reports, for procedural actions and/or follow-up procedures that should be performed in particular conditions, or other criteria.

In some embodiments, the some or all requirements 5107 of the report requirement set 5160 can automatically be determined based on published guidelines by one or more of these entities, for example, based on receiving the published guidelines via network 150 and/or accessing the published guidelines via the Internet. In some cases, requirements 5107 of the report requirement set 5160 can automatically be updated and/or changed to include new and/or different requirements 5107 over time based on new publications by and/or changes to recommendations by one or more of these entities, for example, based on receiving new and/or updated published guidelines via network 150 and/or accessing the published guidelines via the Internet.

Performing the report processing function 5120 can include comparing extracted terms and/or mapped medical codes to some or all requirements 5107 in the report requirement set 5160. Any particular requirements 5107 that are met and/or are otherwise not adhered to can be automatically detected, and the corresponding correction requirement notification data 5132 can include specific edits and/or instructions to rectify these detected requirements 5107 that are not met. For example, the medical report analysis system 5100 only forgoes generating and communicating the correction requirement notification data 5132 when all requirements 5107.1-5107.R in the report requirement set 5160 are determined to have been adhered to. The correction requirement notification data 5132 can indicate correction is required when one or more requirements 5107 are determined not to have been adhered to. The correction requirement notification data 5132 can indicate multiple corrections that are required, for example, when multiple corresponding requirements 5107 are determined not to have been adhered to.

FIGS. 17J-17P illustrate example embodiments of requirements 5107 that can be included in the report requirement set 5160 of FIG. 17I that is utilized by the report processing function 5120 to generate the report analysis data 5122. Any embodiment of the medical report analysis system 5100 discussed herein can determine and/or utilize one or more types of requirements 5107 of FIGS. 17J-17P to generate report analysis data 5122 and/or correction requirement notification data 5132.

As illustrated in FIG. 17J-17M, the report requirement set 5160 can implement one or more of its requirements 5107 as conditional requirements 5162. A conditional requirement 5162 can indicate a requirement for medical reports that is only applicable if a corresponding condition is met. For example, if the corresponding condition is not met, this requirement is deemed not applicable to the report and is not checked and/or is determined to be adhered to based on the condition not being applicable.

As illustrated in FIG. 17J, the report requirement set 5160 can include one or more conditional requirements 5162 that correspond to requirements that one or more procedural actions be performed if a particular corresponding medical condition 5163 is detected. In particular, if the medical report includes mention of and/or indicates presence of the medical condition 5163, the corresponding one or more procedural actions 5164 must be performed. In some embodiments, the medical report must also include mention and/or document the performance of this procedural action when medical report includes mention and/or indicates presence of the corresponding medical condition.

Multiple different medical conditions, such as abnormalities with different characteristics, different measurement criteria, and/or different locations, can be indicated for different conditional requirements 5162. For example, a set of X different medical conditions 5163 have corresponding required procedural actions 5164 to render X conditional requirements 5162.

Performing the report processing function 5120 can include identifying and/or extracting at least one term from the medical report indicating presence of a medical condition 5163. This at least one term can indicate a name of, a type of, a number of, detection of, location of, age of, one or more measurements of, malignancy data for, whether or not the abnormality is new or was previously presented in a prior medical image, growth or shrinkage of the abnormality from a prior medical image and/or other characteristics of a particular abnormality.

The medical condition 5163 of a given conditional requirement 5162 can be denoted by a corresponding pathology label, one or more medical codes 447, and/or other information identifying and/or distinguishing the medical condition. Performing the report processing function 5120 can include determining whether any one or more terms included in text of the medical reports map to, match, and/or otherwise compare favorably to the pathology label, one or more medical codes 447, and/or other information identifying and/or distinguishing the corresponding medical condition 5163.

In some embodiments, some or all of this information indicating medical conditions that is included in a given medical report was written by the medical professional based on utilizing another subsystem 101 that detected, characterized, and/or measured abnormalities in the corresponding medical image, such as the medical scan assisted review system 102. In some embodiments, some or all of the text in the medical report indicating medical conditions was automatically generated as report data 449 by another subsystem 101 that detected, characterized, and/or measured abnormalities in the corresponding medical image, such as the medical scan assisted review system 102, the medical scan diagnosing system 108, medical scan image analysis system 112, and/or the lesion tracking system 3002 of FIGS. 12A-12D.

If the at least one term, and/or a corresponding medical code mapped to the medical term in performing the report processing function 5120, matches a medical condition indicated in a conditional requirement 5162 of the report requirement set, the report processing function 5120 can determine if the medical report includes text indicating performance of the corresponding procedural action. If text is identified in and/or extracted from the report indicating performance of the corresponding procedural action, the conditional requirement 5162 is determined to be adhered to. When the medical report includes text indicating the medical condition, and if text is not identified in and/or not extracted from the report indicating performance of the corresponding procedural action, and/or if the medical report is otherwise determined to include no text indicating performance of the corresponding procedural action 5164, the corresponding conditional requirement 5162 is determined to not be adhered to. Note that this corresponding conditional requirement 5162 is still considered to be adhered to in cases where the corresponding procedural action was not performed, and where the corresponding medical condition was also not detected and/or mentioned.

As a particular example, one conditional requirement 5162.1 can indicate that a volumetric analysis and/or three-dimensional reconstruction be must performed by the medical professional for medical images that include new nodules measured to be greater than or equal to 6 mm. In other embodiments, the volumetric analysis and/or three-dimensional reconstruction must be performed for medical images that include nodules that are greater than or equal to a different diameter and/or that meet other threshold measurement criteria. Other conditional requirements 5162 can optionally indicate the same or different procedural actions and/or other follow up recommendations are required for abnormalities detected that have particular characteristics and/or threshold measurement criteria.

As another particular example, one or more types of abnormalities can be automatically excluded from consideration for inducing procedural actions and/or inducing sending of notifications. For example, calcified nodules can be indicated in the set of report requirements to be excluded from consideration in generating and communicating notifications. In particular, medical conditions indicated in text of the medical report of that correspond to conditional requirements 5162 are automatically ignored, and the conditional requirements 5162 are thus adhered to and/or not checked, when these medical conditions correspond to a type of medical condition excluded from consideration, such as a calcified nodule. In such embodiments, the one conditional requirement 5162.1 can indicate that a volumetric analysis and/or three-dimensional reconstruction be must performed by the medical professional for medical images that include new nodules measured to be greater than or equal to 6 mm, so long as they are not calcified and/or where any nodules that are calcified are excluded from consideration of conditional requirement 5162.1.

Consider the case where the report requirement set 5160 includes this example conditional requirement of FIG. 17J. If report processing function 5120 extracts text from a given medical report that is determined to indicate a new nodule with a measurement greater than or equal to 6 mm, the medical report is only determined to adhere to this conditional requirement 5162.1 when the report processing function 5120 further identifies text in the medical report that is determined to indicate that a volumetric analysis was performed for this nodule. If this conditional requirement 5162.1 is not adhered to, a requirement to perform the volumetric analysis and/or to indicate the performance of volumetric analysis in the medical report will be indicated in the correction requirement notification data 5132.

In some embodiments, the procedural action 5164 required for a given medical condition 5163 in a conditional requirement 5162 can correspond to a follow up action that need not be performed prior to medical report submission, but must and/or should be indicated in the report as a recommended and/or required follow up action. In such cases, if the report processing function 5120 extracts text from a given medical report that is determined to indicate this given medical condition 5163, the given medical report is only determined to adhere to such a conditional requirement 5162 when the report processing function 5120 identifies text in the medical report that is determined to indicate that this follow up action is scheduled to be performed and/or that this follow up action is recommended and/or required to be performed by the same or different medical professional.

In some embodiments, the medical report analysis system 5100 can further determine whether the required procedural action was already performed. This can include retrieving metadata of a corresponding study from the medical picture archive system 2620, for example, as discussed in conjunction with FIG. 17W. This can alternatively or additionally include accessing another database tracking performance of procedural actions based on an identifier of the corresponding study, patient extracted from the medical report and/or based on an identifier of the medical professional. The correction requirement notification data 5132 can be generated to prompt the medical professional to perform the procedural action 5164 if the procedural action 5164 is not mentioned in the report, and if the procedural action 5164 is also not logged in the medical picture archive system 2620 or the other database. The correction requirement notification data 5132 can be generated to prompt the medical professional to simply document their prior performance of the procedural action 5164 if the procedural action 5164 is not mentioned in the report, but if the procedural action 5164 is logged in the medical picture archive system 2620 or the other database.

In some cases, the procedural action does not require documentation in the medical report, and is instead must simply have its performance verified via access to the corresponding study, a log of procedural actions, medical billing system 4010 and/or another log of billing data, and/or other sources in this fashion. For example, a conditional requirement 5162 can be determined to be adhered to and thus not require correction based on identifying text indicating a medical condition 5163 of a conditional requirement 5162, and further based on determining the corresponding procedural action 5164 was performed based on receiving and/or accessing the study, the log of procedural actions, and/or other information denoting performance of the procedural action, even if the procedural action is not described in the text of the medical report.

As illustrated in FIG. 17K, the report requirement set 5160 can include one or more conditional requirements 5162 that correspond to requirements that one or more textual requirements 5165 are required for inclusion in the medical report if a particular procedural action 5164 was performed. In particular, requirements for how some or all procedural actions 5164 are described and/or justified in the medical report may be required, for example, to ensure proper evidence and/or justification for billing of the medical procedures to satisfy insurance company requirements is presented. Thus, if the medical report includes mention of and/or indicates performance of the procedural action 5164 of a conditional requirement 5162 of FIG. 17K, the corresponding one or more textual requirements 5165 must be included in the medical report. These conditional requirements 5162 of FIG. 17K can be included in the report requirement set 5160 instead of or in addition to one or more conditional requirements 5162 of FIG. 17J.

Multiple different procedural actions 5164 can be indicated for different conditional requirements 5162. For example, a set of Y different procedural actions 5164 have corresponding required textual requirements 5165 to render Y conditional requirements 5162.

Performing the report processing function 5120 can include identifying and/or extracting at least one term from the medical report indicating performance of a procedural action 5164. This at least one term can indicate a name of, type of, date and/or time of, results of, and/or other information denoting the procedural action. If the at least one term, and/or a corresponding medical code and/or billing mapped to the term in performing the report processing function 5120, matches a procedural action 5164 indicated in a conditional requirement 5162 of the report requirement set, the report processing function 5120 can determine if the medical report includes text meeting the corresponding textual requirements 5165. If text meeting the corresponding textual requirements 5165 is identified in and/or extracted from the report, the conditional requirement 5162 is determined to be adhered to. When the medical report includes text indicating performance of the procedural action, and if text meeting the corresponding textual requirements 5165 text is not identified in and/or not extracted from the report, and/or if the medical report is otherwise determined to include no text meeting the corresponding textual requirements 5165, the corresponding conditional requirement 5162 is determined to not be adhered to. Note that this corresponding conditional requirement 5162 is still considered to be adhered to in cases where the corresponding required text is not included, and where the corresponding procedural action was also not mention and/or not indicated to have been performed.

As a particular example, one conditional requirement 5162.1 can indicate that a statement of medical necessity is required to be included in the medical report for if a three-dimensional reconstruction and/or volumetric analysis was performed by the medical professional. In other embodiments, same or similar statements of medical necessity must be included for other types of procedural actions indicated to have been performed. Other conditional requirements 5162 can optionally indicate the same or different textual requirements are required to describe, document, and/or justify performance of a corresponding procedural action.

A textual requirement 5165 can indicate a layout, structure, and/or exact words and/or phrases that are request. For example, the statement of medical necessity of conditional requirement 5162.1 can require that a particular statement exists in the report when three-dimensional reconstruction and/or volumetric analysis was performed by the medical professional, such as "3D images were created, reviewed, and interpreted on an independent workstation under radiologist concurrent supervision due to medical necessity."

Consider the case where the report requirement set 5160 includes this example conditional requirement of FIG. 17K. If report processing function 5120 extracts text from a given medical report that is determined to indicate performance of a three-dimensional reconstruction, the medical report is only determined to adhere to this conditional requirement 5162.1 when the report processing function 5120 further identifies the statement "3D images were created, reviewed, and interpreted on an independent workstation under radiologist concurrent supervision due to medical necessity" in the medical report, as indicated by the textual requirement 5165. If this conditional requirement 5162.1 is not adhered to, a requirement to perform include this statement in the medical report will be indicated in the correction requirement notification data 5132.

In some embodiments, correction requirement notification data 5132 can indicate edits and/or revisions automatically generated by the medical report analysis system 5100 to rectify the detected problem. For example, if example conditional requirement 5162.1 is not adhered to, the medical report analysis system 5100 can generate a draft revision of the medical report that includes the required statement for transmission to the medical professional for review in conjunction with the correction requirement notification data 5132. In some embodiments, the medical report analysis system 5100 can alternatively or additionally automatically edit the medical report in the staging module 5110 itself, for example, by send the revision of the medical report that includes a required statement or other textual requirements 5165 to render adherence to a corresponding conditional requirement 5162 to replace the existing medical report in the staging module 5110.

In some embodiments, the correction requirement notification data 5132 can indicate a textual requirement 5165 is required even if the corresponding procedural action was not indicated to be performed, for example, based on another conditional requirement 5162 that indicates required performance of the procedural action being not adhered to. As a particular example, correction requirement notification data 5132 is generated to indicate that three dimensional reconstruction must be performed, and that a statement of medical necessity for this three dimensional reconstruction must be documented in the report, based on determining that a new nodule measuring more than 6 mm is described in the report, and based on determining no mention of performance of three dimensional reconstruction or volumetric analysis is included in the report.

As illustrated in FIG. 17L, the report requirement set 5160 can include one or more conditional requirements 5162 that correspond to requirements that one or more second procedural actions 5164 are required to be performed if a particular first procedural action 5164 was performed. In particular, a given first procedural actions may trigger requirement of performing one or more corresponding second procedural actions. For example, some procedural processes may include multiple steps as multiple procedural actions that must all be performed and/or documented in conjunction. Thus, if the medical report includes mention of and/or indicates performance of a first procedural action 5164 of a conditional requirement 5162 of FIG. 17L, the corresponding second procedural action must be also have been performed and/or must also be indicated in the medical report. These conditional requirements 5162 of FIG. 17L can be included in the report requirement set 5160 instead of or in addition to one or more conditional requirements 5162 of FIG. 17J and/or FIG. 17K.

Multiple procedural actions 5164 can be indicated as requirements for different conditional requirements 5162. For example, a set of Z different first procedural actions 5164 have corresponding second required procedural actions to render Z conditional requirements 5162. A second procedural actions 5164 of a given conditional requirement can be included in another conditional requirement as a first procedural action 5164 or a second procedural action 5164.

Performing the report processing function 5120 can include identifying and/or extracting at least one term from the medical report indicating performance of a first procedural action 5164, such as procedural action 5164.Z, for example, as discussed in conjunction with FIG. 17K. Alternatively, the first procedural action is determined to have been performed based on accessing a corresponding study and/or log of actions to determine if the corresponding action was performed as discussed previously.

If the medical report indicates performance of the procedural action 5164 indicated in a conditional requirement 5162 of the report requirement set, the report processing function 5120 can determine if accompanying, second procedural action, such as procedural action 5164.W, was also performed. This can include determining whether the medical report also includes text indicating performance of this second procedural action as discussed previously. This can alternatively or additionally include accessing a corresponding study and/or log of actions to determine if the corresponding action was performed as discussed previously. In some cases, evidence that the second procedural action was performed via access to information stored via another source is sufficient, for example, in cases where documentation of the second procedural action is not required to be included in the medical report itself.

If the second procedural action is determined to have been performed, the conditional requirement 5162 is determined to be adhered to. When the medical report includes text indicating performance of the first procedural action, and if the second procedural action is determined to have not been performed and/or if its performance cannot be confirmed, the corresponding conditional requirement 5162 is determined to not be adhered to. Note that this corresponding conditional requirement 5162 is still considered to be adhered to in cases where the second procedural action is not determined to have been performed, and where the first procedural action was also not mentioned and/or not determined to have been performed.

As a particular example, one conditional requirement 5162.1 can indicate that a when a three dimensional reconstruction is performed, a screenshot or other image data of the three-dimensional reconstruction must be sent to the medical picture archive system 2620, such as a PACS, for example, in conjunction with the corresponding study. Other conditional requirements 5162 can optionally other types of procedural actions that must be performed in conjunction and/or that are all required steps of a same procedural process.

Consider the case where the report requirement set 5160 includes this example conditional requirement of FIG. 17K. If report processing function 5120 extracts text from a given medical report that is determined to indicate performance of a three-dimensional reconstruction, the medical report is only determined to adhere to this conditional requirement 5162.1 when the medical report analysis system further verifies that a screenshot or other image data of the three-dimensional reconstruction is stored by the medical picture archive system 2620, indicating that the medical profession completed the action of sending the screenshot to the medical picture archive system 2620 for storage. This can include automatically requesting metadata and/or other information of the corresponding study from the medical picture archive system 2620, and analyzing this metadata to determine whether image data of the three-dimensional reconstruction is stored by the medical picture archive system 2620 in conjunction with the study. This can include otherwise accessing the medical picture archive system 2620 based on identifying information of the study and/or corresponding patient to determine whether image data of the three-dimensional reconstruction is stored by the medical picture archive system 2620 in conjunction with the study.

If this conditional requirement 5162.1 is not adhered to, a requirement to send a screenshot of the three-dimensional reconstruction to the medical picture archive system 2620 will be indicated in the correction requirement notification data 5132. In this example, no edits to the medical report are necessary. For example, the medical professional sends a screenshot of the three-dimensional reconstruction to the medical picture archive system 2620 based on receiving the correction requirement notification data 5132, but does not edit the medical report itself as not edits are required. In this example, the original version of the medical report is submitted when the predetermined staging duration elapses based on not being edited, despite correction requirement notification data 5132 requiring other procedural actions be performed.

As another particular example, a conditional requirement 5162 can include determining whether an order for a procedural action is indicated in the medical report or corresponding study, and further determining whether the procedural action was completed by the medical professional. For example, the correction requirement notification data 5132 is generated to indicate that the medical professional must complete the procedural action based on the order to complete the procedural action being identified and further based on determining the procedural action was not completed by the medical professional.

As illustrated in FIG. 17M, the report requirement set 5160 can include one or more conditional requirements 5162 that correspond to requirements that one or more other billing codes 5167 are logged if a particular procedural action 5164 was performed. In particular, some procedural actions may induce particular billing. Thus, if the medical report includes mention of and/or indicates performance of a procedural action 5164 of a conditional requirement 5162 of FIG. 17L, the procedural action must have been billed appropriately. These conditional requirements 5162 of FIG. 17L can be included in the report requirement set 5160 instead of or in addition to one or more conditional requirements 5162 of FIG. 17J FIG. 17K, and/or FIG. 17L.

Performing the report processing function 5120 can include identifying and/or extracting at least one term from the medical report indicating performance of a procedural action 5164, for example, as discussed in conjunction with FIG. 17K and/or FIG. 17L. Alternatively, the first procedural action is determined to have been performed based on accessing a corresponding study and/or log of actions to determine if the corresponding action was performed as discussed previously.

If the medical report indicates performance of the procedural action 5164 indicated in a conditional requirement 5162 of the report requirement set, the report processing function 5120 can determine if a corresponding billing code was logged appropriately. This can include accessing medical billing system 4010 to determine if the billing code was logged for the corresponding study and/or by the corresponding medical professional. This can alternatively or additionally include accessing another log of billing data to determine if the corresponding action was billed appropriately. In some cases, evidence that the procedural action was billed via access to another source is sufficient, for example, in cases where documentation of billing the procedural action is not required to be included in the medical report itself. This can include performing some or all functionality of medical billing verification system 4000 of FIGS. 14A-14E, such as comparison function 4070, to determine whether any discrepancies exist between how the procedural action 5164 should be billed and whether the procedural action 5164 was billed appropriately. For example, the medical report analysis system 5100 is integrated in and/or utilized in conjunction with the medical billing verification system 4000.

If the correct corresponding billing code is identified for performance of the procedural action by the medical professional, the conditional requirement 5162 is determined to be adhered to. When the medical report includes text indicating performance of the procedural action, and if the second procedural action is determined to have not been performed and/or if its performance cannot be confirmed, the corresponding conditional requirement 5162 is determined to not be adhered to. The correction requirement notification data 5132 can be generated to indicate the billing code and/or that correction of the billing data is required. In some cases, the billing data can be automatically corrected via medical billing system 4010 as discussed in conjunction with FIGS. 14A-14E and/or the correction requirement notification data 5132 can be sent to the medical billing system 4010 and/or a client device 120 associated with another user responsible for medical billing.

As illustrated in FIG. 17JN, the report requirement set 5160 can implement one or more of its requirements 5107 as consistency requirements 5166. A consistency requirement 5166 can indicate particular features that must be consistent across some or all instances and/or sections of the medical report. If all these particular features extracted from text in the medical report match and/or are otherwise consistent, the consistency requirement 5166 can be determined be adhered to. If one or more of these particular features extracted from text in the medical report is different from and/or does not match other corresponding features extracted from text in the medical report, the consistency requirement 5166 can be determined to not be adhered to. One or more consistency requirements 5166 of FIG. 17N can be included in report requirement set 5160 instead of and/or in addition to one or more conditional requirements 5162 of FIGS. 17J-17M.

For example, a consistency requirement 5166.1 of report requirement set 5160 can require that measurement units are consistent. Enforcement of consistent units in medical reports via such a consistency requirement 5166 can be particularly important for particular types of measurements indicated in medical reports, such as measurements denoting the measuring the location of intratracheal tubes. For example, text denoting measurements denoting location of anatomical features and/or abnormalities can be automatically and/or extracted from the medical report, and the corresponding units of these measurements can be determined. If different units are used for measurements indicated in the report, this consistency requirement 5166.1 can be determined not to be adhered to, and the correction requirement notification data 5132 can denote the mismatched units and/or can optionally indicate converted measurements generated by the medical report analysis system 5100 to render all measurements under the same unit. Alternatively or in addition, consistency requirement 5166.1 can require that all measurements be in accordance with a standard unit indicated in the consistency requirement 5166.1, such as millimeters. Alternatively or in addition, consistency requirement 5166.1 can require that all measurements of a same abnormality or feature be in accordance with same units, where use of different units for measurements of different abnormalities and/or anatomical features in the report is acceptable. Alternatively or in addition, consistency requirement 5166.1 can require that all measurements be in accordance with a same standard of measure, such as either the Metric system or the Imperial system, where a report is determined to not adhere to consistency requirement 5166.1 based on indicating one measurement under the Metric system and another measurement under the Imperial system.

As another example, a consistency requirement 5166.2 of report requirement set 5160 can require that anatomical regions, features, and/or locations referenced in the medical report are consistent. This can be important in ensuring that anatomical location of the corresponding medical scan and/or anatomical features included in the corresponding medical scan match the anatomical regions, features, and/or locations referenced in the medical report. This can be important in ensuring that the radiologist does not inadvertently reference the wrong anatomical region in the report. For example, a radiologist may accidentally indicate the wrong laterality of a radiology image. If different anatomical features referenced in the medical report, this consistency requirement 5166.2 can be determined not to be adhered to, and the correction requirement notification data 5132 can denote the mismatched anatomical regions and/or can optionally indicate corrected references to the correct anatomical region generated by the medical report analysis system 5100 to render all references to the same anatomical region and/or to match all references to anatomical regions to the anatomical region of the corresponding medical scan. Alternatively or in addition, this consistency requirement 5166.2 can automatically detect discrepancies between "left" and "right" anatomical features, where this consistency requirement 5166.2 can be determined not to be adhered to when a particular anatomical feature that has both a left and right feature is referenced in one set of text in the medical report as the "left" of this particular anatomical feature, and is referenced in another set of text in the medical report as the "right" of this particular anatomical feature.

Alternatively or in addition, this consistency requirement 5166.2 can require that anatomical regions referenced in the report are reflected in the corresponding medical scan, for example, based on: extracting the anatomical region of which the medical scan was captured from DICON headers of the corresponding medical scan and/or other metadata of the corresponding study; performing one or more inference functions upon image data of the medical scan to automatically detect one or more anatomical features captured in the medical scan and to detect discrepancy between these detected anatomical features and the anatomical features described in text of the medical report. Such embodiments are discussed in further detail in conjunction with FIGS. 17V and 17W.

As another example, a consistency requirement 5166.3 of report requirement set 5160 can require that abnormalities referenced in the medical report are consistent. This can be important in ensuring that abnormalities are described consistently and/or are referenced in all appropriate sections of the medical report. These abnormalities can optionally correspond to particular medical conditions 5163 as discussed in conjunction with FIG. 17J.

In some embodiments, if a given abnormality is referenced in multiple portions of the medical report with mismatched descriptions this consistency requirement 5166.3 can be determined not to be adhered to, and the correction requirement notification data 5132 can denote the mismatched descriptions of the abnormality and/or can optionally indicate corrected references to the abnormality generated by the medical report analysis system 5100. For example, consistency requirement 5166.3 is determined not to be adhered to based on identifying that a given abnormality is described in a first set of text of the medical report as having a first location, a first set of characteristics, a first measurement, and/or other first abnormality data 440, while this given abnormality is also described in a second set of text of the medical report as having a second location that is different from the first location, a second set of characteristics that is different from the first set of characteristics, a first measurement that is different from the second measurement, and/or other second abnormality data 440 that is different from the first abnormality data 440.

Alternatively or in addition, this consistency requirement 5166.3 can require that some or all abnormalities reflected in the patient history for the corresponding patient are referenced in the given medical report, for example, based on identifying abnormalities in prior history for the patient detected in study metadata, prior medical reports, and/or prior medical scan and determining whether these previously identified abnormalities are referenced in the given medical report, for example, as having: maintained size and/or presence, grown, shrunken, improved, and/or no longer being present. Alternatively or in addition, this consistency requirement 5166.3 can require that some or all abnormalities detected in the medical scan are referenced in the given medical report, for example, based on performing one or more inference functions upon image data of the medical scan to automatically detect one or more abnormalities and to detect discrepancies between these detected abnormalities and the abnormalities described in text of the medical report. Such embodiments are discussed in further detail in conjunction with FIGS. 17V and 17W.

As illustrated in FIGS. 17O-17P, the report requirement set 5160 can implement one or more of its requirements 5107 as section agreement requirements 5169. A section agreement requirement 5169 can indicate particular features that must be consistent across each of a subset of particular sections 5151 of the medical report. If all these particular features extracted from text in each section of the subset of sections 5151 match and/or are present in all sections of the subset of sections 5151, the section agreement requirement 5169 can be determined be adhered to. If one or more of these particular features extracted from text in one section of the subset of sections 5151 of the medical report is different from and/or does not match the particular features extracted from text in another section of the subset of sections 5151 and/or is missing from being referenced in text in another section of the subset of sections 5151, a section agreement requirement 5169 can be determined to not be adhered to.

One or more section agreement requirements 5169 of FIGS. 17O and 17P can be included in report requirement set 5160 instead of and/or in addition to one or more conditional requirements 5162 of FIGS. 17J-17M, and/or instead of and/or in addition to one or more consistency requirements 1566 of FIG. 17N. As illustrated in FIG. 17O, one or more section agreement requirements 5169 of the report requirement set 5160 can be implemented as one or more corresponding consistency requirements 1566 of FIG. 17N. As illustrated in FIG. 17P, one or more section agreement requirements 5169 of the report requirement set 5160 can be implemented as one or more corresponding conditional requirements 5162 of FIGS. 17J-17M.

A set of sections of the medical report can include: a Procedure section; an Accession section; a Date of Exam section; a Referring Physician section; an Exam section; a Technique section; a Contrast section; a Comparisons section; a Findings section; an Impression section; and/or other sections included in radiology reports and/or other types of medical reports. Some or all of these sections can be denoted with corresponding headers and/or labels in the text of the medical report, such as: "PROCEDURE(S)"; "ACCESSION(S)"; "DATE OF EXAM"; "REFERRING PHYSICIAN"; "EXAM"; "TECHNIQUE"; "CONTRAST"; "COMPARISONS"; "FINDINGS"; "IMPRESSION"; and/or other corresponding labels. In some embodiments, some or all sections of the given medical report can be identified based on extracting the text following the corresponding label and/or the text between the corresponding label and prior to a next corresponding label. In some embodiments, some or all of these sections of the medical report can be required, for example, as corresponding requirements 5107 of the report requirement set 5160, where the report requirement set 5160 is not adhered to if one or more required sections are missing, are blank, and/or are not filled out correctly.

As an example of a section agreement requirement 5169, a section consistency requirement 5169.1 can indicate that any one or more abnormalities referenced in the Findings section of the medical report must agree with the abnormalities described in the Impression section of the medical report. These abnormalities can optionally correspond to particular medical conditions 5163 as discussed in conjunction with FIG. 17J.

As illustrated in FIG. 17O, in some embodiments, this section consistency requirement 5169.1 can be implemented utilizing a consistency requirement 5166, such as consistency requirement 5166.3 of FIG. 17N. However, this section consistency requirement 5169.1 can further require that a description of abnormalities must be present in both the Findings section and the Impression section based on being indicated in the subset of sections 5151 and/or that all abnormalities must have matching descriptions in the Findings section and the Impression section. This section consistency requirement 5169.1 can also allow that the abnormality not be described and/or not be consistent in other sections of the medical report.

As illustrated in FIG. 17P, this section consistency requirement 5169.1 can alternatively or additionally be implemented utilizing a conditional requirement 5162, indicating that if a description of an abnormality is present in the Findings section, a matching description must also be present in the Impression section. While not illustrated in FIG. 17P, a same or different conditional requirement 5162 can further require that if a description of an abnormality is present in the Impression section, a matching description must also be present in the Findings section.

As another example of a section agreement requirement 5169, a section consistency requirement 5169.2 can indicate that anatomical regions, features, and/or locations referenced in the Findings section of the medical report must agree with anatomical regions, features, and/or locations described in the Impression section of the medical report.

As illustrated in FIG. 17O, in some embodiments, this section consistency requirement 5169.2 can be implemented utilizing a consistency requirement 5166, such as consistency requirement 5166.2 of FIG. 17N. However, this section consistency requirement 5169.2 can further require that the same anatomical feature must be indicated in both the Findings section and the Impression section based on being indicated in the subset of sections 5151. This section consistency requirement 5169.2 can also allow that the anatomical region not be described in other sections of the medical report.

As illustrated in FIG. 17P, this section consistency requirement 5169.2 can alternatively or additionally be implemented utilizing a conditional requirement 5162, indicating that if a given anatomical feature, region, and/or location is indicated in the Findings section, the same given anatomical feature, region, and/or location must also be present in the Impression section. While not illustrated in FIG. 17P, a same or different conditional requirement 5162 can further require that if a given anatomical feature, region, and/or location is indicated in the Impression section, a matching given anatomical feature, region, and/or location must also be present in the Findings section.

While not illustrated in FIGS. 17N-17P, other information may be required to be consistent between two or more identified sections of the medical report via one or more corresponding section agreement requirements 5169, such as: medical conditions 5163 indicated in the medical report; procedural actions 5164 identified in the medical report; demographic data and/or patient history data for the patient; information regarding the time, date, and/or location of the corresponding medical scan; information identifying the medical professional and/or corresponding institution; and/or other information included in the medical report.

FIG. 17Q illustrates an example embodiment of the medical report analysis system 5100 of FIG. 17I that performs report processing function 5120 for a report requirement set 5160 that includes one or more section agreement requirements 5169 as discussed in conjunction with FIGS. 17O and 17P. Performing the report processing function 5120 can include performing one or more section processing functions 5123.1-5123.P to extract relevant information, as needed to verify adherence of section agreement requirements 5169, from the relevant sections of corresponding sections subsets 5151 as section data 5124.1-5123.P.

For example, one section processing function 5123.1 can correspond to the Findings section and another section processing function 5123.2 can correspond to the Impression section. The section processing function 5123.1 can identify text corresponding to the Finding section based on identifying a header and/or label for the Finding section in the medical report, and/or based on identifying text following the header and/or label for the Finding section that is prior to a header and/or label of a next section, such as the Impression section. Similarly, the section processing function 5123.2 can identify text corresponding to the Impression section based on identifying a header and/or label for the Impression section in the medical report, and/or based on identifying text following the header and/or label for the Finding section that is prior to a header and/or label of a next section and/or that is prior to the end of the report if the Impression section is a final section of the report.

The section data 5124 for each section can be generated based on text and/or corresponding medical codes indicating one or more: abnormalities; medical conditions 5163; procedural actions 5164; one or more anatomical regions, locations, and/or features; patient data; medical professional date; other data pertaining to the corresponding medical scan; and/or other information relevant for verifying whether one or more section agreement requirements 5169 is met. Generating section data 5124 for a given section can include extracting relevant text corresponding to one or more section agreement requirements 5169 that includes the given section in its section subset 5151; mapping the relevant text to one or more corresponding medical codes; and/or otherwise determining the relevant identified information corresponding to one or more section agreement requirements 5169 that includes the given section in its section subset 5151 based on processing the text for this section.

Performing different section processing functions 5123 can include performing a same natural language processing function upon text from different corresponding sections of the medical report. Performing different section processing functions 5123.1-5123.P can alternatively include performing different natural language processing functions upon text from different corresponding sections of the medical report. For example, different sections of the medical report can have different structure and/or characteristics, and the different natural language processing functions can be different based on the differences in structure and/or characteristics of the corresponding sections. As a particular example, a first natural language processing function can be trained on text included in a first section in a plurality of medical reports, while a second natural language processing function can be trained on text included in a second section in the plurality of medical reports.

A section discrepancy detection function 5129 can be to determine, for one or more section agreement requirements 5169, whether the information in section data 5124 corresponding to the or one or more section agreement requirements 5169 matches for all required sections of the corresponding section subset 5151 and/or is present in all required sections of the corresponding section subset 5151. The section discrepancy detection function 5129 can otherwise be performed to generate section discrepancy data 5131 indicating whether the section agreement requirements 5169 are adhered to based on comparing relevant information in section data 5124 for the appropriate sections, and/or indicating discrepancies between these sections rendering failure to adhere to one or more section agreement requirements 5169.

FIGS. 17R-17U illustrate example correction requirement notification data 5132 generated for sample medical reports. In FIG. 17R, the example medical report includes the statement "there is a new 6 mm nodule along the right major fissure." The report processing function 5120 evaluates an example conditional requirement 5162, which indicates volumetric analysis is required when a new nodule is present measuring greater than or equal to 6 mm. The report processing function 5120 determines this example conditional requirement 5162 is not met based on detecting that text indicating presence of a new nodule greater than or equal to 6 mm, and based on determining no text indicating volumetric analysis is included.

The correction requirement notification data generator 5130 can generate the correction requirement notification data 5132 that includes text for display and/or dictation to the medical professional as instructions and/or recommendations. In this example, the correction requirement notification data 5132 includes a statement that volumetric analysis is recommended, and should be referenced in the report with a statement of medical necessity, because a new nodule greater than or equal to 6 mm was detected. The correction requirement notification data 5132 further indicates that, if the volumetric analysis was already performed, it should be referenced in the report with a statement of medical necessity. The correction requirement notification data 5132 can optionally cite and/or include a link to a publication, for example, published by a medical society from which this recommendation was derived, for review by the medical professional.

In FIG. 17S, the example medical report indicates the right foot in the Findings section, and indicates the left foot in the Impression section. For example, the Findings section also does not indicate the left foot and/or the Impression section also does not indicate the right foot. The right foot can be indicated in the Findings section to denote the anatomical location that the medical scan was captured and/or to denote the location of a corresponding abnormality, while the left foot in the Impression section can similarly denote the anatomical location that the medical scan was captured and/or can similarly denote the location of the corresponding abnormality.

The report processing function 5120 evaluates an example section agreement requirement 5169, which indicates anatomical regions indicated in the Findings section and Impression section must agree. The report processing function 5120 determines this example section agreement requirement 5169 is not met based on detecting text indicating the right foot in the Findings section, and based on detecting text indicating the left foot in the Impression section.

In this example, the correction requirement notification data 5132 includes a statement that the Findings section indicates the right foot while the Impression section indicates the left foot. The correction requirement notification data 5132 can optionally indicates a correction and/or direct edits, such as replacing instances of "right foot" in the Finding section with "left foot" or replacing instances of "left foot" in the Finding section with "right foot." This can include automatically determining whether the left foot or right foot was the correct location, for example, based on metadata of the corresponding study and/or based on inference data generated by performing an inference function upon image data of the corresponding medical scan. Alternatively, automatically determining whether the left foot or right foot was the correct location can be based on a count of the number of instances that mismatched, for example, where "left foot" is determined to be the correct location based on being indicated 6 times in the medical report while "right foot" is referenced only once in the medical report.

In FIG. 17T, the example medical report indicates an oblique fracture of the metatarsal in the Findings section, but no reference of this fracture is included in the Impression section. The report processing function 5120 evaluates an example section agreement requirement 5169, which indicates identified abnormalities indicated in the Findings section must be indicated in the Impression section. The report processing function 5120 determines this example section agreement requirement 5169 is not met based on detecting text indicating the oblique fracture of the metatarsal in the Findings section, and based on not detecting any text indicating this oblique fracture of the metatarsal in the Impression section.

In this example, the correction requirement notification data 5132 includes a statement that the Findings section indicates an oblique fracture of the metatarsal, while the Impression section does not. The correction requirement notification data 5132 indicates that the report must be corrected to include reference to the fracture in the Impression section. The correction requirement notification data 5132 can optionally indicate correction and/or direct edits to the Impression section, such as a revised version of the Impression section that includes reference to the oblique fracture of the metatarsal.

In FIG. 17U, the example medical report includes the term "CT 3-D reconstruction." The report processing function 5120 evaluates an example conditional requirement 5162, indicating a statement of medical necessity is required when three-dimensional reconstruction is performed. The report processing function 5120 determines this example conditional requirement 5162 is not met based on detecting that text indicating performance of a three-dimensional reconstruction, and based on determining no text that indicates the statement of medical necessity.

The correction requirement notification data generator 5130 can generate the correction requirement notification data 5132 to includes direct edits for inclusion in the revised medical report to the medical professional as instructions and/or recommendations. In this example, the correction requirement notification data 5132 includes an edit to the report to include the statement of medical necessity indicated in the example conditional requirement 5162: "3D images were created, reviewed, and interpreted on an independent workstation under radiologist concurrent supervision due to medical necessity." This can be displayed and/or dictated to the medical professional as instructions to include these edits in the medical report. Alternatively or in addition, a draft revision of the medical report including these edits is sent to the medical report for review, subsequent editing, and creation as a revision to the prior medical report.

FIG. 17V illustrates an embodiment of the medical report analysis system 5100 that utilizes inference data 5126 generated via an inference function 5125 performed upon medical scan image data 410 of a medical scan corresponding to the medical report, such as the medical scan reviewed by the medical professional in conjunction with generating the medical report. Some of all features and/or functionality of the medical report analysis system 5100 of FIG. 17V can be utilized to implement the medical report analysis system 5100 of FIGS. 17B, 17C, and/or 17D, and/or any other embodiment of the medical report analysis system 5100 described herein.

Identification of and/or retrieval of the corresponding medical scan image data 410 can be based on an accession number extracted from the medical report. Identification of and/or retrieval of the corresponding medical scan image data 410 can be based on other linking information identifying the corresponding study and/or patient. For example, an identifier of the corresponding medical scan, time and/or data of the corresponding medical scan, and/or name or other identifier of the patient is extracted from the corresponding report via the report processing function 5120, and this extracted information is utilized to retrieve the corresponding study from the medical scan database 342 and/or the medical picture archive system 2620.

The inference data 5126 can include abnormality data 440, lesion measurement data 3041 and/or lesion change measurement data 3055, and/or other inference data generated via performance of an inference function and/or medical scan analysis function described herein. For example, the medical report analysis system 5100 implements and/or communicates with another subsystem 101 to generate the inference function via performance of at least one via inference function 5125 upon image data of a medical scan, such as medical scan diagnosing system 108, medical scan image analysis system 112, lesion tracking system 3002, and/or any other subsystem 101 described herein.

The report processing function 5120 can generate report analysis data 5122 indicating required corrections based on discrepancies between the inference data 5126 and the medical report. The required corrections can indicate changes to the medical report required to rectify discrepancies with the medical scan image data. This inference data 5126 can be utilized in determining whether or not one or more consistency requirements 5166 of FIG. 17N are adhered to, for example, based on whether abnormalities and/or anatomical regions indicated in the inference data 5126 match abnormalities and/or anatomical regions referenced in text of the medical report.

For example, the medical report analysis system 5100 implements and/or communicates with the retroactive discrepancy flagging system 3100 of FIGS. 13A-14F to detect discrepancies between the medical report and image data. In particular, in addition to being implemented to detect discrepancies retroactively via access to reports that are already submitted and stored, the functionality of the retroactive discrepancy flagging system 3100 can optionally be extended and/or utilized in conjunction with the medical report analysis system 5100 to detect discrepancies prior to formal submission of medical reports, enabling some or all of these discrepancies to be corrected more rapidly and/or to be corrected in the medical report prior to the medical report being stored in the medical report analysis system 5100 via generation and communication of corresponding correction requirement notification data 5132 prior to elapsing of the predetermined staging duration.

The inference function 5125 of FIG. 17V can be performed by performing the inference function 3110 of FIG. 13A, and/or report processing function 5120 can be performed by performing extraction function 3120 and/or the consensus function 3195. The medical report analysis system 5100 can otherwise detect any discrepancies between medical reports and medical scans discussed in conjunction with FIGS. 13A-16C and/or can generate the correction requirement notification data 5132 to indicate the detected discrepancy and/or indicate an instruction to resolve the detected discrepancy.

FIG. 17W illustrates an embodiment of the medical report analysis system 5100 that utilizes extracted data 5128 extracted from study metadata retrieved from medical picture archive system 2620 and/or another database accessible by medical report analysis system. Some of all features and/or functionality of the medical report analysis system 5100 of FIG. 17W can be utilized to implement the medical report analysis system 5100 of FIGS. 17B, 17C, and/or 17D, and/or any other embodiment of the medical report analysis system 5100 described herein.

The study metadata can correspond to metadata of a study reviewed by the medical professional to generate the given medical report and/or a study that includes one or more medical scans reviewed by the medical professional to generate the given medical report. Study metadata can alternatively or additionally be retrieved from another database, such as a log of procedural actions and/or a medical billing system 4010.

Identification of and/or retrieval of the corresponding study metadata can be based on an accession number extracted from the medical report. Identification of and/or retrieval of the corresponding study metadata can be based on other linking information identifying the corresponding study and/or patient. For example, an identifier of the corresponding study, time and/or data of the corresponding study, and/or name or other identifier of the patient is extracted from the corresponding report via the report processing function 5120, and this extracted information is utilized to retrieve the corresponding study from the medical scan database 342 and/or the medical picture archive system 2620.

The study metadata can correspond to DICOM metadata and/or any other metadata associated with the study. The metadata can indicate types of procedural actions for the study and/or images that are stored in the medical picture archive system 2620, such as whether a screenshot of a three dimensional reconstruction is stored in the medical picture archive system 2620 as discussed in conjunction with the example of FIG. 17L.

An extraction function 5127 can be performed to render extracted data 5128 extracted from the received study metadata. The extraction function 5127 can include extracting required information relevant to a particular requirement 5107 and/or extracting information from one or more fields of the metadata, for example, based on a known structure of the metadata.

The extracted data 5128 can be utilized to determine if discrepancies exist in the medical report that must be corrected, for example, as discussed in conjunction with FIG. 17V. This extracted data 5128 can be utilized in determining whether or not one or more consistency requirements 5166 of FIG. 17N are adhered to, for example, based on whether abnormalities and/or anatomical regions indicated in the extracted data 5128 match abnormalities and/or anatomical regions referenced in text of the medical report. Alternatively or in addition, the extracted data 5128 can indicate procedural actions that were performed previously. For example, the medical report analysis system 5100 confirms submission of a screenshot of a three dimensional reconstruction that is required for a conditional requirement as discussed in conjunction with the example of FIG. 17L based on determining the extracted data 5128 indicates storage of a screenshot of a three dimensional reconstruction for the study.

FIG. 17X illustrates a flow diagram of a method for execution, for example, in conjunction with utilizing the medical report analysis system 5100 and/or one or more other subsystems 101 described herein. As indicated in step 5171, a medical scan can be acquired and sent to a radiologist or other medical professional for review, for example, via their client device 120. As indicated in step 5172, the radiologist can then analyze the received medical scan to create a corresponding medical report. As indicated in step 5173, the completed report is sent to a staging module for a predetermined duration of time, such as four minutes and/or the predetermined staging duration. As indicated in step 5177, the report is sent by to the RIS and/or another medical report database 392 when the predetermined duration of time elapses.

As indicated in step 5174, a system, such as the medical report analysis system 5100 of FIGS. 17B-17W and/or another subsystem 101, generates report analysis data for the report while being staged in the staging module. Step 5175 can be performed prior step 5177 being performed and after step 5173 being performed. As indicated in step 5174, if the report analysis data for the report indicates a discrepancy, missing requirements, potential follow up, typographical errors, and/or other required corrections and/or actions by the radiologist, the radiologist is notified of the required corrections, as indicated in step 5176. If the report analysis data for the report does not indicate any discrepancy, missing requirements, potential follow up, typographical errors and/or other required corrections and/or actions by the radiologist, the radiologist is not notified, and the medical report will be sent to the RIS upon elapsing of the predetermined duration of time as it stands.

After the radiologist is notified of required corrections in step 5176, the radiologist can recreate and/or edit the medical report for the medical scan in step 5172, and steps 5173, 5174, 5175, 5176, can be repeated for this new version of the medical report. Furthermore steps 5174, 5175, and 5176 can be performed prior to the report being submitted in step 5177. When the recreated and/or edits to the medical report are sent to the staging module, they can replace the prior version of the medical report in the staging module, where only the most recently updated version of the medical report is submitted in step 5177 upon elapsing of the duration of time.

In various embodiments, a medical report analysis system includes least one processor and at least one memory. The at least one memory includes operational instructions that, when executed by the at least one processor of the medical report analysis system, cause the medical report analysis system to: receive a medical report created by a medical professional at a creation time; automatically generate report analysis data for the medical report by performing a report processing function prior to elapsing of a fixed-length time frame starting at the creation time; generate correction requirement notification data based on the report analysis data indicating at least one correction requirement; and facilitate communication of the correction requirement notification data to the medical professional.

FIG. 17Y illustrates a flow diagram of a method for execution by the medical report analysis system 5100 and/or one or more other subsystems 101 described herein. For example, the medical report analysis system 5100 includes at least one memory that includes operational instructions that, when executed by the at least one processor of the medical report analysis system 5100, cause the medical report analysis system to perform some or all steps of FIG. 17Y.

Step 5182 includes receiving a medical report created by a medical professional at a creation time. Receiving the medical report in step 5182 can include receiving the medical report from the staging module or from the client device 120. For example, the medical report is written by the medical professional via interaction with a client device 120. The medical report can be created at the creation time based on being sent by the client module 120 to a staging module such as staging module 5110. The report is optionally not received from a RIS or other medical report database based on not yet being submitted to and/or not yet being stored in the RIS or other medical report database.

Step 5184 includes, prior to elapsing of a fixed-length time frame starting at the creation time, automatically generating report analysis data for the medical report by performing a report processing function. The fixed-length time frame can be implemented as the fixed-length time frame 5119. In various embodiments, a fixed-length duration of the fixed-length time frame is equal to and/or is approximately equal to four minutes. The time frame can be based on or can be in accordance with a predetermined staging duration associated with a staging module storing the medical report, such as predetermined staging duration 5114. The report analysis data can be implemented as report analysis data 5122. The report processing function can be implemented as report processing function 5120.

Step 5186 includes, prior to elapsing of the fixed-length time frame, generating correction requirement notification data based on the report analysis data indicating at least one correction requirement. The correction requirement notification data can be implemented as correction requirement notification data 5132. The correction requirement notification data can be generated via correction requirement notification data generator 5130.

Step 5188 includes, prior to elapsing of the fixed-length time frame, facilitating communication of the correction requirement notification data to the medical professional. This can include displaying and/or dictating the correction requirement notification data to the medical professional via a display device and/or speakers. This can include identifying contact information and/or instructions associated with the medical professional and sending the correction requirement notification data to the medical professional in accordance with the contact information and/or instructions. This can include transmitting the correction requirement notification data to a client device associated with the medical professional. For example, the medical professional receives the correction requirement notification data via display and/or dictation of the correction requirement notification data via a display device and/or speakers of the client device. The correction requirement notification data can be transmitted to a same client device utilized to write the medical report and/or a same client device that sent the medical report to the staging module and/or the medical report analysis system. The correction requirement notification data can alternatively be transmitted to a different client device utilized to write the medical report and/or a different client device that sent the medical report to the staging module and/or the medical report analysis system.

In various embodiments, the medical report is received by a staging module at the creation time. The medical report is transmitted from the staging module to a Radiology Information System (RIS) based on elapsing of a predetermined staging duration associated with the staging module. The method can further include determining the fixed-length time frame based on the predetermined staging duration associated with the staging module.

In various embodiments, the medical report is updated by the medical professional prior to elapsing of the fixed-length time frame to include at least one edit based on the communication of the correction requirement notification data to the medical professional. This updated medical report that includes the at least one edit can be transmitted to the RIS for storage based on elapsing of the predetermined staging duration. In various embodiments, a timer corresponding to countdown of the predetermined staging time frame is paused during updating of the medical report by the medical professional to include the at least one edit.

In various embodiments, performing the report processing function upon the medical report includes automatically extracting at least one pathology label from the medical report. In various embodiments, the report analysis data indicates the at least one correction requirement based on the medical report failing to meet at least one corresponding requirement of a set of predefined report requirements. In various embodiments, the at least one corresponding requirement is based on a requirement for a procedural action when a corresponding medical condition exists.

Generating the report analysis data can include automatically identifying text in the medical report indicating the corresponding medical condition exists based on the set of predefined report requirements and/or automatically determining whether the text indicating the procedural action was performed is included in the medical report based on identifying text in the medical report indicating the corresponding medical condition exists. Generating the correction requirement notification data includes indicating performance of the procedural action is required based on determining the medical report does not include text indicating the procedural action was performed, and/or documentation of performance of the procedural action is required in the medical report based on determining the medical report does not include text indicating the procedural action was performed.

In various embodiments, the at least one corresponding requirement includes a requirement that corresponding medical condition corresponds to presence of a nodule that is greater than a predetermined size, such as a predetermined diameter of 6 mm. The procedural action can correspond to performance of a volumetric analysis and/or three dimensional reconstruction. Generating the correction requirement notification data can include indicating performance of the volumetric analysis is required based on automatically identifying text in the medical report indicating presence of a nodule that is greater than the predetermined size and further based on determining the medical report does not include text indicating the volumetric analysis was performed.

In various embodiments, the at least one corresponding requirement includes a requirement that the medical report include a statement of medical necessity if the medical report indicates a three-dimensional reconstruction was performed. In various embodiments, generating the report analysis data includes automatically identifying text in the medical report indicating the three-dimensional reconstruction was performed and further includes automatically determining the medical report includes no text associated with the statement of medical necessity. The at least one correction requirement can indicate inclusion of the statement of medical necessity in the medical report is required and/or can include an edit to the report that includes the statement of medical necessity.

In various embodiments, the at least one corresponding requirement includes a requirement that, if the medical report indicates a three-dimensional reconstruction was performed, a screenshot of the three-dimensional reconstruction be sent to a Picture Archive and Communication System (PACS). Generating the report analysis data can include automatically identifying text in the medical report indicating the three-dimensional reconstruction was performed and can further include automatically determining a screenshot of the three-dimensional reconstruction was not sent to the PACS. The at least one correction requirement can indicate transmission of the screenshot of the three-dimensional reconstruction to the PACS is required. In various embodiments, automatically determining a screenshot of the three-dimensional reconstruction was not sent to the PACS is based on processing metadata of a study corresponding to the medical report.

In various embodiments, the at least one corresponding requirement includes a requirement that anatomical features indicated in a findings section of the medical report must match anatomical features indicated in an impression section of the medical report. Generating the report analysis data can include automatically identifying a first subset of text of the medical report corresponding to the findings section of the medical report, and automatically generating finding section data indicating a first anatomical feature based on the first subset of text. Generating the report analysis data can further include automatically identifying a second subset of text of the medical report corresponding to the impression section of the medical repot, and automatically generating impression section data indicating a second anatomical feature based on the second subset of text. The at least one correction requirement can indicate discrepancy between the findings section and the impression section based on the first anatomical feature being different from the second anatomical feature.

In various embodiments, the at least one corresponding requirement includes a requirement that abnormalities indicated in a findings section of the medical report must also be indicated in an impression section of the medical report. Generating the report analysis data can include automatically identifying a first subset of text of the medical report corresponding to the findings section of the medical report, and automatically generating finding section data describing an abnormality based on the first subset of text. Generating the report analysis data can further include automatically identifying a second subset of text of the medical report corresponding to the impression section of the medical repot, and automatically generating impression section data based on the second subset of text. The impression section data can indicate that the abnormality is not described in the impression section based on the second subset of text: not including any text describing the abnormality, including text describing a different abnormality, and/or including text that describing the abnormality differently than the findings section. The at least one correction requirement can indicate discrepancy between the findings section and the impression section based on the abnormality being described in the findings section, and based on the abnormality not being described in the impression section.

In various embodiments, the method includes receiving a second medical report created by a second medical professional at a second creation time. Prior to elapsing of the fixed-length time frame starting at the second creation time, second report analysis data is automatically for the second medical report by performing a report processing function upon the second medical report. The method can include foregoing generating and/or facilitating communication of correction requirement notification data for the second medical report based on the second report analysis data indicating no correction requirements. The medical report can be transmitted to a Radiology Information System (RIS) for storage in response to elapsing of the fixed-length time frame and/or in response to elapsing of a predetermined staging duration associated with the fixed-length time frame.

In various embodiments, facilitating communication of the correction requirement notification data to the medical professional includes displaying the correction requirement notification data via a display device. In various embodiments, facilitating communication of the correction requirement notification data to the medical professional includes transmitting the correction requirement notification data to a client device associated with the medical professional. In various embodiments, the medical report was created by the medical professional via a second client device associated with the medical professional that is different from the client device. In various embodiments, the client device is a cellular device, and facilitating transmission of the correction requirement notification data to the client device associated with the medical professional includes transmitting a text message to the client device via a cellular network.

In various embodiments, the method includes receiving a second medical report created by a second medical professional at a second creation time. prior to elapsing of the fixed-length time frame starting at the second creation time, the method includes generating report analysis completion time estimate data indicating an estimated time that second report analysis data corresponding to the second medical report will be completed. When the report analysis completion time estimate data indicates the estimated time will occur after the elapsing of the fixed-length time frame, the method includes generating report analysis delay notification data based on the report analysis completion time estimate data indicates the estimated time will occur after the elapsing of the fixed-length time frame. The method includes facilitating communication of the report analysis delay notification data to the medical professional.

In various embodiments, the method includes receive a plurality of medical reports created at a plurality of corresponding creation times, and further includes generating each of a plurality of report analysis data prior to elapsing of the fixed-length time frame for each corresponding one of the plurality of medical reports based on generating the plurality of report analysis data in accordance with a temporal ordering of the plurality of corresponding creation times.

It is noted that terminologies as may be used herein such as bit stream, stream, signal sequence, etc. (or their equivalents) have been used interchangeably to describe digital information whose content corresponds to any of a number of desired types (e.g., data, video, speech, text, graphics, audio, etc. any of which may generally be referred to as 'data').

As may be used herein, the terms "substantially" and "approximately" provides an industry-accepted tolerance for its corresponding term and/or relativity between items. For some industries, an industry-accepted tolerance is less than one percent and, for other industries, the industry-accepted tolerance is 10 percent or more. Other examples of industry-accepted tolerance range from less than one percent to fifty percent. Industry-accepted tolerances correspond to, but are not limited to, component values, integrated circuit process variations, temperature variations, rise and fall times, thermal noise, dimensions, signaling errors, dropped packets, temperatures, pressures, material compositions, and/or performance metrics. Within an industry, tolerance variances of accepted tolerances may be more or less than a percentage level (e.g., dimension tolerance of less than +/−1%). Some relativity between items may range from a difference of less than a percentage level to a few percent. Other relativity between items may range from a difference of a few percent to magnitude of differences.

As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to".

As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may be used herein, one or more claims may include, in a specific form of this generic form, the phrase "at least one of a, b, and c" or of this generic form "at least one of a, b, or c", with more or less elements than "a", "b", and "c". In either phrasing, the phrases are to be interpreted identically. In particular, "at least one of a, b, and c" is equivalent to "at least one of a, b, or c" and shall mean a, b, and/or c. As an example, it means: "a" only, "b" only, "c" only, "a" and "b", "a" and "c", "b" and "c", and/or "a", "b", and "c".

As may also be used herein, the terms "processing module", "processing circuit", "processor", "processing circuitry", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, processing circuitry, and/or processing unit may be, or further include, memory and/or an integrated memory element, which may be a single memory device, a plurality of memory devices, and/or embedded circuitry of another processing module, module, processing circuit, processing circuitry, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, processing circuitry, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, processing circuitry and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, processing circuitry and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with one or more other routines. In addition, a flow diagram may include an "end" and/or "continue" indication. The "end" and/or "continue" indications reflect that the steps presented can end as described and shown or optionally be incorporated in or otherwise used in conjunction with one or more other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, a quantum register or other quantum memory and/or any other device that stores data in a non-transitory manner. Furthermore, the memory device may be in a form of a solid-state memory, a hard drive memory or other disk storage, cloud memory, thumb drive, server memory, computing device memory, and/or other non-transitory medium for storing data. The storage of data includes temporary storage (i.e., data is lost when power is removed from the memory element) and/or persistent storage (i.e., data is retained when power is removed from the memory element). As used herein, a transitory medium shall mean one or more of: (a) a wired or wireless medium for the transportation of data as a signal from one computing device to another computing device for temporary storage or persistent storage; (b) a wired or wireless medium for the transportation of data as a signal within a computing device from one element of the computing device to another element of the computing device for temporary storage or persistent storage; (c) a wired or wireless medium for the transportation of data as a signal from one computing device to another computing device for processing the data by the other computing device; and (d) a wired or wireless medium for the transportation of data as a signal within a computing device from one element of the computing device to another element of the computing device for processing the data by the other element of the computing device. As may be used herein, a non-transitory computer readable memory is substantially equivalent to a computer readable memory. A non-transitory computer readable memory can also be referred to as a non-transitory computer readable storage medium.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A medical report analysis system comprising:
at least one processor; and
at least one memory that stores operational instructions that, when executed by the at least one processor, cause the processor to:
receive a medical report created by a medical professional at a creation time;
prior to elapsing of a fixed-length time frame starting at the creation time:
automatically generate report analysis data for the medical report by performing a report processing function, the report analysis data to indicate at least one correction requirement to the medical report to resolve at least one detected error;
based on the report analysis data indicating at least one correction requirement to the medical report to resolve at least one detected error, automatically generate correction requirement notification data; and
facilitate communication of the correction requirement notification data to the medical professional, wherein the report analysis data indicates the at least one correction requirement based on the medical report failing to meet at least one corresponding requirement of a set of predefined report requirements, and wherein the at least one corresponding requirement is based on a requirement for a procedural action when a corresponding medical condition exists, wherein generating the report analysis data includes:
automatically identifying text in the medical report indicating the corresponding medical condition exists based on the set of predefined report requirements;
automatically determining whether the text indicating the procedural action was performed is included in the medical report based on identifying text in the medical report indicating the corresponding medical condition exists; and
wherein generating the correction requirement notification data includes indicating at least one of: performance of the procedural action is required based on determining the medical report does not include text indicating the procedural action was performed, or documentation of performance of the procedural action is required in the medical report based on determining the medical report does not include text indicating the procedural action was performed.

2. The medical report analysis system of claim 1, wherein the at least one corresponding requirement includes a requirement that the corresponding medical condition corresponds to presence of a nodule that is greater than a predetermined size, wherein the procedural action corresponds to performance of a volumetric analysis, and wherein generating the correction requirement notification data includes indicating performance of the volumetric analysis is required based on automatically identifying text in the medical report indicating a presence of a nodule that is greater than the predetermined size and further based on determining the medical report does not include text indicating the volumetric analysis was performed.

3. A medical report analysis system comprising:
at least one processor; and
at least one memory that stores operational instructions that, when executed by the at least one processor, cause the processor to:
receive a medical report created by a medical professional at a creation time;

prior to elapsing of a fixed-length time frame starting at the creation time:
automatically generate report analysis data for the medical report by performing a report processing function, the report analysis data to indicate at least one correction requirement to the medical report to resolve at least one detected error;
based on the report analysis data indicating at least one correction requirement to the medical report to resolve at least one detected error, automatically generate correction requirement notification data; and
facilitate communication of the correction requirement notification data to the medical professional, wherein the report analysis data indicates the at least one correction requirement based on the medical report failing to meet at least one corresponding requirement of a set of predefined report requirements, and wherein the at least one corresponding requirement includes a requirement that the medical report include a statement of medical necessity if the medical report indicates a three-dimensional reconstruction was performed;
wherein generating the report analysis data includes automatically identifying text in the medical report indicating the three-dimensional reconstruction was performed and further includes automatically determining the medical report includes no text associated with the statement of medical necessity; and
wherein the at least one correction requirement indicates inclusion of the statement of medical necessity in the medical report is required.

4. A medical report analysis system comprising:
at least one processor; and
at least one memory that stores operational instructions that, when executed by the at least one processor, cause the processor to:
receive a medical report created by a medical professional at a creation time;
prior to elapsing of a fixed-length time frame starting at the creation time:
automatically generate report analysis data for the medical report by performing a report processing function, the report analysis data to indicate at least one correction requirement to the medical report to resolve at least one detected error;
based on the report analysis data indicating at least one correction requirement to the medical report to resolve at least one detected error, automatically generate correction requirement notification data; and
facilitate communication of the correction requirement notification data to the medical professional, wherein the report analysis data indicates the at least one correction requirement based on the medical report failing to meet at least one corresponding requirement of a set of predefined report requirements, and wherein the at least one corresponding requirement includes a requirement that, if the medical report indicates a three-dimensional reconstruction was performed, a screenshot of the three-dimensional reconstruction be sent to a Picture Archive and Communication System (PACS);
wherein generating the report analysis data includes automatically identifying text in the medical report indicating the three-dimensional reconstruction was performed and further includes automatically determining a screenshot of the three-dimensional reconstruction was not sent to the PACS; and
wherein the at least one correction requirement indicates transmission of the screenshot of the three-dimensional reconstruction to the PACS is required.

5. The medical report analysis system of claim 4, wherein automatically determining a screenshot of the three-dimensional reconstruction was not sent to the PACS is based on processing metadata of a study corresponding to the medical report.

6. A medical report analysis system comprising:
at least one processor; and
at least one memory that stores operational instructions that, when executed by the at least one processor, cause the processor to:
receive a medical report created by a medical professional at a creation time;
prior to elapsing of a fixed-length time frame starting at the creation time:
automatically generate report analysis data for the medical report by performing a report processing function, the report analysis data to indicate at least one correction requirement to the medical report to resolve at least one detected error;
based on the report analysis data indicating at least one correction requirement to the medical report to resolve at least one detected error, automatically generate correction requirement notification data; and
facilitate communication of the correction requirement notification data to the medical professional, wherein the report analysis data indicates the at least one correction requirement based on the medical report failing to meet at least one corresponding requirement of a set of predefined report requirements, and wherein the at least one corresponding requirement includes a requirement that anatomical features indicated in a findings section of the medical report must match anatomical features indicated in an impression section of the medical report;
wherein generating the report analysis data includes:
automatically identifying a first subset of text of the medical report corresponding to the findings section of the medical report;
automatically generating finding section data indicating a first anatomical feature based on the first subset of text;
automatically identifying a second subset of text of the medical report corresponding to the impression section of the medical report; and
automatically generating impression section data indicating a second anatomical feature based on the second subset of text; and
wherein the at least one correction requirement indicates discrepancy between the findings section and the impression section based on the first anatomical feature being different from the second anatomical feature.

7. A medical report analysis system comprising:
at least one processor; and
at least one memory that stores operational instructions that, when executed by the at least one processor, cause the processor to:

receive a medical report created by a medical professional at a creation time;
prior to elapsing of a fixed-length time frame starting at the creation time:
automatically generate report analysis data for the medical report by performing a report processing function, the report analysis data to indicate at least one correction requirement to the medical report to resolve at least one detected error;
based on the report analysis data indicating at least one correction requirement to the medical report to resolve at least one detected error, automatically generate correction requirement notification data; and
facilitate communication of the correction requirement notification data to the medical professional, wherein the operational instructions, when executed by the at least one processor, further cause the processor to:
receive a second medical report created by a second medical professional at a second creation time;
prior to elapsing of the fixed-length time frame starting at the second creation time:
generate report analysis completion time estimate data indicating an estimated time that second report analysis data corresponding to the second medical report will be completed;
when the report analysis completion time estimate data indicates the estimated time will occur after the elapsing of the fixed-length time frame:
generate report analysis delay notification data based on the report analysis completion time estimate data indicates the estimated time will occur after the elapsing of the fixed-length time frame; and
facilitate communication of the report analysis delay notification data to the medical professional.

* * * * *